(12) United States Patent
Stoessel et al.

(10) Patent No.: US 11,737,352 B2
(45) Date of Patent: Aug. 22, 2023

(54) MATERIALS FOR ORGANIC ELECTROLUMINESCENT DEVICES

(71) Applicant: Merck Patent GmbH, Darmstadt (DE)

(72) Inventors: Philipp Stoessel, Frankfurt am Main (DE); Nils Koenen, Griesheim (DE); Christian Ehrenreich, Darmstadt (DE); Philipp Harbach, Muehltal (DE); Lara-Isabel Rodriguez, Darmstadt (DE); Rouven Linge, Darmstadt (DE); Sebastian Meyer, Aschaffenburg (DE); Aaron Lackner, Mannheim (DE)

(73) Assignee: Merck Patent GmbH, Darmstadt (DE)

( * ) Notice: Subject to any disclaimer, the term of this patent is extended or adjusted under 35 U.S.C. 154(b) by 655 days.

(21) Appl. No.: 16/479,662

(22) PCT Filed: Jan. 22, 2018

(86) PCT No.: PCT/EP2018/051411
§ 371 (c)(1),
(2) Date: Jul. 22, 2019

(87) PCT Pub. No.: WO2018/134392
PCT Pub. Date: Jul. 26, 2018

(65) Prior Publication Data
US 2021/0367155 A1 Nov. 25, 2021

(30) Foreign Application Priority Data

Jan. 23, 2017 (EP) .................................... 17152547

(51) Int. Cl.
```
H10K 85/60      (2023.01)
C07F 15/00      (2006.01)
C07J 9/00       (2006.01)
C07J 43/00      (2006.01)
C09K 11/06      (2006.01)
H10K 85/30      (2023.01)
H10K 50/11      (2023.01)
H10K 101/10     (2023.01)
```

(52) U.S. Cl.
CPC ....... *H10K 85/626* (2023.02); *C07F 15/0033* (2013.01); *C07J 9/00* (2013.01); *C07J 43/003* (2013.01); *C09K 11/06* (2013.01); *H10K 85/342* (2023.02); *H10K 85/622* (2023.02); *H10K 85/624* (2023.02); *H10K 85/654* (2023.02); *H10K 85/6572* (2023.02); *H10K 85/6574* (2023.02); *C09K 2211/1007* (2013.01); *C09K 2211/1011* (2013.01); *C09K 2211/1025* (2013.01); *C09K 2211/1029* (2013.01); *C09K 2211/1037* (2013.01); *C09K 2211/1044* (2013.01); *C09K 2211/1055* (2013.01); *C09K 2211/1074* (2013.01); *C09K 2211/185* (2013.01); *H10K 50/11* (2023.02); *H10K 2101/10* (2023.02)

(58) Field of Classification Search
CPC ................................................... H01L 51/0058
See application file for complete search history.

(56) References Cited

U.S. PATENT DOCUMENTS

| | | | | |
|---|---|---|---|---|
| 3,772,099 A | * | 11/1973 | Ryan | C06B 23/008 102/314 |
| 4,539,507 A | * | 9/1985 | VanSlyke | H01L 51/0068 548/137 |
| 2003/0173563 A1 | | 9/2003 | Grizzi | |
| 2008/0177059 A1 | * | 7/2008 | Bittman | C07J 43/00 540/4 |
| 2011/0236603 A1 | | 9/2011 | Hagio et al. | |
| 2011/0260114 A1 | | 10/2011 | Wu et al. | |
| 2014/0058061 A1 | | 2/2014 | Bellemin-Laponnaz et al. | |
| 2017/0125676 A1 | | 5/2017 | Anmian et al. | |

FOREIGN PATENT DOCUMENTS

| | | |
|---|---|---|
| CN | 103073444 A | 5/2013 |
| CN | 106058048 A | 10/2016 |
| DE | 102007063051 A1 | 7/2009 |
| EP | 0924724 A2 | 6/1999 |
| WO | WO-9420589 A2 | 9/1994 |

OTHER PUBLICATIONS

Kulkarni et al, Dipole-Moment-Driven Cooperative Supramolecular Polymerization, 2015, J. Am. Chem. Soc., 137, 3924-3932.*
International Search Report for PCT/EP2018/051411 dated Mar. 28, 2018.
Kabe, R., et al., "Afterglow Organic Light-Emitting Diode", Advanced Materials, vol. 28, No. 4, (2016), pp. 655-660.
Kulkarni, C., et al., "Dipole-Moment-Driven Cooperative Supramolecular Polymerization", Journal of the American Chemical Society, vol. 137, No. 11, (2015), pp. 3924-3932.
Written Opinion of the International Searching Authority for PCT/EP2018/051411 dated Mar. 28, 2018.

(Continued)

*Primary Examiner* — William D Young
(74) *Attorney, Agent, or Firm* — Faegre Drinker Biddle & Reath LLP

(57) ABSTRACT

The present invention relates to compounds of the formulae (1) to (4), which are suitable for use in electronic devices, in particular organic electroluminescent devices, to intermediate compounds for the compounds or formulae (1) to (4) and to electronic devices, which comprise the compounds of formulae (1) to (4).

15 Claims, No Drawings

(56) References Cited

OTHER PUBLICATIONS

Zhao, L., et al., "Horizontal molecular orientation in solution-processed organic light-emitting diodes", Applied Physics Letters, vol. 106, No. 6, (2015), pp. 063301-1 to 063301-5.
Roder et al., "Potential adrenal gland imaging agents. II. Radioiodination of p-hydroxyphenyl derivatives of digitoxigenin, dihydrodigitoxigenin, and scillarenin," Arch Pharm, vol. 318, No. 10, Nov. 2022, pp. 882-888.
Xu et al., "Excited State Modulation for Organic Afterglow: Materials and Applications," Advanced Materials, vol. 28, No. 45, Dec. 7, 2016, pp. 9920-9940.

* cited by examiner

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2018/051411, filed Jan. 22, 2018, which claims benefit of European Application No. 17152547.0, filed Jan. 23, 2017, both of which are incorporated herein by reference in their entirety.

The present invention relates to a compound of one of the formulae (1) to (4), to the use of the compound in an electronic device, and to an electronic device comprising at least one compound of one of the formulae (1) to (4). The present invention furthermore relates to a process for the preparation of compounds of the formulae (1) to (4) and to a formulation comprising one or more compounds of the formulae (1) to (4).

The development of functional compounds for use in electronic devices is currently the subject of intensive research. The aim is, in particular, the development of compounds with which improved properties of electronic devices in one or more relevant points can be achieved, such as, for example, efficiency and lifetime of the device as well as colour coordinates of the emitted light.

In accordance with the present invention, the term electronic device is taken to mean, inter alia, organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the last-mentioned electronic devices called OLEDs. The general structure and the functional principle of OLEDs are known to the person skilled in the art and are described, for example, in U.S. Pat. No. 4,539,507.

An OLED comprises different layers, which are usually applied either by vapour deposition in a vacuum chamber or are processed from solution. The processes based on vapour deposition lead to good results but such processes are complex and thus expensive and unsuitable, in particular, for relatively high-molecular-weight compounds, such as, for example, polymers.

In the case of low-molecular-weight organic compounds (so-called "Small Molecules"), processing from solution is also desirable owing to the high technical complexity in the case of vacuum processing. Small molecules have a molecular weight equal or inferior to 3000 g/mol. When they are processed from solution, they should have good solubility properties in the solution that comprises them.

The present invention is thus based on the technical object of providing compounds which are suitable for use in electronic devices, such as OLEDs, which can be employed as fluorescent emitting compounds, phosphorescent emitting compounds, hosts for fluorescent emitting compounds and hosts for phosphorescent emitting compounds and which are suitable for solution processing.

It has been found here that small molecules comprising at least one terpene group exhibit good properties with regard to solubility and at the same time, lead to OLEDs that have improved properties, particularly in terms of efficiency.

Without wishing to be bound by theory, the inventors of the present application believe that the terpene substituents, due to their rod-shape, control the orientation of the functional materials to which they are appended, without influencing the electronic properties of the groups to which they are appended. This leads to OLED having improved performances in terms of efficiency. The term orientation means here the horizontal molecular orientation of the compounds, as explained in Zhao et al., Horizontal molecular orientation in solution-processed organic light-emitting diodes, Appl. Phys. Lett. 106063301, 2015.

The invention thus relates to a compound of one of the formulae (1) to (4),

Formula (1)

Formula (2)

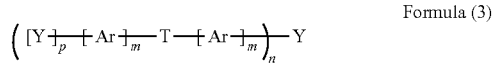

Formula (3)

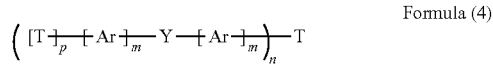

Formula (4)

where the following applies to the symbols and indices used:

Y is selected from the group consisting of fluorescent emitting groups, phosphorescent emitting groups, host groups for fluorescent emitting compounds and host groups for phosphorescent emitting compound, having a molecular weight equal or inferior to 3000 g/mol, and which may in each case be substituted by one or more radicals $R^1$;

Ar is on each occurrence, identically or differently, selected from the group consisting of aromatic or heteroaromatic ring systems having 5 to 60 aromatic ring atoms, which may in each case also be substituted by one or more radicals R, where two groups Ar are allowed to be connected via a single bond or a divalent bridge;

T is on each occurrence, identically or differently selected from the group consisting of terpene and terpenoid groups, which may in each case be substituted by one or more radicals $R^1$;

R, $R^1$ stand on each occurrence, identically or differently, for H, D, F, Cl, Br, I, CHO, CN, $NO_2$, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals $R^2$, where in each case one or more non-adjacent $CH_2$ groups may be replaced by $R^2C=CR^2$, CEO, C=O, C=S, SO, $SO_2$, O or S and where one or more H atoms may be replaced by D, F, Cl, Br, I, CN or $NO_2$, an aromatic or heteroaromatic ring systems having 5 to 60 aromatic ring atoms, which may in each case be substituted by one or more radicals $R^2$, or an aryloxy groups having 5 to 60 aromatic ring atoms, which may be substituted by one or more radicals $R^2$, where two adjacent substituents R and/or two adjacent substituents $R^1$ may form a mono- or polycyclic, aliphatic ring system or aromatic ring system, which may be substituted by one or more radicals $R^2$;

$R^2$ stands on each occurrence, identically or differently, for H, D, F, Cl, Br, I, CN, a straight-chain alkyl, alkoxy or thioalkyl groups having 1 to 20 C atoms or branched or cyclic alkyl, alkoxy or thioalkyl groups having 3 to 20 C atoms, where in each case one or more non-adjacent $CH_2$ groups may be replaced by SO, $SO_2$, O, S and where one or more H atoms may be replaced by D, F, Cl, Br or I, or an aromatic or heteroaromatic ring system having 5 to 24 C atoms;

m is on each occurrence, identically or differently, 0, 1, 2, 3 or 4;

n is an integer selected from 1 to 8; and p is on each occurrence, identically or differently, 0 or 1, with the proviso that at least one p is equal to 1 in formulae (1) and (2).

Adjacent substituents in the sense of the present invention are substituents which are bonded to atoms which are linked directly to one another or which are bonded to the same atom.

Furthermore, the expression according to which at least one p is equal to 1 in formulae (1) and (2), means that there is at least one group T present in the compounds of formulae (1) and (2). Thus if, n is equal to 1 in formulae (1) and (2), then p is also equal to 1. If n is equal to 2 in formulae (1) and (2), then the index p occurs two times and one of them must be equal to 1. The other one is then equal to 0 or 1.

In accordance with the invention, if n is 1 in formula (1), then there is one group —(Ar)$_m$-(T)$_p$, where p is 1, which is bonded to the group Y. If n is an integer equal to 2 or more, in formula (1), then there are 2 or more groups —(Ar)$_m$-(T)$_p$, where at least one p is 1, which are bonded to the group Y as represented in the examples below:

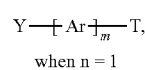

Formula (1)

when n = 1

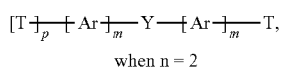

Formula (1)

when n = 2

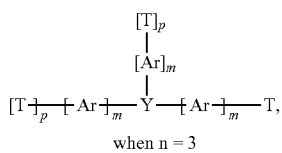

Formula (1)

when n = 3

In accordance with the invention, if n is 1 in formula (2), then there is one group —(Ar)$_m$—(Y)$_p$, where p is 1, which is bonded to the group T. If n is an integer equal to 2 or more, in formula (2), then there are 2 or more groups —(Ar)$_m$—(Y)$_p$, where at least one p is 1, which are bonded to the group T as represented in the examples below:

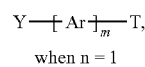

Formula (2)

when n = 1

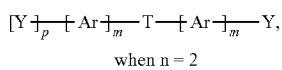

Formula (2)

when n = 2

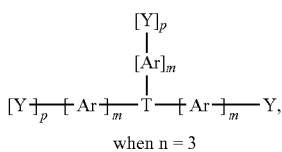

Formula (2)

when n = 3

In the same way, if n is 1 in formula (3), then there is one group —(Ar)$_m$-T-(Ar)$_m$—(Y)$_p$, which is bonded to the group Y. If n is an integer equal to 2 or more, in formula (3), then there are 2 or more groups —(Ar)$_m$-T-(Ar)$_m$—(Y)$_p$, which are bonded to the same group Y.

In still the same way, if n is 1 in formula (4), then there is one group —(Ar)$_m$—Y—(Ar)$_m$-(T)$_p$, which is bonded to the group T. If n is an integer equal to 2 or more, in formula (2), then there are 2 or more groups —(Ar)$_m$—Y—(Ar)$_m$-(T)$_p$, which are bonded to the same group T.

Furthermore, the following definitions of chemical groups apply for the purposes of the present application:

An aryl group in the sense of this invention contains 6 to 60 aromatic ring atoms, preferably 6 to 40 aromatic ring atoms, more preferably 6 to 20 aromatic ring atoms; a heteroaryl group in the sense of this invention contains 5 to 60 aromatic ring atoms, preferably 5 to 40 aromatic ring atoms, more preferably 5 to 20 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system, preferably 6 to 40 C atoms, more preferably 6 to 20 C atoms. A heteroaromatic ring system in the sense of this invention contains 5 to 60 aromatic ring atoms, preferably 5 to 40 aromatic ring atoms, more preferably 5 to 20 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an spa-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. This is illustrated by the following schemes:

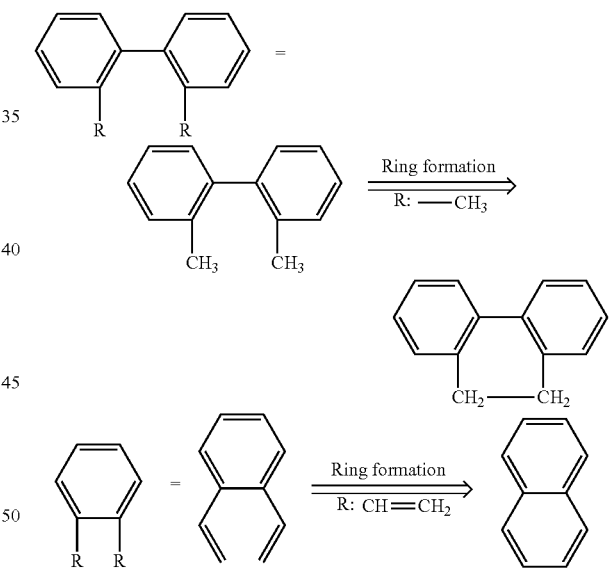

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

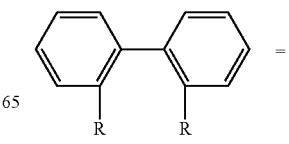

-continued

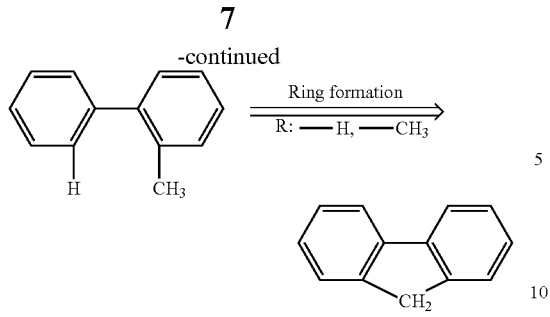

In accordance with a preferred embodiment, m is on each occurrence, identically or differently 0, 1 or 2, more preferably 1 or 2.

In accordance with a preferred embodiment, the index n, in formulae (1) to (4), is an integer selected from 1 to 4, more preferably 1 to 3, very more preferably 1 or 2.

In accordance with a preferred embodiment, the compound according to the invention is a compound of formula (1) or (2). More preferably, it is a compound according to formula (1) or (2), where p is on each occurrence equal to 1, and m is on each occurrence equal to one.

The group Ar is preferably selected from aromatic and heteroaromatic ring systems having 5 to 25 aromatic ring atoms, preferably 6 to 18 aromatic ring atoms, which may in each case also be substituted by one or more radicals R, where two groups Ar are allowed to be connected via a single bond or a divalent bridge.

The formulation that two groups Ar may be connected via a single bond or a divalent bridge is, for the purposes of the present application, intended to be taken to mean, inter alia, that the two groups are linked to one another. This is illustrated by the following schemes:

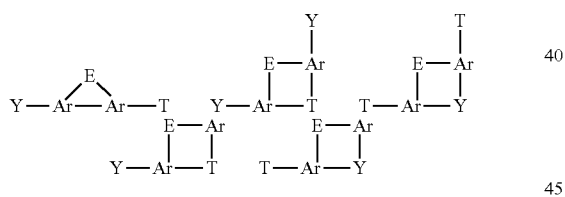

where the group E is a single bond or a divalent bridge, for example —C(R)$^2$—, —O—, —S— and —N(R)—. The group E is preferably a single bond or a group —C(R)$^2$—.

The group Ar is very preferably selected from aromatic ring systems having 6 to 18 aromatic ring atoms, which may in each case also be substituted by one or more radicals R. The group Ar is particularly preferably selected from benzene, biphenyl, naphtyl and fluorene, which may in each case also be substituted by one or more radicals R.

Examples of suitable divalent groups Ar are the groups of formulae (Ar-1) to (Ar 24),

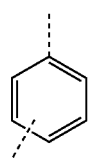

Ar-1

Ar-2

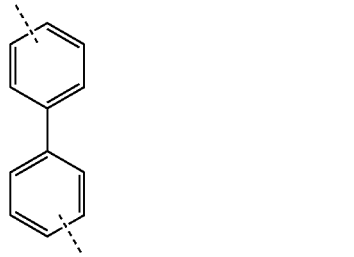

Ar-3

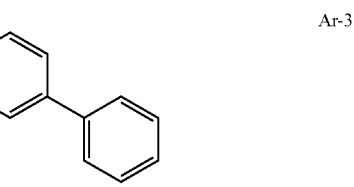

Ar-4

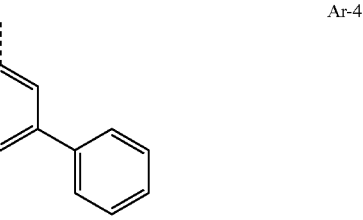

Ar-5


Ar-6


Ar-7

Ar-8


Ar-9

Ar-10

Ar-11 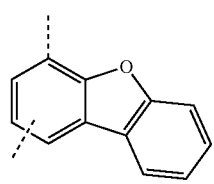
Ar-12 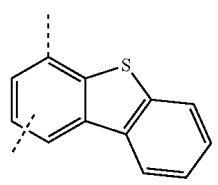
Ar-13 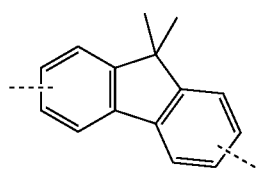
Ar-14 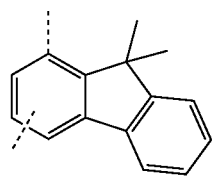
Ar-15 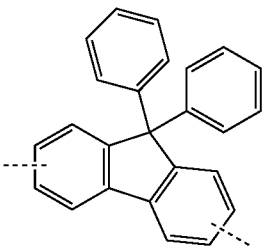
Ar-16 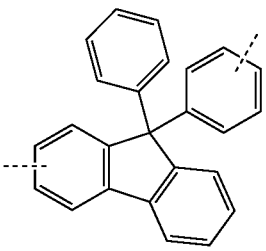
Ar-17 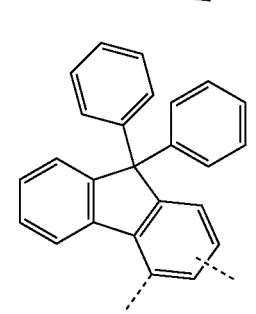
Ar-18 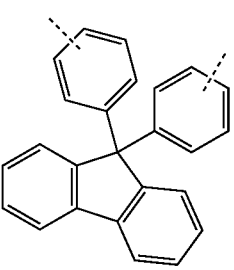
Ar-19 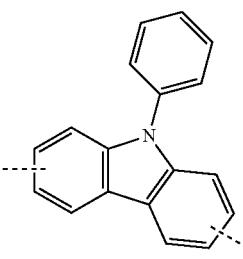
Ar-20 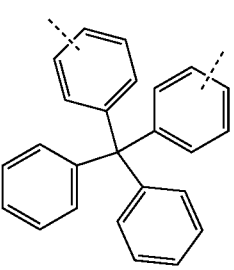
Ar-21 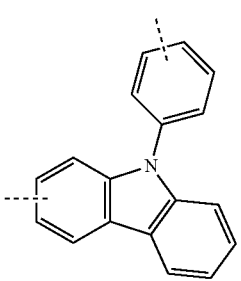
Ar-22 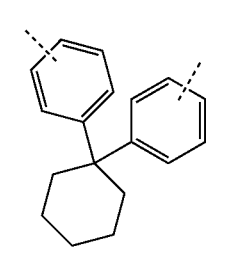
Ar-23 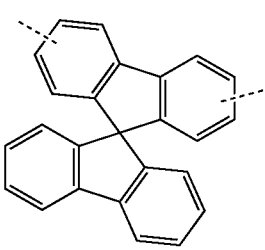

-continued

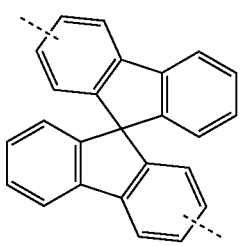
Ar-24 where the dashed bonds indicate the bonds to:

T and Y when m=1; or

T and another group Ar when m≥1; or

Y and another group Ar when m≥1.

Examples of suitable monovalent groups Ar are the groups of formulae (Ar-25) to (Ar-33),

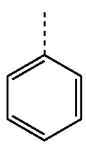
Ar-25

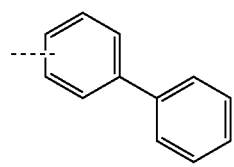
Ar-26

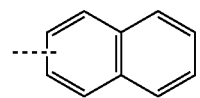
Ar-27

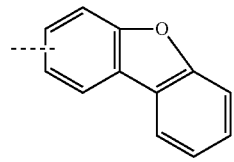
Ar-28

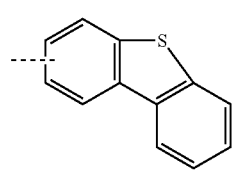
Ar-29

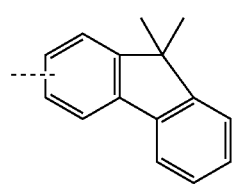
Ar-30

-continued

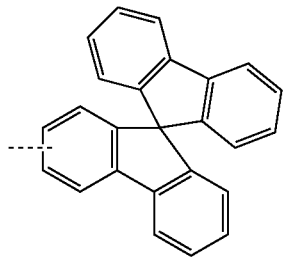
Ar-31

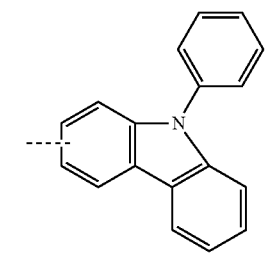
Ar-32

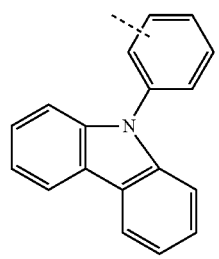
Ar-33 where the dashed bond indicates the bond to Y, T or an adjacent Ar.

In accordance with a preferred embodiment, the group T, when m is 0, is bonded to the group Y via a carbon-carbon bond or the group Ar, when m is 1, is bonded to the group Y via a carbon-carbon bond.

In accordance with a preferred embodiment, the group Y is a phosphorescent emitting group.

A phosphorescent emitting group according to the present invention encompasses groups, in which the light emission takes place through a spin-forbidden transition, for example a transition from an excited triplet state or a state having a relatively high spin quantum number, for example a quintet state. The phosphorescent emitting group can emit light, in the visible region, near UV or near IR, on suitable excitation and in addition contains at least one atom having an atomic number greater than 20, preferably greater than 38 and less than 84, particularly preferably greater than 56 and less than 80.

The phosphorescent emitting groups are preferably compounds which contain copper, molybdenum, tungsten, rhenium, ruthenium, osmium, rhodium, iridium, palladium, platinum, silver, gold or europium, in particular compounds which contain iridium, platinum or copper.

When the group Y is a phosphorescent emitting group, it is preferably selected from iridium, platinum or copper complexes. All luminescent iridium, platinum or copper complexes are regarded as phosphorescent compounds in the sense of the present invention.

Examples of suitable groups Y, when Y is a phosphorescent emitting group, are the groups listed in the following table:

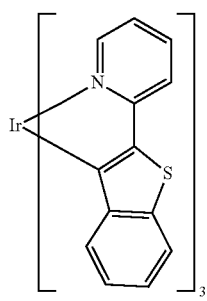
P1
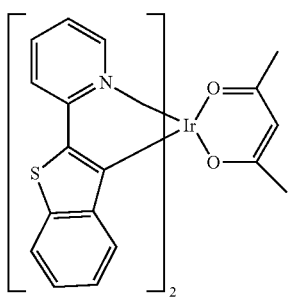
P2
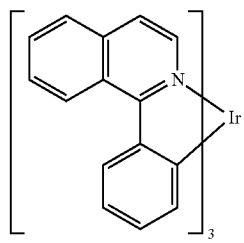
P3
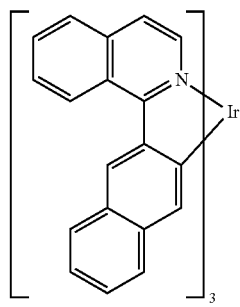
P4
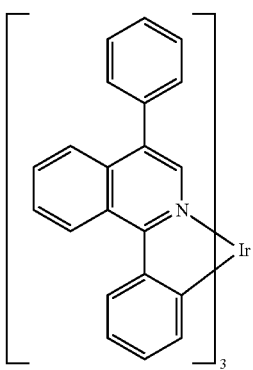
P5

-continued
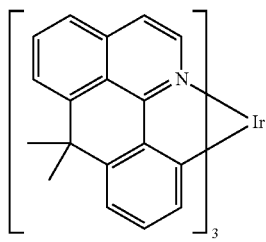
P6
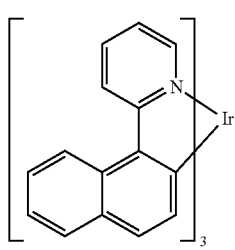
P7
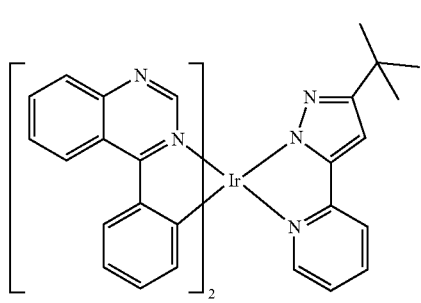
P8
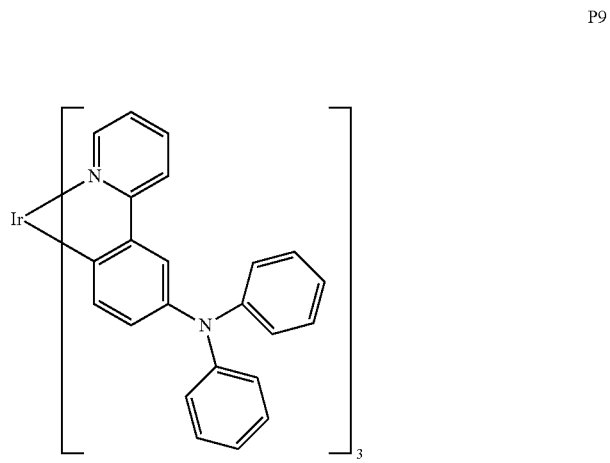
P9
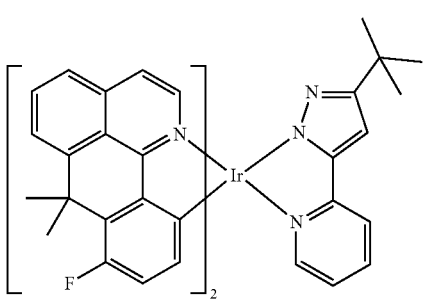
P10

-continued
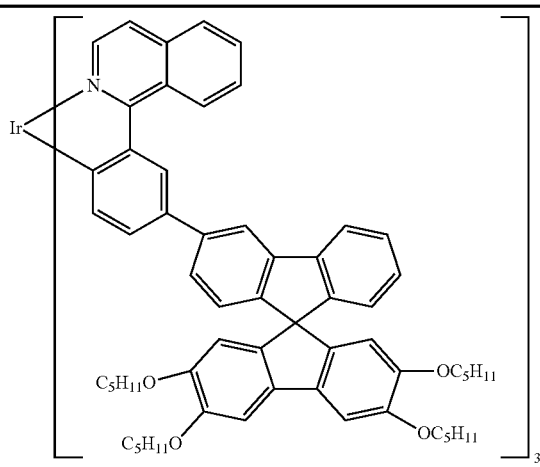
P11
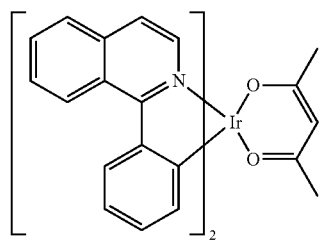
P12
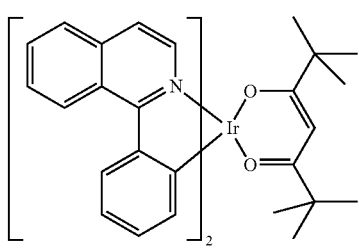
P13
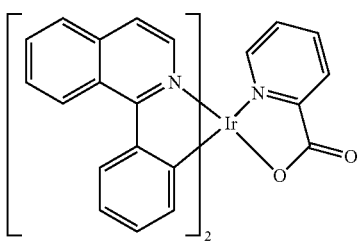
P14
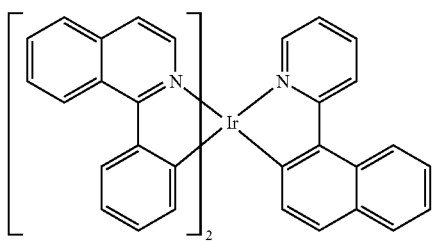
P15

-continued
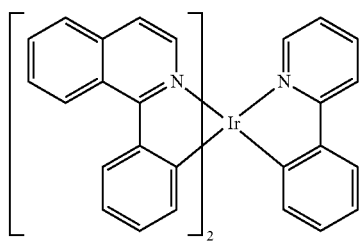
P16
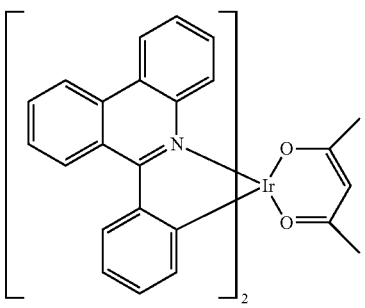
P17
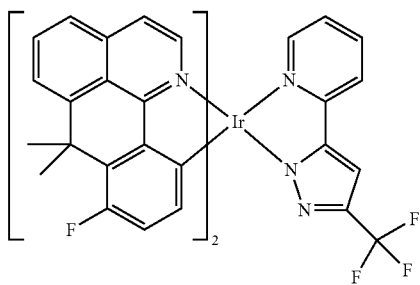
P18
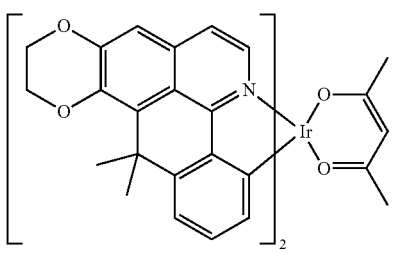
P19
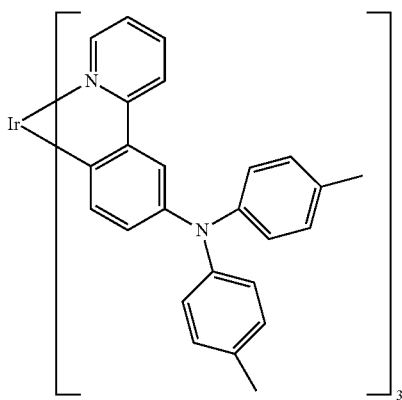
P20

-continued
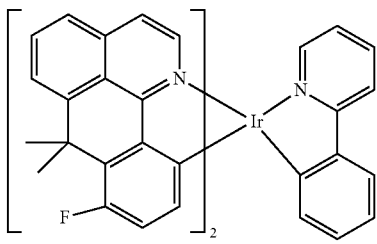
P21
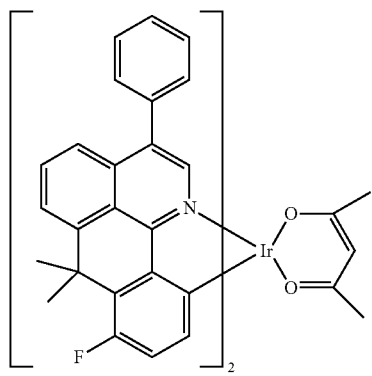
P22
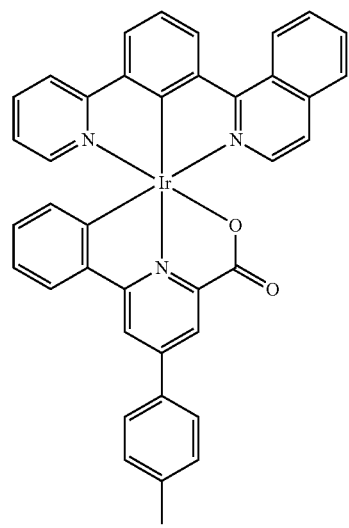
P23
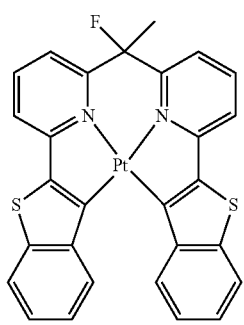
P24

-continued
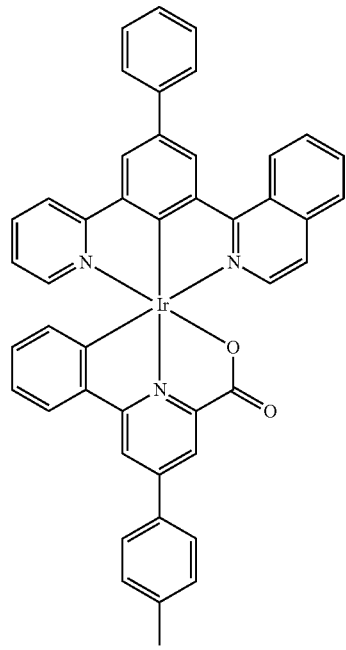
P25
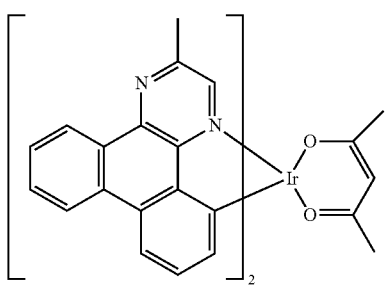
P26
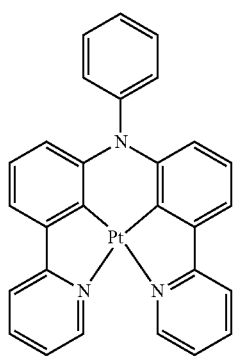
P27
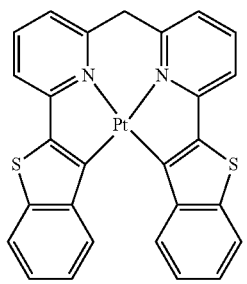
P28

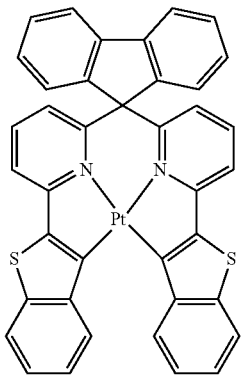
P29
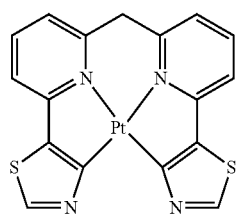
P30
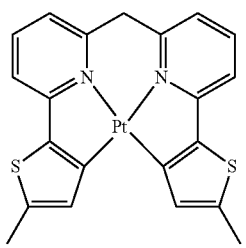
P31
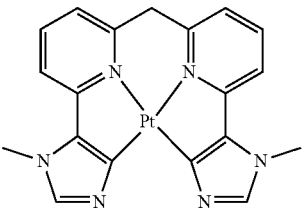
P32
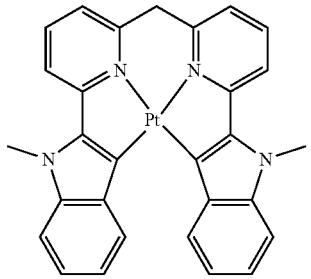
P33

-continued
P34
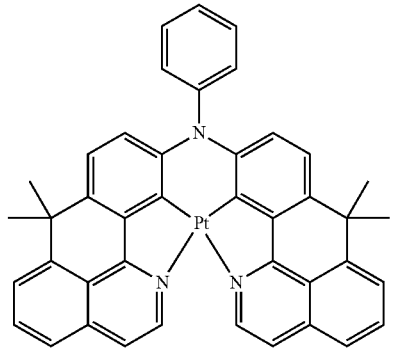
P35
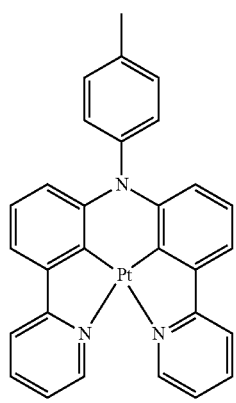
P36
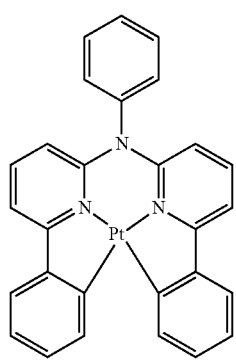
P37
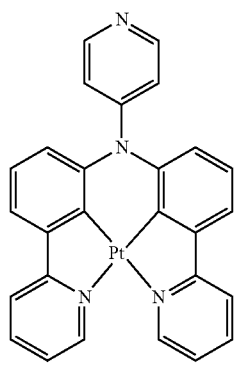

-continued
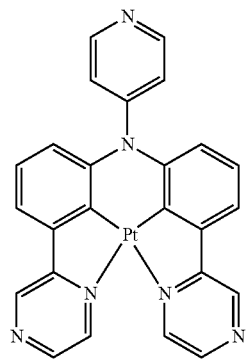
P38
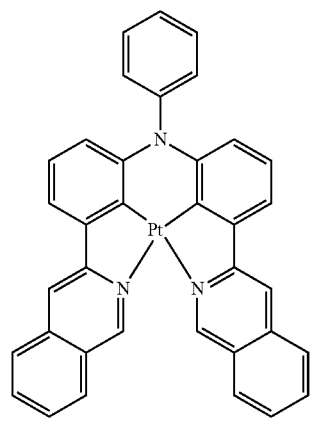
P39
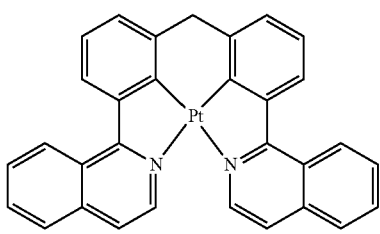
P40
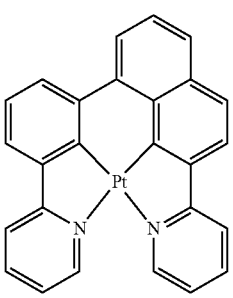
P41
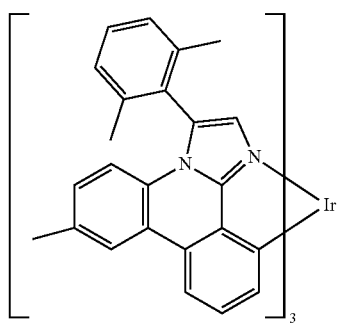
P42

-continued
P43
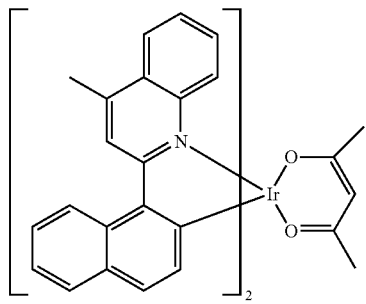
P44
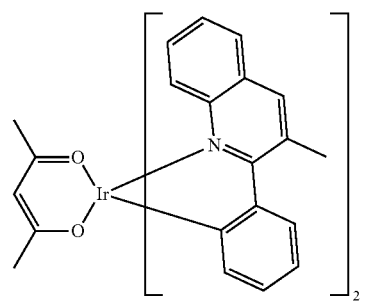
P45
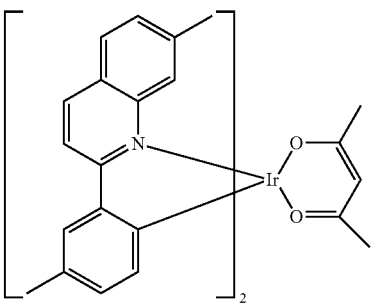
P46
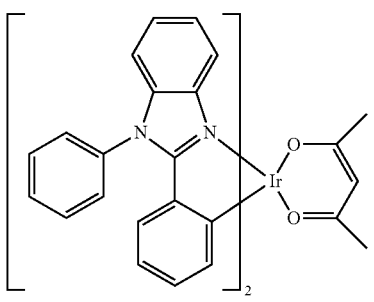

-continued
P47
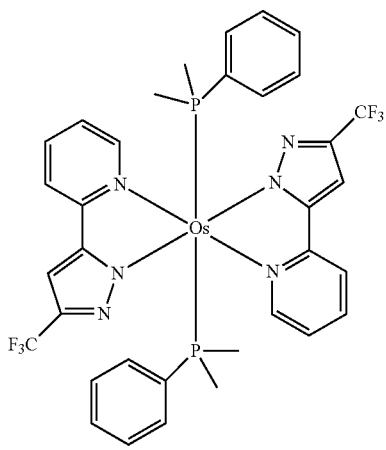
P48
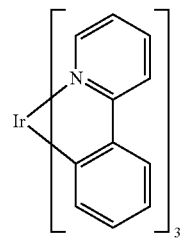
P49
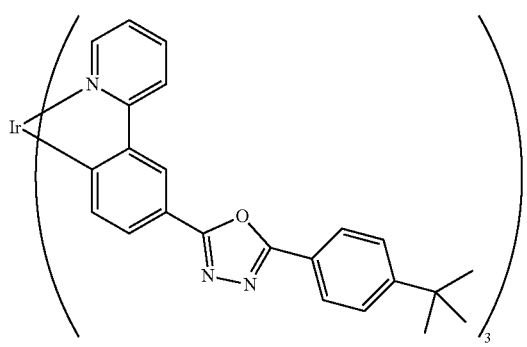
P50
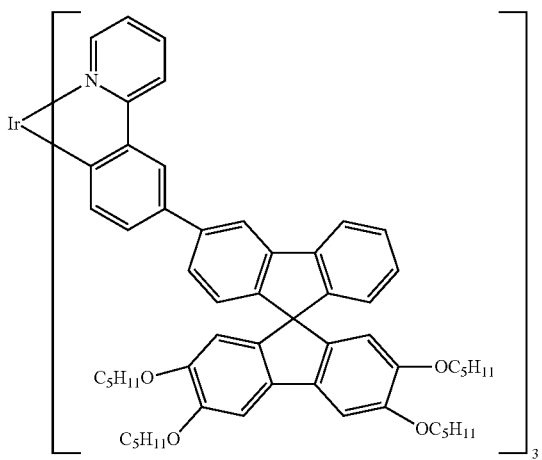

-continued
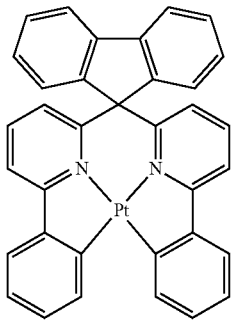
P51
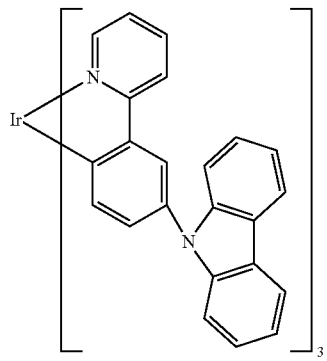
P52
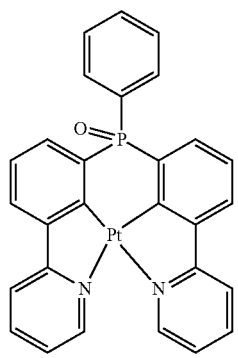
P53
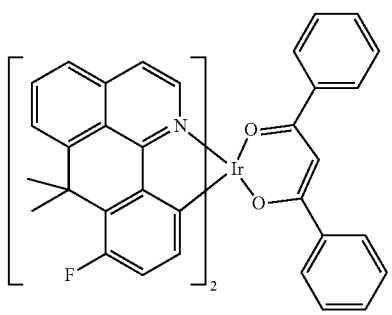
P54
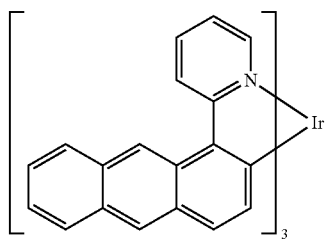
P55

-continued
P56
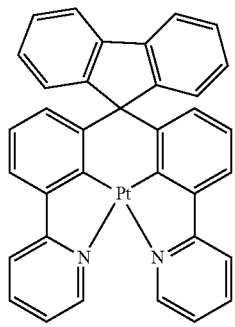
P57
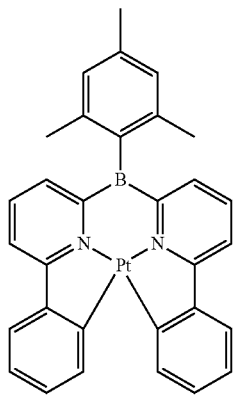
P58
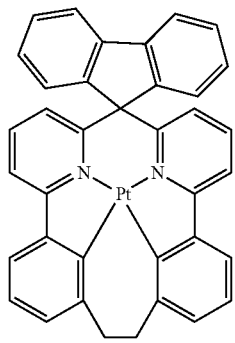
P59
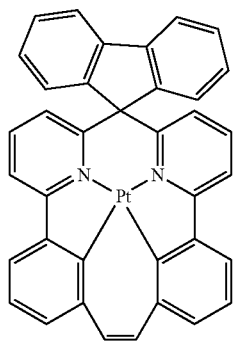

-continued
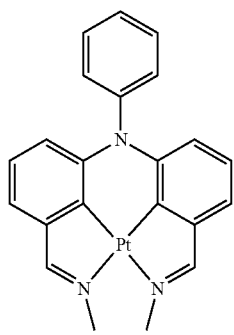
P60
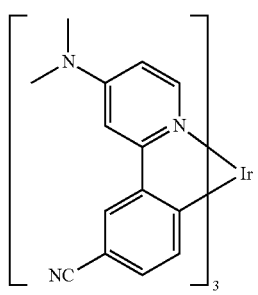
P61
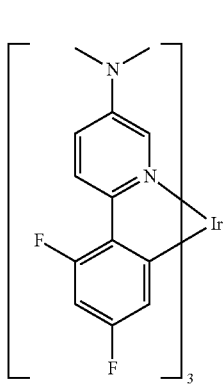
P62
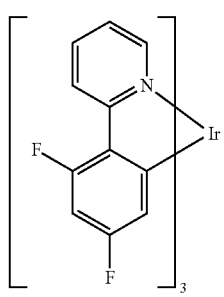
P63
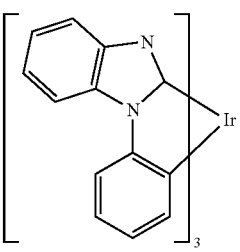
P64

-continued
P65
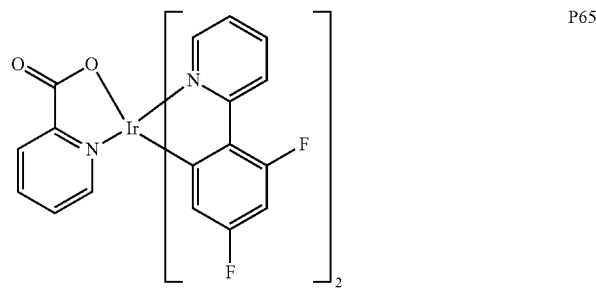
P66
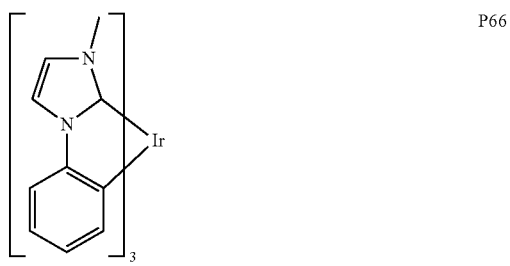
P67
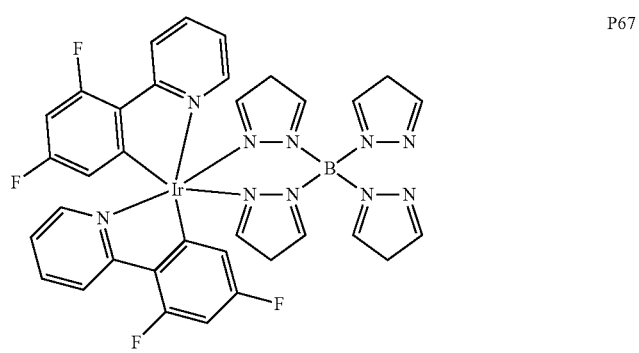
P68
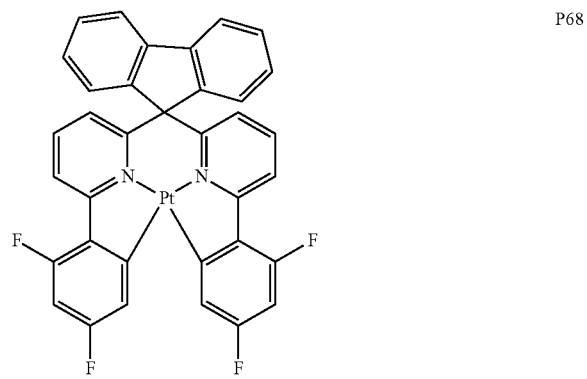
P69
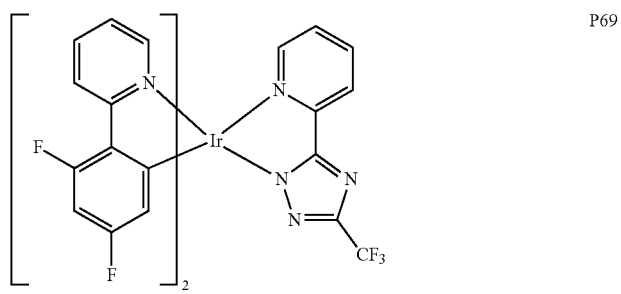

-continued
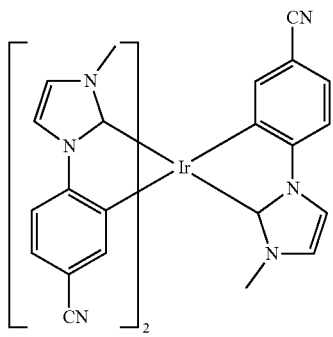
P70
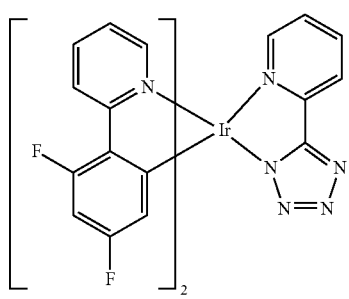
P71
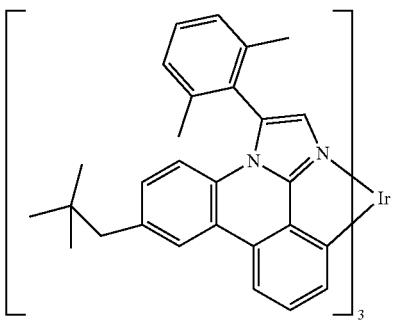
P72
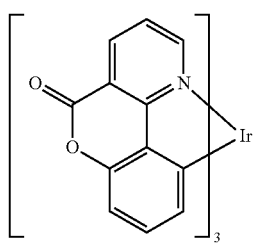
P73
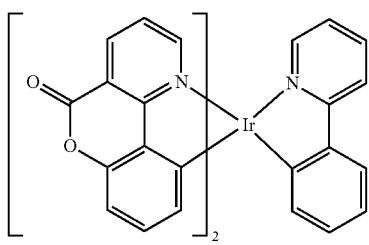
P74

-continued
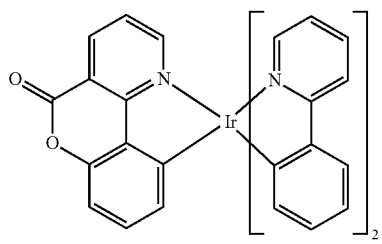
P75
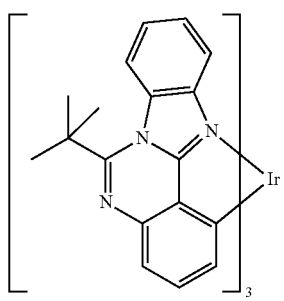
P76
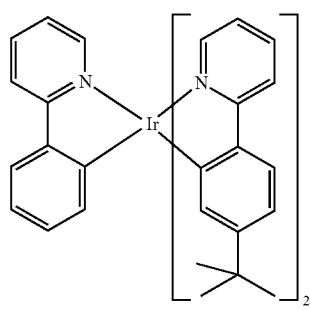
P77
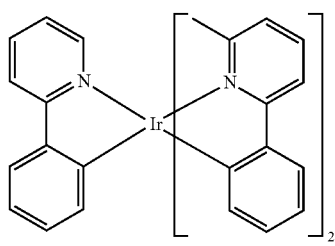
P78
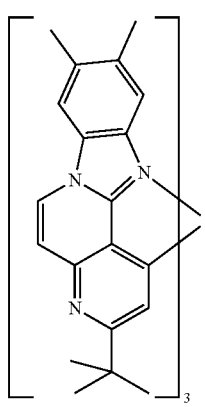
P79

-continued
P80
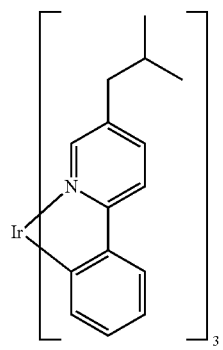
P81
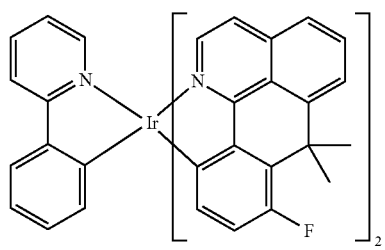
P82
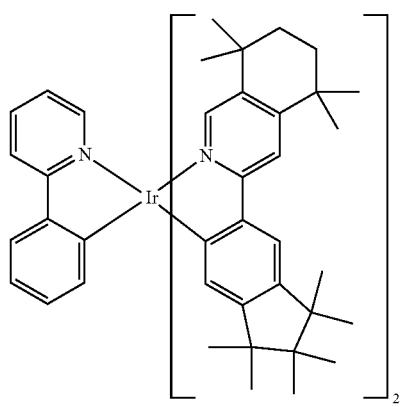
P83
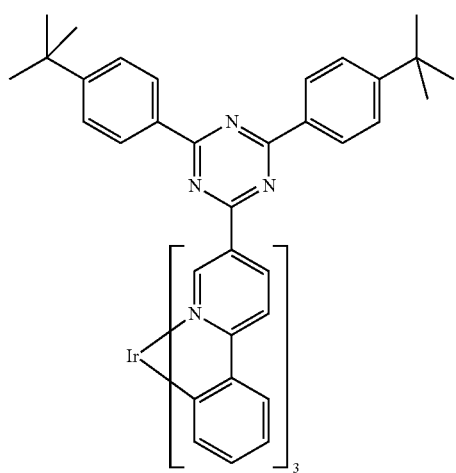

-continued
P84
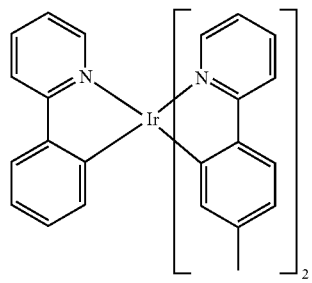
P85
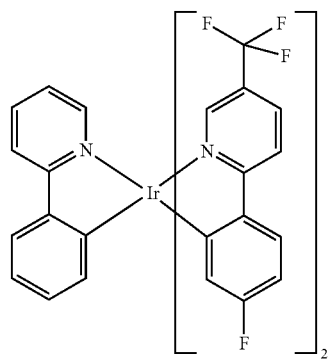
P86
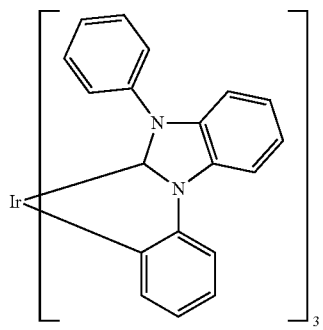
P87
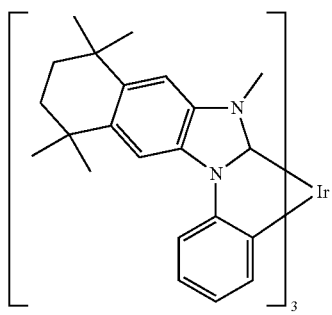

P88
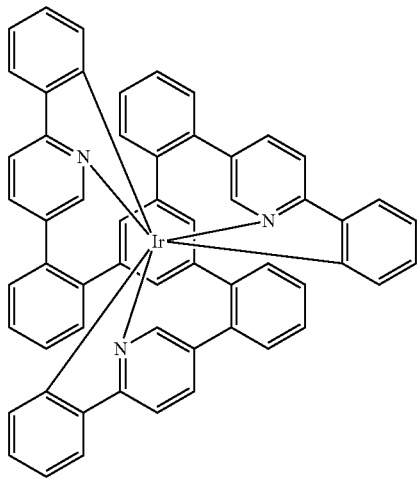
P89
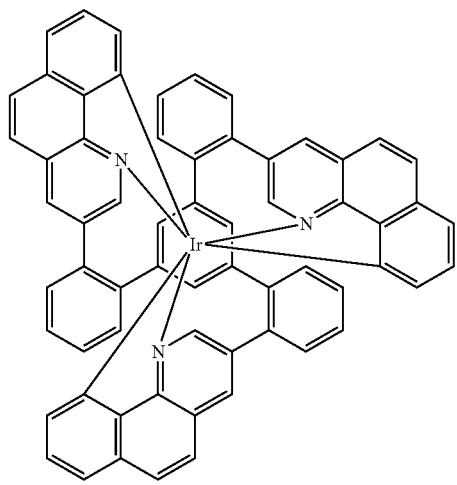
P90
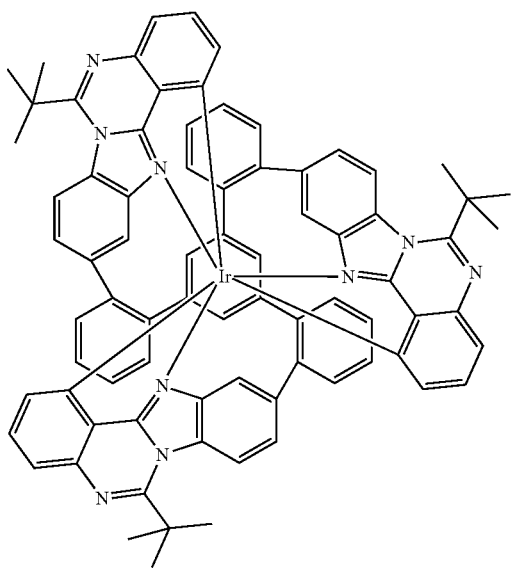

-continued
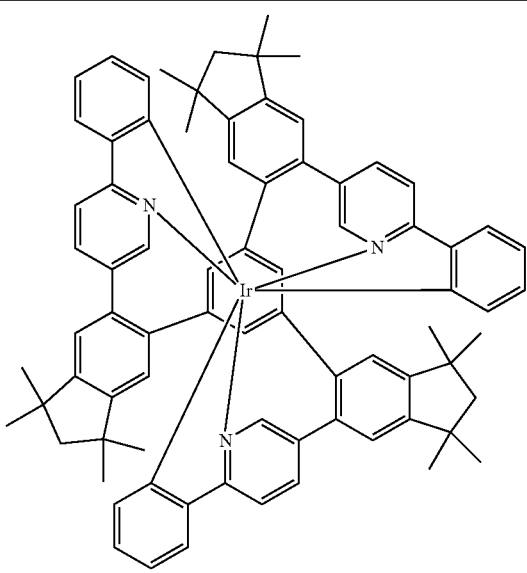
P91
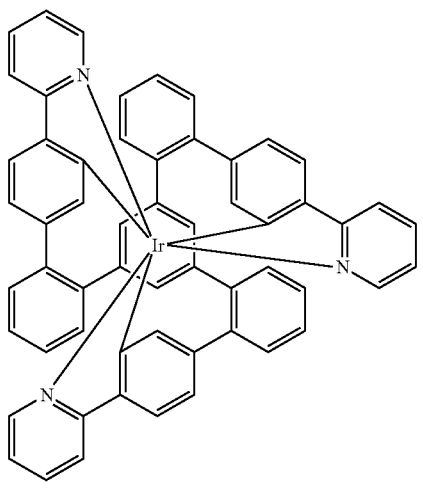
P92
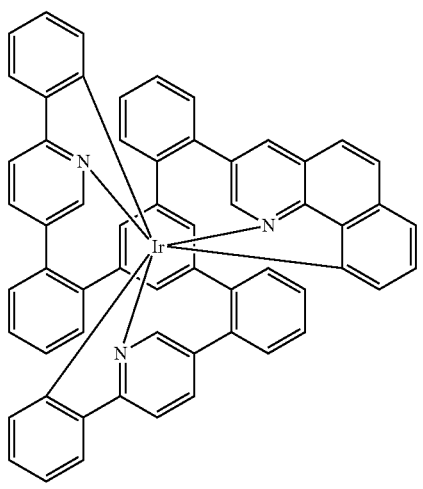
P93

-continued
P94
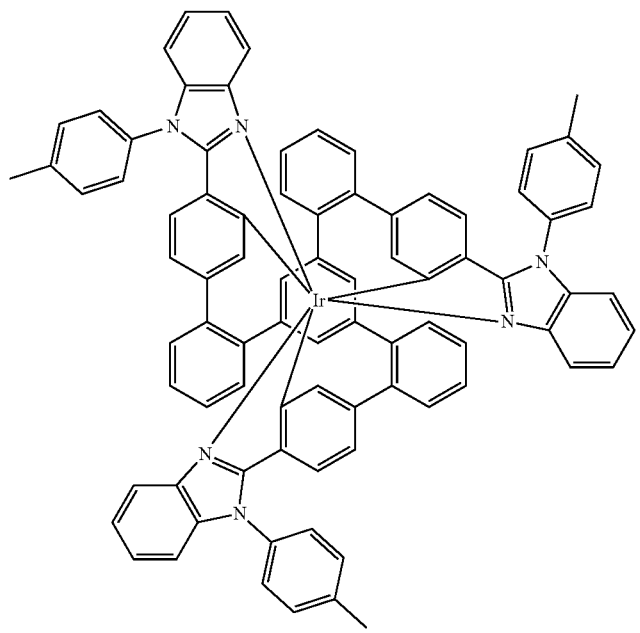
P95
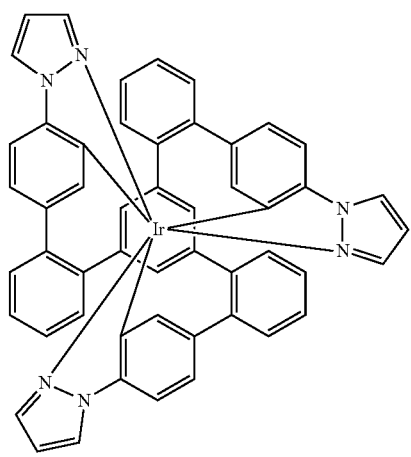
P96
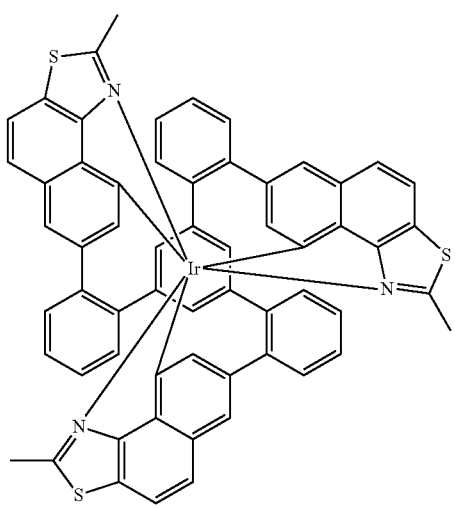

P97
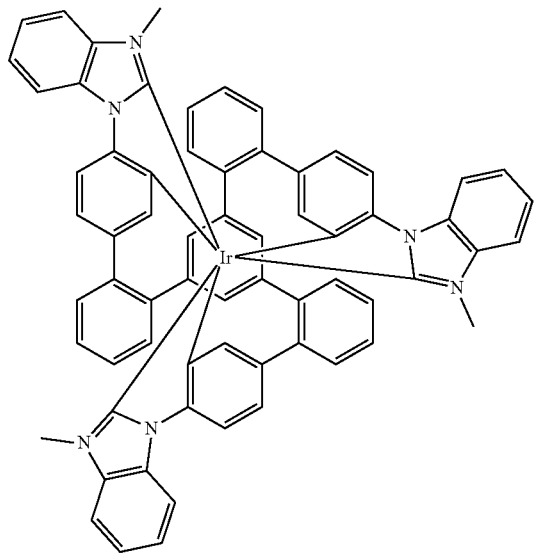
P98
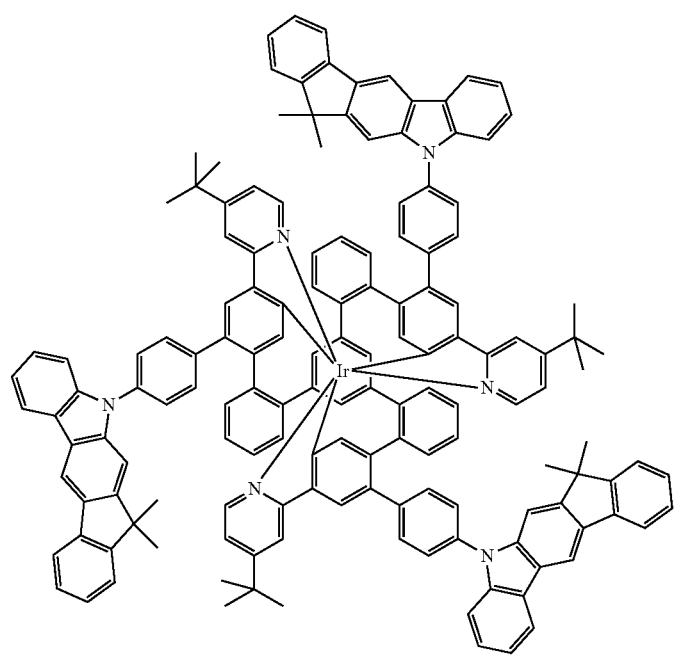

-continued
P99
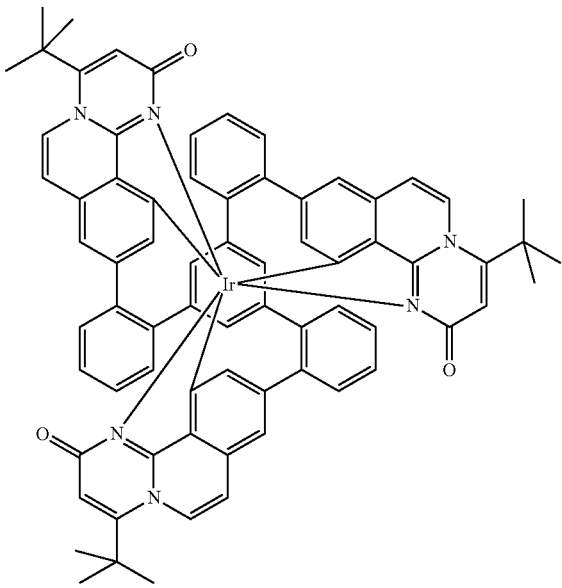
P100
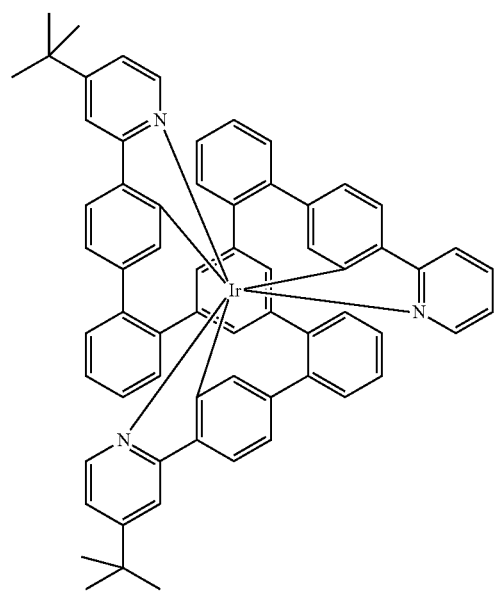

-continued
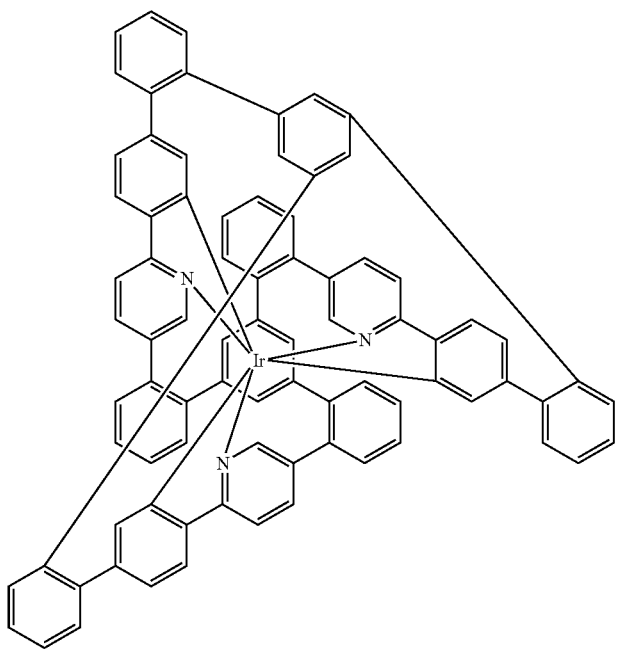
P101
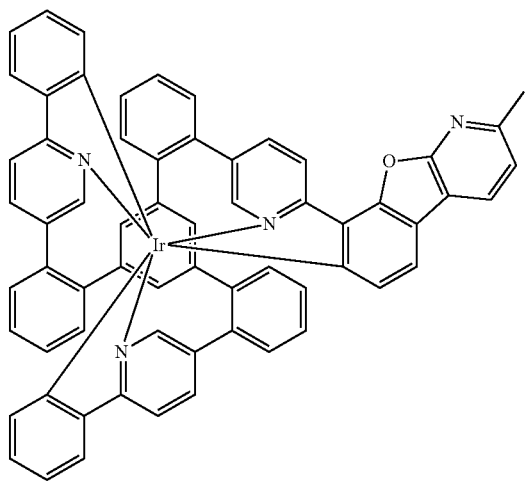
P102
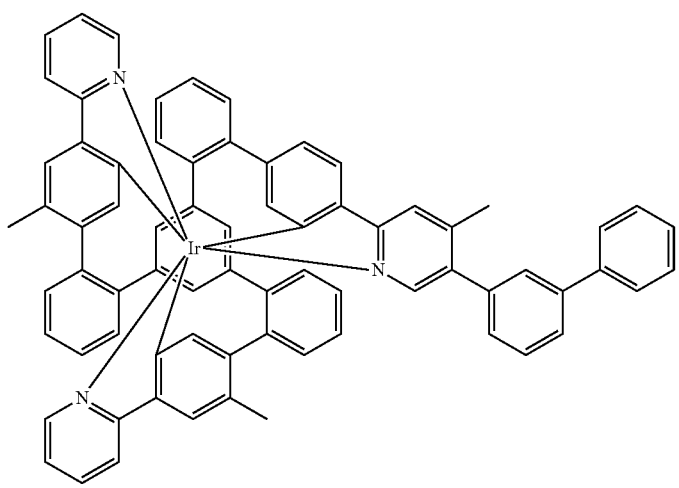
P103 where at least one group T may be appended at any free position of the group (P1) to (P103), directly or via a group Ar, and where the groups (P1) to (P103) may further be substituted at any free position by a radical $R^1$ as defined above.

Examples of suitable phosphorescent emitting compounds substituted by at least one terpene or terpenoid group are represented in the table below:

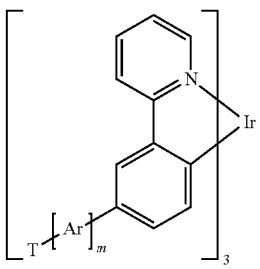
PT-1

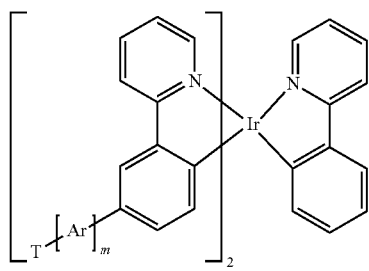
PT-2

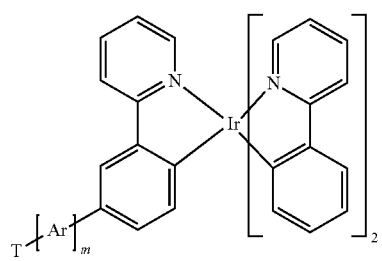
PT-3

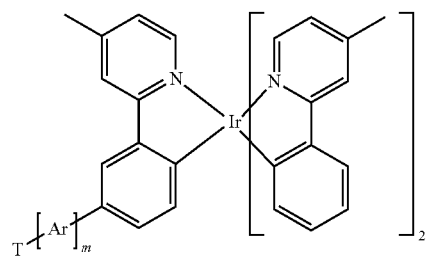
PT-4

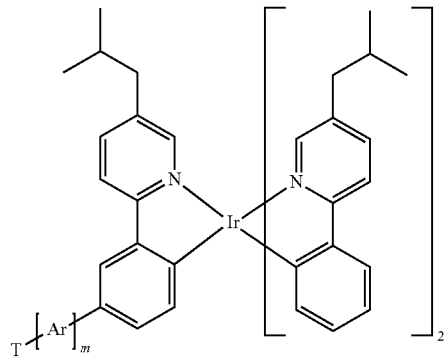
PT-5

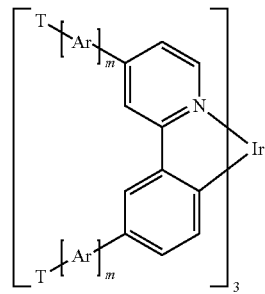
PT-6
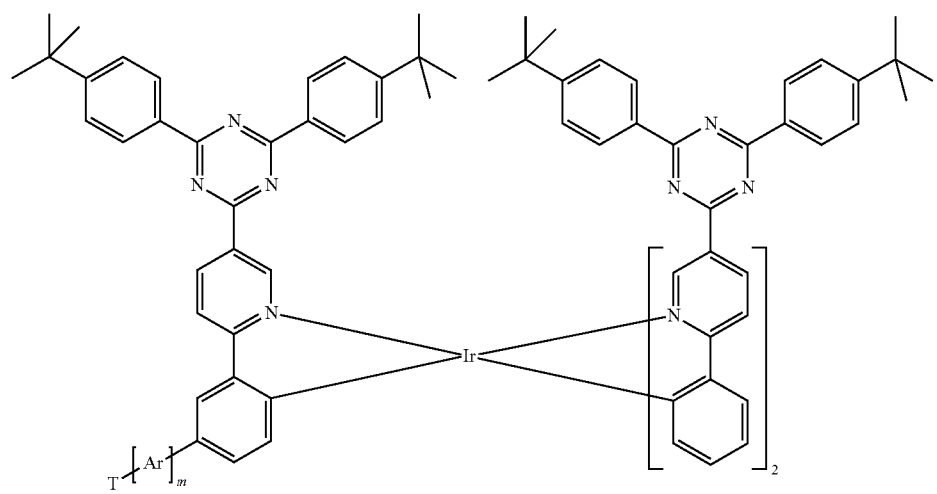
PT-7
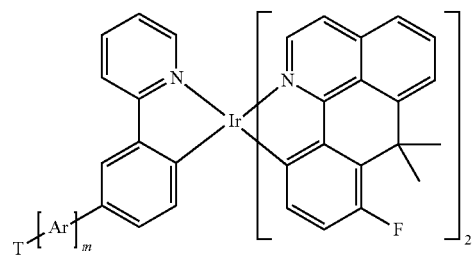
PT-8
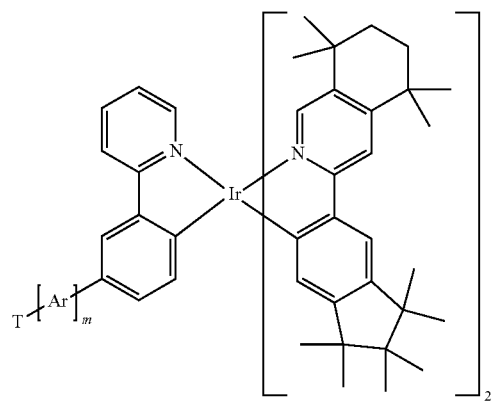
PT-9

-continued
PT-10
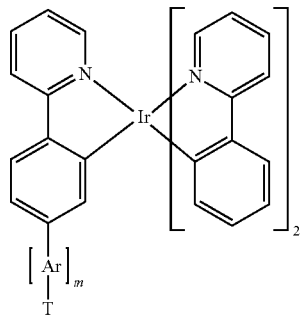
PT-11
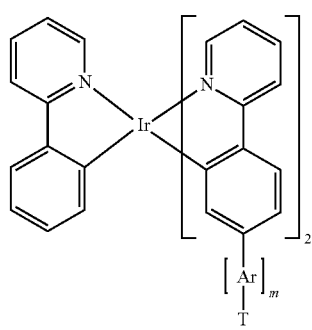
PT-12
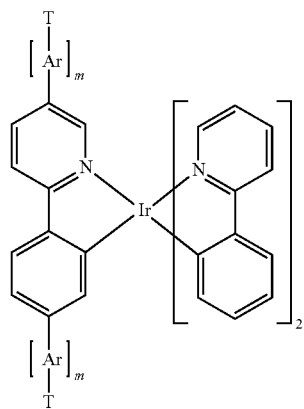
PT-13
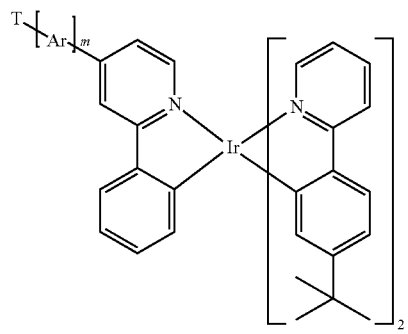

-continued
PT-14
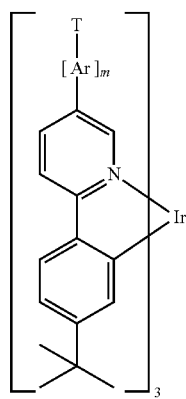
PT-15
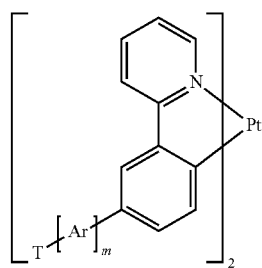
PT-16
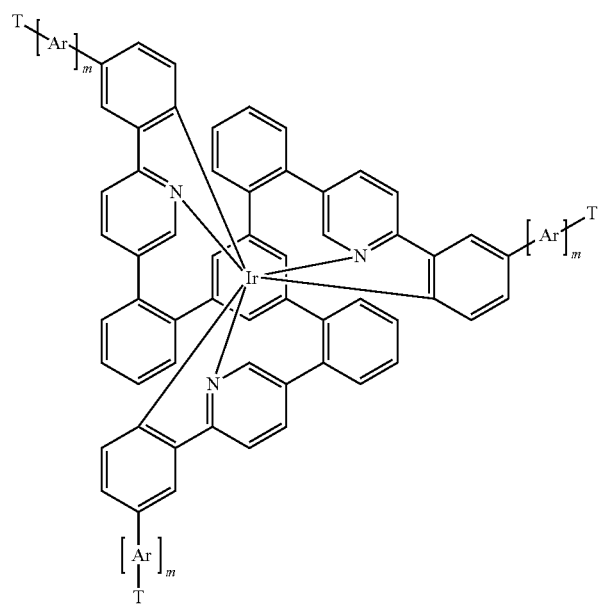

PT-17
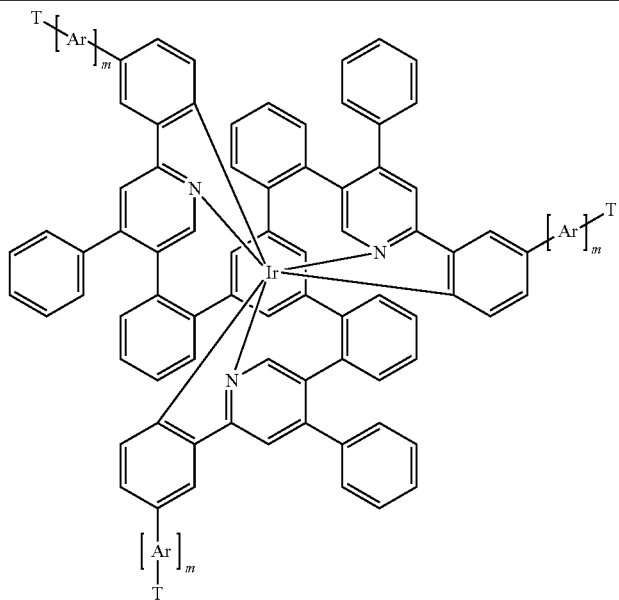
PT-18
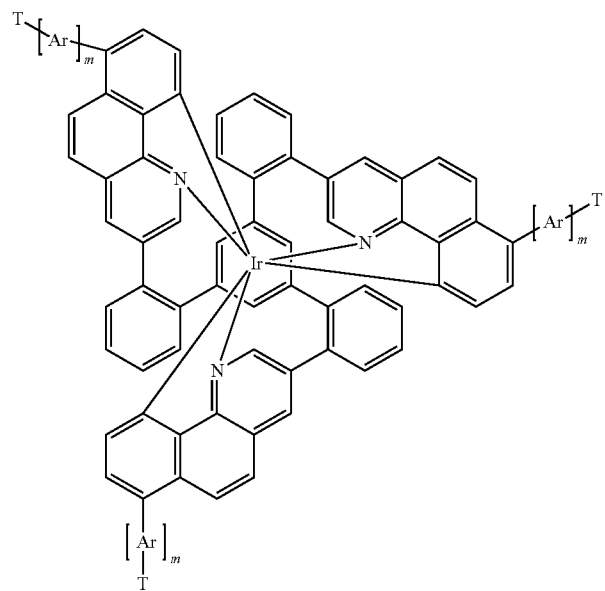

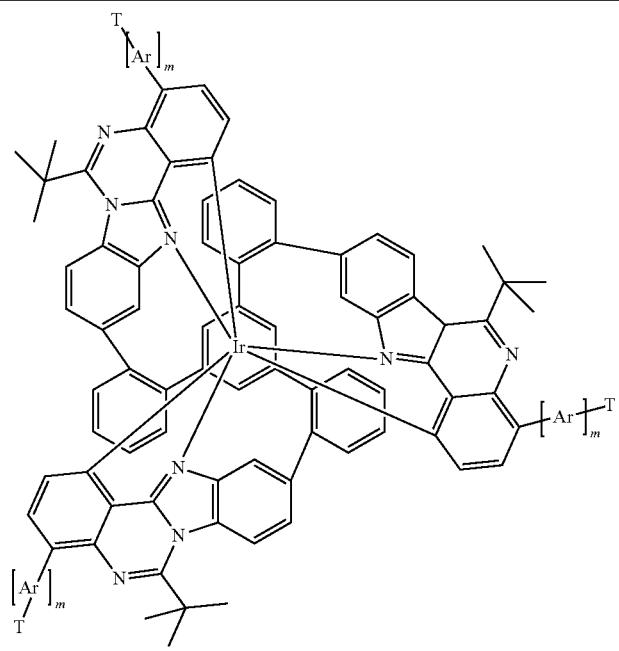
PT-19
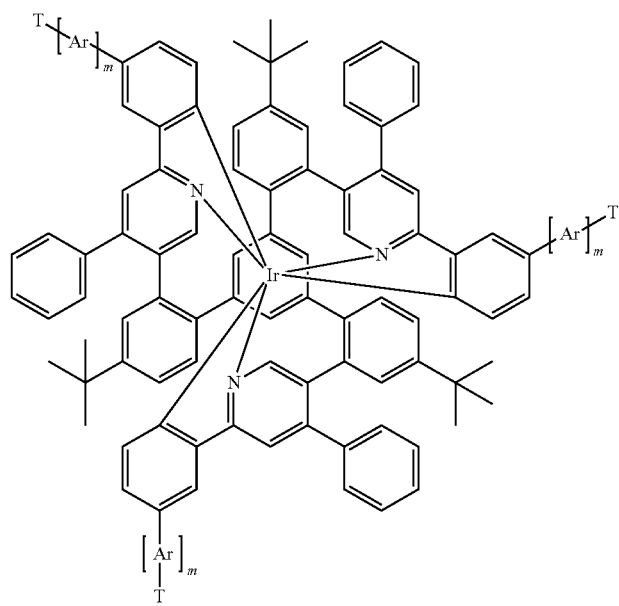
PT-20

-continued
PT-21
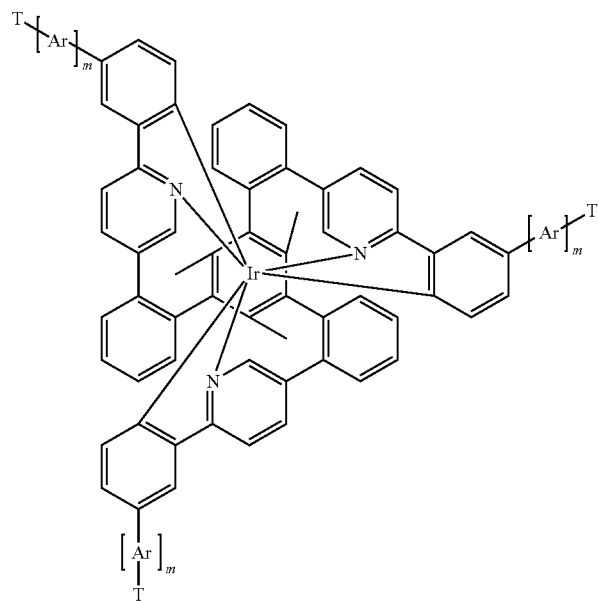
PT-22
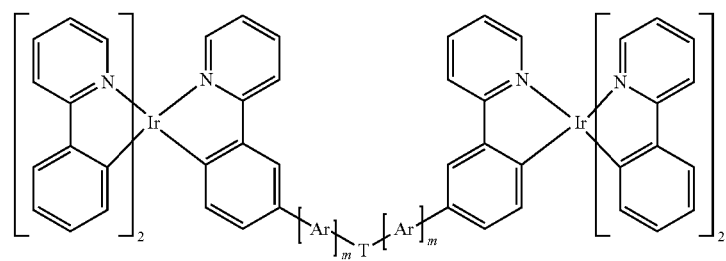

-continued

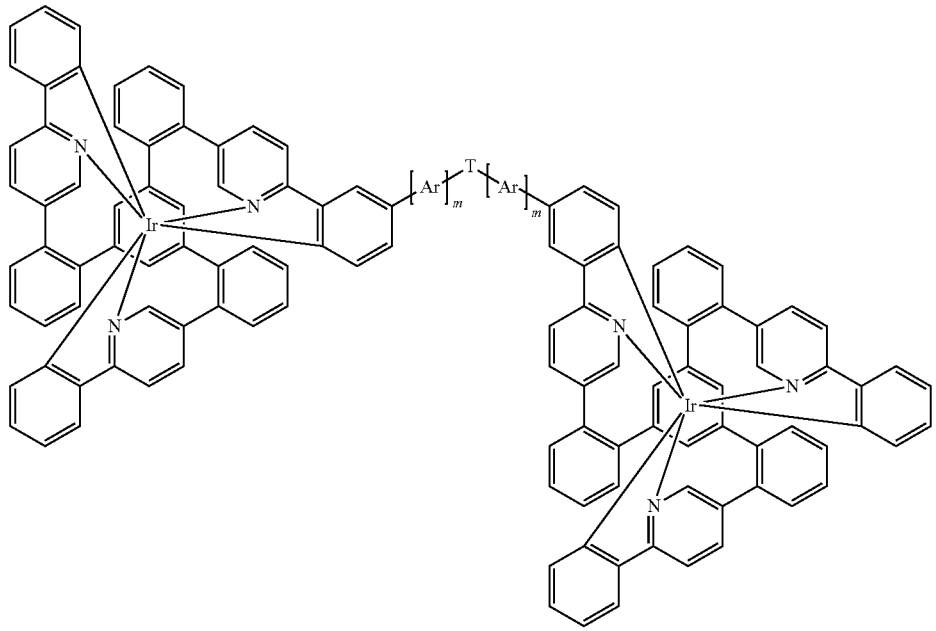

PT-23

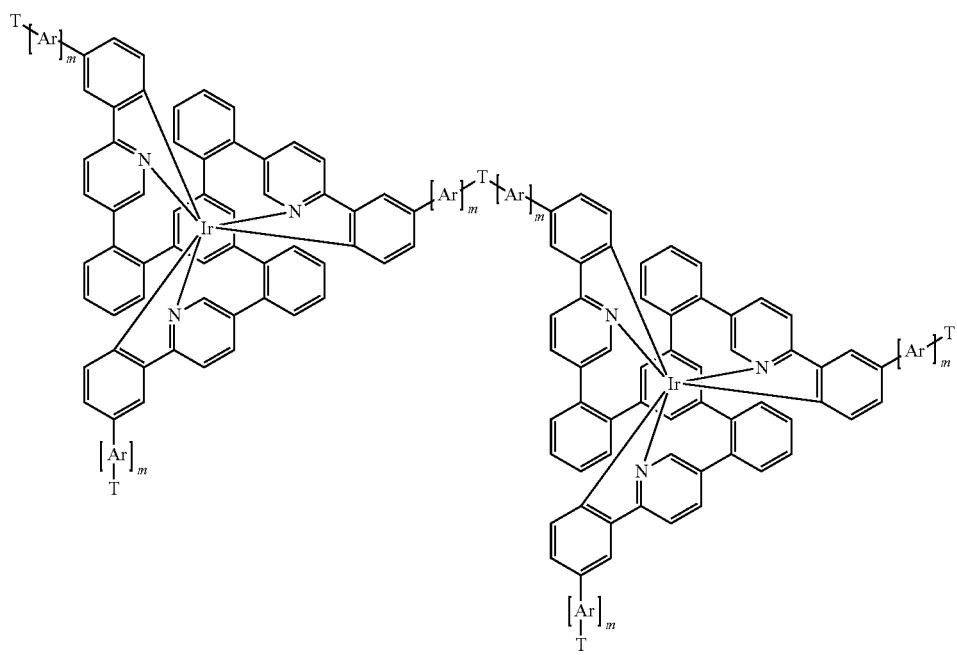

PT-24 where the symbols Ar, T and the index m have the same meaning as above and where the compounds represented in the table above may be further substituted by a group $R^1$, as defined above, at any free position.

In accordance with another preferred embodiment, the group Y is a fluorescent emitting group.

A fluorescent emitting group here is taken to mean a group, which emits light, in the visible region, near UV or near IR, on suitable excitation via a fluorescence process.

When the group Y is a fluorescent emitting group, it is preferably selected from arylamines, indenofluorene derivatives or anthracene derivatives.

An arylamine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms.

Preferred examples thereof are aromatic anthracenamines, aromatic anthracenediamines, aromatic pyrenamines, aromatic pyrenediamines, aromatic chrysenamines or aromatic chrysenediamines.

An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Further preferred fluorescent emitting groups are indenofluorene derivatives like indenofluorenamines, indenofluorenediamines, benzoindenofluorenamines, benzoindenofluorenediamines, dibenzoindenofluorenamines or dibenzoindeno-fluorenediamines and the indenofluorene derivatives containing condensed aryl groups.

Examples of suitable groups Y, when Y is a fluorescent emitting group, are the groups listed in the following table:

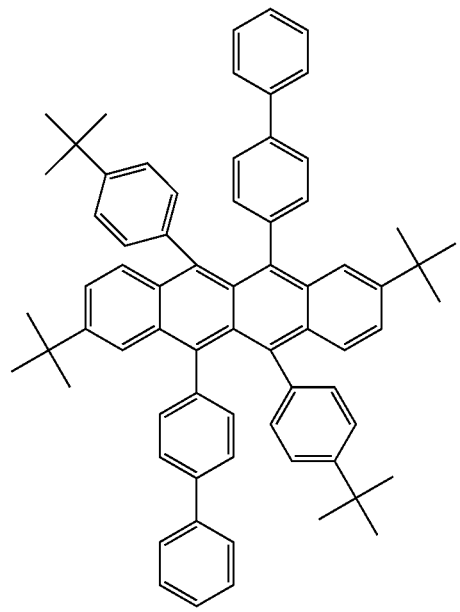 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]

F1

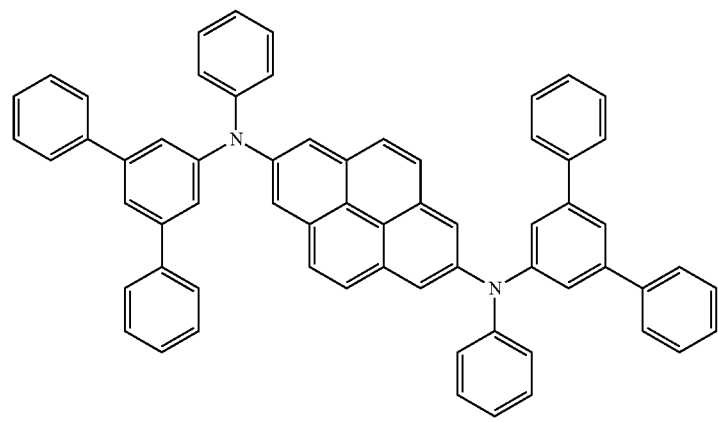 [SMILES: c1ccc(-c2cc(-c3ccccc3)cc(N(c3ccccc3)c3cc4ccc5cc(N(c6ccccc6)c6cc(-c7ccccc7)cc(-c7ccccc7)c6)cc6ccc(c3)c4c56)c2)cc1]

F2

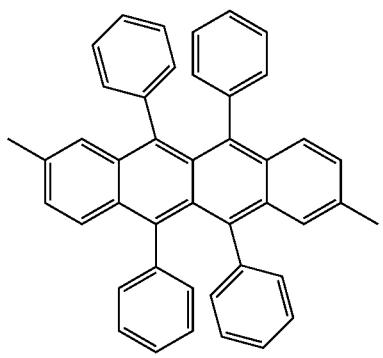

F3

F4
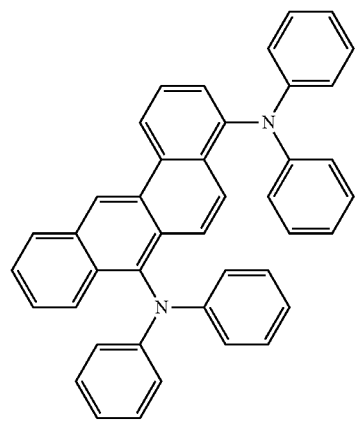 [SMILES: c1ccc(N(c2ccccc2)c2cccc3c2ccc2c(N(c4ccccc4)c4ccccc4)c4ccccc4cc23)cc1]
F5
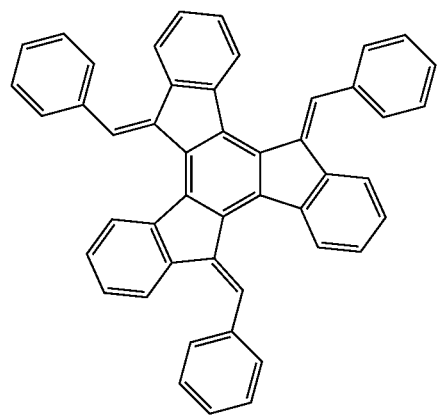 [SMILES: C(=C1/c2ccccc2-c2c1c1c(c3c2/C(=C/c2ccccc2)c2ccccc2-3)/C(=C/c2ccccc2)c2ccccc2-1)/c1ccccc1]
F6
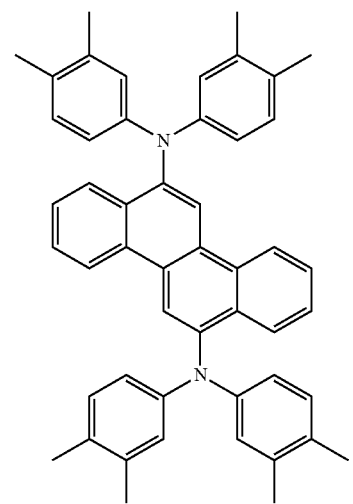

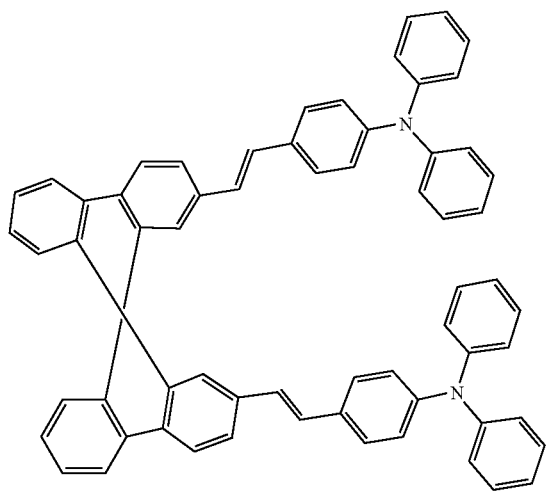 [SMILES: C(=C\c1ccc2c(c1)-c1ccccc1-c1ccc(/C=C/c3ccc(N(c4ccccc4)c4ccccc4)cc3)cc1-c1ccccc1-2)/c1ccc(N(c2ccccc2)c2ccccc2)cc1]
F7
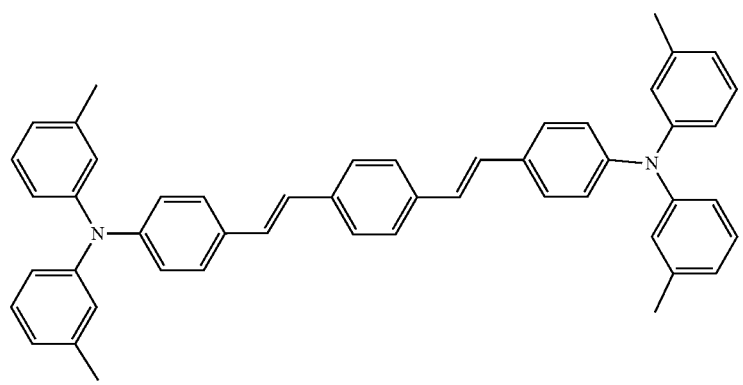 [SMILES: Cc1cccc(N(c2ccc(/C=C/c3ccc(/C=C/c4ccc(N(c5cccc(C)c5)c5cccc(C)c5)cc4)cc3)cc2)c2cccc(C)c2)c1]
F8
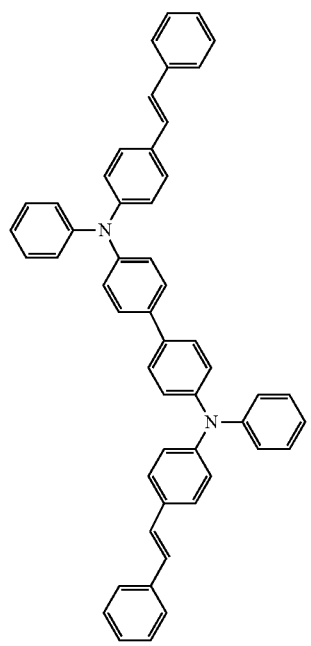 [SMILES: C(=C\c1ccc(N(c2ccccc2)c2ccc(-c3ccc(N(c4ccccc4)c4ccc(/C=C/c5ccccc5)cc4)cc3)cc2)cc1)/c1ccccc1]
F9

-continued
F10
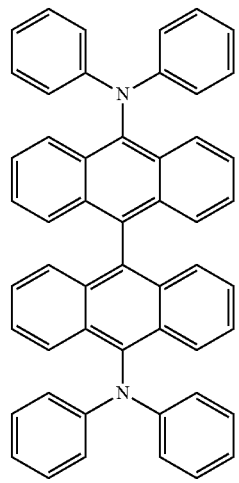 [SMILES: c1ccc(N(c2ccccc2)c2c3ccccc3c(-c3c4ccccc4c(N(c4ccccc4)c4ccccc4)c4ccccc34)c3ccccc23)cc1]
F11
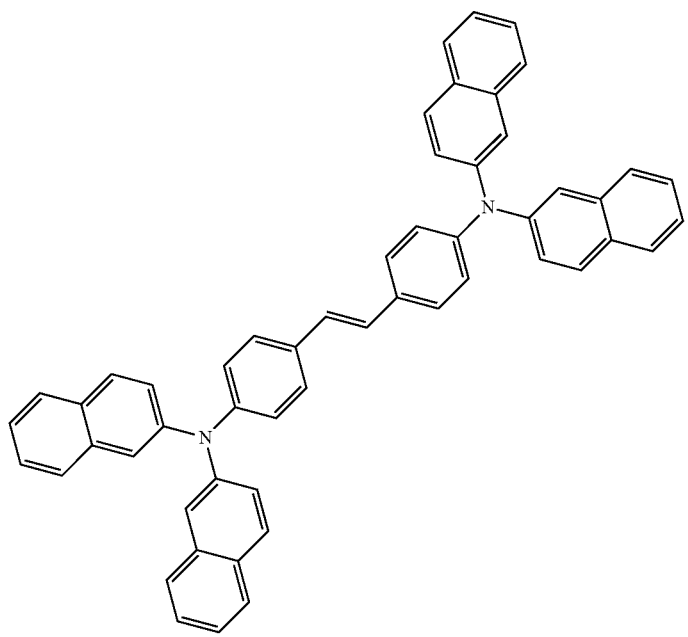 [SMILES: C(=C\c1ccc(N(c2ccc3ccccc3c2)c2ccc3ccccc3c2)cc1)/c1ccc(N(c2ccc3ccccc3c2)c2ccc3ccccc3c2)cc1]

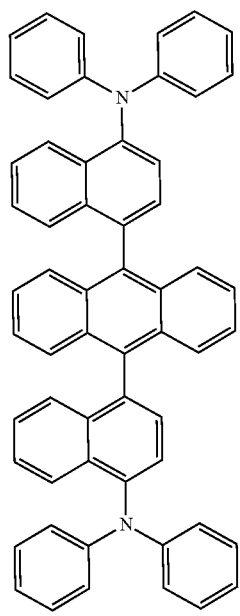 [SMILES: c1ccc(N(c2ccccc2)c2ccc(-c3c4ccccc4c(-c4ccc(N(c5ccccc5)c5ccccc5)c5ccccc45)c4ccccc34)c3ccccc23)cc1]
F12
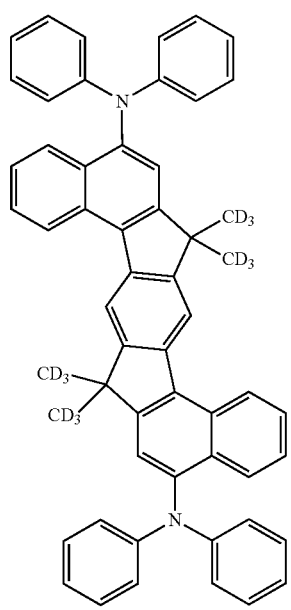 [SMILES: [2H]C([2H])([2H])C1(C([2H])([2H])[2H])c2cc3c(cc2-c2c1cc(N(c1ccccc1)c1ccccc1)c1ccccc21)C(C([2H])([2H])[2H])(C([2H])([2H])[2H])c1cc(N(c2ccccc2)c2ccccc2)c2ccccc2c1-3]
F13
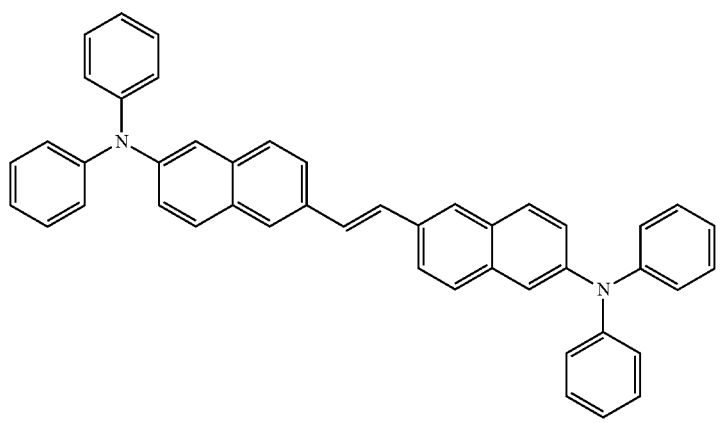 [SMILES: C(=C\c1ccc2cc(N(c3ccccc3)c3ccccc3)ccc2c1)/c1ccc2cc(N(c3ccccc3)c3ccccc3)ccc2c1]
F14

F15
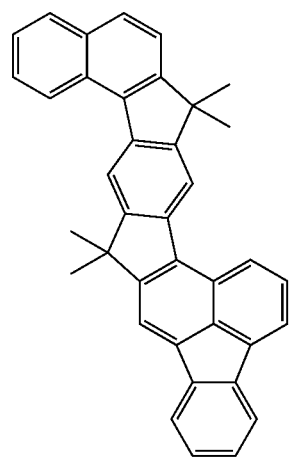 [SMILES: CC1(C)c2cc3c(cc2-c2c1ccc1ccccc21)C(C)(C)c1cc2c4c(cccc4c1-3)-c1ccccc1-2]
F16
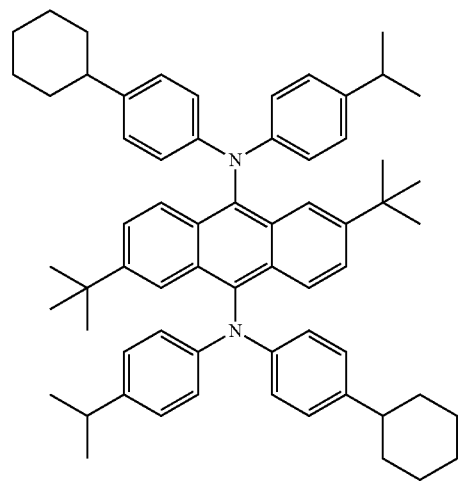 [SMILES: CC(C)c1ccc(N(c2ccc(C3CCCCC3)cc2)c2c3ccc(C(C)(C)C)cc3c(N(c3ccc(C(C)C)cc3)c3ccc(C4CCCCC4)cc3)c3ccc(C(C)(C)C)cc23)cc1]
F17
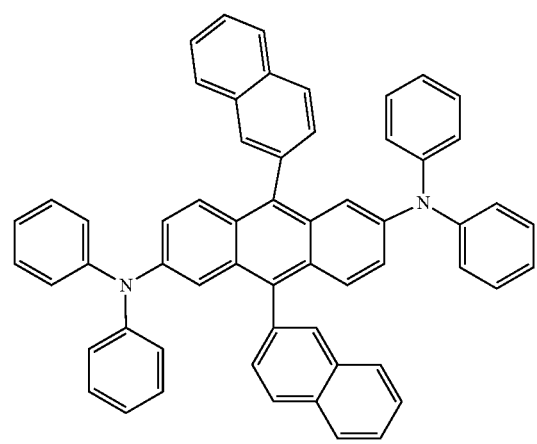 [SMILES: c1ccc(N(c2ccccc2)c2ccc3c(-c4ccc5ccccc5c4)c4cc(N(c5ccccc5)c5ccccc5)ccc4c(-c4ccc5ccccc5c4)c3c2)cc1]

F18
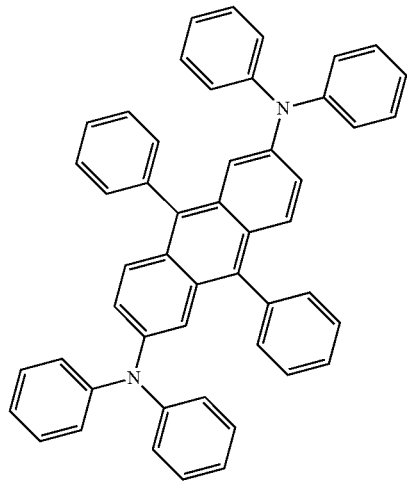 [SMILES: c1ccc(-c2c3ccc(N(c4ccccc4)c4ccccc4)cc3c(-c3ccccc3)c3ccc(N(c4ccccc4)c4ccccc4)cc23)cc1]
F19
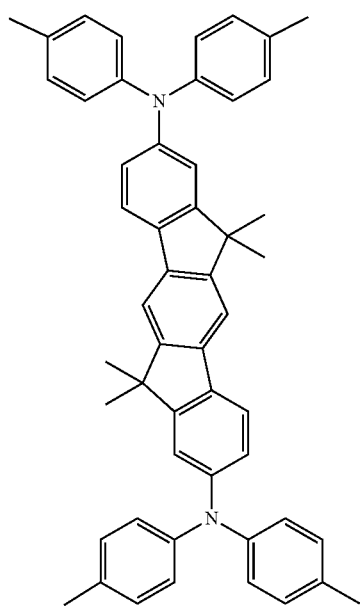
F20
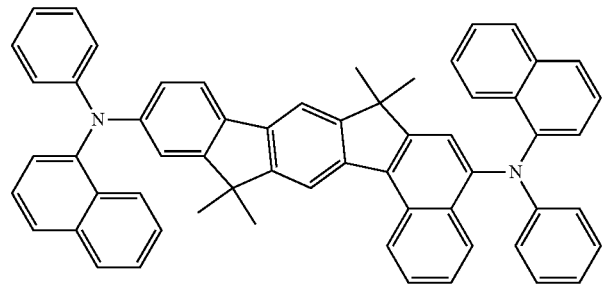 [SMILES: CC1(C)c2cc(N(c3ccccc3)c3cccc4ccccc34)ccc2-c2cc3c(cc21)-c1c(cc(N(c2ccccc2)c2cccc4ccccc24)c2ccccc12)C3(C)C]

F21
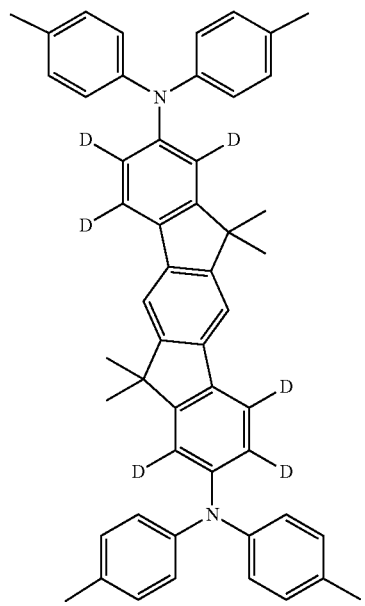
F22
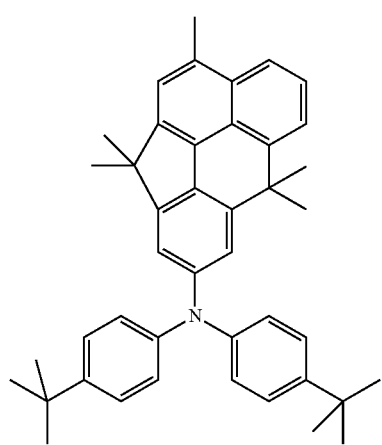 [SMILES: Cc1cc2c3c4c(cccc14)C(C)(C)c1cc(N(c4ccc(C(C)(C)C)cc4)c4ccc(C(C)(C)C)cc4)cc(c1-3)C2(C)C]

-continued
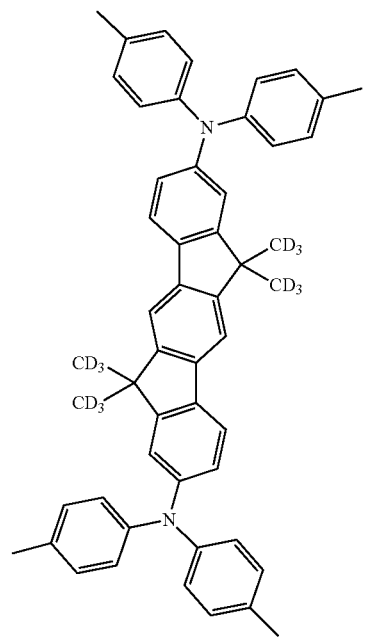
F23
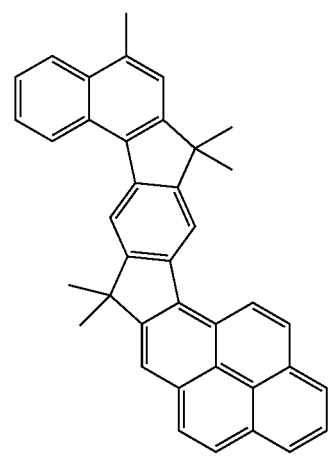 [SMILES: Cc1cc2c(c3ccccc13)-c1cc3c(cc1C2(C)C)-c1c(cc2ccc4cccc5ccc1c2c45)C3(C)C]
F24
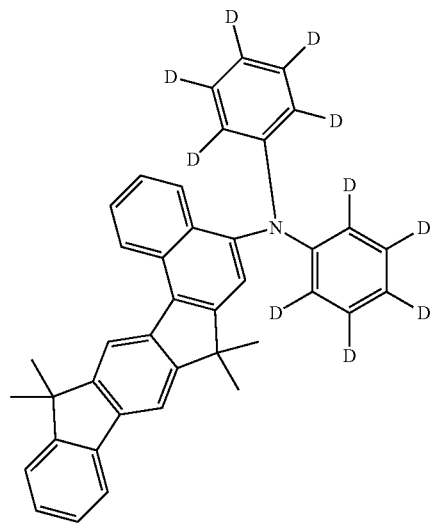 [SMILES: [2H]c1c([2H])c([2H])c(N(c2c([2H])c([2H])c([2H])c([2H])c2[2H])c2cc3c(c4ccccc24)-c2cc4c(cc2C3(C)C)-c2ccccc2C4(C)C)c([2H])c1[2H]]
F25

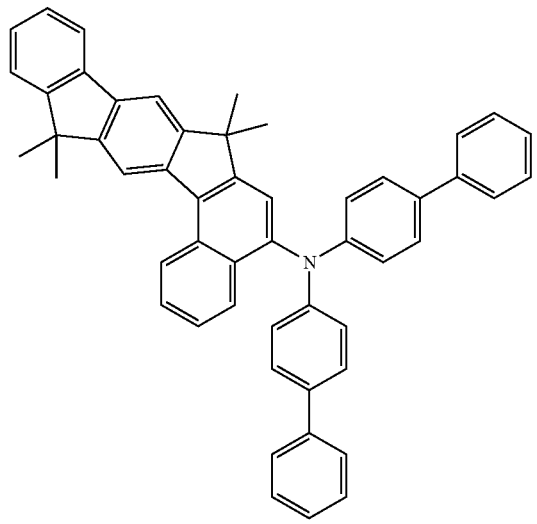 [SMILES: CC1(C)c2ccccc2-c2cc3c(cc21)-c1c(cc(N(c2ccc(-c4ccccc4)cc2)c2ccc(-c4ccccc4)cc2)c2ccccc12)C3(C)C]
F26
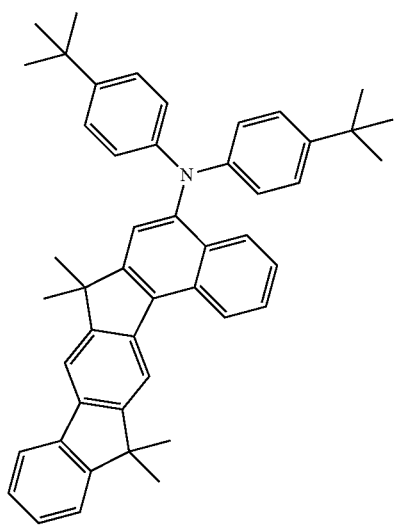 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]
F27
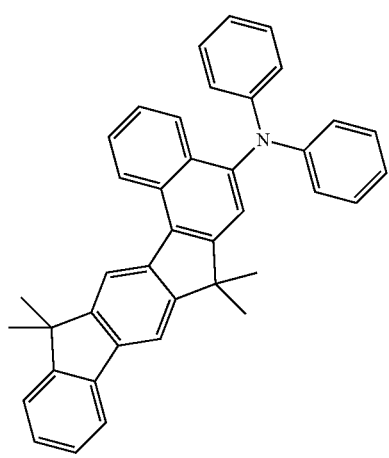 [SMILES: CC1(C)c2ccccc2-c2cc3c(cc21)-c1c(cc(N(c2ccccc2)c2ccccc2)c2ccccc12)C3(C)C]
F28

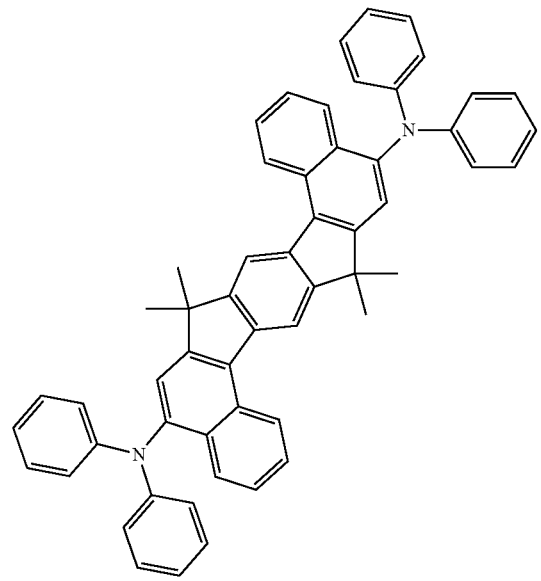 [SMILES: CC1(C)c2cc3c(cc2-c2c1cc(N(c1ccccc1)c1ccccc1)c1ccccc21)C(C)(C)c1cc(N(c2ccccc2)c2ccccc2)c2ccccc2c1-3]
F29
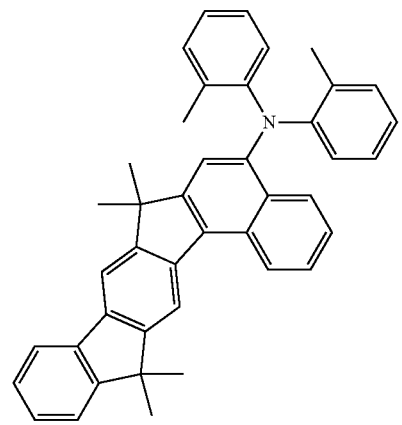 [SMILES: Cc1ccccc1N(c1ccccc1C)c1cc2c(c3ccccc13)-c1cc3c(cc1C2(C)C)-c1ccccc1C3(C)C]
F30
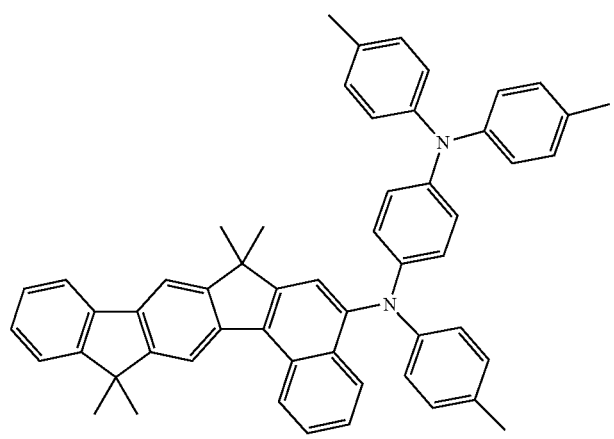 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]
F31

-continued
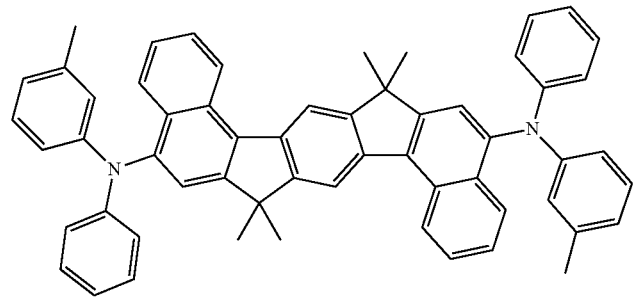 [SMILES: Cc1cccc(N(c2ccccc2)c2cc3c(c4ccccc24)-c2cc4c(cc2C3(C)C)-c2c(cc(N(c3ccccc3)c3cccc(C)c3)c3ccccc23)C4(C)C)c1]
F32
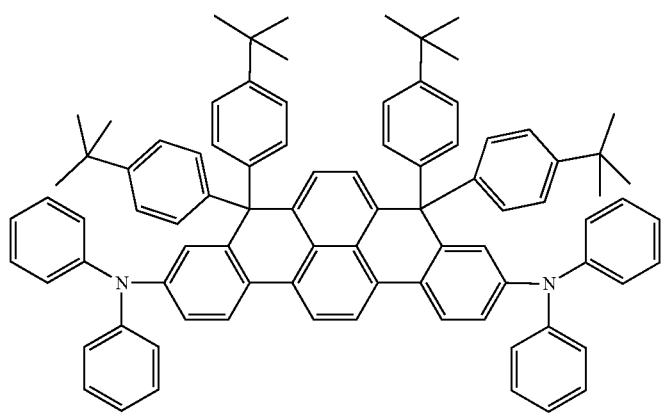 [SMILES: CC(C)(C)c1ccc(C2(c3ccc(C(C)(C)C)cc3)c3cc(N(c4ccccc4)c4ccccc4)ccc3-c3ccc4c5c(ccc2c35)C(c2ccc(C(C)(C)C)cc2)(c2ccc(C(C)(C)C)cc2)c2cc(N(c3ccccc3)c3ccccc3)ccc2-4)cc1]
F33
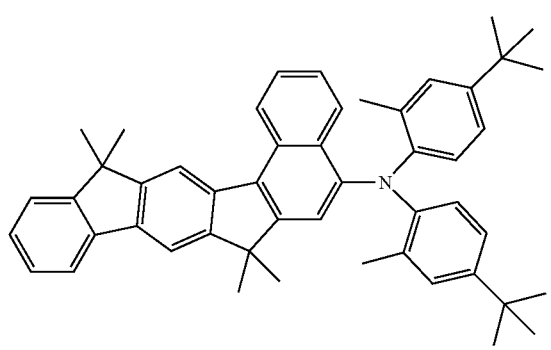 [SMILES: Cc1cc(C(C)(C)C)ccc1N(c1ccc(C(C)(C)C)cc1C)c1cc2c(c3ccccc13)-c1cc3c(cc1C2(C)C)-c1ccccc1C3(C)C]
F34
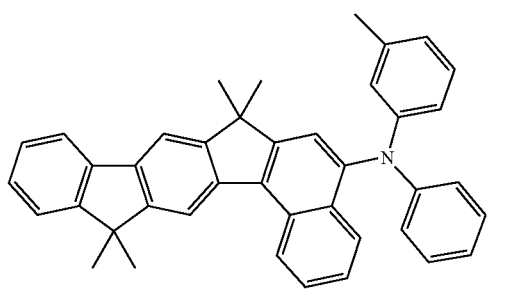 [SMILES: Cc1cccc(N(c2ccccc2)c2cc3c(c4ccccc24)-c2cc4c(cc2C3(C)C)-c2ccccc2C4(C)C)c1]
F35
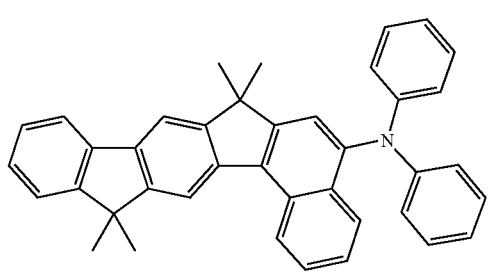 [SMILES: CC1(C)c2ccccc2-c2cc3c(cc21)-c1c(cc(N(c2ccccc2)c2ccccc2)c2ccccc12)C3(C)C]
F36

-continued
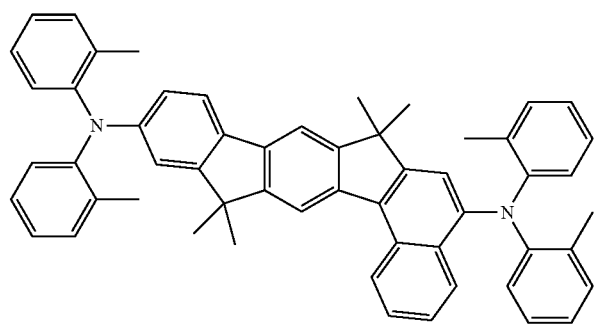 [SMILES: Cc1ccccc1N(c1ccc2c(c1)C(C)(C)c1cc3c(cc1-2)C(C)(C)c1cc(N(c2ccccc2C)c2ccccc2C)c2ccccc2c1-3)c1ccccc1C]
F37
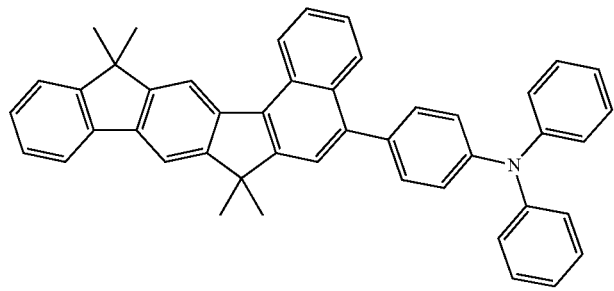 [SMILES: CC1(C)c2ccccc2-c2cc3c(cc21)-c1c(cc(-c2ccc(N(c4ccccc4)c4ccccc4)cc2)c2ccccc12)C3(C)C]
F38
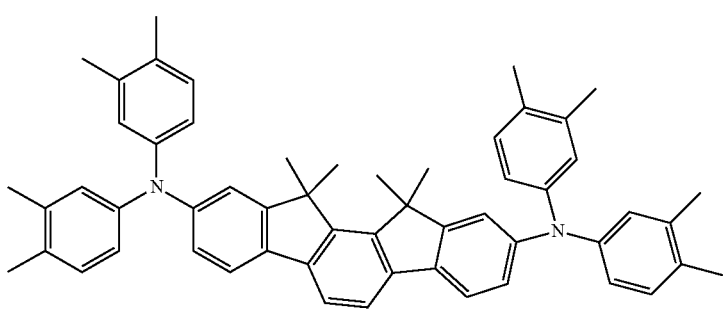
F39
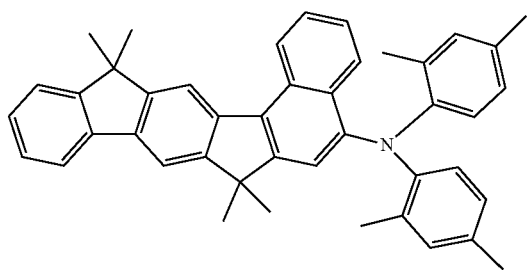 [SMILES: Cc1ccc(N(c2ccc(C)cc2C)c2cc3c(c4ccccc24)-c2cc4c(cc2C3(C)C)-c2ccccc2C4(C)C)c(C)c1]
F40
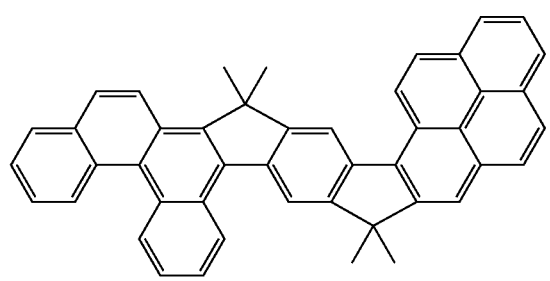 [SMILES: CC1(C)c2cc3c(cc2-c2c1cc1ccc4cccc5ccc2c1c45)C(C)(C)c1c-3c2ccccc2c2c1ccc1ccccc12]
F41

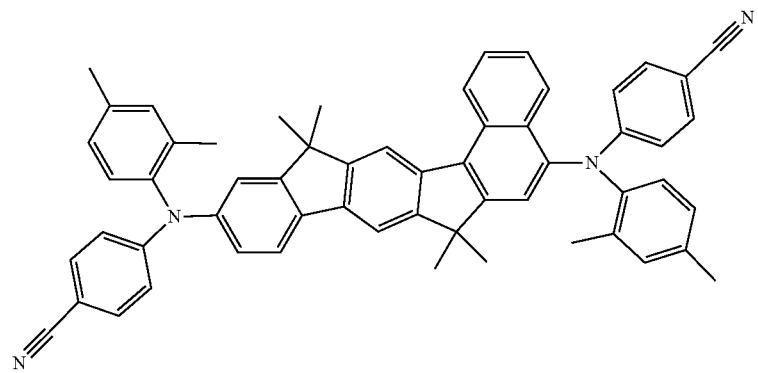 [SMILES: Cc1ccc(N(c2ccc(C#N)cc2)c2ccc3c(c2)C(C)(C)c2cc4c(cc2-3)C(C)(C)c2cc(N(c3ccc(C#N)cc3)c3ccc(C)cc3C)c3ccccc3c2-4)c(C)c1]
F42
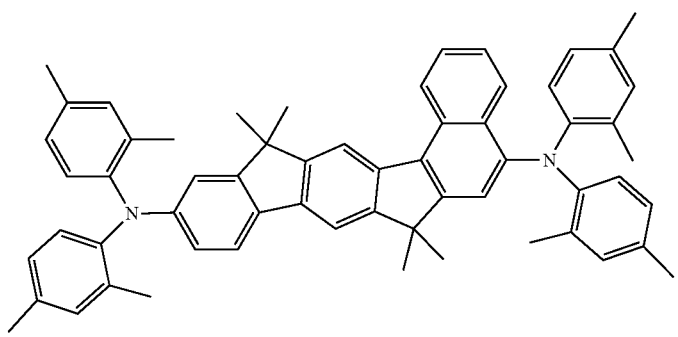
F43
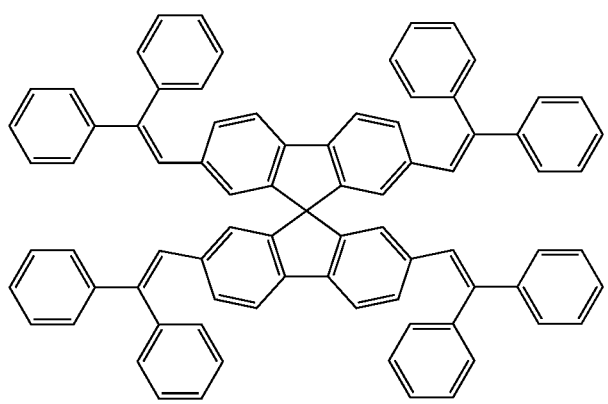 [SMILES: C(=C(c1ccccc1)c1ccccc1)c1ccc2c(c1)C1(c3cc(C=C(c4ccccc4)c4ccccc4)ccc3-2)c2cc(C=C(c3ccccc3)c3ccccc3)ccc2-c2ccc(C=C(c3ccccc3)c3ccccc3)cc21]
F44
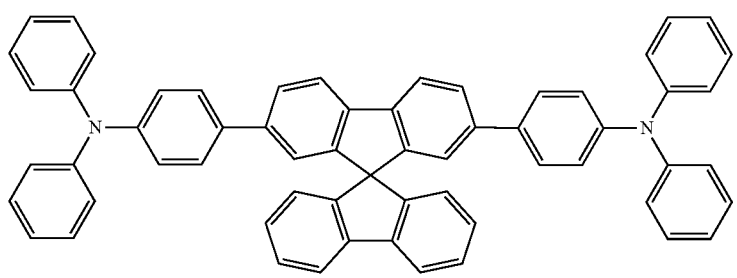 [SMILES: c1ccc(N(c2ccccc2)c2ccc(-c3ccc4c(c3)C3(c5ccccc5-c5ccccc53)c3cc(-c5ccc(N(c6ccccc6)c6ccccc6)cc5)ccc3-4)cc2)cc1]
F45

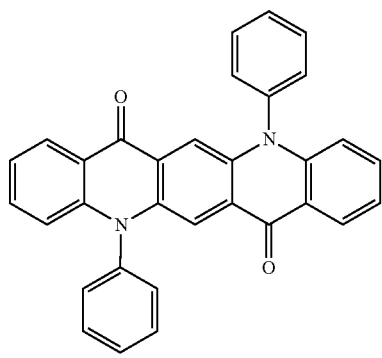 [SMILES: O=c1c2ccccc2n(-c2ccccc2)c2cc3c(=O)c4ccccc4n(-c4ccccc4)c3cc12]
F46
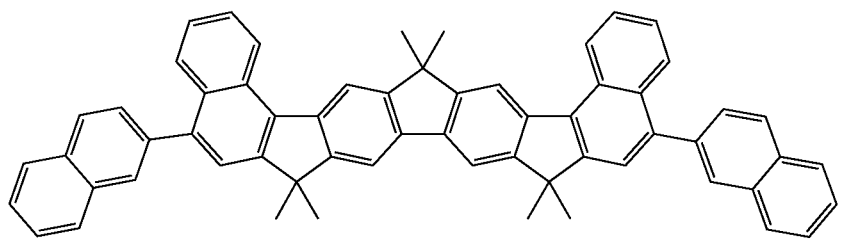 [SMILES: CC1(C)c2cc3c(cc2-c2cc4c(cc21)-c1c(cc(-c2ccc5ccccc5c2)c2ccccc12)C4(C)C)C(C)(C)c1cc(-c2ccc4ccccc4c2)c2ccccc2c1-3]
F47
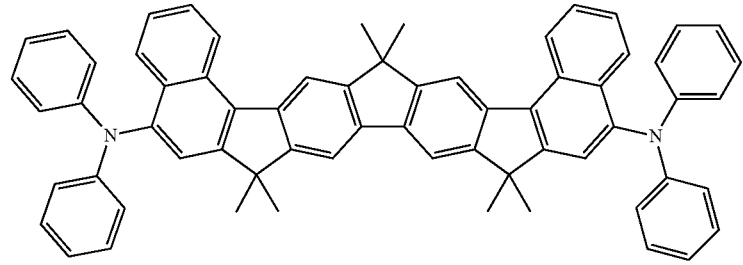 [SMILES: CC1(C)c2cc3c(cc2-c2cc4c(cc21)-c1c(cc(N(c2ccccc2)c2ccccc2)c2ccccc12)C4(C)C)C(C)(C)c1cc(N(c2ccccc2)c2ccccc2)c2ccccc2c1-3]
F48
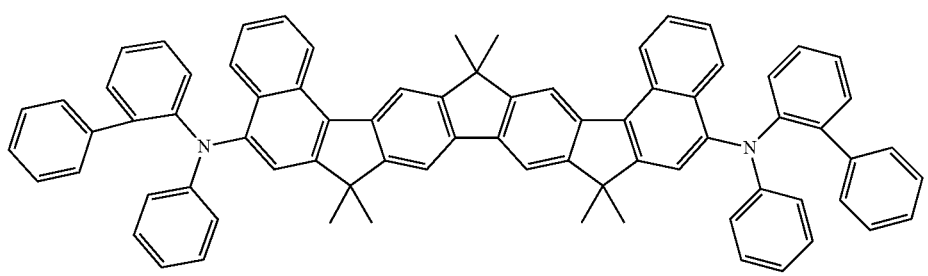 [SMILES: CC1(C)c2cc3c(cc2-c2cc4c(cc21)-c1c(cc(N(c2ccccc2)c2ccccc2-c2ccccc2)c2ccccc12)C4(C)C)C(C)(C)c1cc(N(c2ccccc2)c2ccccc2-c2ccccc2)c2ccccc2c1-3]
F49
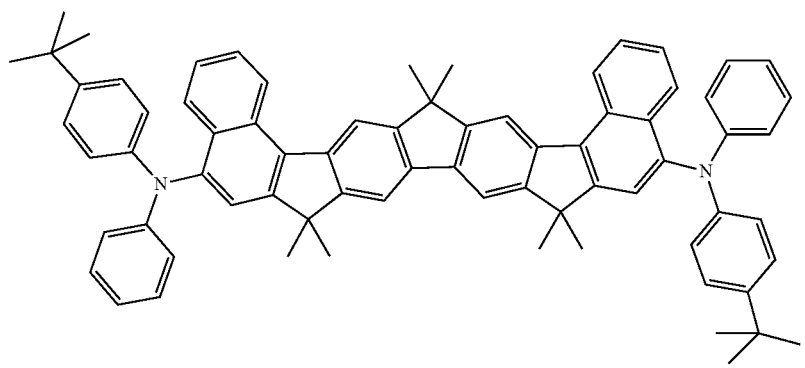 [SMILES: CC(C)(C)c1ccc(N(c2ccccc2)c2cc3c(c4ccccc24)-c2cc4c(cc2C3(C)C)-c2cc3c(cc2C4(C)C)-c2c(cc(N(c4ccccc4)c4ccc(C(C)(C)C)cc4)c4ccccc24)C3(C)C)cc1]
F50

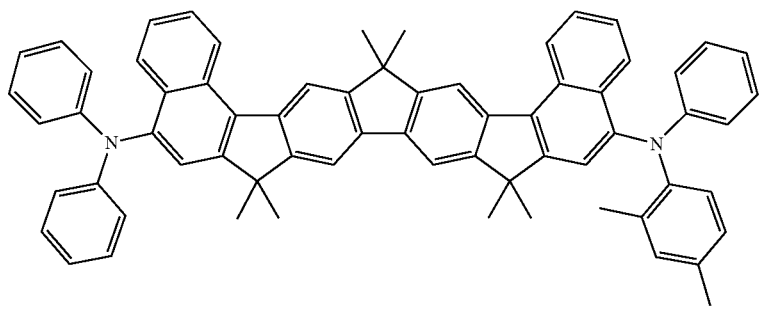 [SMILES: Cc1ccc(N(c2ccccc2)c2cc3c(c4ccccc24)-c2cc4c(cc2C3(C)C)-c2cc3c(cc2C4(C)C)-c2c(cc(N(c4ccccc4)c4ccccc4)c4ccccc24)C3(C)C)c(C)c1]
F51
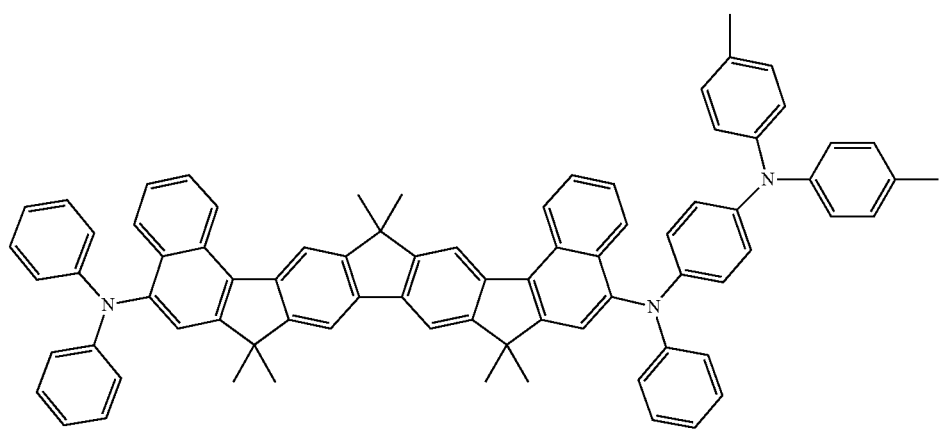 [SMILES: Cc1ccc(N(c2ccc(C)cc2)c2ccc(N(c3ccccc3)c3cc4c(c5ccccc35)-c3cc5c(cc3C4(C)C)-c3cc4c(cc3C5(C)C)-c3c(cc(N(c5ccccc5)c5ccccc5)c5ccccc35)C4(C)C)cc2)cc1]
F52
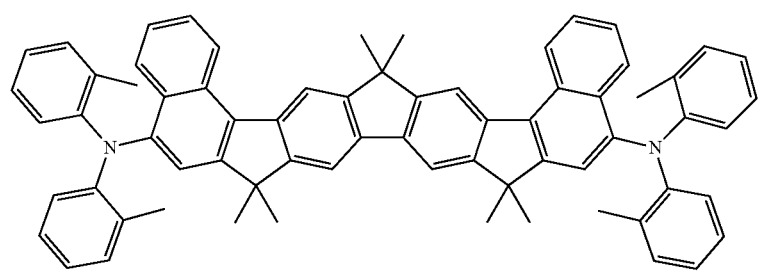 [SMILES: Cc1ccccc1N(c1ccccc1C)c1cc2c(c3ccccc13)-c1cc3c(cc1C2(C)C)-c1cc2c(cc1C3(C)C)-c1c(cc(N(c3ccccc3C)c3ccccc3C)c3ccccc13)C2(C)C]
F53
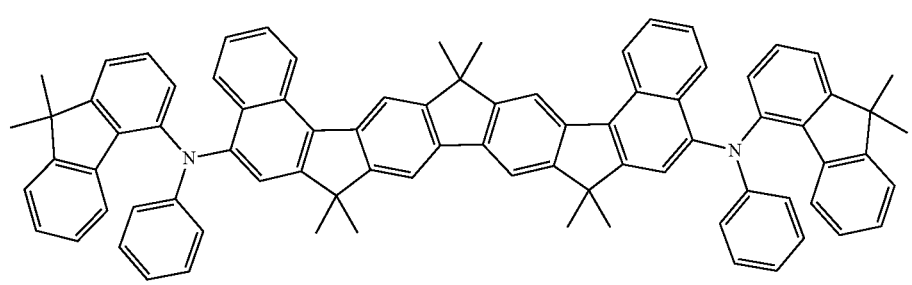
F54
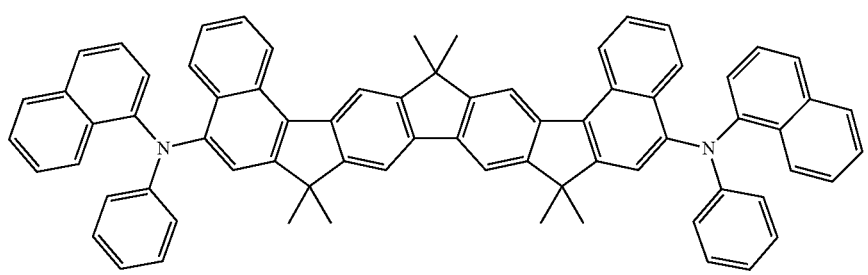 [SMILES: CC1(C)c2cc3c(cc2-c2cc4c(cc21)-c1c(cc(N(c2ccccc2)c2cccc5ccccc25)c2ccccc12)C4(C)C)C(C)(C)c1cc(N(c2ccccc2)c2cccc4ccccc24)c2ccccc2c1-3]
F55

-continued
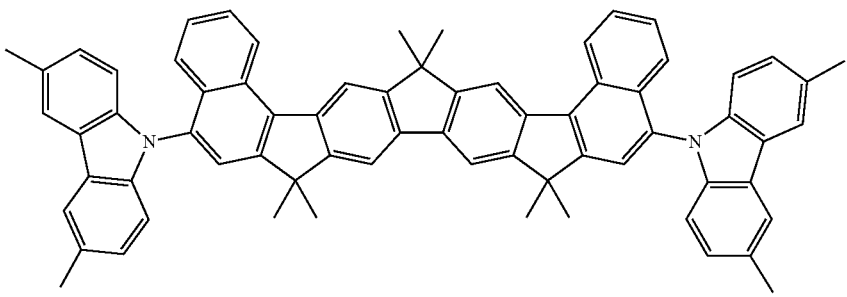
F56
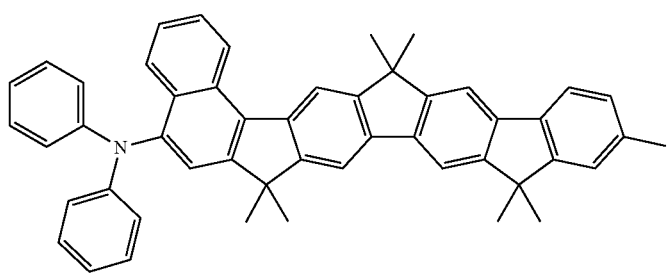 [SMILES: Cc1ccc2c(c1)C(C)(C)c1cc3c(cc1-2)C(C)(C)c1cc2c(cc1-3)C(C)(C)c1cc(N(c3ccccc3)c3ccccc3)c3ccccc3c1-2]
F57
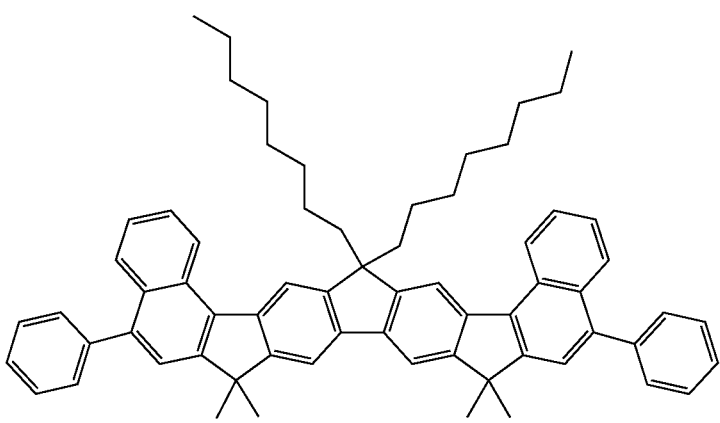 [SMILES: CCCCCCCCC1(CCCCCCCC)c2cc3c(cc2-c2cc4c(cc21)-c1c(cc(-c2ccccc2)c2ccccc12)C4(C)C)C(C)(C)c1cc(-c2ccccc2)c2ccccc2c1-3]
F58
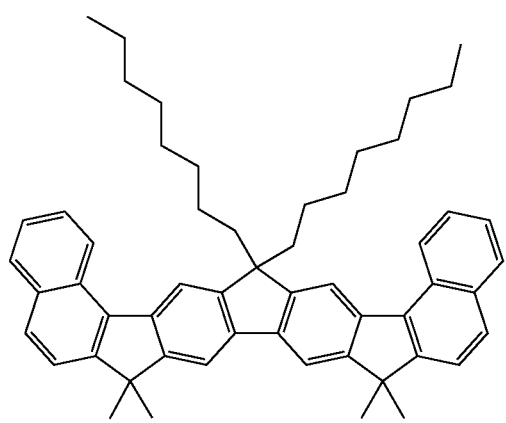 [SMILES: CCCCCCCCC1(CCCCCCCC)c2cc3c(cc2-c2cc4c(cc21)-c1c(ccc2ccccc12)C4(C)C)C(C)(C)c1ccc2ccccc2c1-3]
F59

F60
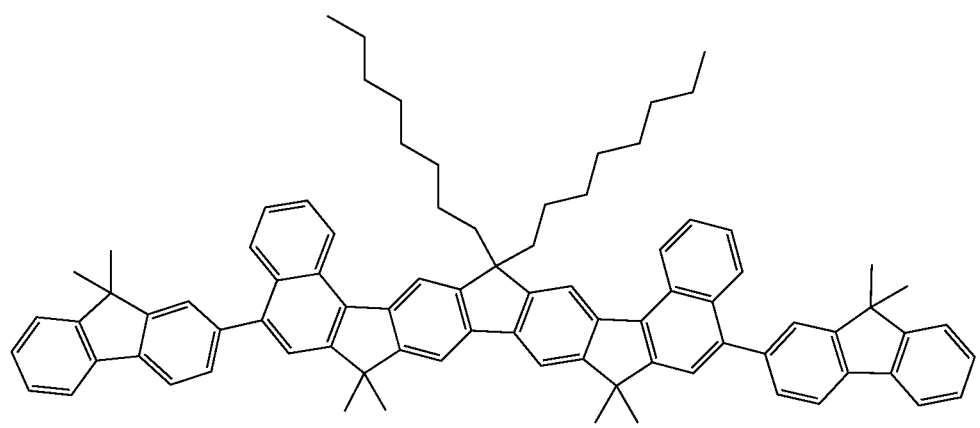 [SMILES: CCCCCCCCC1(CCCCCCCC)c2cc3c(cc2-c2cc4c(cc21)-c1c(cc(-c2ccc5c(c2)C(C)(C)c2ccccc2-5)c2ccccc12)C4(C)C)C(C)(C)c1cc(-c2ccc4c(c2)C(C)(C)c2ccccc2-4)c2ccccc2c1-3]
F61
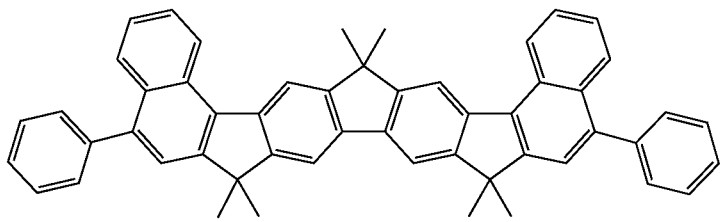 [SMILES: CC1(C)c2cc3c(cc2-c2cc4c(cc21)-c1c(cc(-c2ccccc2)c2ccccc12)C4(C)C)C(C)(C)c1cc(-c2ccccc2)c2ccccc2c1-3]
F62
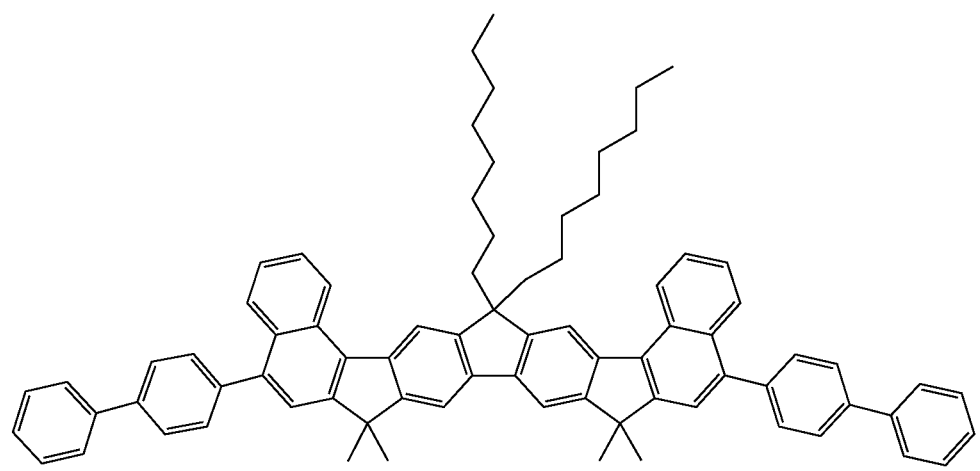 [SMILES: CCCCCCCCC1(CCCCCCCC)c2cc3c(cc2-c2cc4c(cc21)-c1c(cc(-c2ccc(-c5ccccc5)cc2)c2ccccc12)C4(C)C)C(C)(C)c1cc(-c2ccc(-c4ccccc4)cc2)c2ccccc2c1-3]
F63
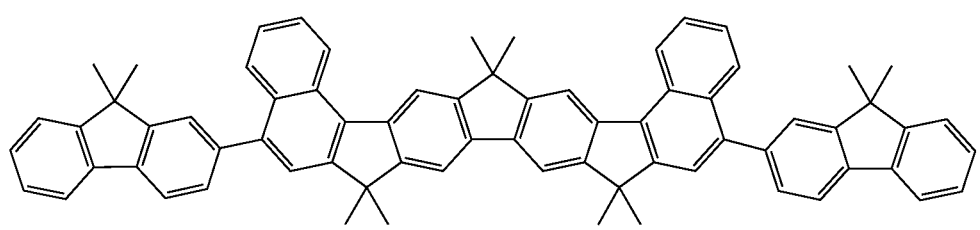 [SMILES: CC1(C)c2ccccc2-c2ccc(-c3cc4c(c5ccccc35)-c3cc5c(cc3C4(C)C)-c3cc4c(cc3C5(C)C)-c3c(cc(-c5ccc6c(c5)C(C)(C)c5ccccc5-6)c5ccccc35)C4(C)C)cc21]

-continued
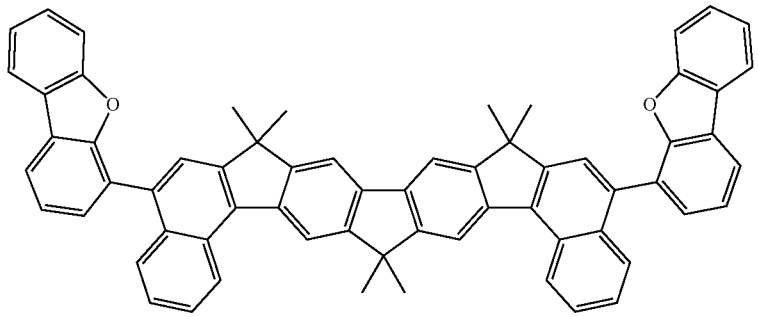 [SMILES: CC1(C)c2cc3c(cc2-c2cc4c(cc21)-c1c(cc(-c2cccc5c2oc2ccccc25)c2ccccc12)C4(C)C)C(C)(C)c1cc(-c2cccc4c2oc2ccccc24)c2ccccc2c1-3]
F64
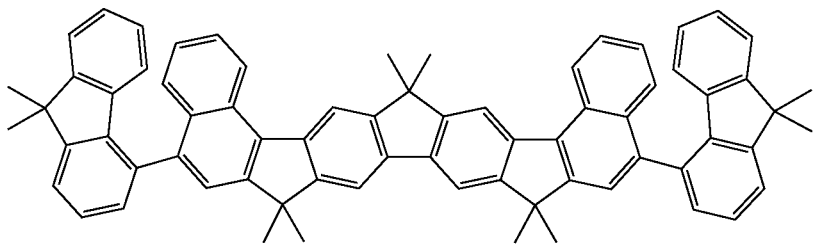
F65
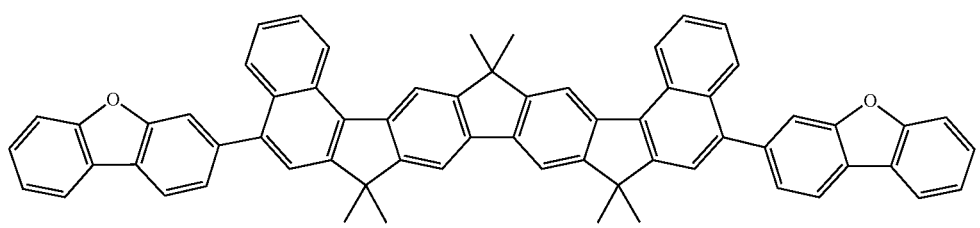 [SMILES: CC1(C)c2cc3c(cc2-c2cc4c(cc21)-c1c(cc(-c2ccc5c(c2)oc2ccccc25)c2ccccc12)C4(C)C)C(C)(C)c1cc(-c2ccc4c(c2)oc2ccccc24)c2ccccc2c1-3]
F66
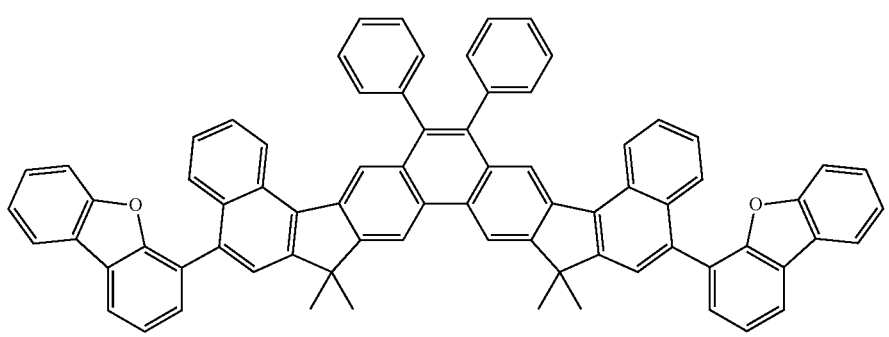 [SMILES: CC1(C)c2cc3c(cc2-c2c1cc(-c1cccc4c1oc1ccccc14)c1ccccc21)c(-c1ccccc1)c(-c1ccccc1)c1cc2c(cc13)C(C)(C)c1cc(-c3cccc4c3oc3ccccc34)c3ccccc3c1-2]
F67
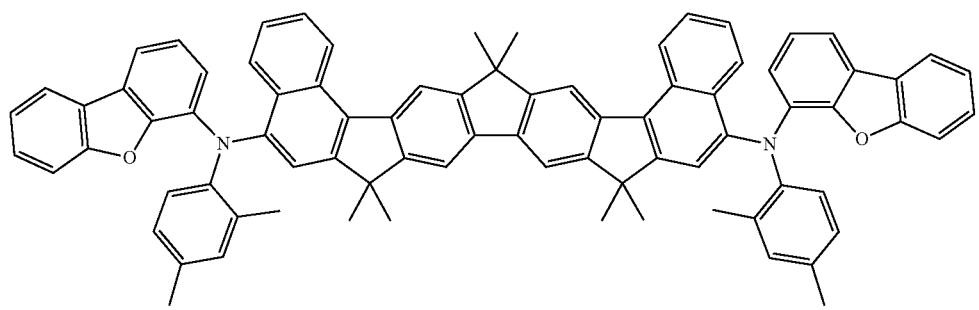 [SMILES: Cc1ccc(N(c2cc3c(c4ccccc24)-c2cc4c(cc2C3(C)C)-c2cc3c(cc2C4(C)C)-c2c(cc(N(c4ccc(C)cc4C)c4cccc5c4oc4ccccc45)c4ccccc24)C3(C)C)c2cccc3c2oc2ccccc23)c(C)c1]
F68

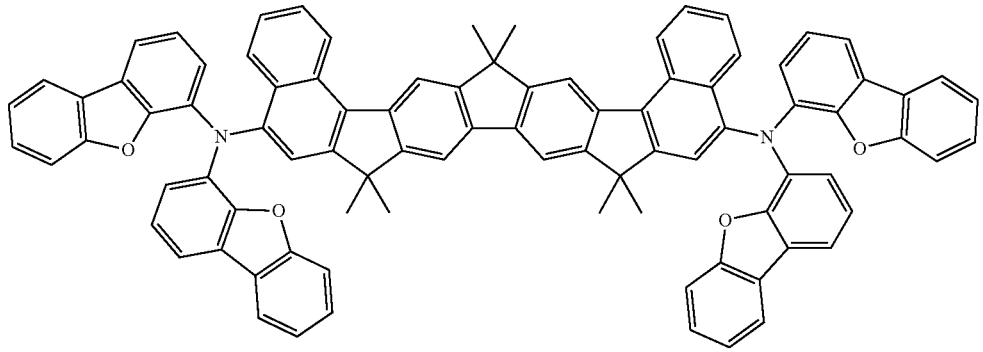 [SMILES: CC1(C)c2cc3c(cc2-c2cc4c(cc21)-c1c(cc(N(c2cccc5c2oc2ccccc25)c2cccc5c2oc2ccccc25)c2ccccc12)C4(C)C)C(C)(C)c1cc(N(c2cccc4c2oc2ccccc24)c2cccc4c2oc2ccccc24)c2ccccc2c1-3]
F69
where at least one group T may be appended at any free position of the group (F1) to (F69), directly or via a group Ar, and where the groups (F1) to (F69) may further be substituted at any free position by a radical $R^1$ as defined above.
Examples of suitable fluorescent emitting groups substituted by at least one terpene or terpenoid group are represented in the table below:
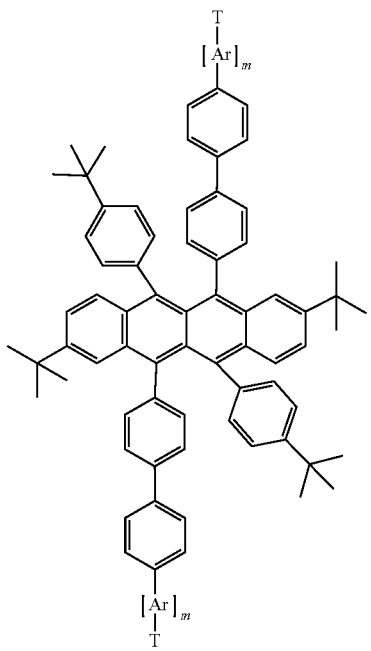
FT-1

-continued
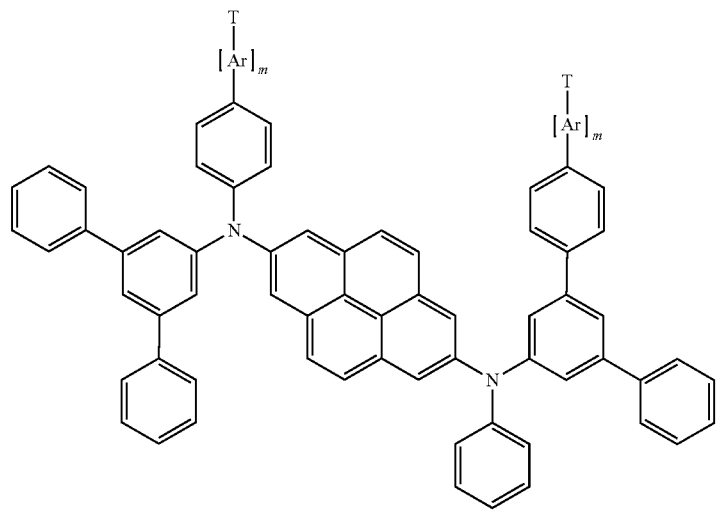
FT-2
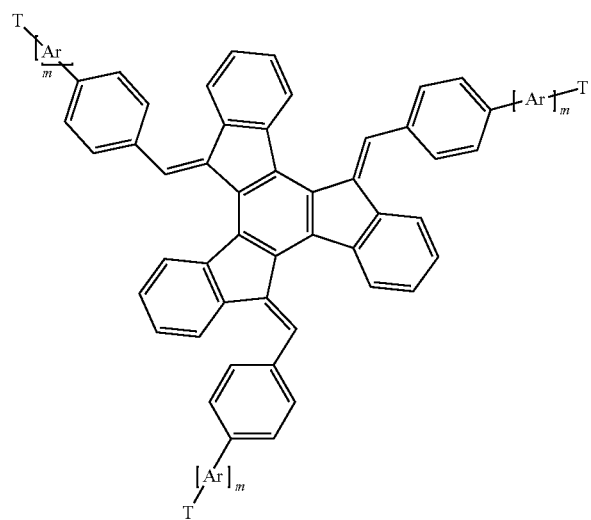
FT-3
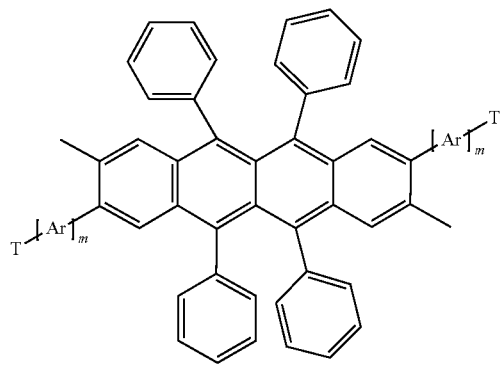
FT-4

FT-5
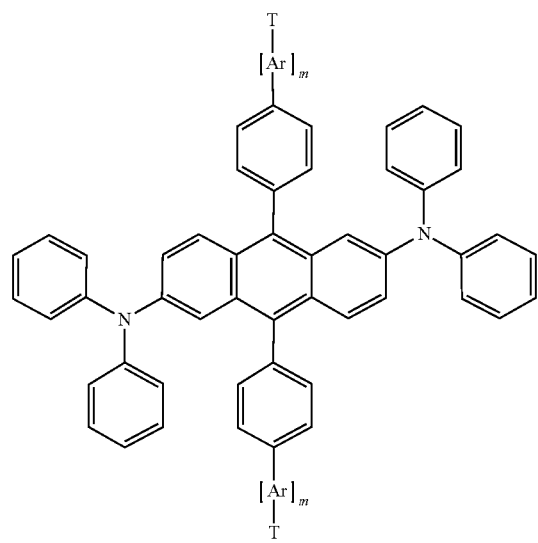
FT-6
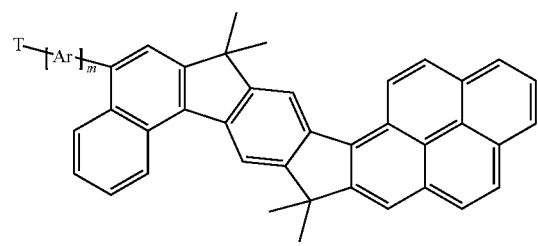
FT-7
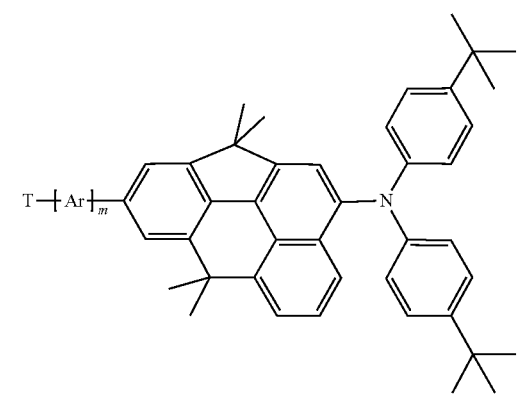

FT-8
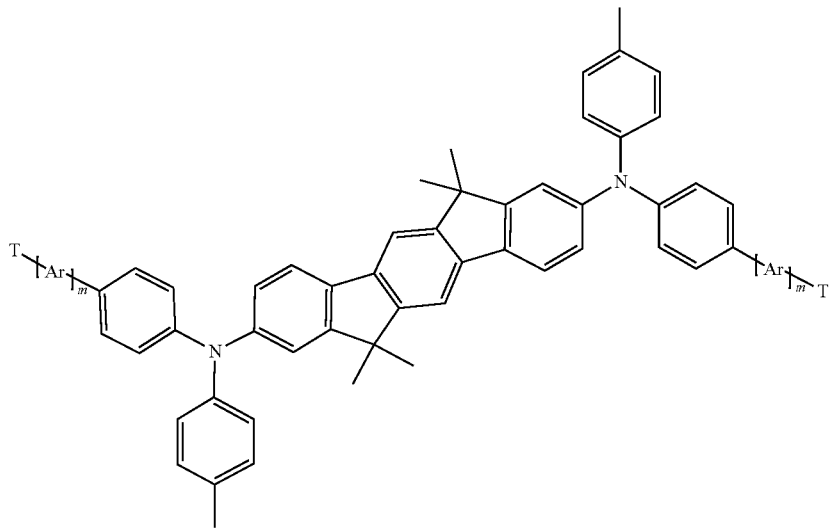
FT-9
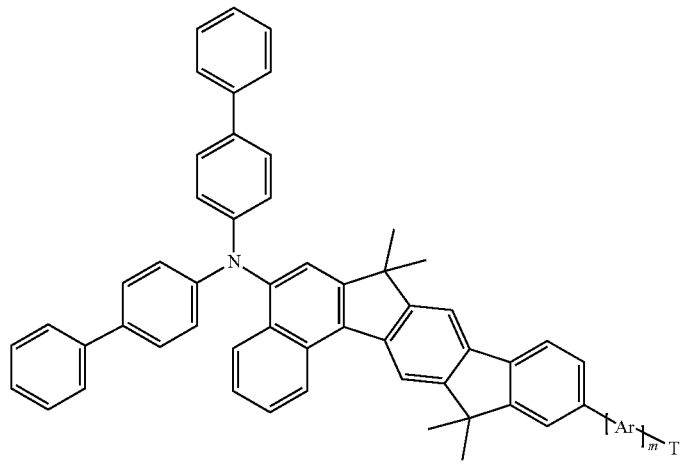
FT-10
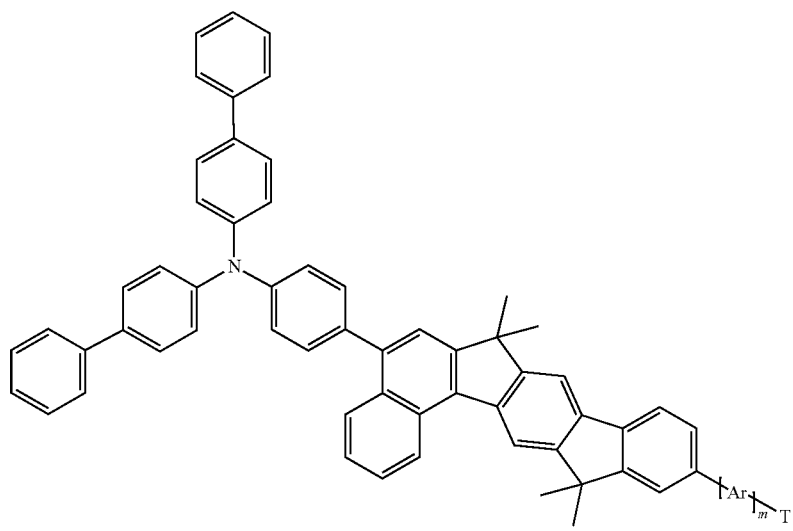

-continued
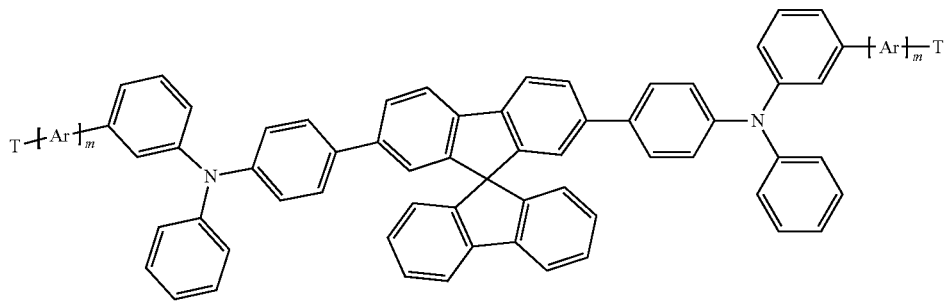
FT-11
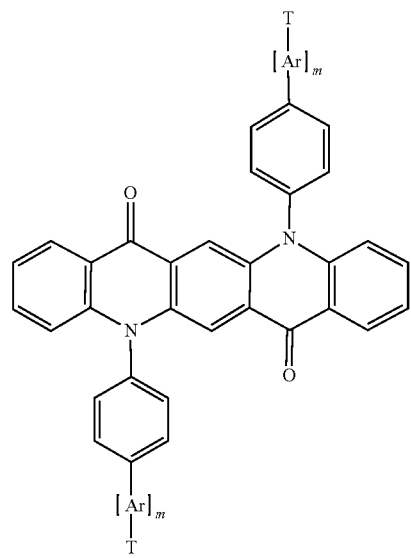
FT-12
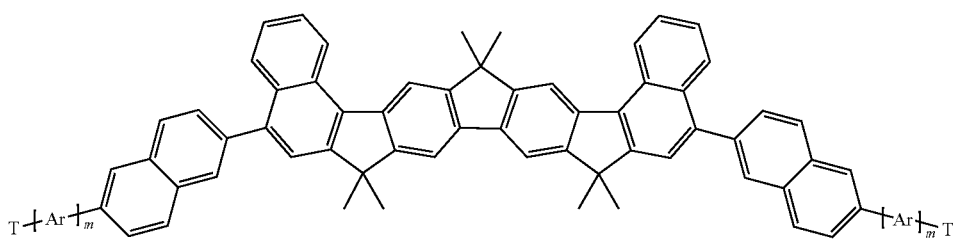
FT-13
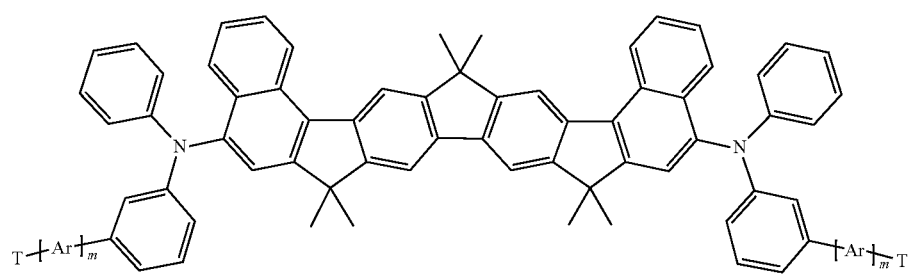
FT-14
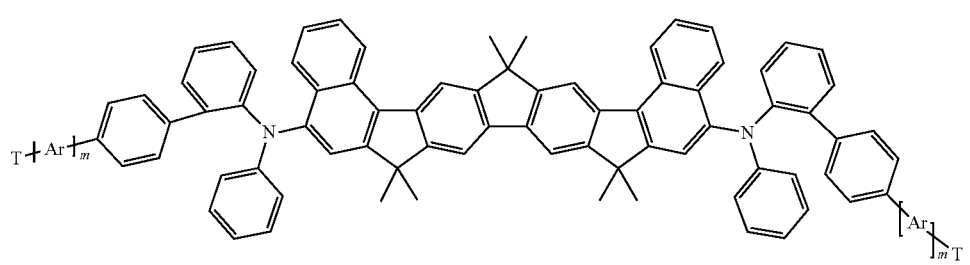
FT-15

-continued
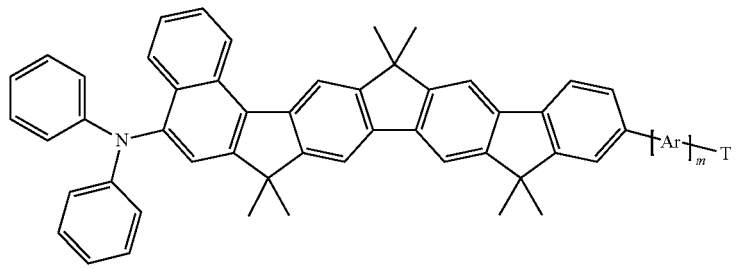
FT-16
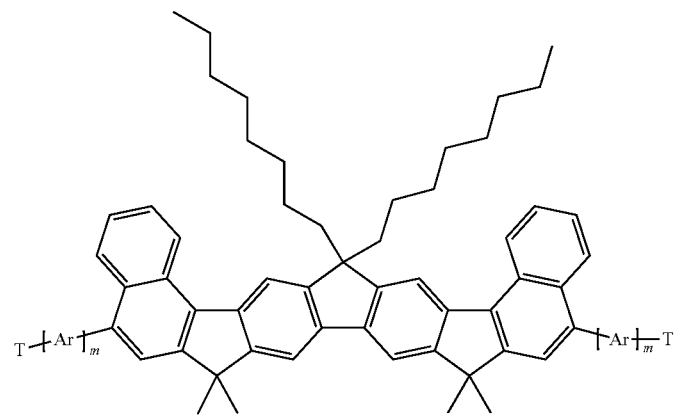
FT-17
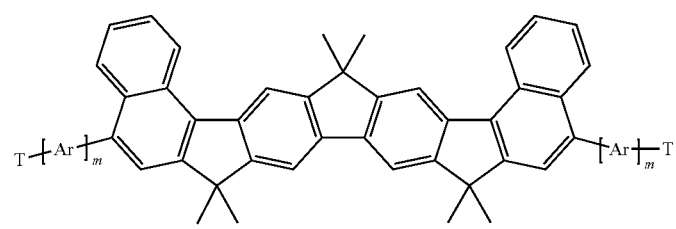
FT-18
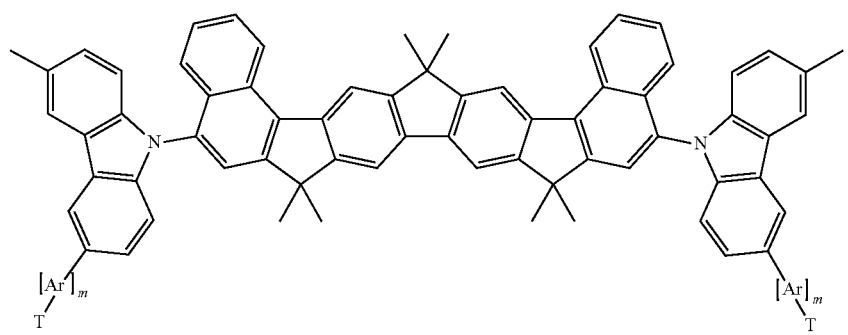
FT-19
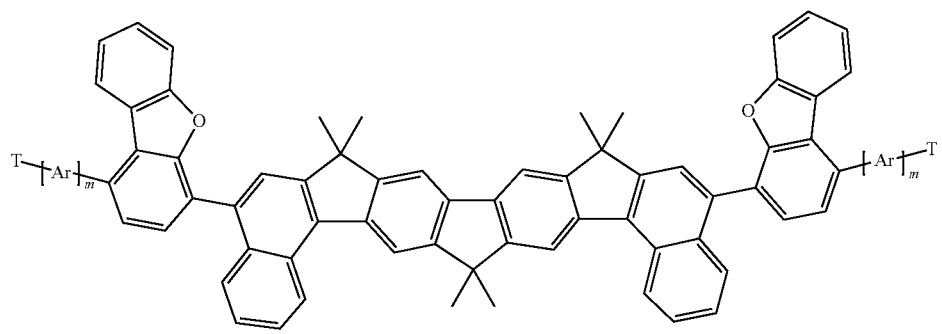
FT-20

-continued
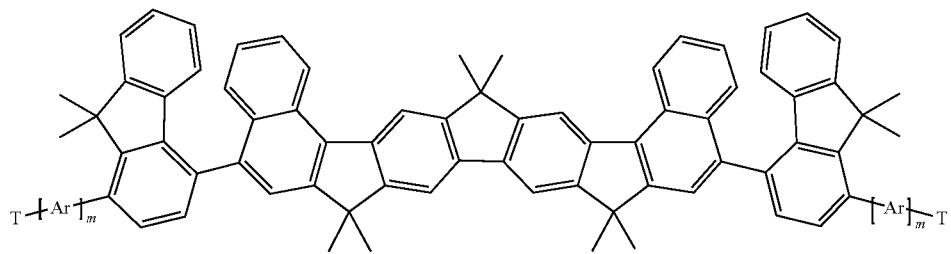
FT-21
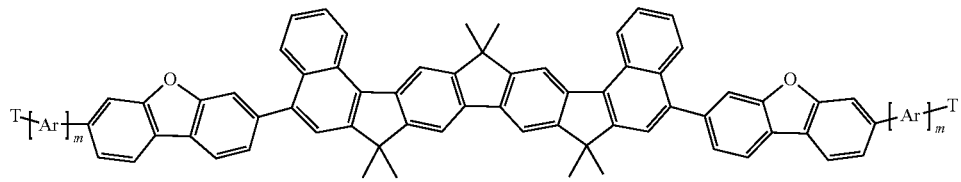
FT-22
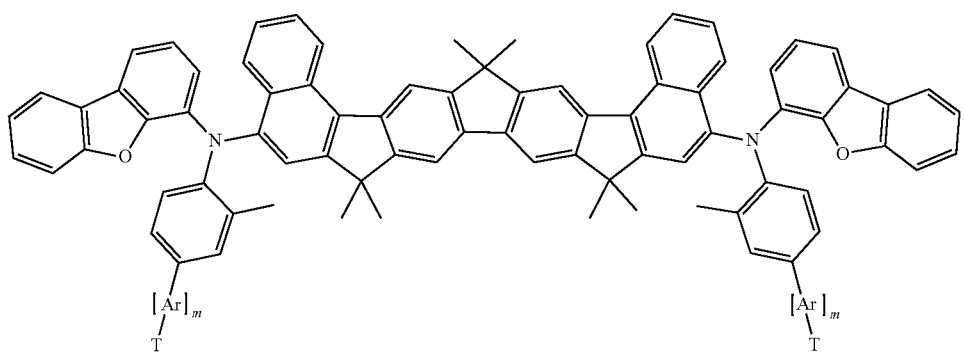
FT-23
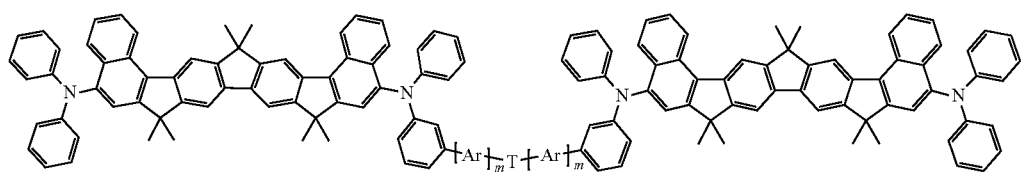
FT-24
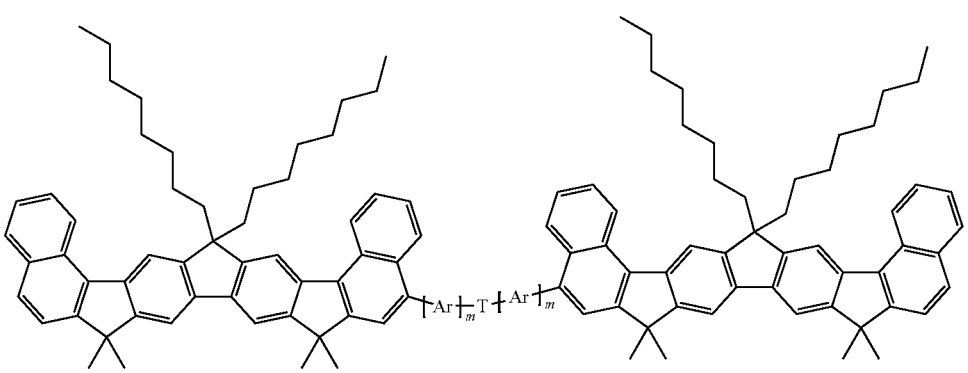
FT-25
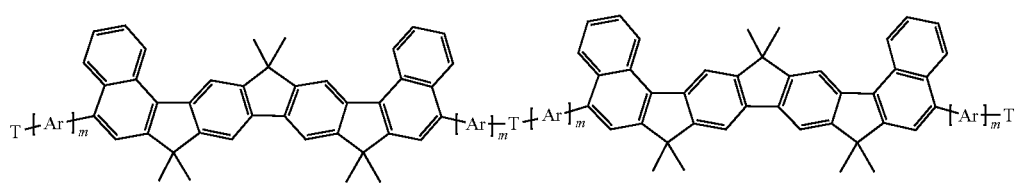
FT-26 where the symbols Ar, T and the index m have the same meaning as above and where the compounds represented in the table above may be further substituted by a group R¹, as defined above, at any free position.

In accordance with another preferred embodiment, the group Y is a host group for a phosphorescent emitting compound.

A host group for a phosphorescent emitting compound here is taken to mean a material, which is present in the emitting layer comprising a phosphorescent emitting compound, preferably as the principal component, and which does not emit light on operation of the device.

When the group Y is a host group for a phosphorescent emitting compound, it is preferably selected from spirobifluorene amines, aromatic ketones, aromatic phosphine oxides or aromatic sulfoxides or sulfones, triarylamines, carbazole derivatives, indolocarbazole derivatives, indenocarbazole derivatives, azacarbazole derivatives, silanes, azaboroles or boronic esters, triazine derivatives, zinc complexes, fluorene derivatives, diazasilole or tetraazasilole derivatives, diazaphosphole derivatives or bridged carbazole derivatives.

Examples of suitable groups Y, when Y is a host group for a phosphorescent emitting compounds, are the groups listed in the following table:

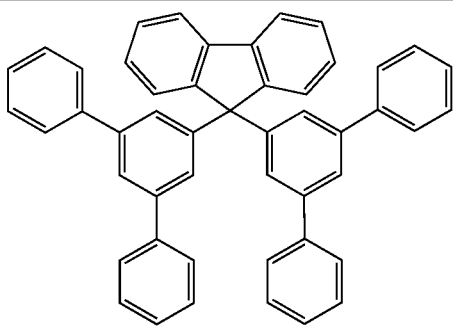 [SMILES: c1ccc(-c2cc(-c3ccccc3)cc(C3(c4cc(-c5ccccc5)cc(-c5ccccc5)c4)c4ccccc4-c4ccccc43)c2)cc1]

HP1

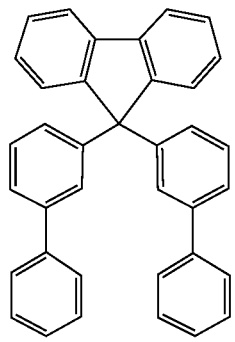 [SMILES: c1ccc(-c2cccc(C3(c4cccc(-c5ccccc5)c4)c4ccccc4-c4ccccc43)c2)cc1]

HP2

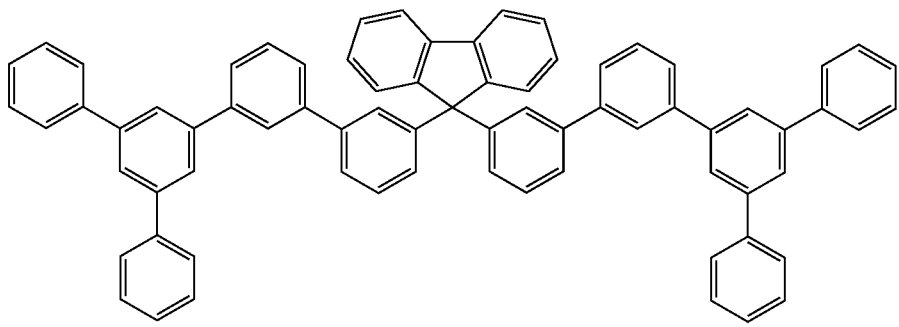 [SMILES: c1ccc(-c2cc(-c3ccccc3)cc(-c3cccc(-c4cccc(C5(c6cccc(-c7cccc(-c8cc(-c9ccccc9)cc(-c9ccccc9)c8)c7)c6)c6ccccc6-c6ccccc65)c4)c3)c2)cc1]

HP3

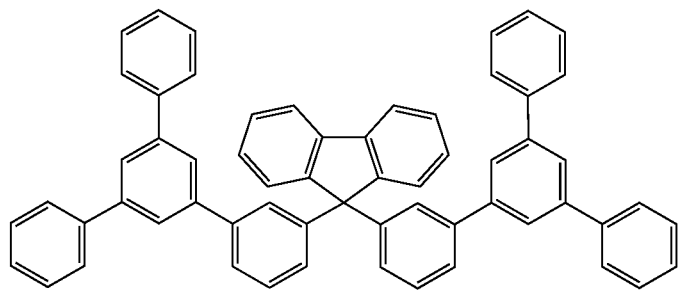 [SMILES: c1ccc(-c2cc(-c3ccccc3)cc(-c3cccc(C4(c5cccc(-c6cc(-c7ccccc7)cc(-c7ccccc7)c6)c5)c5ccccc5-c5ccccc54)c3)c2)cc1]

HP4

HP5
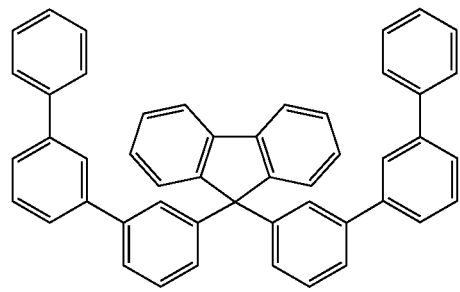 [SMILES: c1ccc(-c2cccc(-c3cccc(C4(c5cccc(-c6cccc(-c7ccccc7)c6)c5)c5ccccc5-c5ccccc54)c3)c2)cc1]
HP6
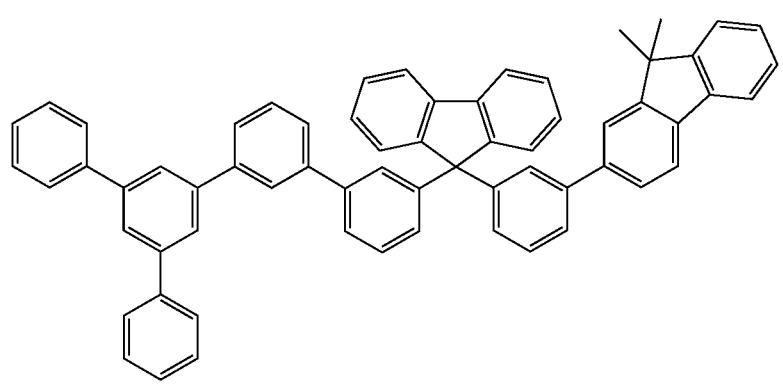 [SMILES: CC1(C)c2ccccc2-c2ccc(-c3cccc(C4(c5cccc(-c6cccc(-c7cc(-c8ccccc8)cc(-c8ccccc8)c7)c6)c5)c5ccccc5-c5ccccc54)c3)cc21]
HP7
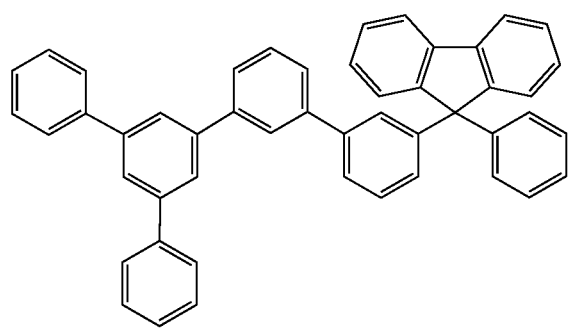 [SMILES: c1ccc(-c2cc(-c3ccccc3)cc(-c3cccc(-c4cccc(C5(c6ccccc6)c6ccccc6-c6ccccc65)c4)c3)c2)cc1]
HP8
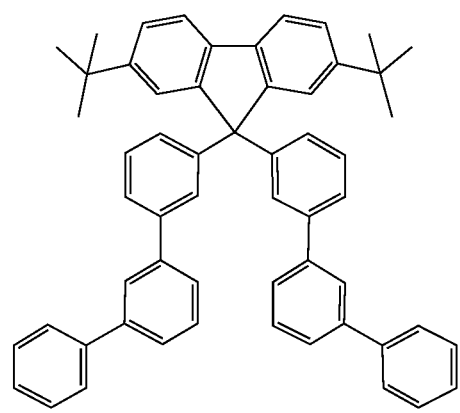 [SMILES: CC(C)(C)c1ccc2c(c1)C(c1cccc(-c3cccc(-c4ccccc4)c3)c1)(c1cccc(-c3cccc(-c4ccccc4)c3)c1)c1cc(C(C)(C)C)ccc1-2]

HP9
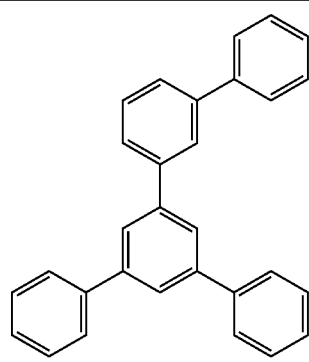
HP10
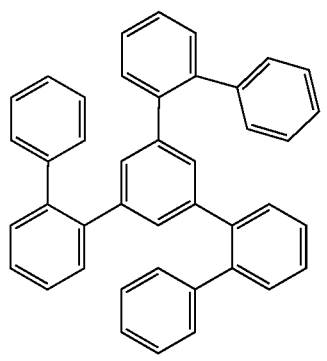 [SMILES: c1ccc(-c2ccccc2-c2cc(-c3ccccc3-c3ccccc3)cc(-c3ccccc3-c3ccccc3)c2)cc1]
HP11
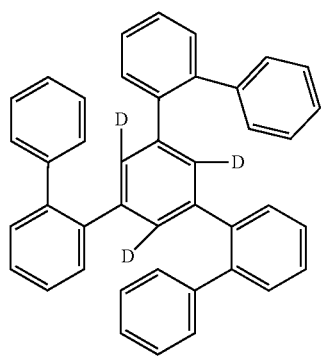 [SMILES: [2H]c1c(-c2ccccc2-c2ccccc2)c([2H])c(-c2ccccc2-c2ccccc2)c([2H])c1-c1ccccc1-c1ccccc1]
HP12
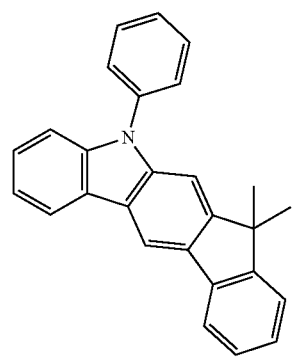 [SMILES: CC1(C)c2ccccc2-c2cc3c4ccccc4n(-c4ccccc4)c3cc21]

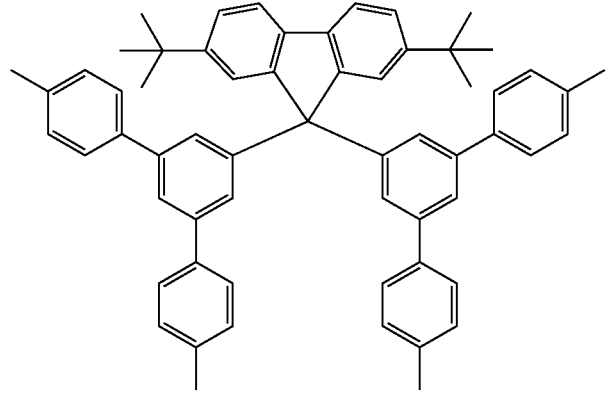
HP13
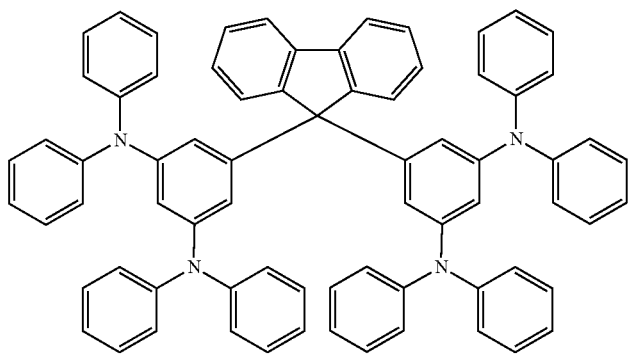 [SMILES: c1ccc(N(c2ccccc2)c2cc(N(c3ccccc3)c3ccccc3)cc(C3(c4cc(N(c5ccccc5)c5ccccc5)cc(N(c5ccccc5)c5ccccc5)c4)c4ccccc4-c4ccccc43)c2)cc1]
HP14
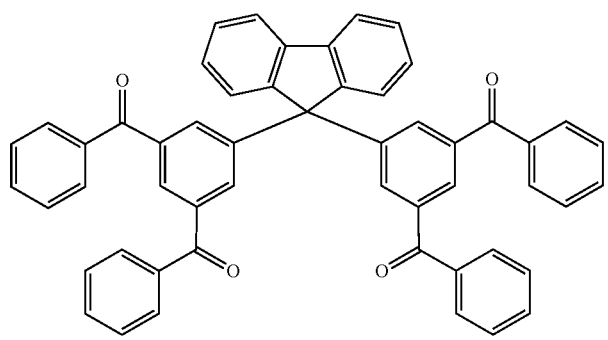 [SMILES: O=C(c1ccccc1)c1cc(C(=O)c2ccccc2)cc(C2(c3cc(C(=O)c4ccccc4)cc(C(=O)c4ccccc4)c3)c3ccccc3-c3ccccc32)c1]
HP15
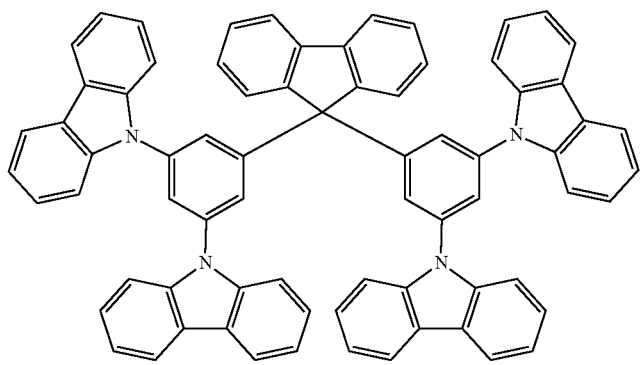 [SMILES: c1ccc2c(c1)-c1ccccc1C2(c1cc(-n2c3ccccc3c3ccccc32)cc(-n2c3ccccc3c3ccccc32)c1)c1cc(-n2c3ccccc3c3ccccc32)cc(-n2c3ccccc3c3ccccc32)c1]
HP16

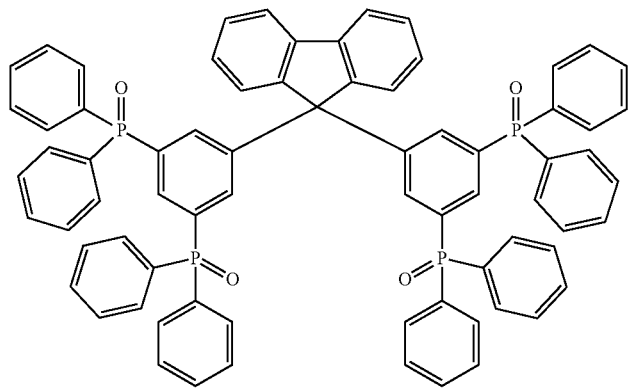 [SMILES: O=P(c1ccccc1)(c1ccccc1)c1cc(C2(c3cc(P(=O)(c4ccccc4)c4ccccc4)cc(P(=O)(c4ccccc4)c4ccccc4)c3)c3ccccc3-c3ccccc32)cc(P(=O)(c2ccccc2)c2ccccc2)c1]
HP17
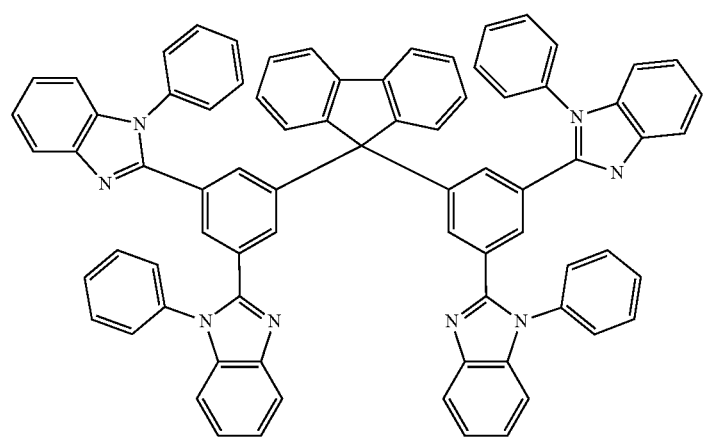
HP18
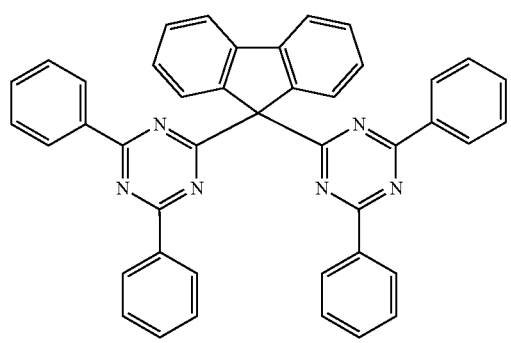 [SMILES: c1ccc(-c2nc(-c3ccccc3)nc(C3(c4nc(-c5ccccc5)nc(-c5ccccc5)n4)c4ccccc4-c4ccccc43)n2)cc1]
HP19
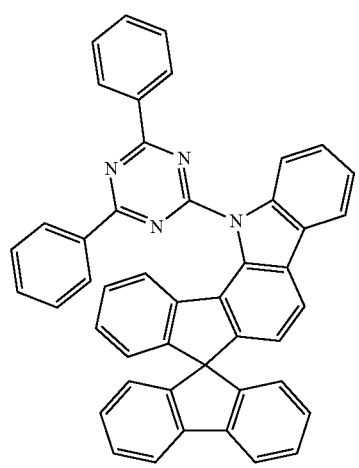 [SMILES: c1ccc(-c2nc(-c3ccccc3)nc(-n3c4ccccc4c4ccc5c(c43)-c3ccccc3C53c4ccccc4-c4ccccc43)n2)cc1]
HP20

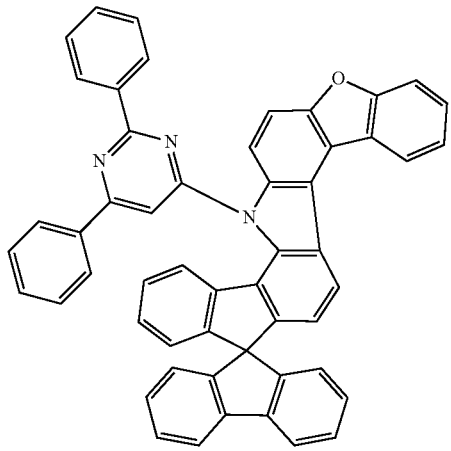 [SMILES: c1ccc(-c2cc(-n3c4ccc5oc6ccccc6c5c4c4ccc5c(c43)-c3ccccc3C53c4ccccc4-c4ccccc43)nc(-c3ccccc3)n2)cc1]
HP21
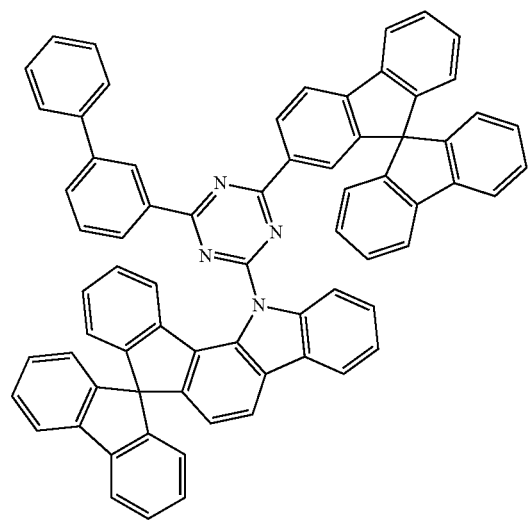 [SMILES: c1ccc(-c2cccc(-c3nc(-c4ccc5c(c4)C4(c6ccccc6-c6ccccc64)c4ccccc4-5)nc(-n4c5ccccc5c5ccc6c(c54)-c4ccccc4C64c5ccccc5-c5ccccc54)n3)c2)cc1]
HP22
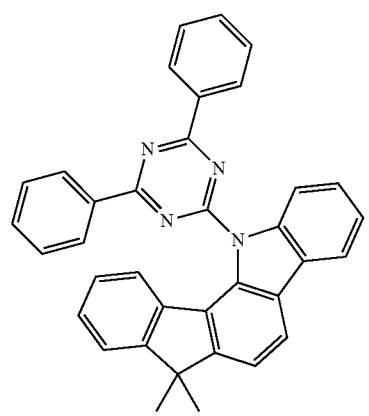 [SMILES: CC1(C)c2ccccc2-c2c1ccc1c3ccccc3n(-c3nc(-c4ccccc4)nc(-c4ccccc4)n3)c21]
HP23

-continued
HP24
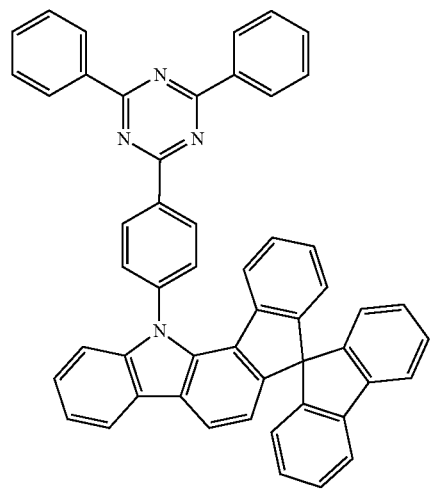 [SMILES: c1ccc(-c2nc(-c3ccccc3)nc(-c3ccc(-n4c5ccccc5c5ccc6c(c54)-c4ccccc4C64c5ccccc5-c5ccccc54)cc3)n2)cc1]
HP25
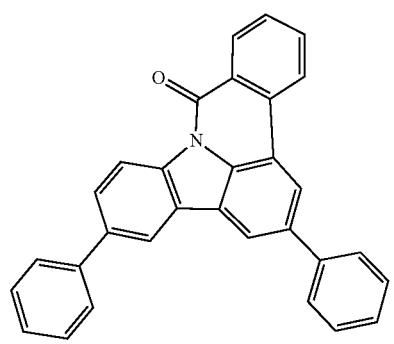 [SMILES: O=c1c2ccccc2c2cc(-c3ccccc3)cc3c4cc(-c5ccccc5)ccc4n1c23]
HP26
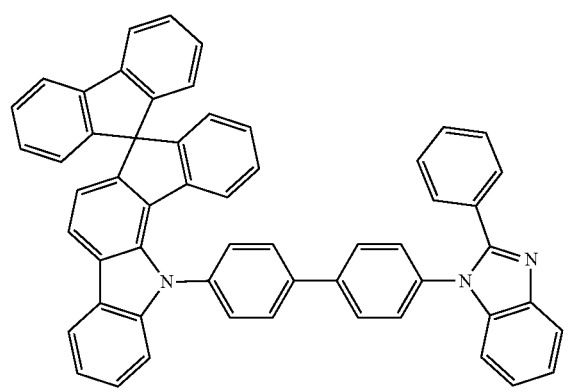 [SMILES: c1ccc(-c2nc3ccccc3n2-c2ccc(-c3ccc(-n4c5ccccc5c5ccc6c(c54)-c4ccccc4C64c5ccccc5-c5ccccc54)cc3)cc2)cc1]

HP27
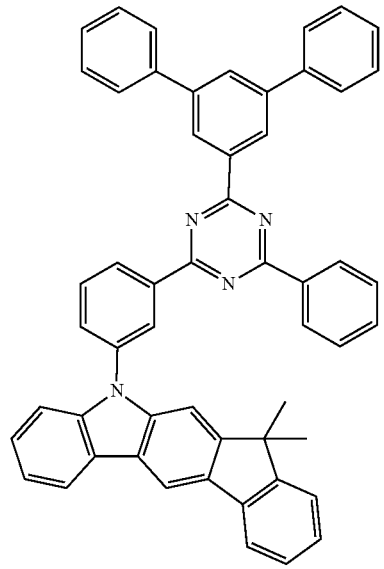 [SMILES: CC1(C)c2ccccc2-c2cc3c4ccccc4n(-c4cccc(-c5nc(-c6ccccc6)nc(-c6cc(-c7ccccc7)cc(-c7ccccc7)c6)n5)c4)c3cc21]
HP28
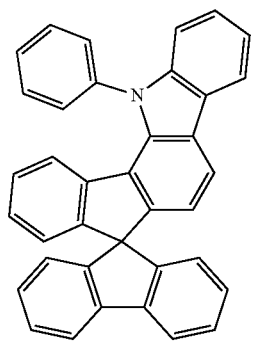 [SMILES: c1ccc(-n2c3ccccc3c3ccc4c(c32)-c2ccccc2C42c3ccccc3-c3ccccc32)cc1]
HP29
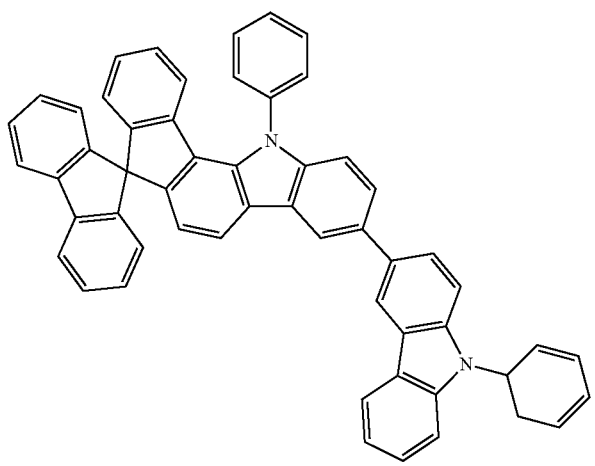 [SMILES: C1=CCC(n2c3ccccc3c3cc(-c4ccc5c(c4)c4ccc6c(c4n5-c4ccccc4)-c4ccccc4C64c5ccccc5-c5ccccc54)ccc32)C=C1]

HP30
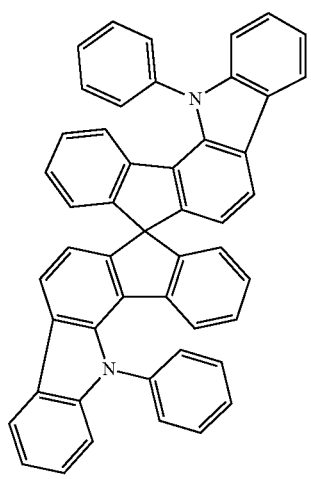 [SMILES: c1ccc(-n2c3ccccc3c3ccc4c(c32)-c2ccccc2C42c3ccccc3-c3c2ccc2c4ccccc4n(-c4ccccc4)c32)cc1]
HP31
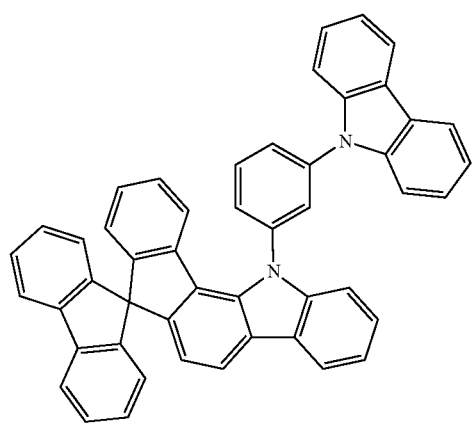 [SMILES: c1cc(-n2c3ccccc3c3ccccc32)cc(-n2c3ccccc3c3ccc4c(c32)-c2ccccc2C42c3ccccc3-c3ccccc32)c1]
HP32
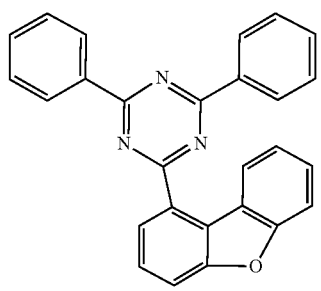 [SMILES: c1ccc(-c2nc(-c3ccccc3)nc(-c3cccc4oc5ccccc5c34)n2)cc1]
HP33
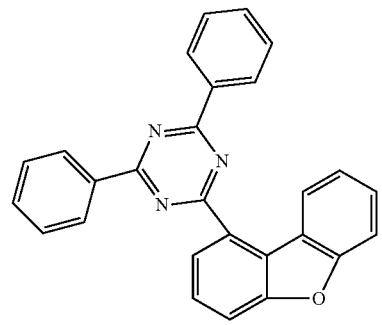 [SMILES: c1ccc(-c2nc(-c3ccccc3)nc(-c3cccc4oc5ccccc5c34)n2)cc1]

HP34
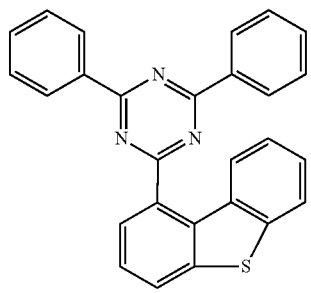 [SMILES: c1ccc(-c2nc(-c3ccccc3)nc(-c3cccc4sc5ccccc5c34)n2)cc1]
HP35
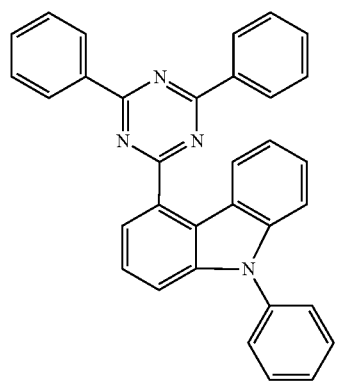 [SMILES: c1ccc(-c2nc(-c3ccccc3)nc(-c3cccc4c3c3ccccc3n4-c3ccccc3)n2)cc1]
HP36
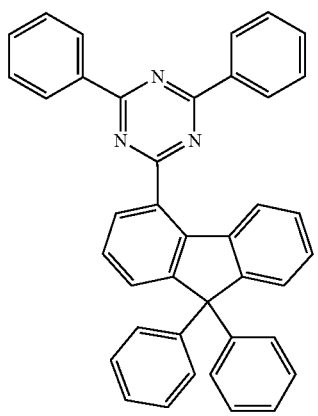 [SMILES: c1ccc(-c2nc(-c3ccccc3)nc(-c3cccc4c3-c3ccccc3C4(c3ccccc3)c3ccccc3)n2)cc1]
HP37
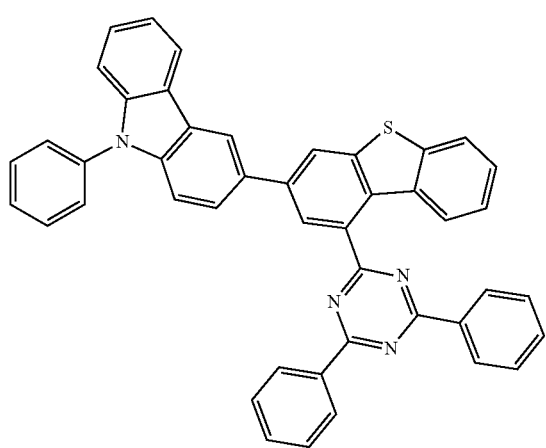 [SMILES: c1ccc(-c2nc(-c3ccccc3)nc(-c3cc(-c4ccc5c(c4)c4ccccc4n5-c4ccccc4)cc4sc5ccccc5c34)n2)cc1]

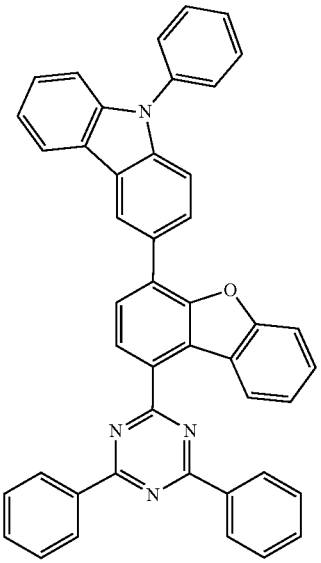 [SMILES: c1ccc(-c2nc(-c3ccccc3)nc(-c3ccc(-c4ccc5c(c4)c4ccccc4n5-c4ccccc4)c4oc5ccccc5c34)n2)cc1]
HP38
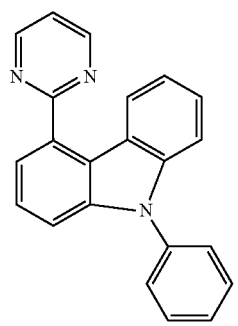 [SMILES: c1ccc(-n2c3ccccc3c3c(-c4ncccn4)cccc32)cc1]
HP39
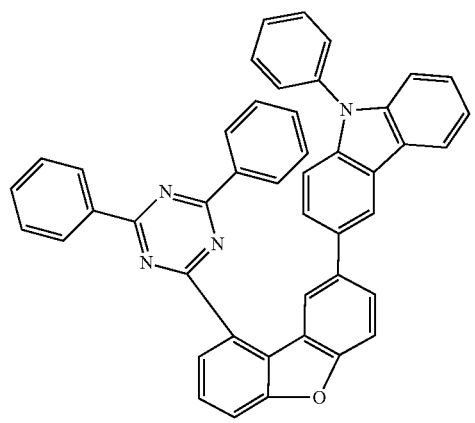 [SMILES: c1ccc(-c2nc(-c3ccccc3)nc(-c3cccc4oc5ccc(-c6ccc7c(c6)c6ccccc6n7-c6ccccc6)cc5c34)n2)cc1]
HP40
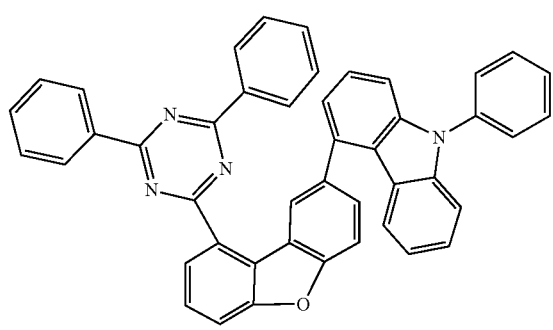 [SMILES: c1ccc(-c2nc(-c3ccccc3)nc(-c3cccc4oc5ccc(-c6cccc7c6c6ccccc6n7-c6ccccc6)cc5c34)n2)cc1]
HP41

HP42
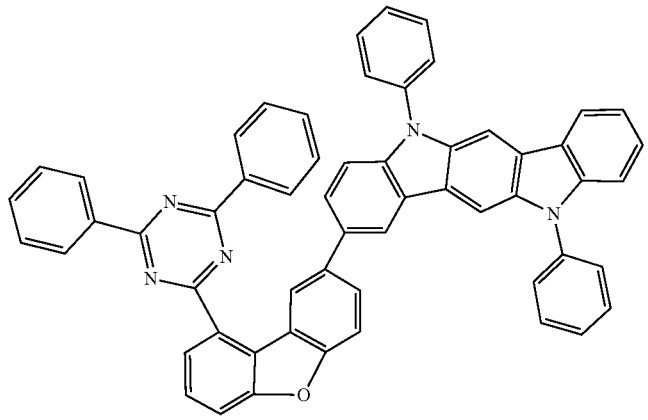 [SMILES: c1ccc(-c2nc(-c3ccccc3)nc(-c3cccc4oc5ccc(-c6ccc7c(c6)c6cc8c(cc6n7-c6ccccc6)c6ccccc6n8-c6ccccc6)cc5c34)n2)cc1]
HP43
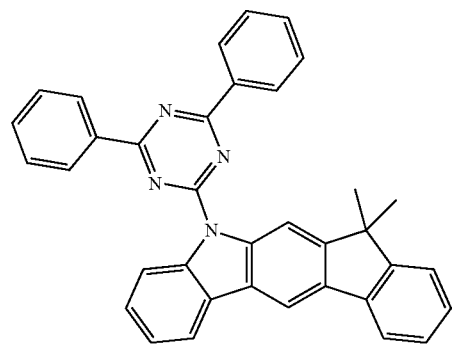 [SMILES: CC1(C)c2ccccc2-c2cc3c4ccccc4n(-c4nc(-c5ccccc5)nc(-c5ccccc5)n4)c3cc21]
HP44
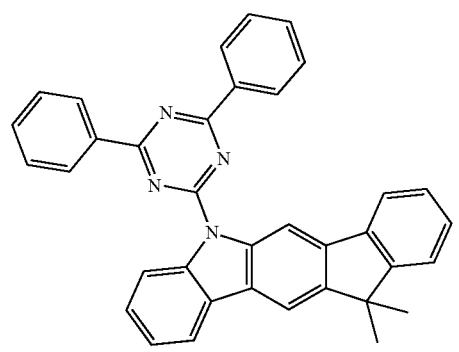 [SMILES: CC1(C)c2ccccc2-c2cc3c(cc21)c1ccccc1n3-c1nc(-c2ccccc2)nc(-c2ccccc2)n1]
HP45
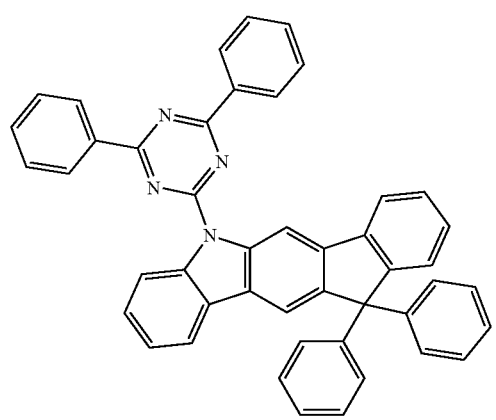 [SMILES: c1ccc(-c2nc(-c3ccccc3)nc(-n3c4ccccc4c4cc5c(cc43)-c3ccccc3C5(c3ccccc3)c3ccccc3)n2)cc1]

HP46
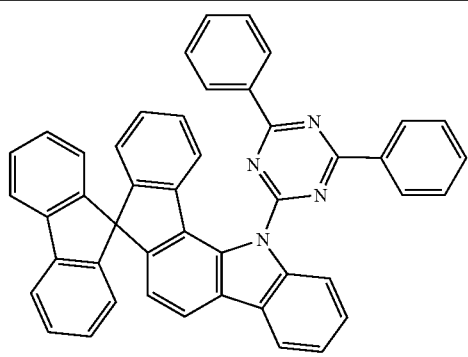
HP47
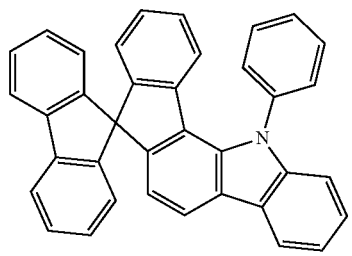 [SMILES: c1ccc(-n2c3ccccc3c3ccc4c(c32)-c2ccccc2C42c3ccccc3-c3ccccc32)cc1]
HP48
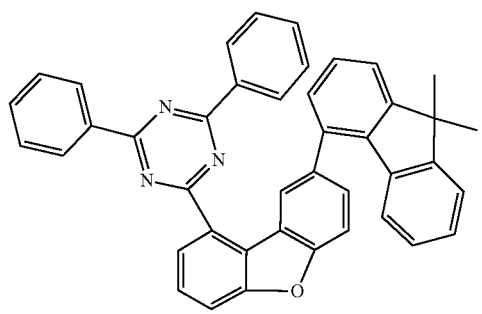 [SMILES: CC1(C)c2ccccc2-c2c(-c3ccc4oc5cccc(-c6nc(-c7ccccc7)nc(-c7ccccc7)n6)c5c4c3)cccc21]
HP49
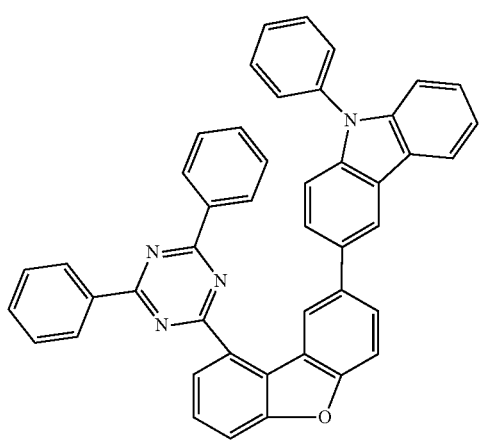 [SMILES: c1ccc(-c2nc(-c3ccccc3)nc(-c3cccc4oc5ccc(-c6ccc7c(c6)c6ccccc6n7-c6ccccc6)cc5c34)n2)cc1]

HP50
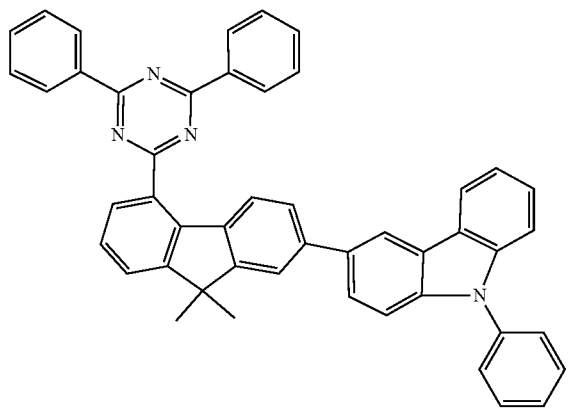 [SMILES: CC1(C)c2cc(-c3ccc4c(c3)c3ccccc3n4-c3ccccc3)ccc2-c2c(-c3nc(-c4ccccc4)nc(-c4ccccc4)n3)cccc21]
HP51
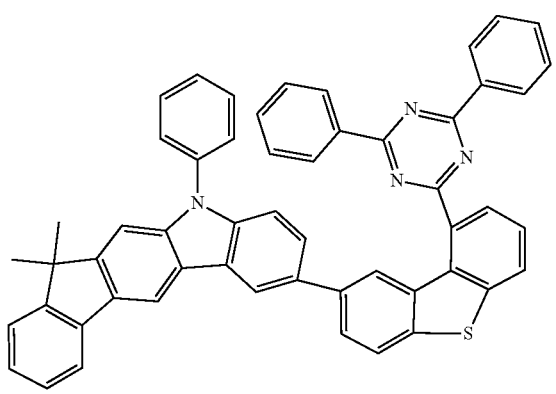 [SMILES: CC1(C)c2ccccc2-c2cc3c4cc(-c5ccc6sc7cccc(-c8nc(-c9ccccc9)nc(-c9ccccc9)n8)c7c6c5)ccc4n(-c4ccccc4)c3cc21]
HP52
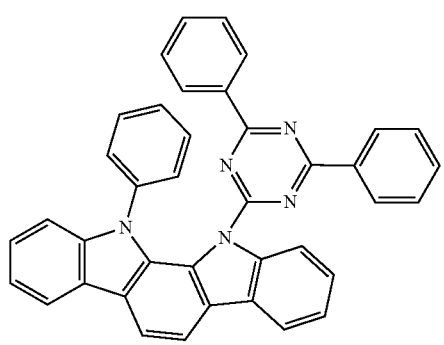 [SMILES: c1ccc(-c2nc(-c3ccccc3)nc(-n3c4ccccc4c4ccc5c6ccccc6n(-c6ccccc6)c5c43)n2)cc1]
HP53
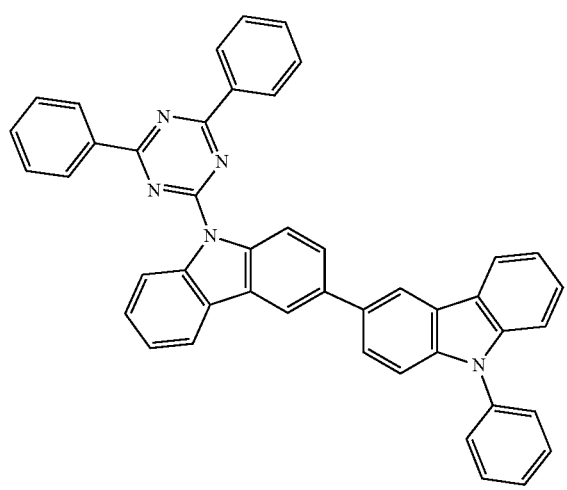 [SMILES: c1ccc(-c2nc(-c3ccccc3)nc(-n3c4ccccc4c4cc(-c5ccc6c(c5)c5ccccc5n6-c5ccccc5)ccc43)n2)cc1]

-continued
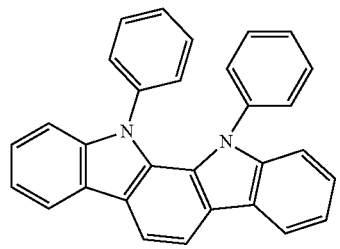 [SMILES: c1ccc(-n2c3ccccc3c3ccc4c5ccccc5n(-c5ccccc5)c4c32)cc1]
HP54
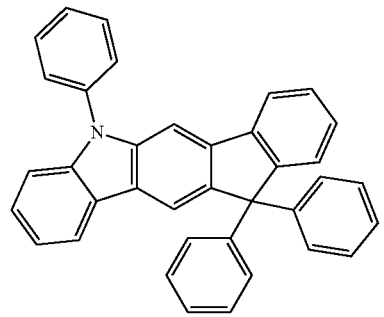 [SMILES: c1ccc(-n2c3ccccc3c3cc4c(cc32)-c2ccccc2C4(c2ccccc2)c2ccccc2)cc1]
HP55
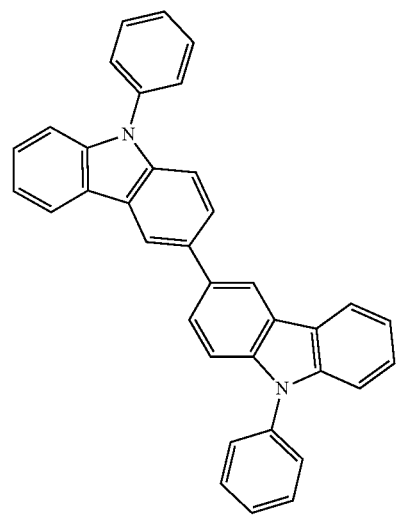 [SMILES: c1ccc(-n2c3ccccc3c3cc(-c4ccc5c(c4)c4ccccc4n5-c4ccccc4)ccc32)cc1]
HP56
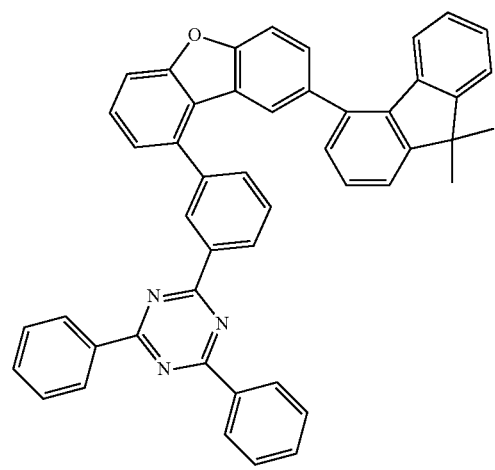 [SMILES: CC1(C)c2ccccc2-c2c(-c3ccc4oc5cccc(-c6cccc(-c7nc(-c8ccccc8)nc(-c8ccccc8)n7)c6)c5c4c3)cccc21]
HP57

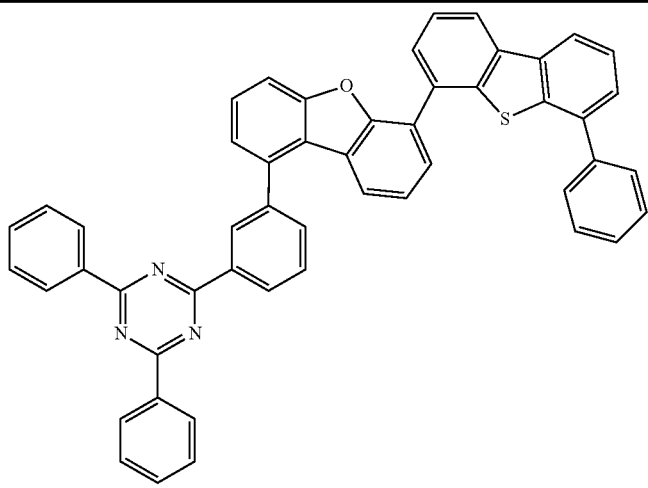
HP58
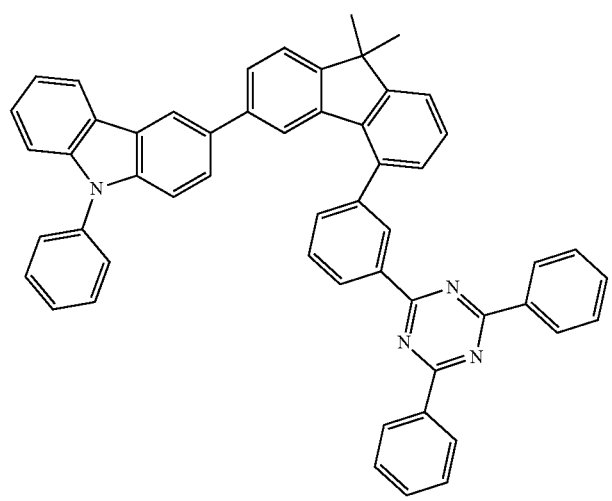 [SMILES: CC1(C)c2ccc(-c3ccc4c(c3)c3ccccc3n4-c3ccccc3)cc2-c2c(-c3cccc(-c4nc(-c5ccccc5)nc(-c5ccccc5)n4)c3)cccc21]
HP59
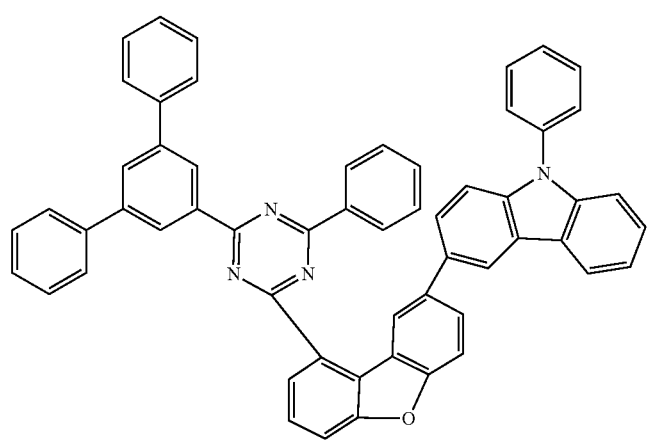 [SMILES: c1ccc(-c2cc(-c3ccccc3)cc(-c3nc(-c4ccccc4)nc(-c4cccc5oc6ccc(-c7ccc8c(c7)c7ccccc7n8-c7ccccc7)cc6c45)n3)c2)cc1]
HP60
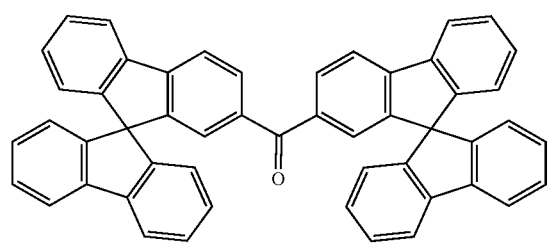 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2]
HP61

HP62
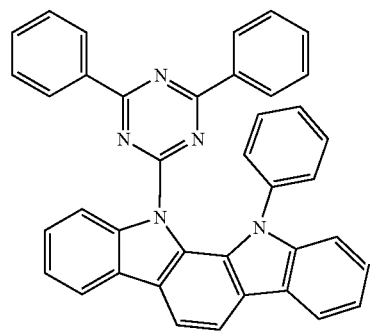 [SMILES: C=Cc1c(/C=C\C)c2ccc3c4ccccc4n(-c4nc(-c5ccccc5)nc(-c5ccccc5)n4)c3c2n1-c1ccccc1]
HP63
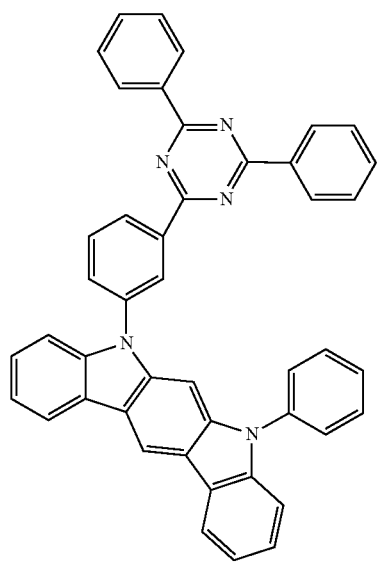 [SMILES: c1ccc(-c2nc(-c3ccccc3)nc(-c3cccc(-n4c5ccccc5c5cc6c7ccccc7n(-c7ccccc7)c6cc54)c3)n2)cc1]
HP64
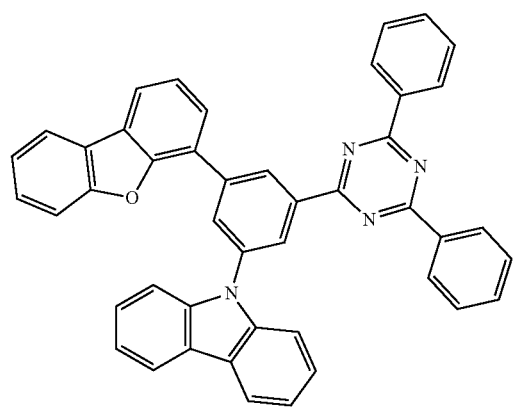 [SMILES: c1ccc(-c2nc(-c3ccccc3)nc(-c3cc(-c4cccc5c4oc4ccccc45)cc(-n4c5ccccc5c5ccccc54)c3)n2)cc1]

-continued
HP65
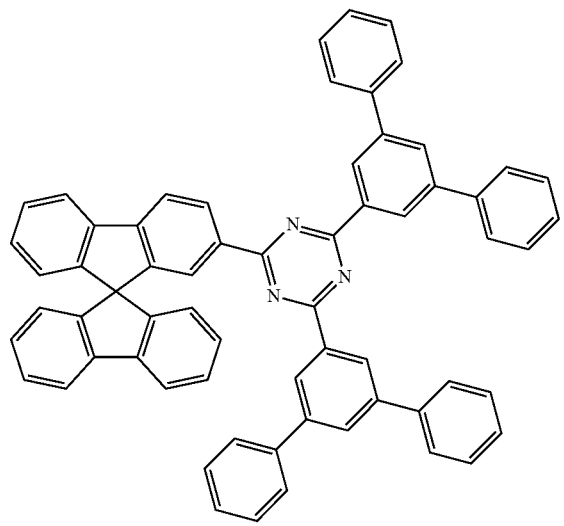 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
HP66
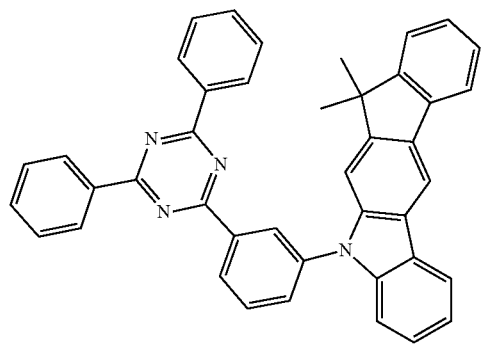 [SMILES: CC1(C)c2ccccc2-c2cc3c4ccccc4n(-c4cccc(-c5nc(-c6ccccc6)nc(-c6ccccc6)n5)c4)c3cc21]
HP67
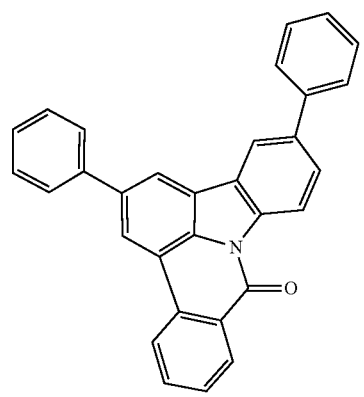 [SMILES: O=c1c2ccccc2c2cc(-c3ccccc3)cc3c4cc(-c5ccccc5)ccc4n1c23]

-continued
HP68
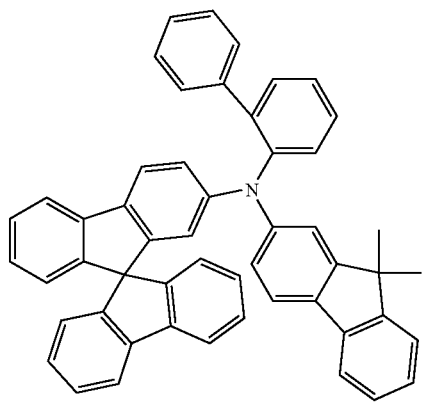 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
HP69
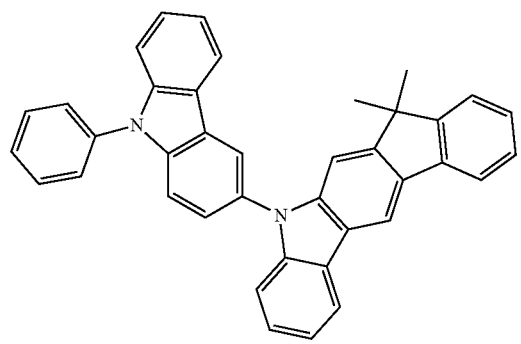 [SMILES: CC1(C)c2ccccc2-c2cc3c4ccccc4n(-c4ccc5c(c4)c4ccccc4n5-c4ccccc4)c3cc21]
HP70
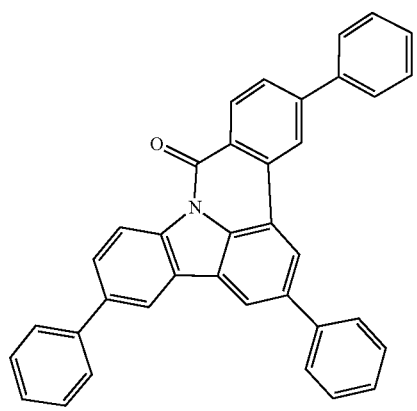 [SMILES: O=c1c2ccc(-c3ccccc3)cc2c2cc(-c3ccccc3)cc3c4cc(-c5ccccc5)ccc4n1c23]
HP71
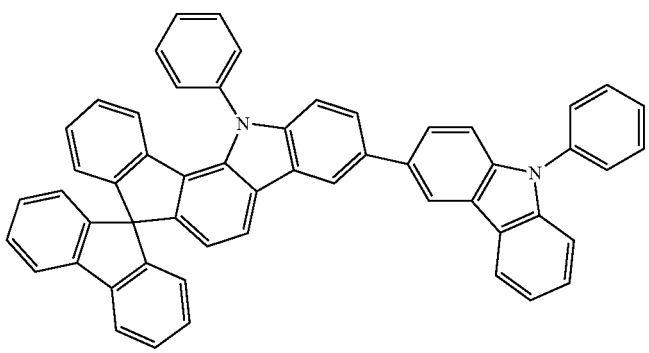 [SMILES: c1ccc(-n2c3ccccc3c3cc(-c4ccc5c(c4)c4ccc6c(c4n5-c4ccccc4)-c4ccccc4C64c5ccccc5-c5ccccc54)ccc32)cc1]

-continued
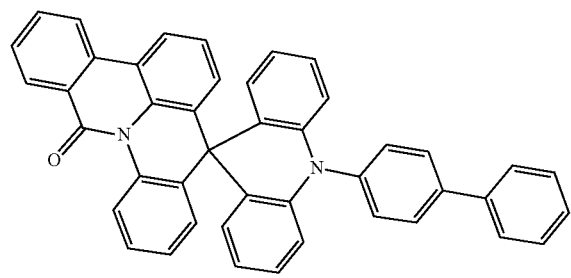 [SMILES: O=c1c2ccccc2c2cccc3c2n1-c1ccccc1C31c2ccccc2N(c2ccc(-c3ccccc3)cc2)c2ccccc21]
HP72
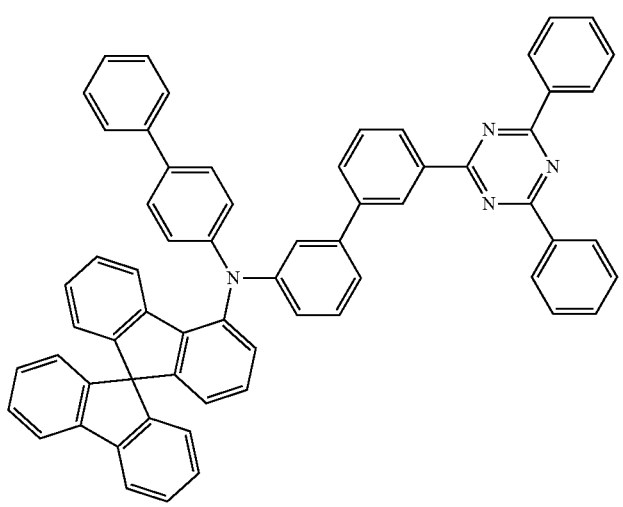 [SMILES: c1ccc(-c2ccc(N(c3cccc(-c4cccc(-c5nc(-c6ccccc6)nc(-c6ccccc6)n5)c4)c3)c3cccc4c3-c3ccccc3C43c4ccccc4-c4ccccc43)cc2)cc1]
HP73
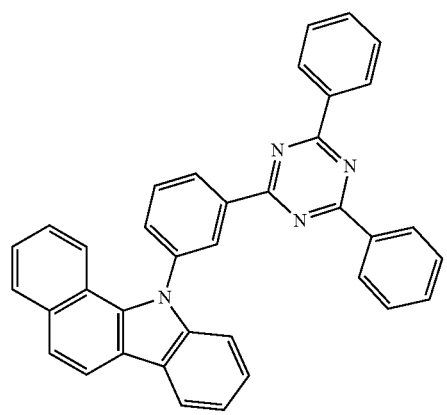 [SMILES: c1ccc(-c2nc(-c3ccccc3)nc(-c3cccc(-n4c5ccccc5c5ccc6ccccc6c54)c3)n2)cc1]
HP74
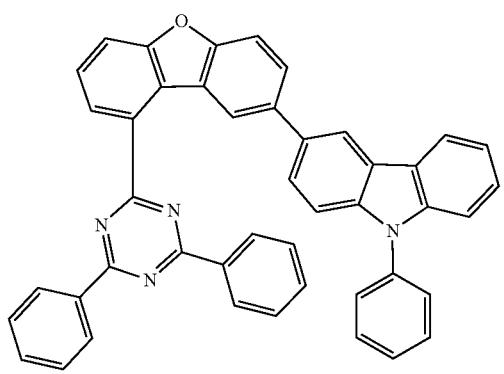 [SMILES: c1ccc(-c2nc(-c3ccccc3)nc(-c3cccc4oc5ccc(-c6ccc7c(c6)c6ccccc6n7-c6ccccc6)cc5c34)n2)cc1]
HP75

HP76
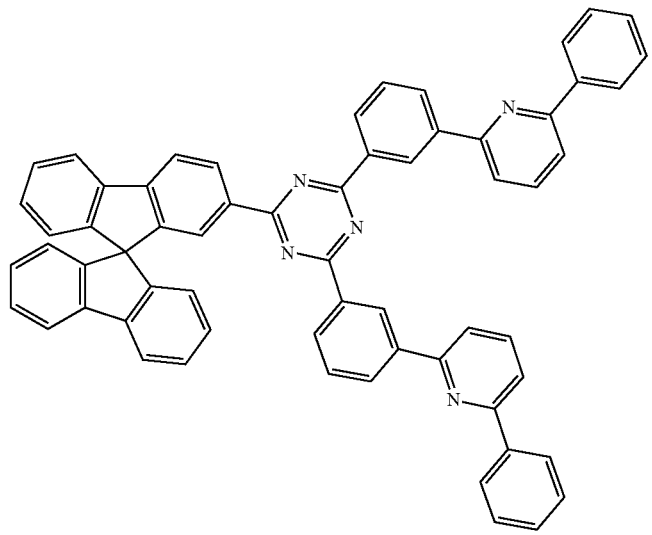 [SMILES: c1ccc(-c2cccc(-c3cccc(-c4nc(-c5cccc(-c6cccc(-c7ccccc7)n6)c5)nc(-c5ccc6c(c5)C5(c7ccccc7-c7ccccc75)c5ccccc5-6)n4)c3)n2)cc1]
HP77
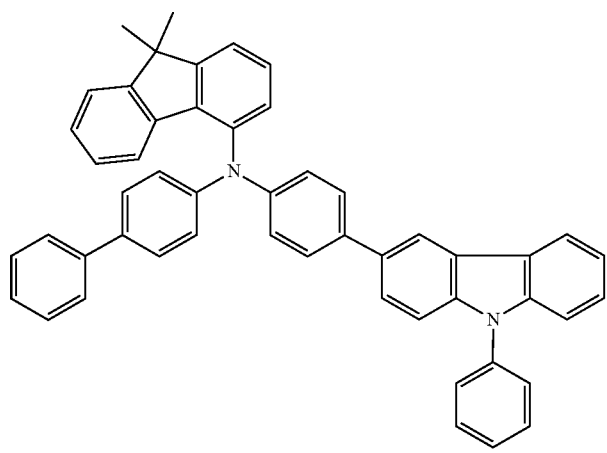 [SMILES: CC1(C)c2ccccc2-c2c(N(c3ccc(-c4ccccc4)cc3)c3ccc(-c4ccc5c(c4)c4ccccc4n5-c4ccccc4)cc3)cccc21]
HP78
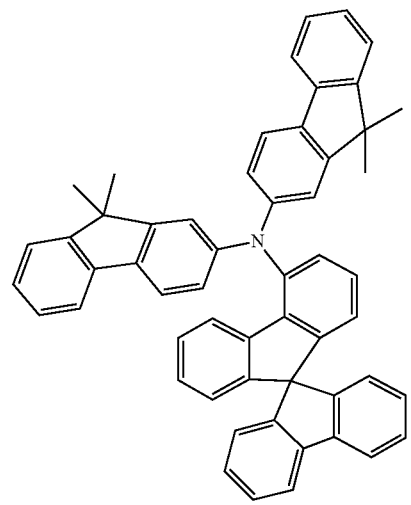 [SMILES: CC1(C)c2ccccc2-c2ccc(N(c3ccc4c(c3)C(C)(C)c3ccccc3-4)c3cccc4c3-c3ccccc3C43c4ccccc4-c4ccccc43)cc21]

HP79
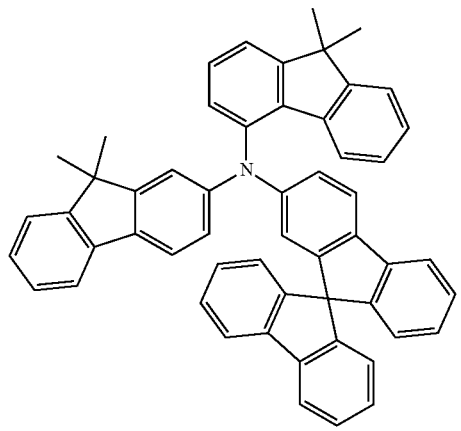 [SMILES: CC1(C)c2ccccc2-c2ccc(N(c3ccc4c(c3)C3(c5ccccc5-c5ccccc53)c3ccccc3-4)c3cccc4c3-c3ccccc3C4(C)C)cc21]
HP80
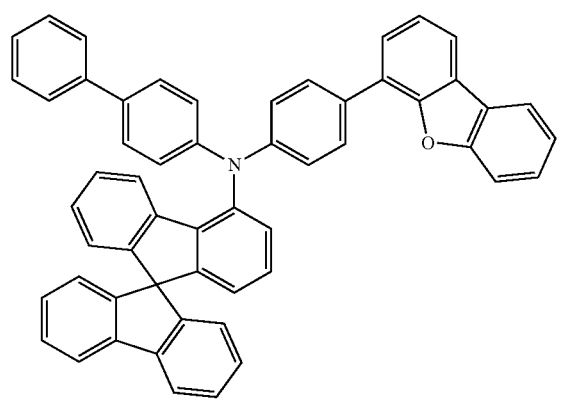 [SMILES: c1ccc(-c2ccc(N(c3ccc(-c4cccc5c4oc4ccccc45)cc3)c3cccc4c3-c3ccccc3C43c4ccccc4-c4ccccc43)cc2)cc1]
HP81
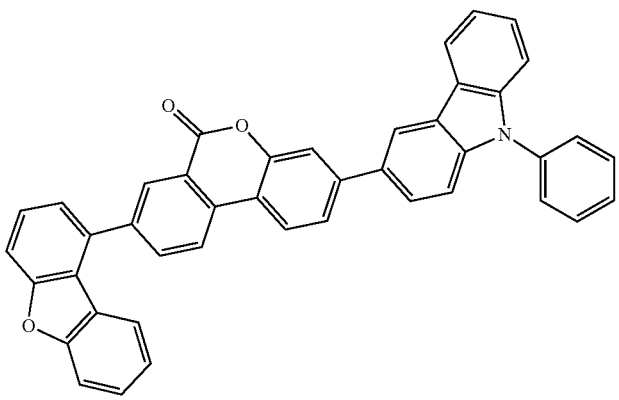 [SMILES: O=c1oc2cc(-c3ccc4c(c3)c3ccccc3n4-c3ccccc3)ccc2c2ccc(-c3cccc4oc5ccccc5c34)cc12]
HP82
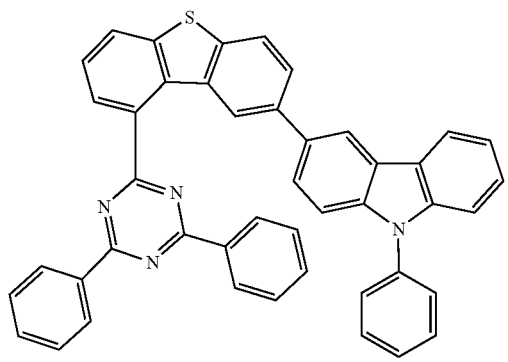 [SMILES: c1ccc(-c2nc(-c3ccccc3)nc(-c3cccc4sc5ccc(-c6ccc7c(c6)c6ccccc6n7-c6ccccc6)cc5c34)n2)cc1]

HP83
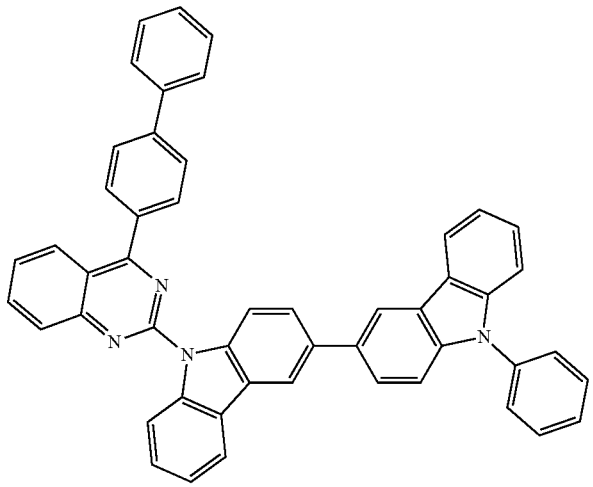 [SMILES: c1ccc(-c2ccc(-c3nc(-n4c5ccccc5c5cc(-c6ccc7c(c6)c6ccccc6n7-c6ccccc6)ccc54)nc4ccccc34)cc2)cc1]
HP84
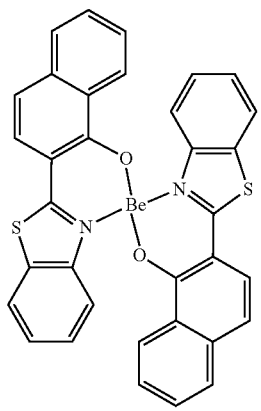
HP85
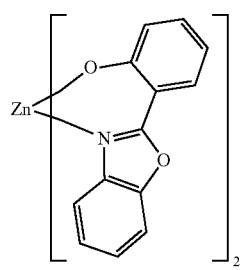
HP86
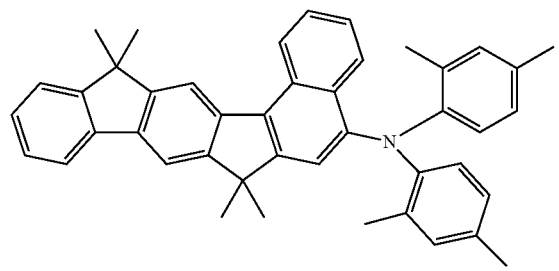 [SMILES: Cc1ccc(N(c2ccc(C)cc2C)c2cc3c(c4ccccc24)-c2cc4c(cc2C3(C)C)-c2ccccc2C4(C)C)c(C)c1]

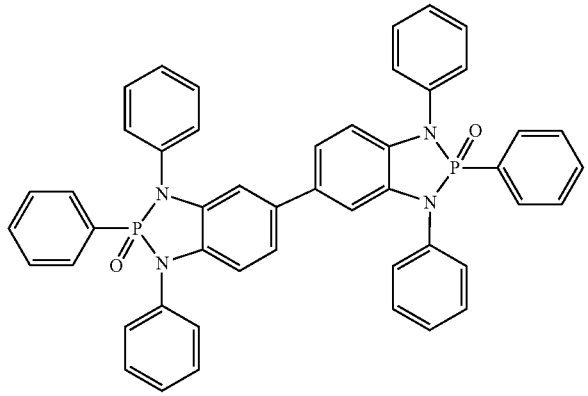 [SMILES: O=P1(c2ccccc2)N(c2ccccc2)c2ccc(-c3ccc4c(c3)N(c3ccccc3)P(=O)(c3ccccc3)N4c3ccccc3)cc2N1c1ccccc1]

HP87

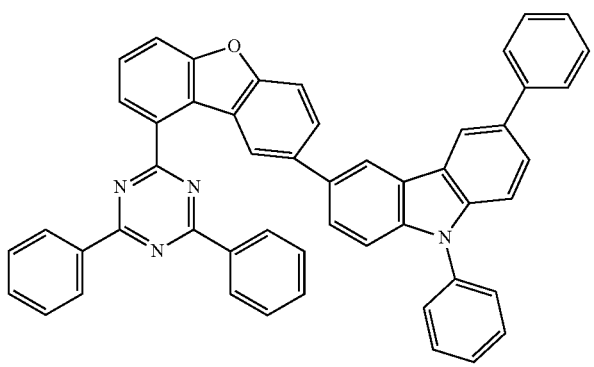 [SMILES: c1ccc(-c2ccc3c(c2)c2cc(-c4ccc5oc6cccc(-c7nc(-c8ccccc8)nc(-c8ccccc8)n7)c6c5c4)ccc2n3-c2ccccc2)cc1]

HP88 where at least one group T may be appended at any free position of the group (HP1) to (HP88), directly or via a group Ar, and where the groups (HP1) to (HP88) may further be substituted at any free position by a radical $R^1$ as defined above.

Example of suitable host groups for phosphorescent emitting compounds, substituted by at least one terpene or terpenoid group, are represented in the table below:

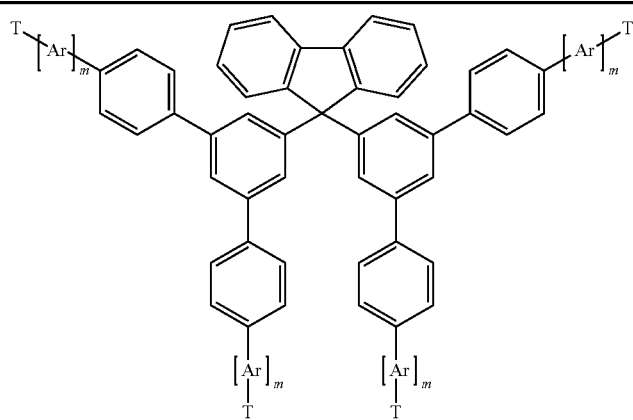

HPT-1

-continued
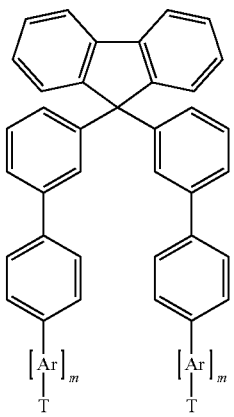
HPT-2
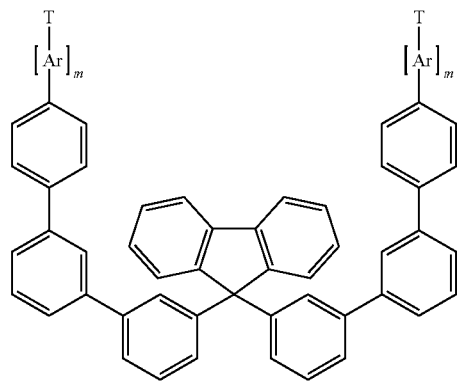
HPT-3
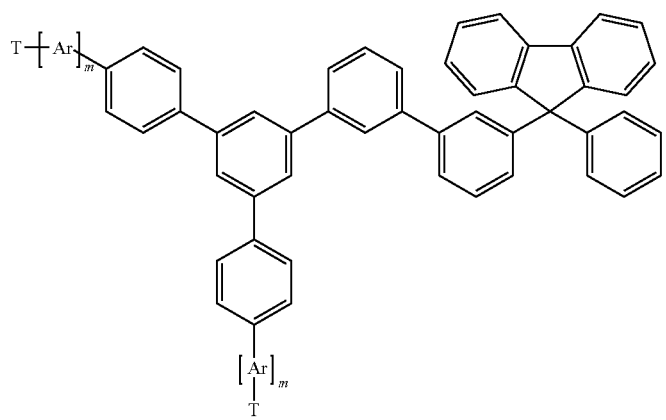
HPT-4
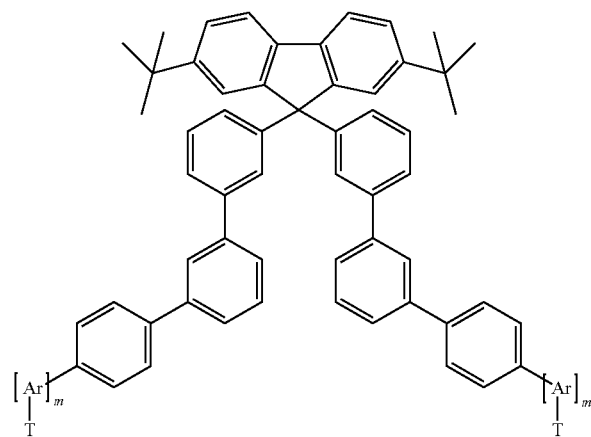
HPT-5

-continued
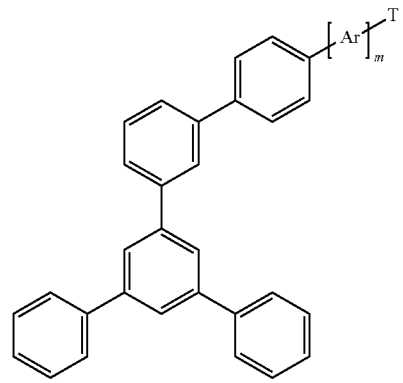
HPT-6
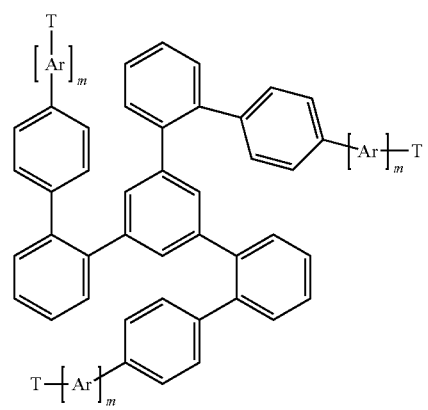
HPT-7
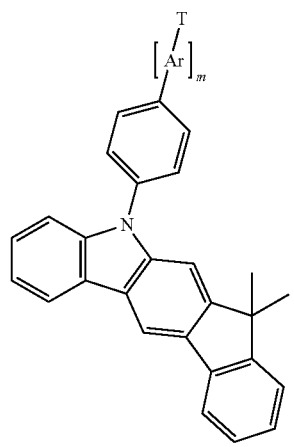
HPT-8

-continued
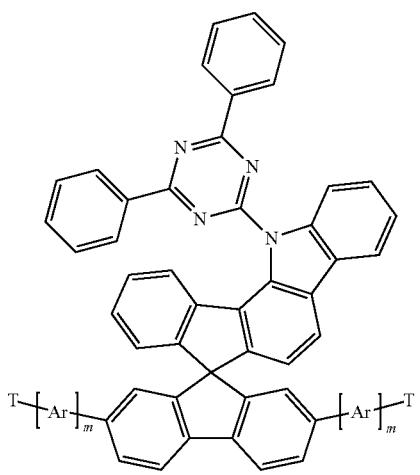
HPT-9
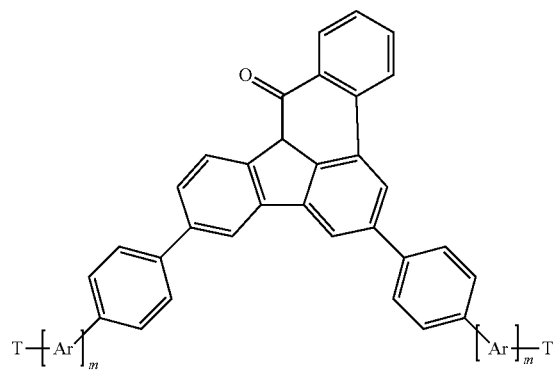
HPT-10
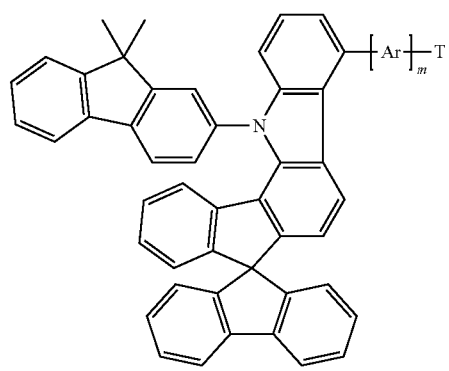
HPT-11
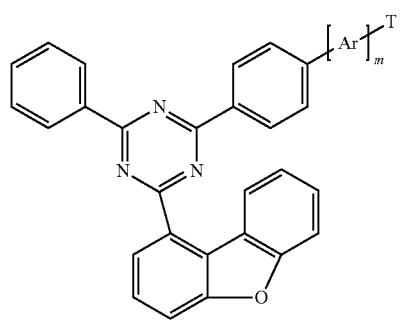
HPT-12

-continued
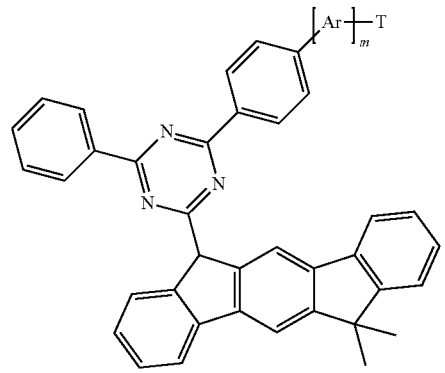
HPT-13
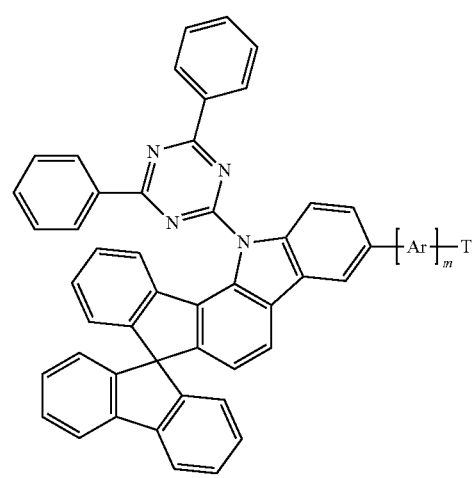
HPT-14
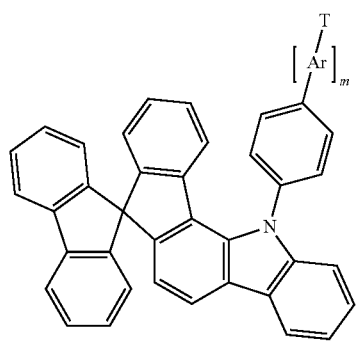
HPT-15
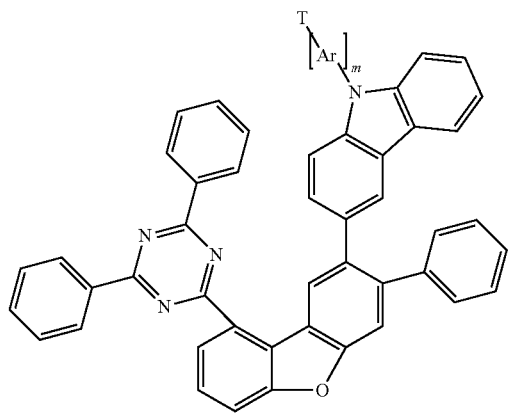
HPT-16

HPT-17
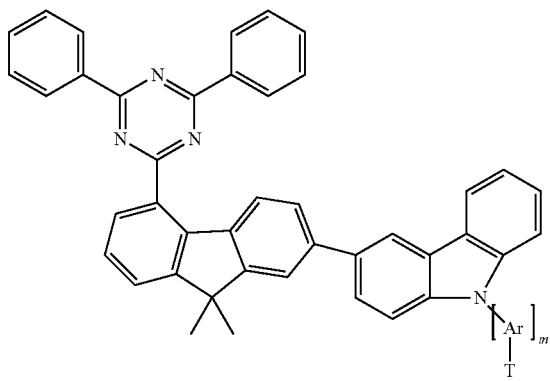
HPT-18
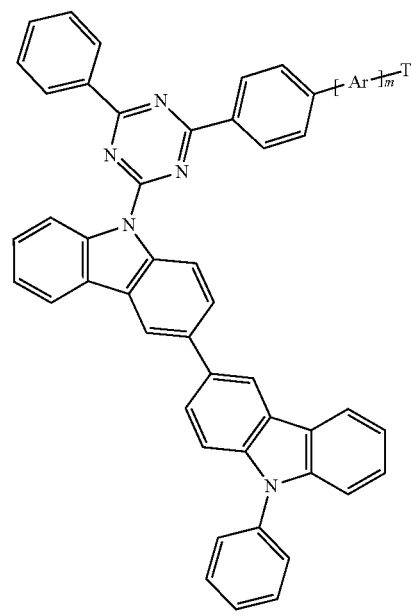
HPT-19
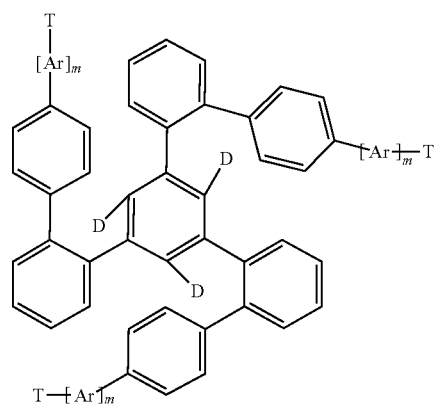

-continued
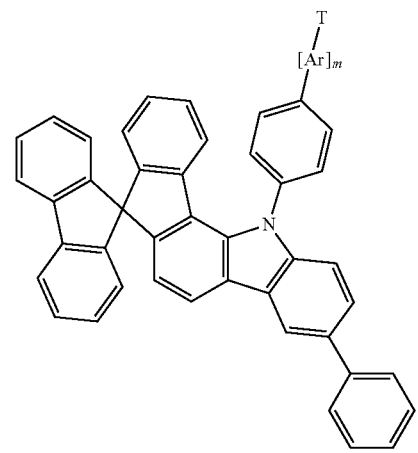
HPT-20
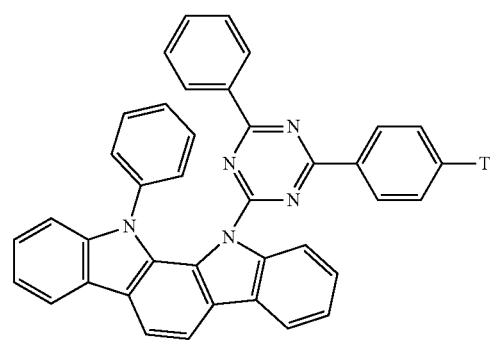
HPT-21
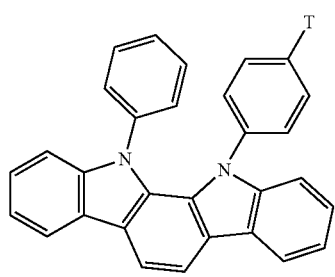
HPT-22
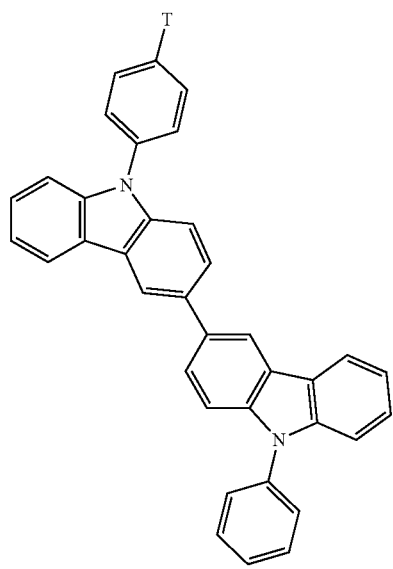
HPT-23

-continued
HPT-24
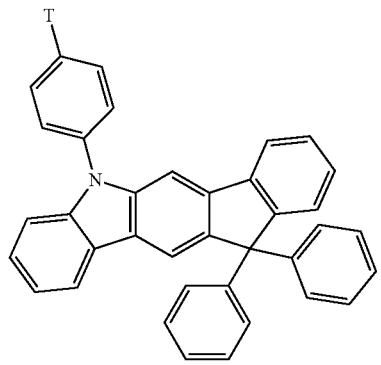
HPT-25
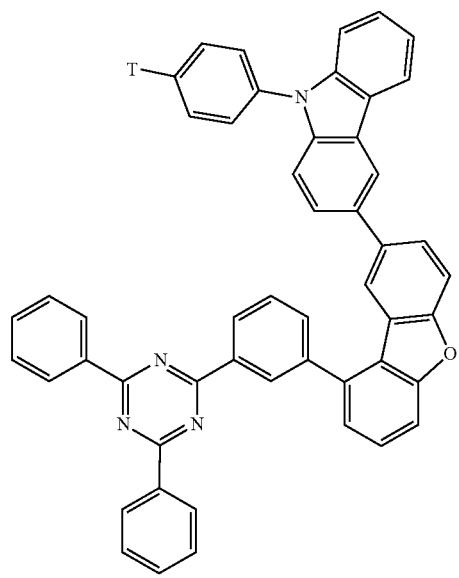
HPT-26
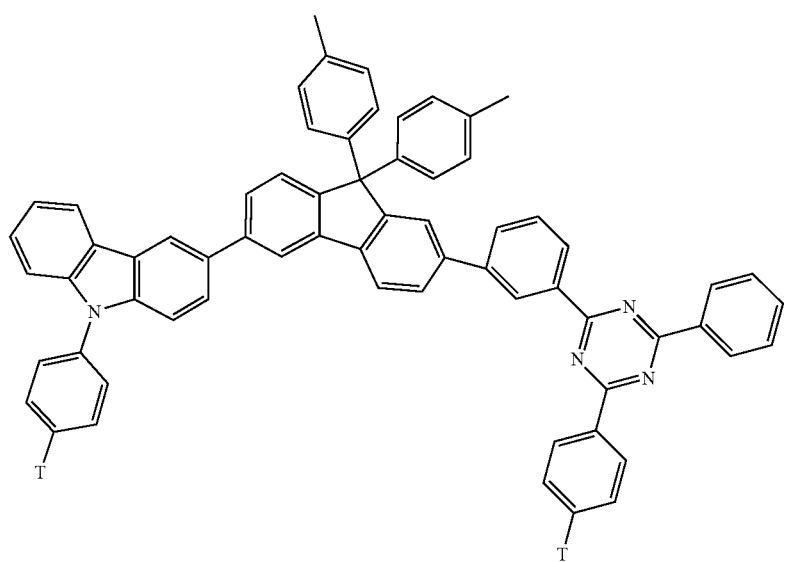

-continued
HPT-27
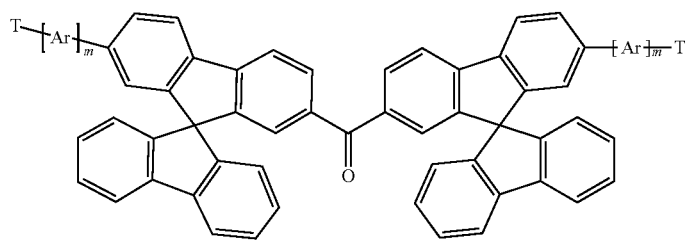
HPT-28
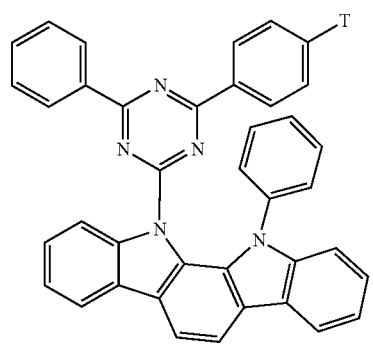
HPT-29
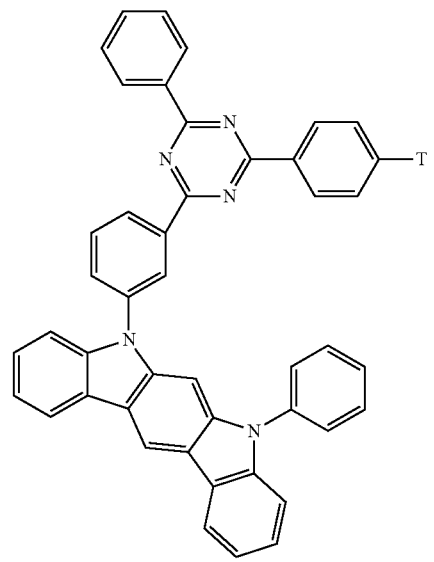

-continued
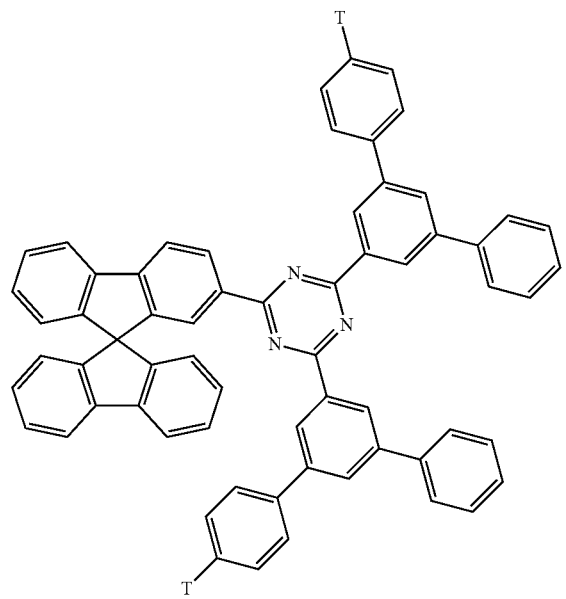
HPT-30
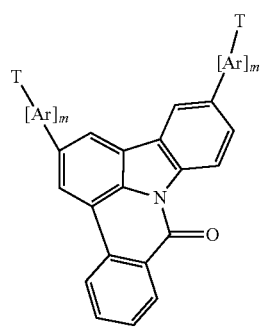
HPT-31
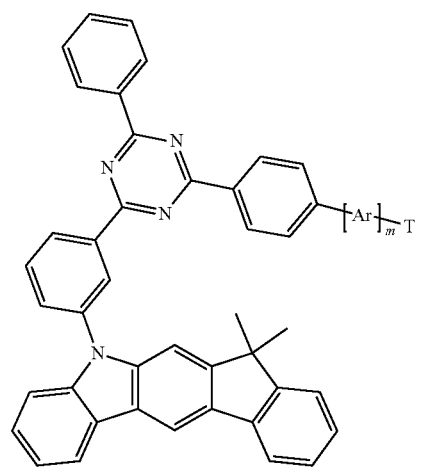
HPT-32

-continued
HPT-33
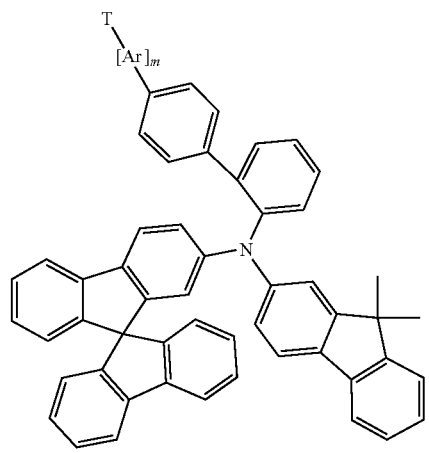
HPT-34
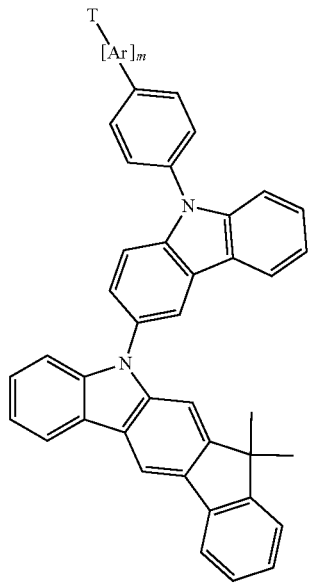
HPT-35
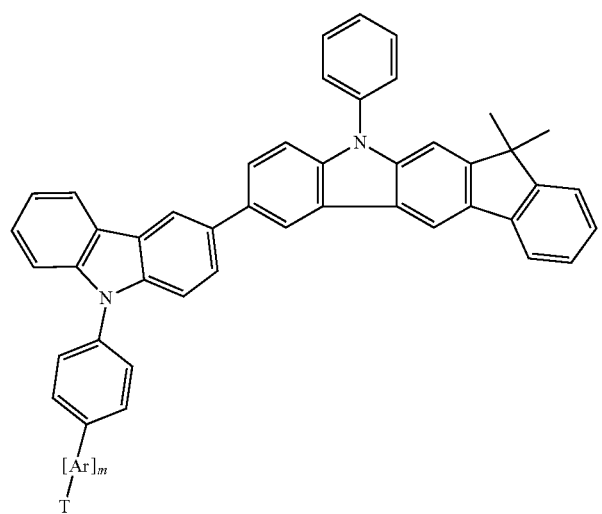

HPT-36
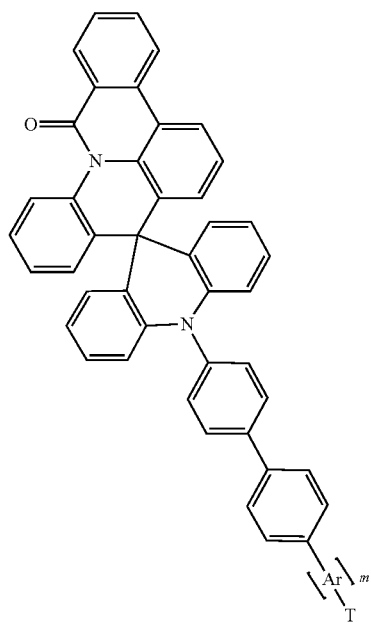
HPT-37
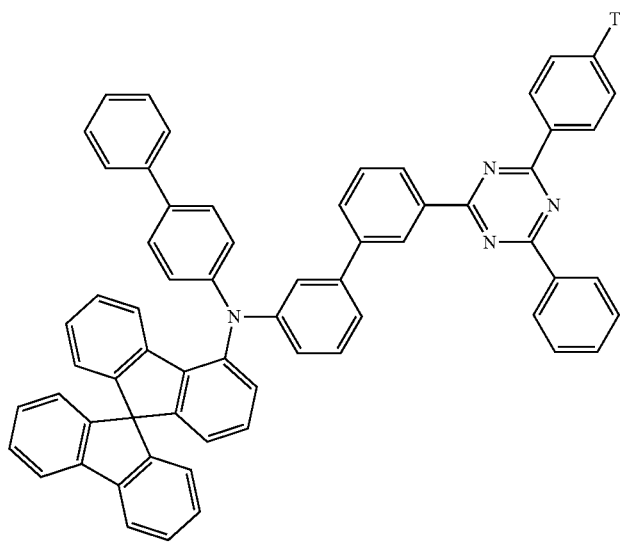
HPT-38
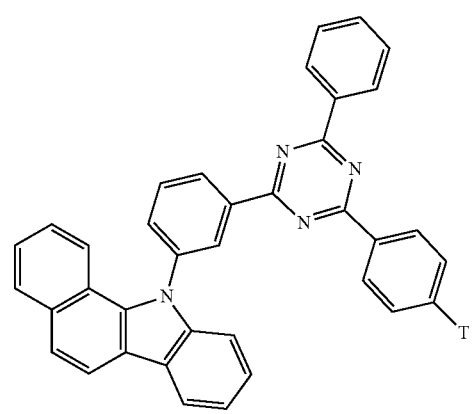

-continued
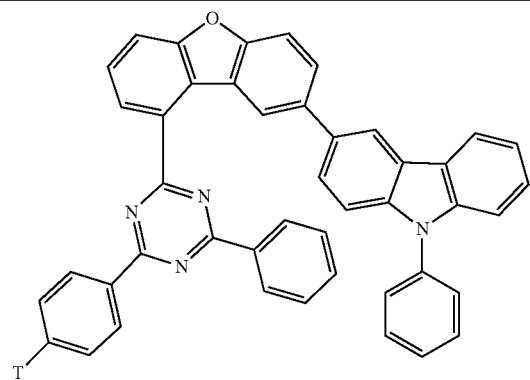
HPT-39
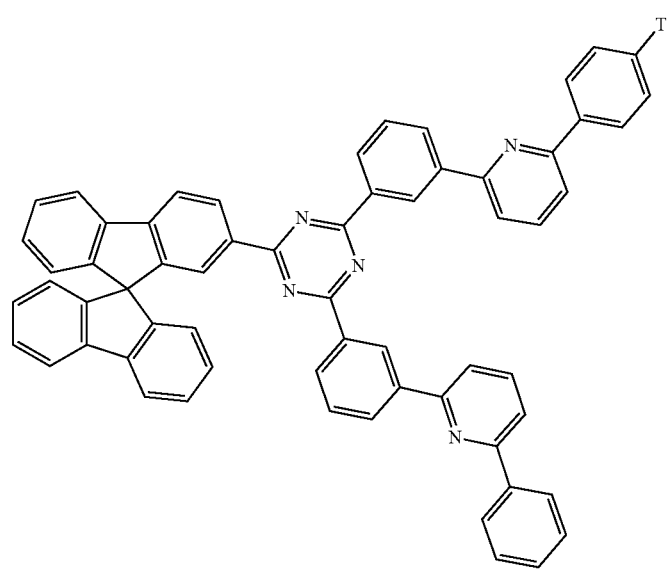
HPT-40
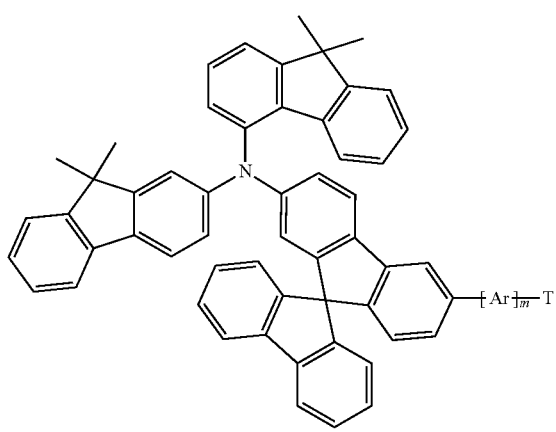
HPT-41
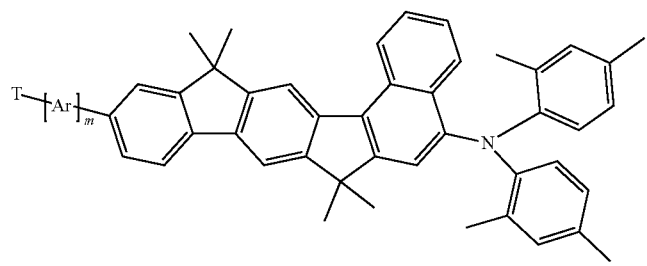
HPT-42

HPT-43
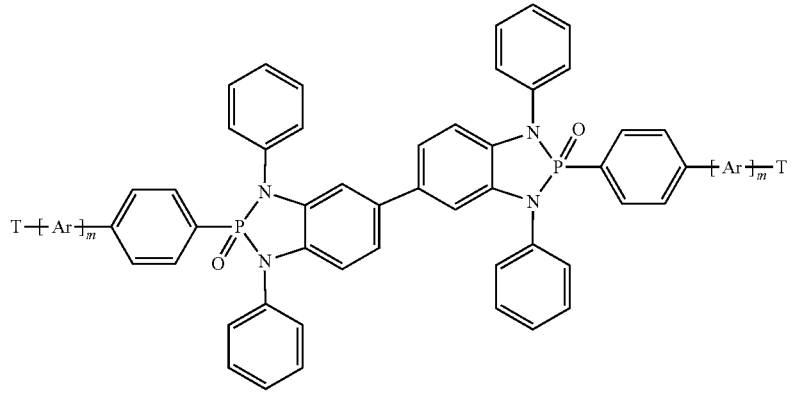
HPT-44
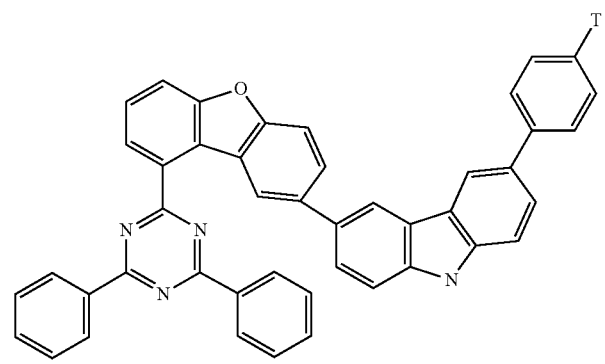
HPT-45
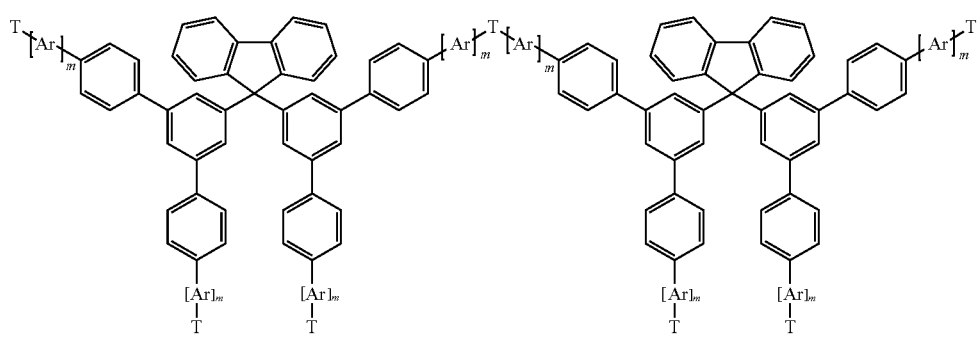
HPT-46
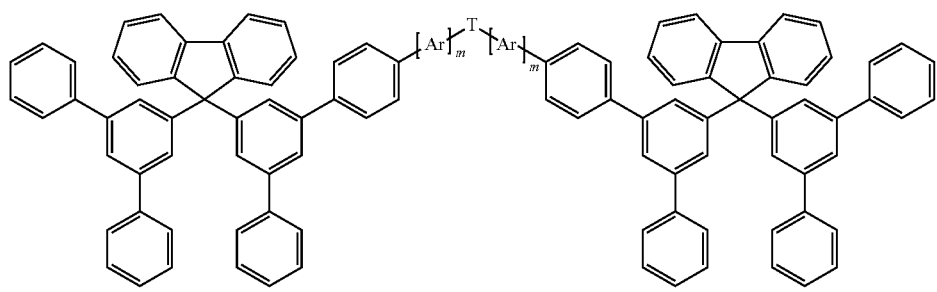

-continued

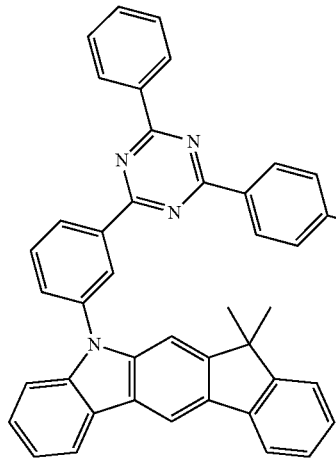 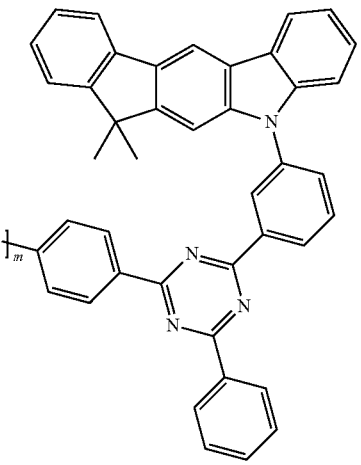

HPT-47 where the symbols Ar, T and the index m have the same meaning as above and where the compounds represented in the table above may be further substituted by a group $R^1$, as defined above, at any free position.

In accordance with another preferred embodiment, the group Y is a host group for a fluorescent emitting compound.

A host group for a fluorescent emitting compound here is taken to mean a material which is present in the emitting layer comprising a fluorescent emitting compound, preferably as the principal component, and which does not emit light on operation of the device.

When the group Y is a host group for a fluorescent emitting compound, it is preferably selected from oligoarylenes, in particular oligoarylenes containing condensed aromatic groups, oligoarylenevinylenes, polypodal metal complexes, hole-conducting compounds, electron-conducting compounds, in particular ketones, phosphine oxides and sulfoxides, boronic acid derivatives and benzanthracenes. When the functional material, which is substituted by a terpene or terpenoid group, is a host material for a fluorescent emitting material, it is very preferably selected from oligoarylenes, comprising naphthalene, anthracene, benzanthracene, benzophenanthrene or pyrene, oligoarylenevinylenes, indenofluorene derivatives, ketones, phosphine oxides and sulfoxides.

An oligoarylene in the sense of this invention is intended to be taken to mean a compound in which at least three aryl or arylene groups are bonded to one another.

Examples of suitable groups Y, when Y is a host group for a fluorescent emitting compound, are the groups listed in the following table:

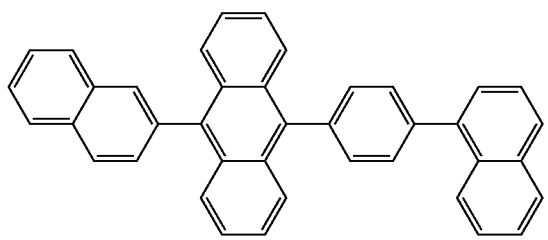 [SMILES: c1ccc2cc(-c3c4ccccc4c(-c4ccc(-c5cccc6ccccc56)cc4)c4ccccc34)ccc2c1]

HF1

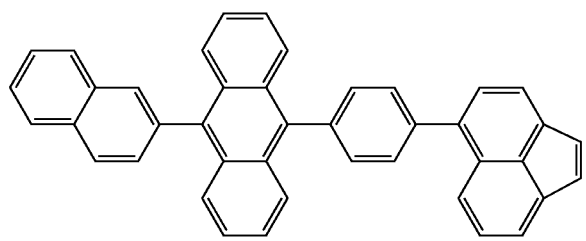 [SMILES: C1=Cc2ccc(-c3ccc(-c4c5ccccc5c(-c5ccc6ccccc6c5)c5ccccc45)cc3)c3cccc1c23]

HF2

-continued
HF3
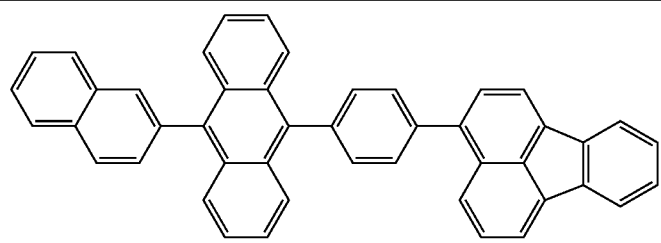
HF4
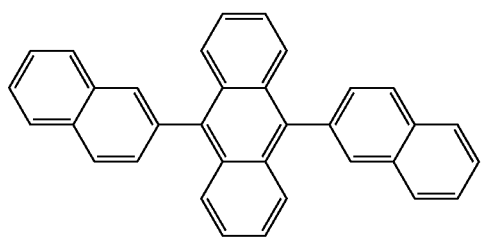 [SMILES: c1ccc2cc(-c3c4ccccc4c(-c4ccc5ccccc5c4)c4ccccc34)ccc2c1]
HF5
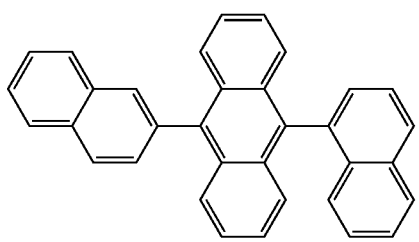 [SMILES: c1ccc2cc(-c3c4ccccc4c(-c4cccc5ccccc45)c4ccccc34)ccc2c1]
HF6
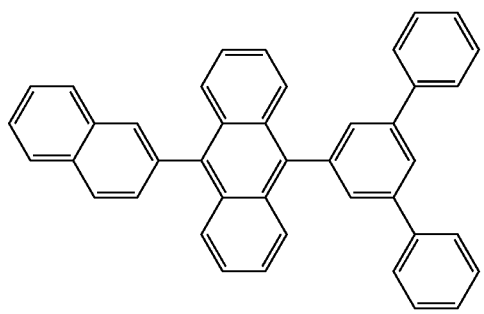 [SMILES: c1ccc(-c2cc(-c3ccccc3)cc(-c3c4ccccc4c(-c4ccc5ccccc5c4)c4ccccc34)c2)cc1]
HF7
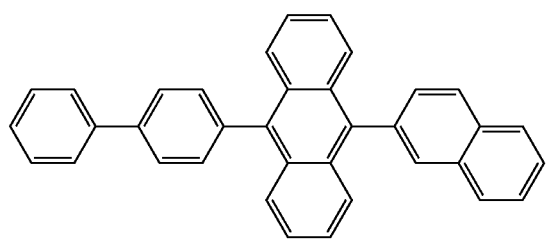 [SMILES: c1ccc(-c2ccc(-c3c4ccccc4c(-c4ccc5ccccc5c4)c4ccccc34)cc2)cc1]
HF8
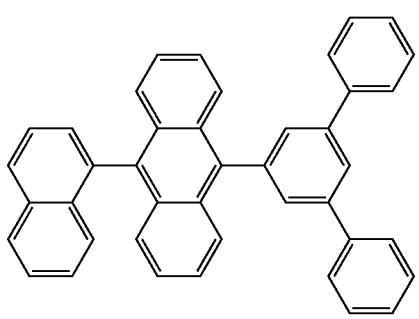 [SMILES: c1ccc(-c2cc(-c3ccccc3)cc(-c3c4ccccc4c(-c4cccc5ccccc45)c4ccccc34)c2)cc1]

HF9
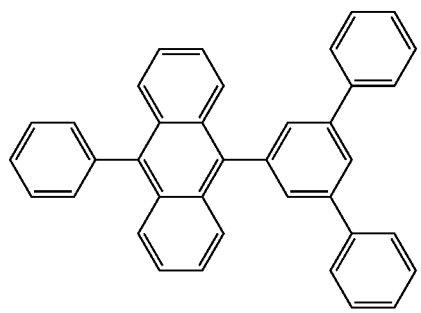 [SMILES: c1ccc(-c2cc(-c3ccccc3)cc(-c3c4ccccc4c(-c4ccccc4)c4ccccc34)c2)cc1]
HF10
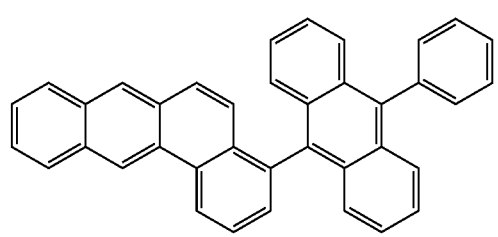 [SMILES: c1ccc(-c2c3ccccc3c(-c3cccc4c3ccc3cc5ccccc5cc34)c3ccccc23)cc1]
HF11
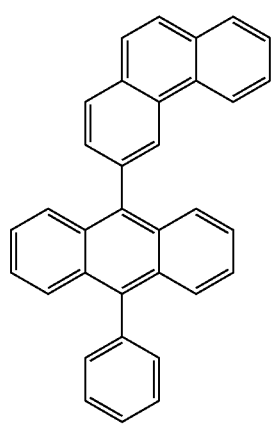 [SMILES: c1ccc(-c2c3ccccc3c(-c3ccc4ccc5ccccc5c4c3)c3ccccc23)cc1]
HF12
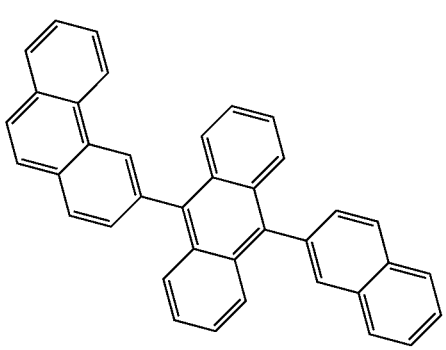 [SMILES: c1ccc2cc(-c3c4ccccc4c(-c4ccc5ccc6ccccc6c5c4)c4ccccc34)ccc2c1]
HF13
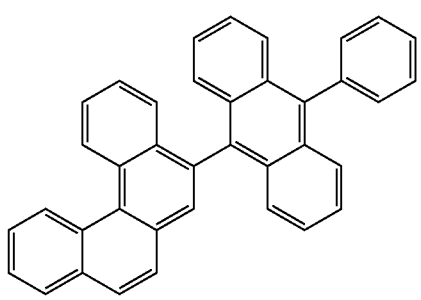 [SMILES: c1ccc(-c2c3ccccc3c(-c3cc4ccc5ccccc5c4c4ccccc34)c3ccccc23)cc1]

HF14
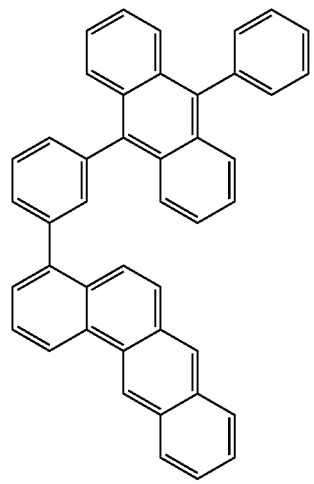 [SMILES: c1ccc(-c2c3ccccc3c(-c3cccc(-c4cccc5c4ccc4cc6ccccc6cc45)c3)c3ccccc23)cc1]
HF15
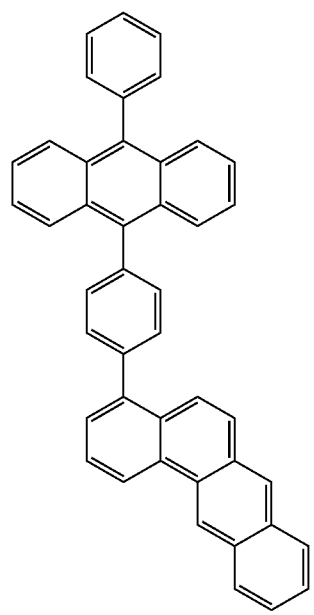 [SMILES: c1ccc(-c2c3ccccc3c(-c3ccc(-c4cccc5c4ccc4cc6ccccc6cc45)cc3)c3ccccc23)cc1]
HF16
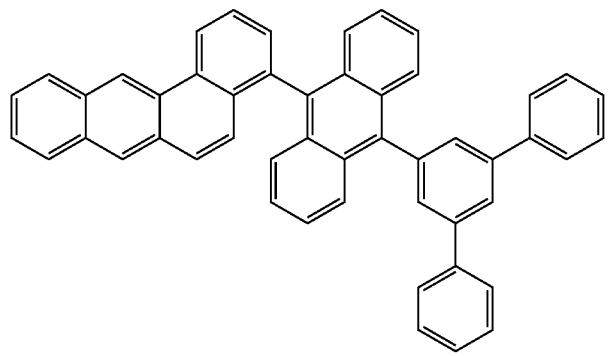 [SMILES: c1ccc(-c2cc(-c3ccccc3)cc(-c3c4ccccc4c(-c4cccc5c4ccc4cc6ccccc6cc45)c4ccccc34)c2)cc1]

-continued
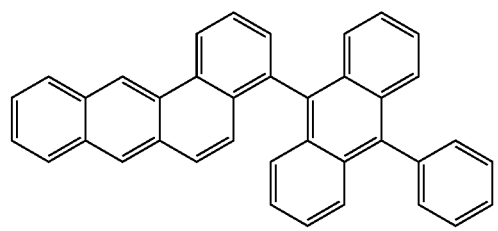 [SMILES: c1ccc(-c2c3ccccc3c(-c3cccc4c3ccc3cc5ccccc5cc34)c3ccccc23)cc1]
HF17
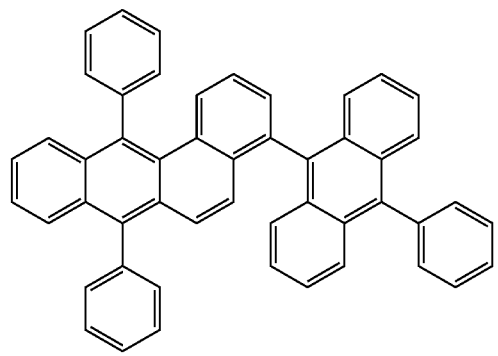 [SMILES: c1ccc(-c2c3ccccc3c(-c3cccc4c3ccc3c(-c5ccccc5)c5ccccc5c(-c5ccccc5)c34)c3ccccc23)cc1]
HF18
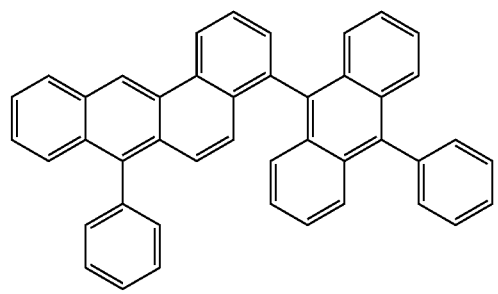 [SMILES: c1ccc(-c2c3ccccc3c(-c3cccc4c3ccc3c(-c5ccccc5)c5ccccc5cc34)c3ccccc23)cc1]
HF19
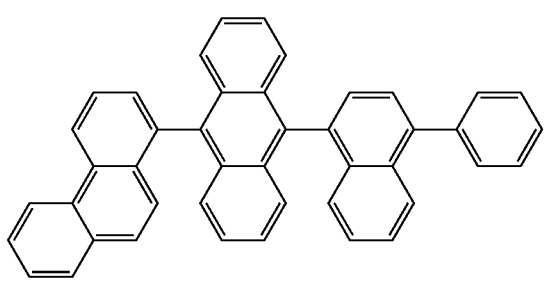 [SMILES: c1ccc(-c2ccc(-c3c4ccccc4c(-c4cccc5c4ccc4ccccc45)c4ccccc34)c3ccccc23)cc1]
HF20
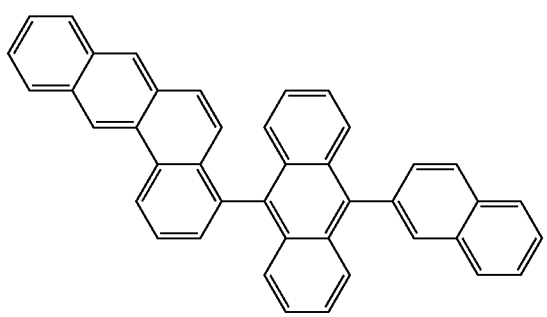 [SMILES: c1ccc2cc(-c3c4ccccc4c(-c4cccc5c4ccc4cc6ccccc6cc45)c4ccccc34)ccc2c1]
HF21

HF22
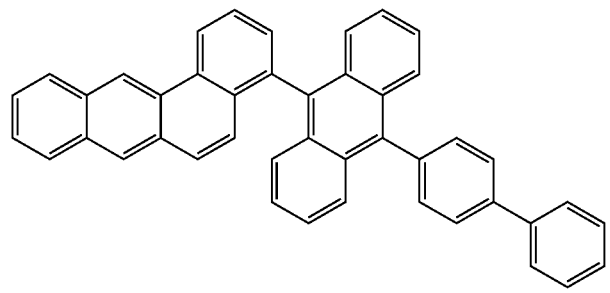 [SMILES: c1ccc(-c2ccc(-c3c4ccccc4c(-c4cccc5c4ccc4cc6ccccc6cc45)c4ccccc34)cc2)cc1]
HF23
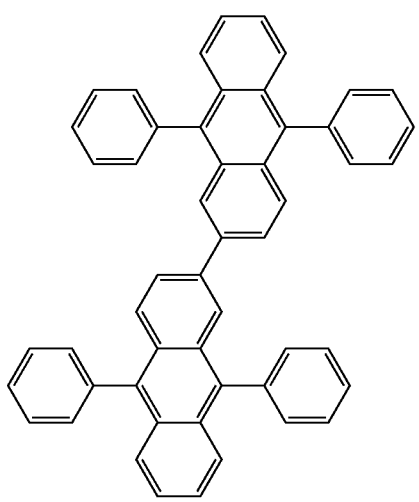 [SMILES: c1ccc(-c2c3ccccc3c(-c3ccccc3)c3cc(-c4ccc5c(-c6ccccc6)c6ccccc6c(-c6ccccc6)c5c4)ccc23)cc1]
HF24
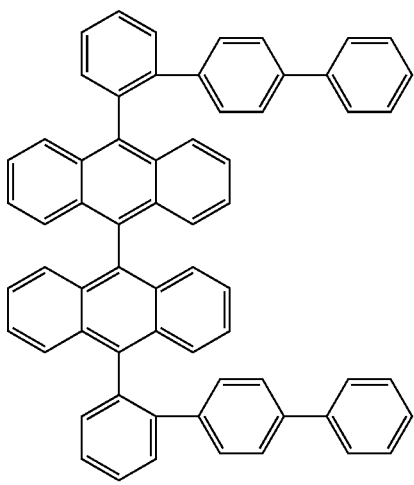 [SMILES: c1ccc(-c2ccc(-c3ccccc3-c3c4ccccc4c(-c4c5ccccc5c(-c5ccccc5-c5ccc(-c6ccccc6)cc5)c5ccccc45)c4ccccc34)cc2)cc1]
HF25
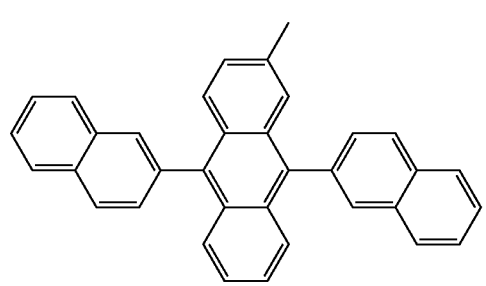 [SMILES: Cc1ccc2c(-c3ccc4ccccc4c3)c3ccccc3c(-c3ccc4ccccc4c3)c2c1]

-continued
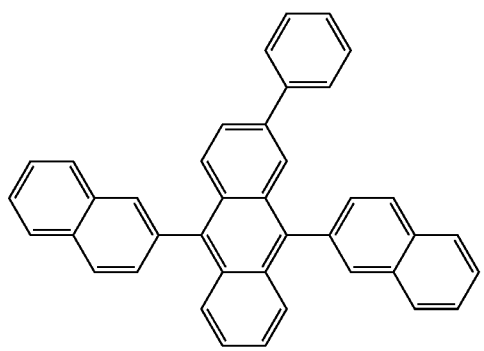 [SMILES: c1ccc(-c2ccc3c(-c4ccc5ccccc5c4)c4ccccc4c(-c4ccc5ccccc5c4)c3c2)cc1]
HF26
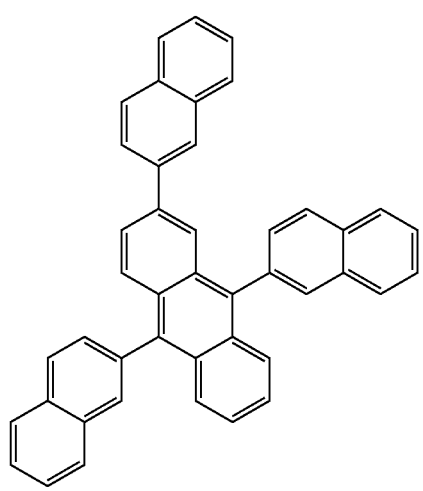 [SMILES: c1ccc2cc(-c3ccc4c(-c5ccc6ccccc6c5)c5ccccc5c(-c5ccc6ccccc6c5)c4c3)ccc2c1]
HF27
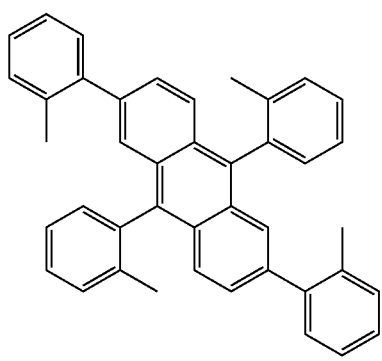 [SMILES: Cc1ccccc1-c1ccc2c(-c3ccccc3C)c3cc(-c4ccccc4C)ccc3c(-c3ccccc3C)c2c1]
HF28
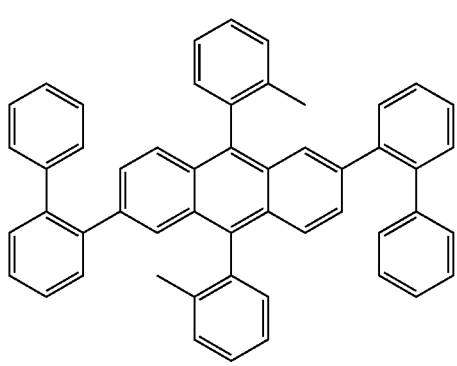 [SMILES: Cc1ccccc1-c1c2ccc(-c3ccccc3-c3ccccc3)cc2c(-c2ccccc2C)c2ccc(-c3ccccc3-c3ccccc3)cc12]
HF29

-continued
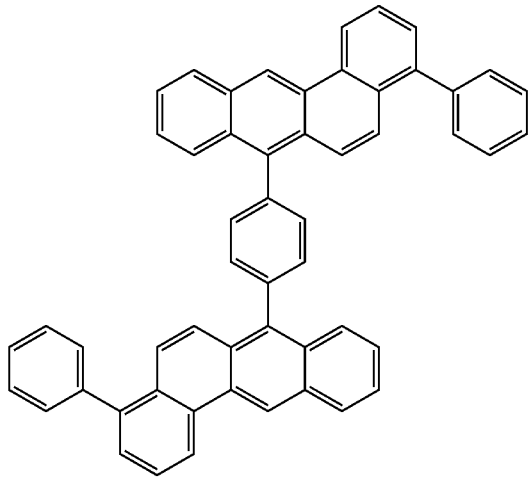 [SMILES: c1ccc(-c2cccc3c2ccc2c(-c4ccc(-c5c6ccccc6cc6c5ccc5c(-c7ccccc7)cccc56)cc4)c4ccccc4cc23)cc1]
HF30
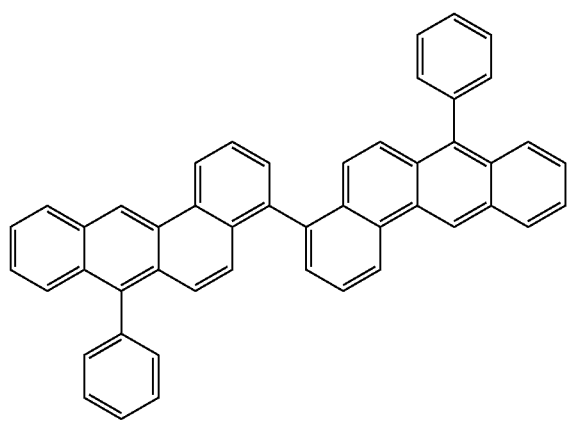 [SMILES: c1ccc(-c2c3ccccc3cc3c2ccc2c(-c4cccc5c4ccc4c(-c6ccccc6)c6ccccc6cc45)cccc23)cc1]
HF31
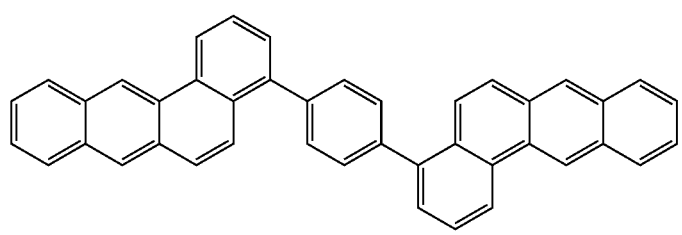 [SMILES: c1ccc2cc3c(ccc4c(-c5ccc(-c6cccc7c6ccc6cc8ccccc8cc67)cc5)cccc43)cc2c1]
HF32

-continued
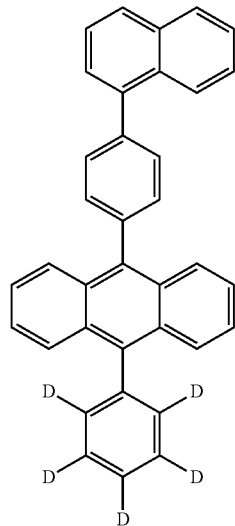 [SMILES: [2H]c1c([2H])c([2H])c(-c2c3ccccc3c(-c3ccc(-c4cccc5ccccc45)cc3)c3ccccc23)c([2H])c1[2H]]
HF33
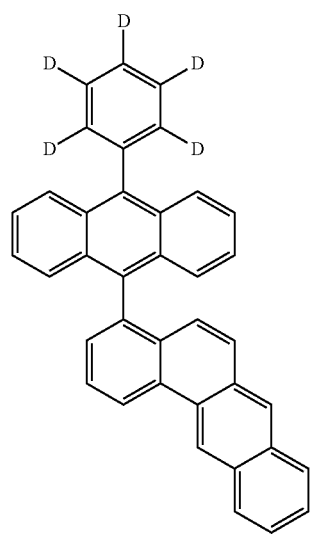 [SMILES: [2H]c1c([2H])c([2H])c(-c2c3ccccc3c(-c3cccc4c3ccc3cc5ccccc5cc34)c3ccccc23)c([2H])c1[2H]]
HF34
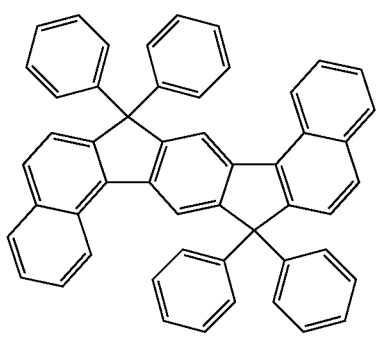 [SMILES: c1ccc(C2(c3ccccc3)c3cc4c(cc3-c3c2ccc2ccccc32)C(c2ccccc2)(c2ccccc2)c2ccc3ccccc3c2-4)cc1]
HF35
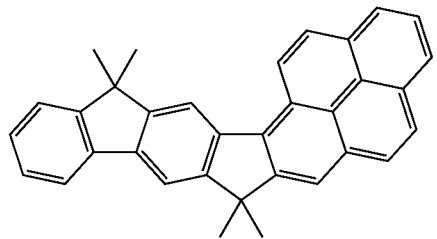 [SMILES: CC1(C)c2ccccc2-c2cc3c(cc21)-c1c(cc2ccc4cccc5ccc1c2c45)C3(C)C]
HF36

-continued
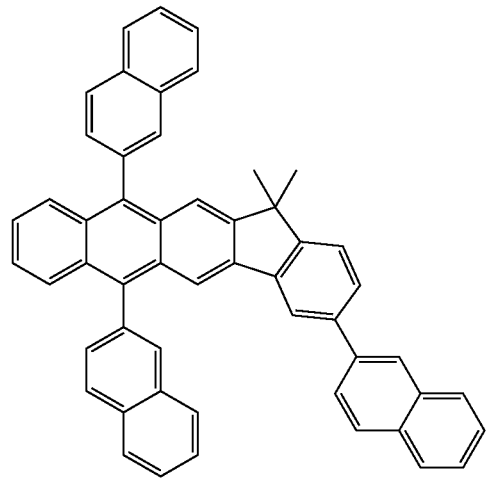 [SMILES: CC1(C)c2ccc(-c3ccc4ccccc4c3)cc2-c2cc3c(-c4ccc5ccccc5c4)c4ccccc4c(-c4ccc5ccccc5c4)c3cc21]
HF37
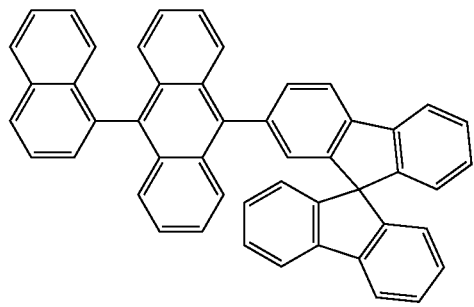 [SMILES: c1ccc2c(c1)-c1ccccc1C21c2ccccc2-c2ccc(-c3c4ccccc4c(-c4cccc5ccccc45)c4ccccc34)cc21]
HF38
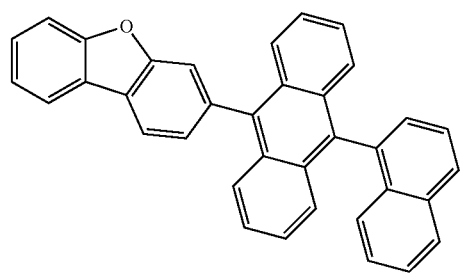 [SMILES: c1ccc2c(-c3c4ccccc4c(-c4ccc5c(c4)oc4ccccc45)c4ccccc34)cccc2c1]
HF39
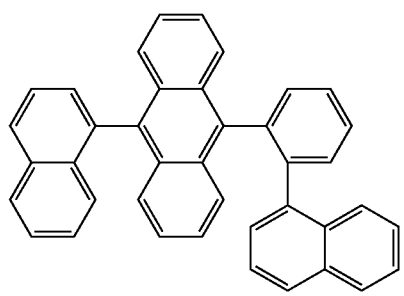 [SMILES: c1ccc(-c2c3ccccc3c(-c3cccc4ccccc34)c3ccccc23)c(-c2cccc3ccccc23)c1]
HF40
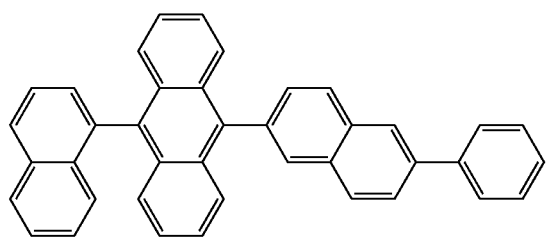 [SMILES: c1ccc(-c2ccc3cc(-c4c5ccccc5c(-c5cccc6ccccc56)c5ccccc45)ccc3c2)cc1]
HF41

-continued
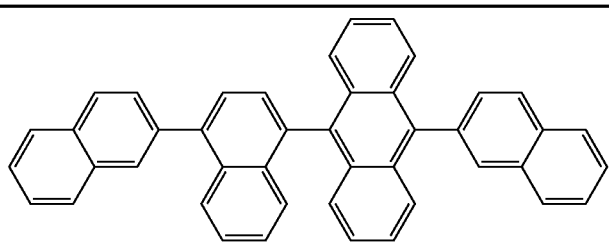
HF42
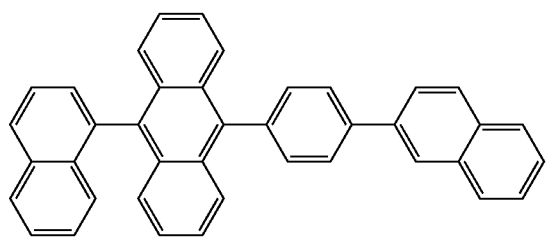 [SMILES: c1ccc2cc(-c3ccc(-c4c5ccccc5c(-c5cccc6ccccc56)c5ccccc45)cc3)ccc2c1]
HF43
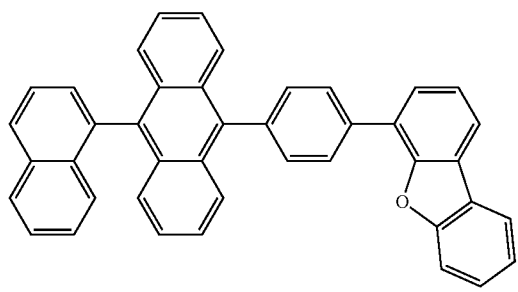 [SMILES: c1ccc2c(-c3c4ccccc4c(-c4ccc(-c5cccc6c5oc5ccccc56)cc4)c4ccccc34)cccc2c1]
HF44
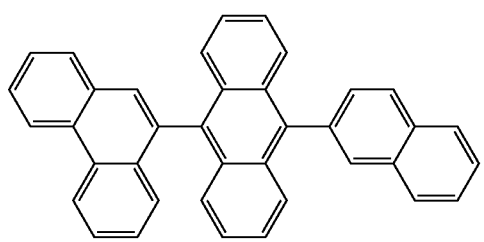 [SMILES: c1ccc2cc(-c3c4ccccc4c(-c4cc5ccccc5c5ccccc45)c4ccccc34)ccc2c1]
HF45
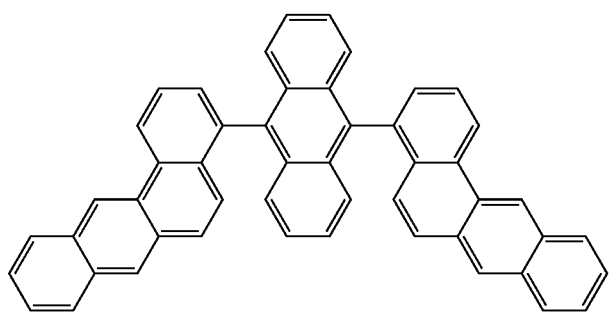 [SMILES: c1ccc2cc3c(ccc4c(-c5c6ccccc6c(-c6cccc7c6ccc6cc8ccccc8cc67)c6ccccc56)cccc43)cc2c1]
HF46
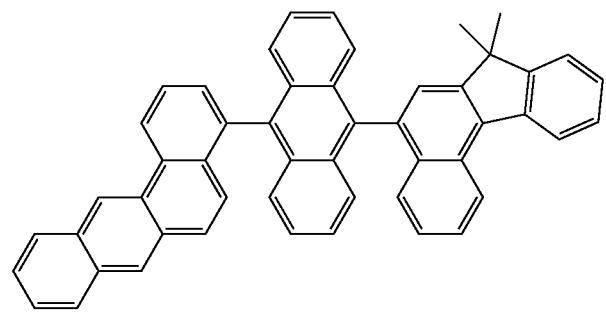 [SMILES: CC1(C)c2ccccc2-c2c1cc(-c1c3ccccc3c(-c3cccc4c3ccc3cc5ccccc5cc34)c3ccccc13)c1ccccc21]
HF47

-continued
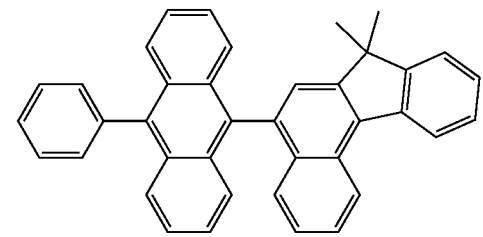 [SMILES: CC1(C)c2ccccc2-c2c1cc(-c1c3ccccc3c(-c3ccccc3)c3ccccc13)c1ccccc21]
HF48
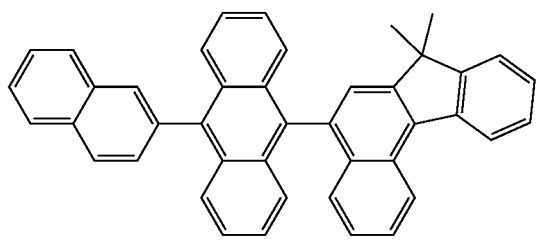 [SMILES: CC1(C)c2ccccc2-c2c1cc(-c1c3ccccc3c(-c3ccc4ccccc4c3)c3ccccc13)c1ccccc21]
HF49
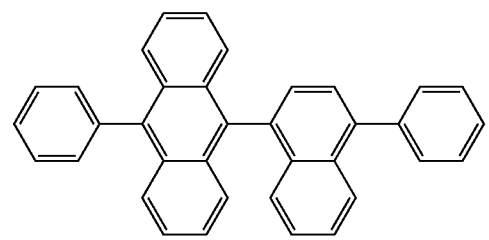 [SMILES: c1ccc(-c2ccc(-c3c4ccccc4c(-c4ccccc4)c4ccccc34)c3ccccc23)cc1]
HF50
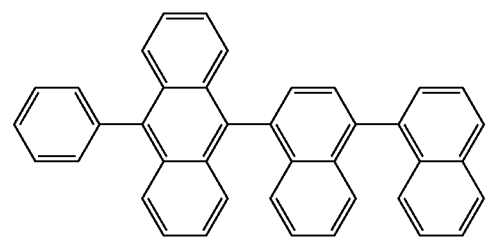 [SMILES: c1ccc(-c2c3ccccc3c(-c3ccc(-c4cccc5ccccc45)c4ccccc34)c3ccccc23)cc1]
HF51
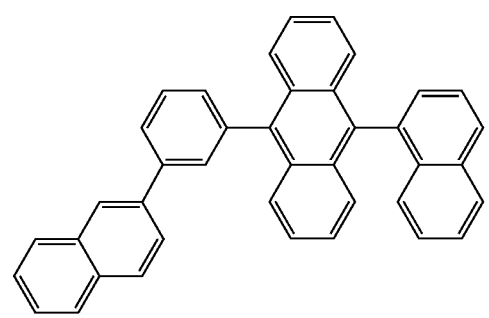 [SMILES: c1cc(-c2ccc3ccccc3c2)cc(-c2c3ccccc3c(-c3cccc4ccccc34)c3ccccc23)c1]
HF52
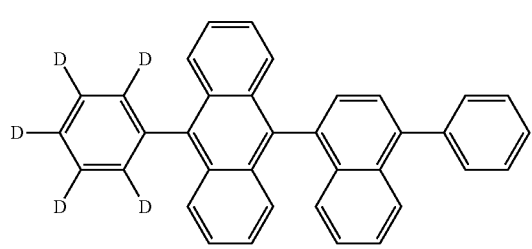 [SMILES: [2H]c1c([2H])c([2H])c(-c2c3ccccc3c(-c3ccc(-c4ccccc4)c4ccccc34)c3ccccc23)c([2H])c1[2H]]
HF53

HF54
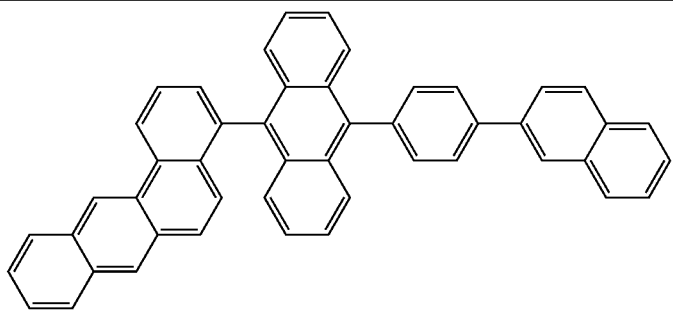
HF55
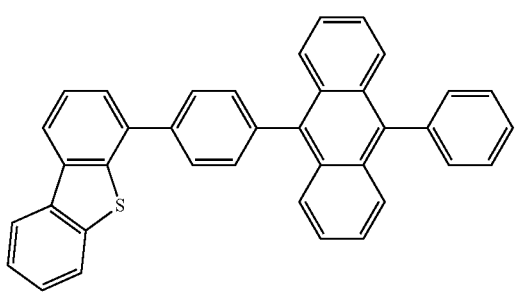 [SMILES: c1ccc(-c2c3ccccc3c(-c3ccc(-c4cccc5c4sc4ccccc45)cc3)c3ccccc23)cc1]
HF56
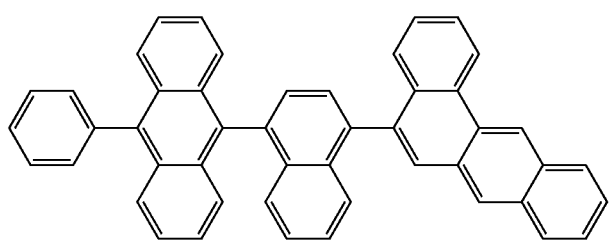 [SMILES: c1ccc(-c2c3ccccc3c(-c3ccc(-c4cc5cc6ccccc6cc5c5ccccc45)c4ccccc34)c3ccccc23)cc1]
HF57
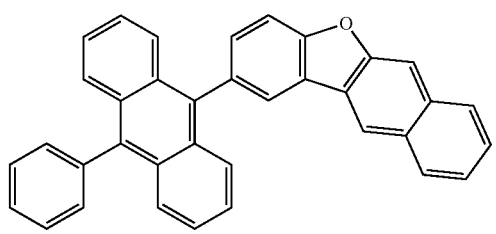 [SMILES: c1ccc(-c2c3ccccc3c(-c3ccc4oc5cc6ccccc6cc5c4c3)c3ccccc23)cc1]
HF58
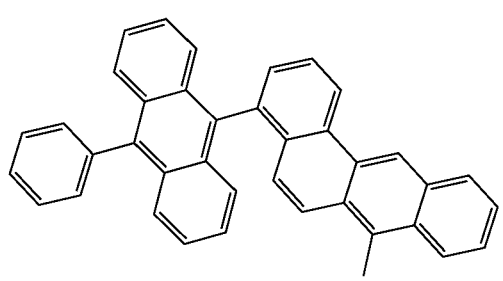 [SMILES: Cc1c2ccccc2cc2c1ccc1c(-c3c4ccccc4c(-c4ccccc4)c4ccccc34)cccc12]
HF59
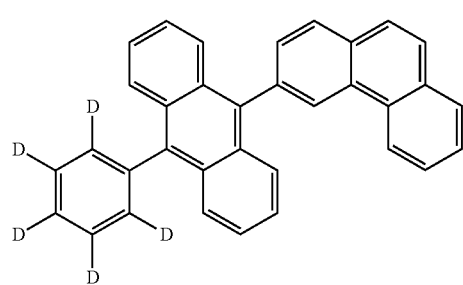 [SMILES: [2H]c1c([2H])c([2H])c(-c2c3ccccc3c(-c3ccc4ccc5ccccc5c4c3)c3ccccc23)c([2H])c1[2H]]

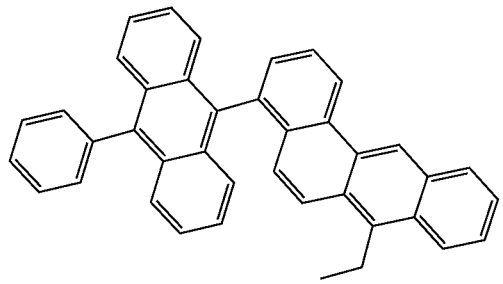 [SMILES: CCc1c2ccccc2cc2c1ccc1c(-c3c4ccccc4c(-c4ccccc4)c4ccccc34)cccc12]

HF60

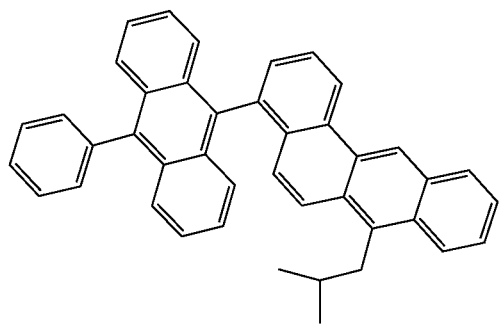 [SMILES: CC(C)Cc1c2ccccc2cc2c1ccc1c(-c3c4ccccc4c(-c4ccccc4)c4ccccc34)cccc12]

HF61 where at least one group T may be appended at any free position of the group (HF1) to (HF61), directly or via a group Ar, and where the groups (HF61) to (HF61) may further be substituted at any free position by a radical $R^1$ as defined above.

Examples of suitable host groups for fluorescent emitting compounds, substituted by at least one terpene or terpenoid group, are represented in the table below:

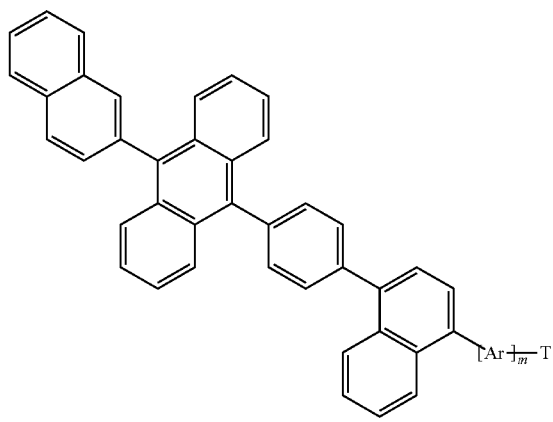

HFT-1

-continued
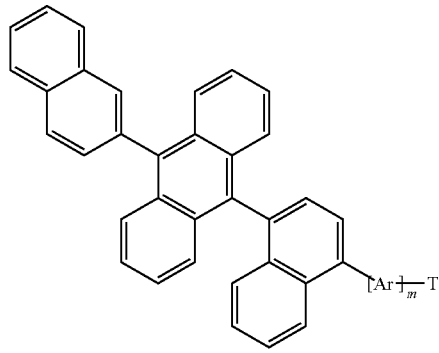
HFT-2
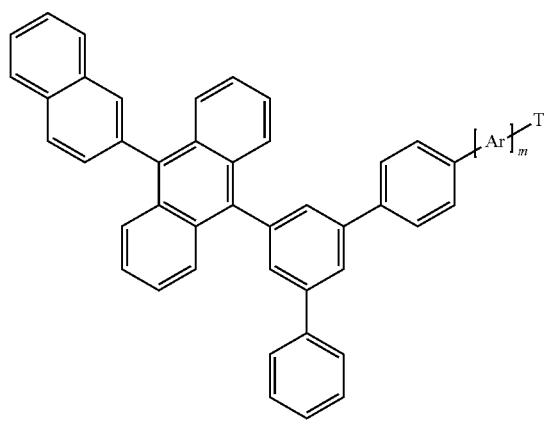
HFT-3
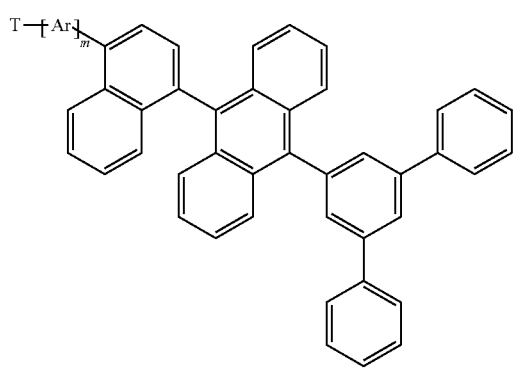
HFT-4
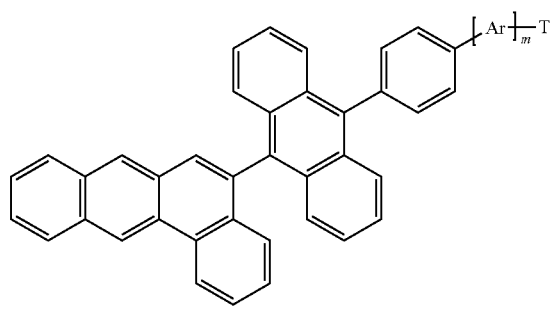
HFT-5

-continued
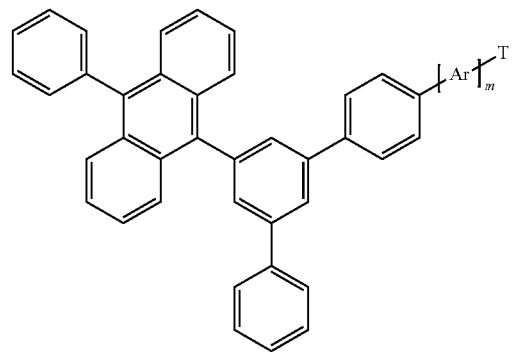
HFT-6
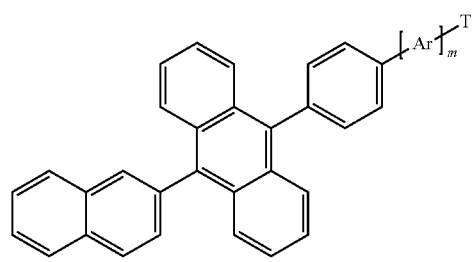
HFT-7
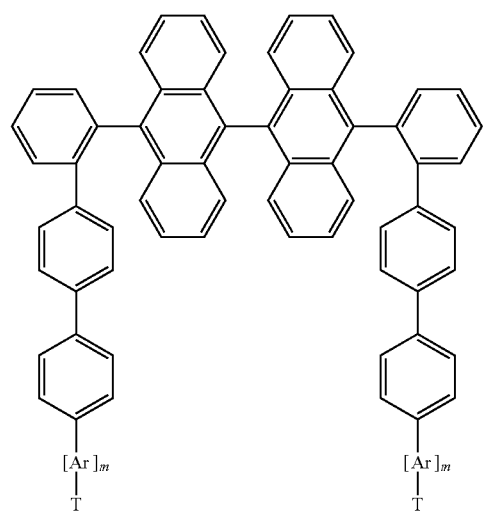
HFT-8
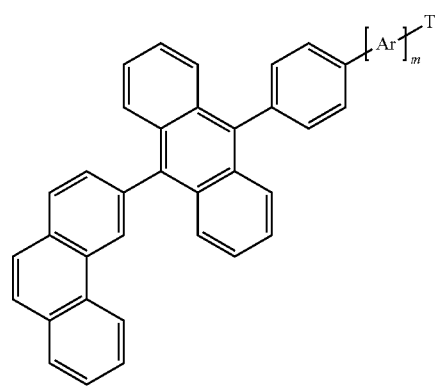
HFT-9

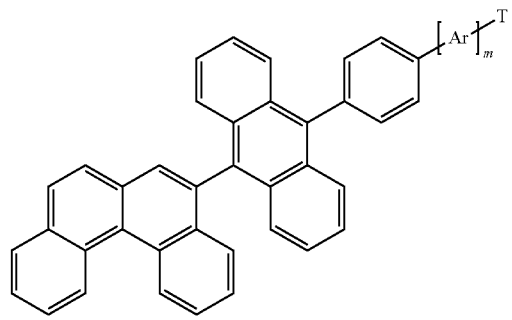
HFT-10
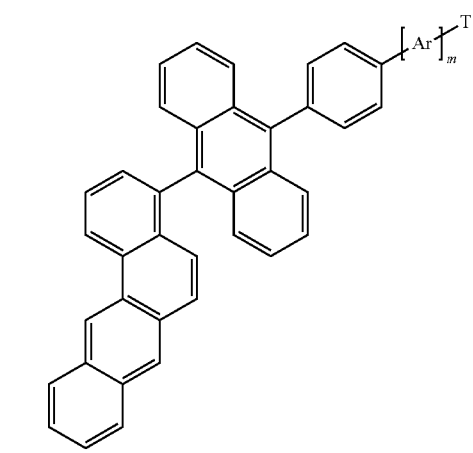
HFT-11
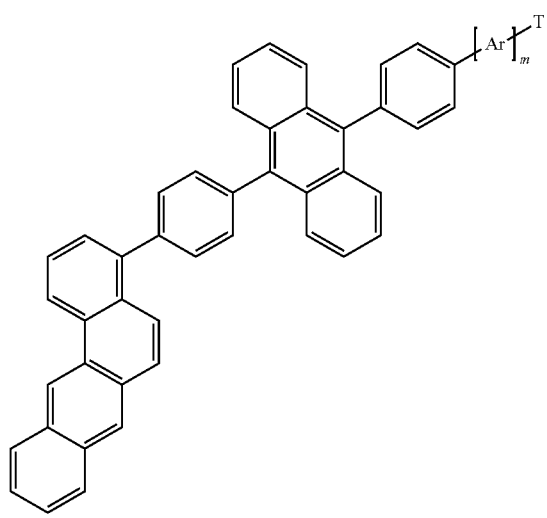
HFT-12
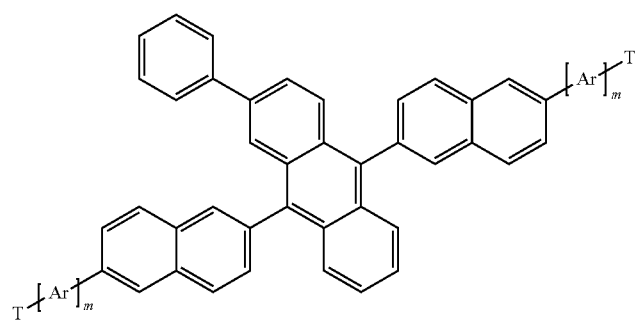
HFT-12

-continued
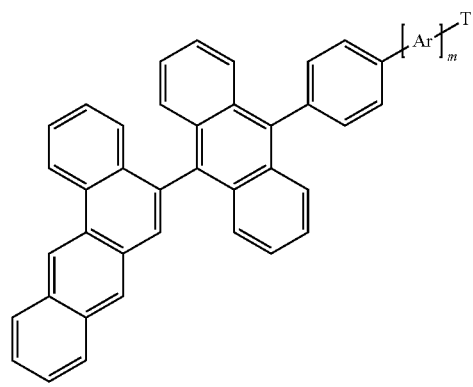
HFT-13
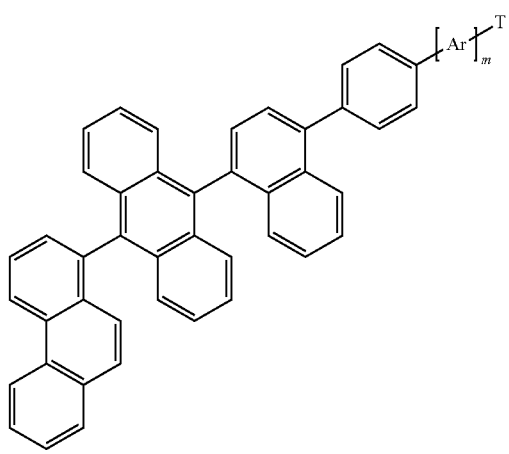
HFT-14
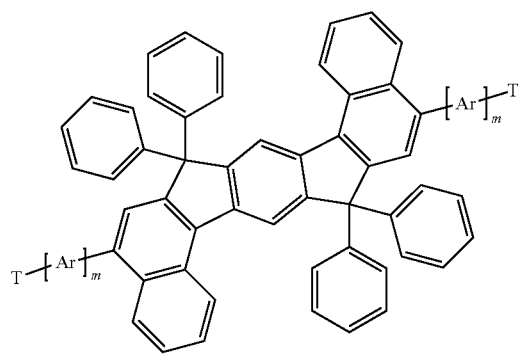
HFT-15
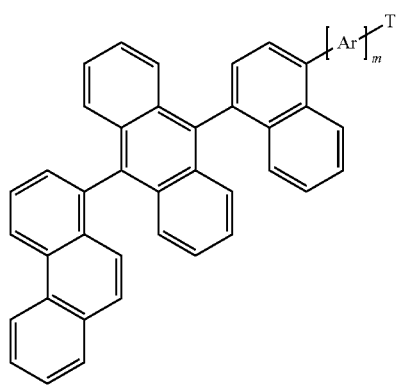
HFT-16

HFT-17
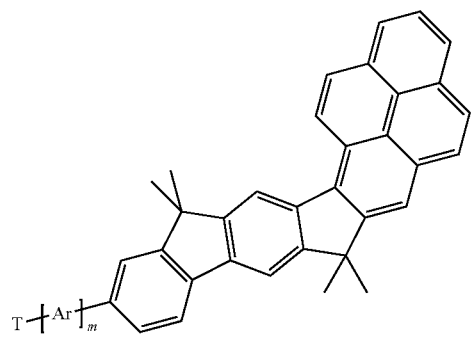
HFT-18
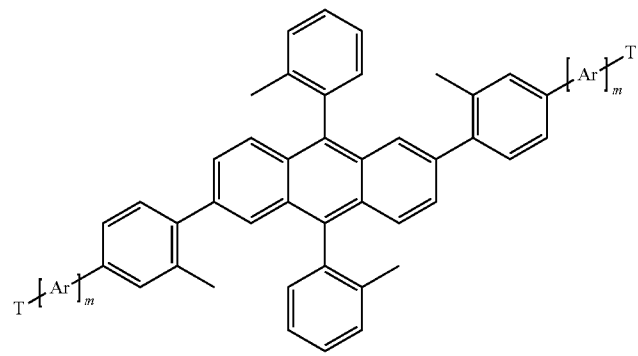
HFT-19
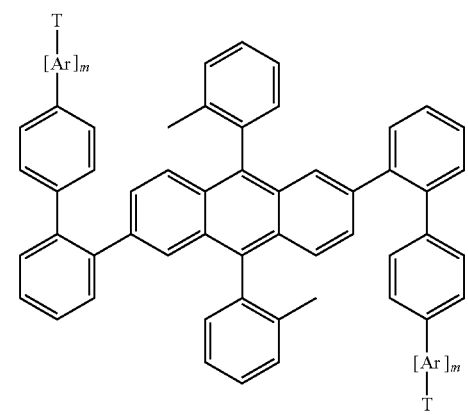

-continued
HFT-20
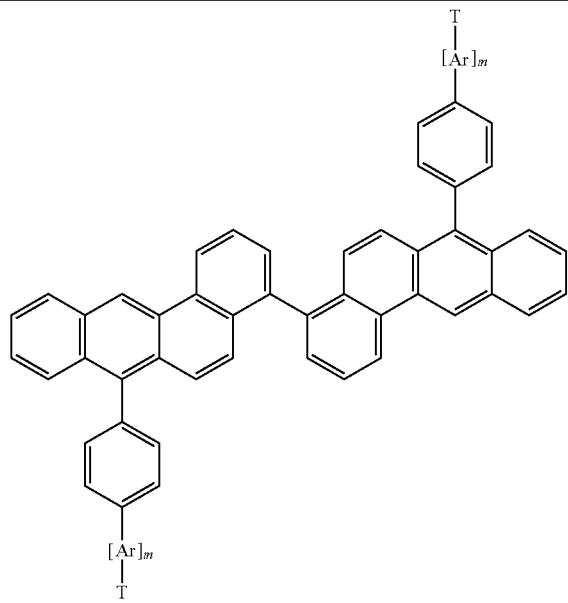
HFT-21
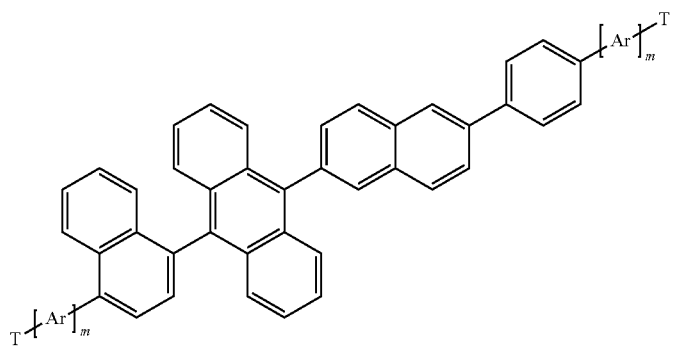
HFT-22
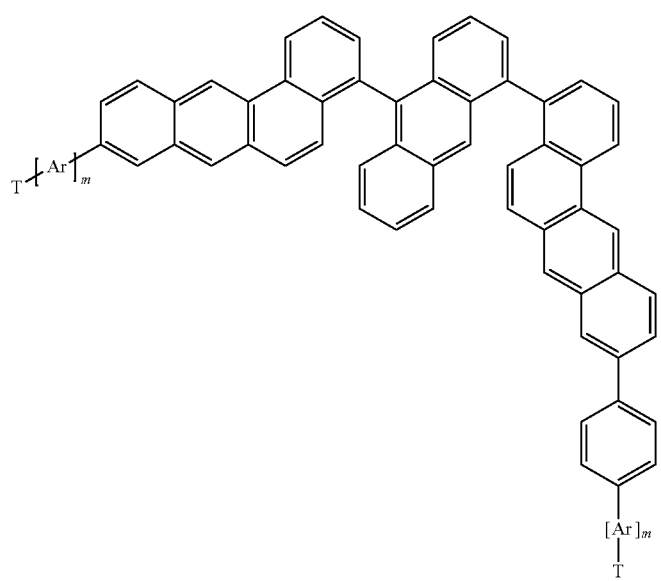

-continued
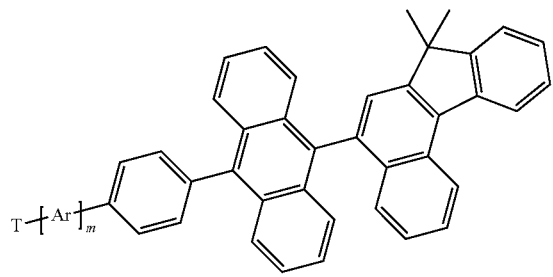
HFT-23
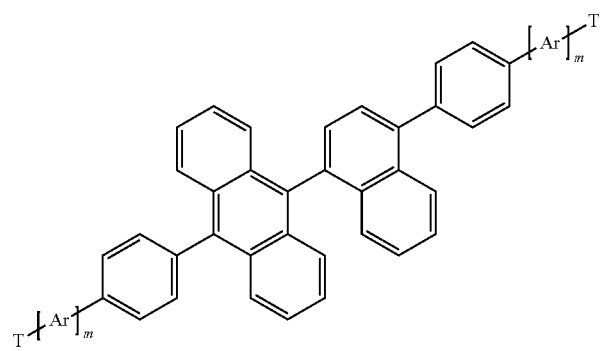
HFT-24
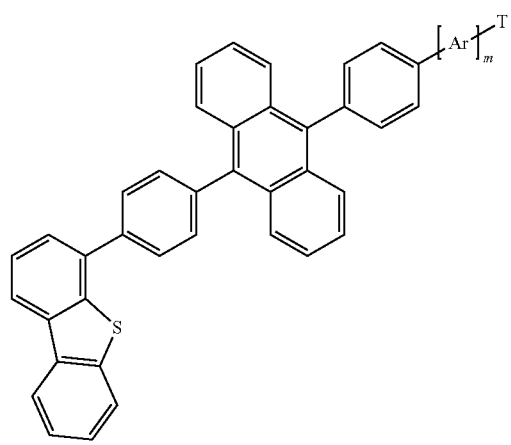
HFT-25
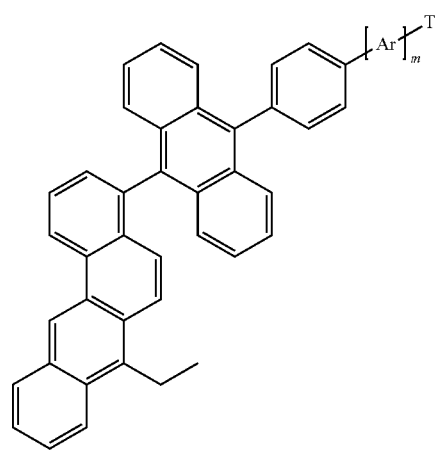
HFT-26

-continued

HFT-27

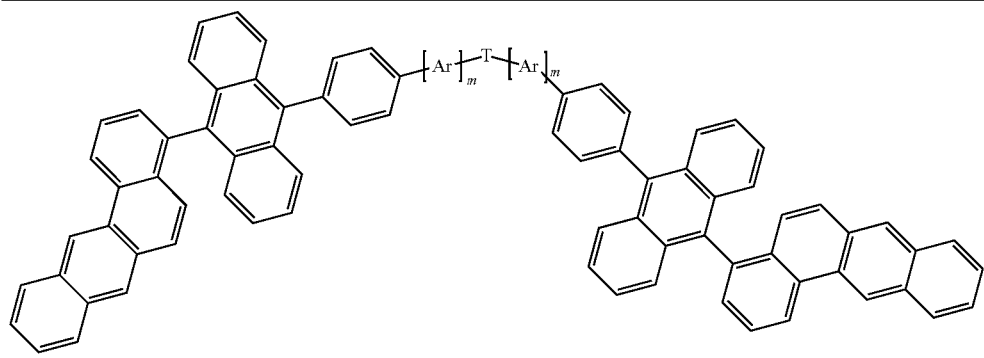

HFT-28

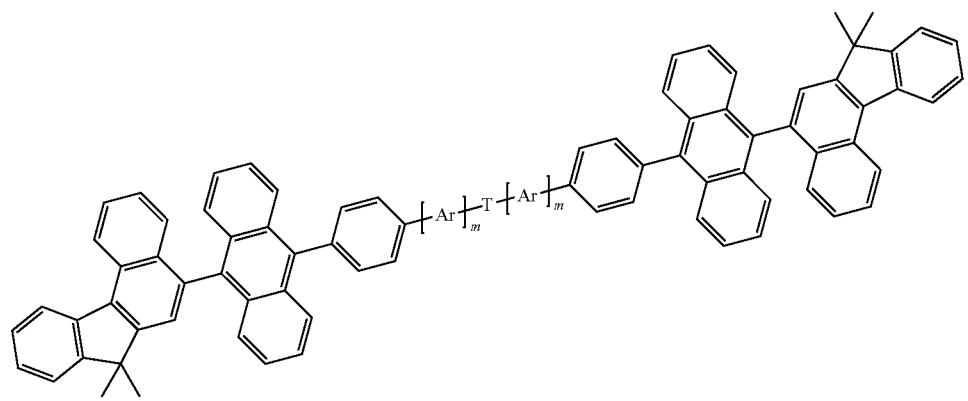

HFT-29

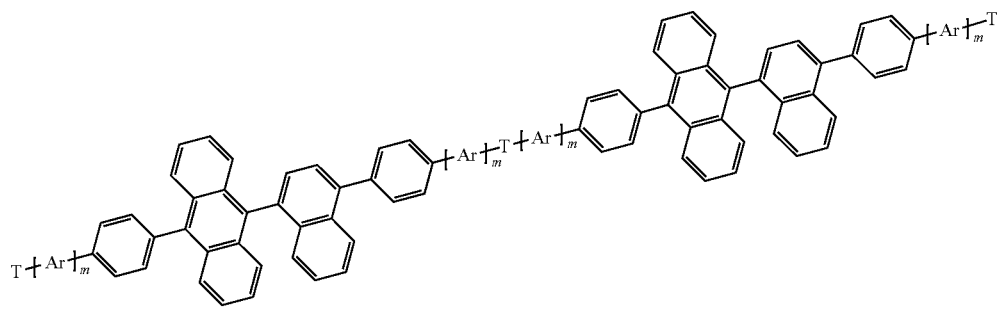

where the symbols Ar, T and the index m have the same meaning as above and where the compounds represented in the table above may be further substituted by a group $R^1$, as defined above, at any free position.

In accordance with a preferred embodiment, the terpene or terpenoid group appended to the functional material, has a molecular weight equal or superior to 350 g/mol.

It is furthermore preferred that the terpene or terpenoid group, appended to the functional material, is selected from tetracyclic terpene or tetracyclic terpenoid. The terpene or terpenoid group, appended to the functional material, is very preferably selected from sterane derivatives. The terpene or terpenoid group, appended to the functional material, is particularly preferably selected from gonane, estrane, androstane, norandrostane (etiane), cholane, cholestane, ergostane, pregnane, and stigmastane derivatives, preferably cholestanes and their derivatives. It is very particularly preferred that T is a cholestane derivative, which comprises the following substituted or unsubstituted moiety:

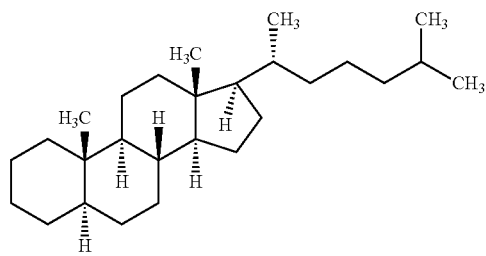

Example of suitable terpene or terpenoide groups T, which can be appended to the functional material are listed in the following table:

| 249 | 250 -continued |
|---|---|
| 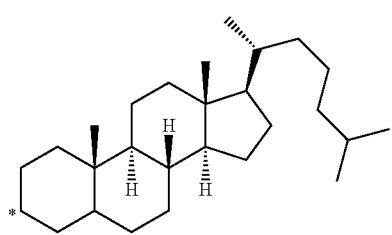 T1 | 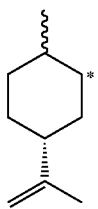 T8 |
| 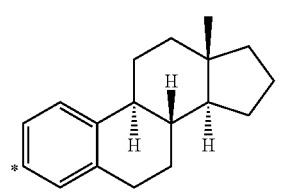 T2 | 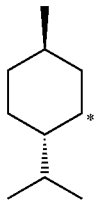 T9 |
| 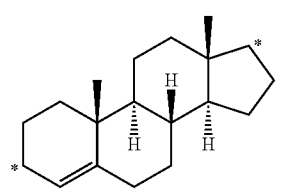 T3 |  T10 |
| 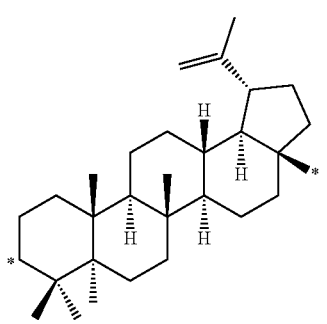 T4 |  T11 |
| |  T12 |
| 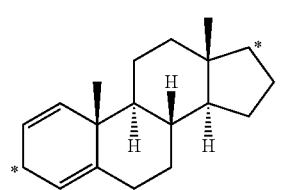 T5 | 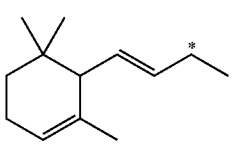 T13 |
| | 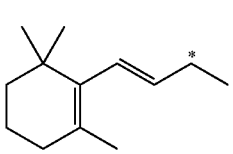 T14 |
| 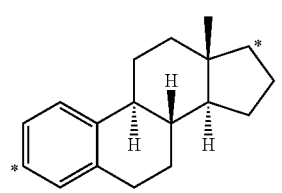 T6 | 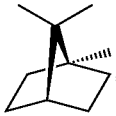 T15 |
| |  T16 |
| 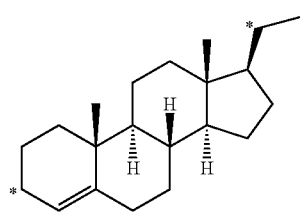 T7 | 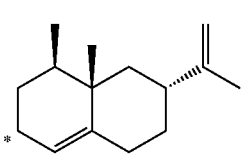 T17 |

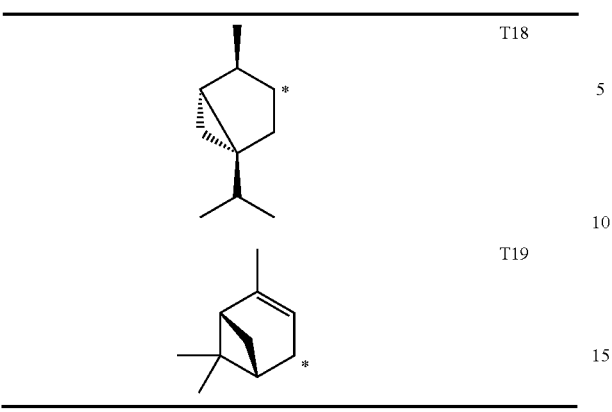
where the symbol(s) * in T1 to T19 indicates the bonding to the group(s) —(Ar)$_m$—Y in formulae (1) to (4).
Among T1 to T19, the groups T1, T2, T6, T9, T10, T11, T12, T15, T16 and T18 are preferred, the groups T1, T2 and T6 are very preferred and the group T1 and T2 are particularly preferred.
Other examples of suitable compounds according to the invention are the structures shown below:
Fluorscent hosts
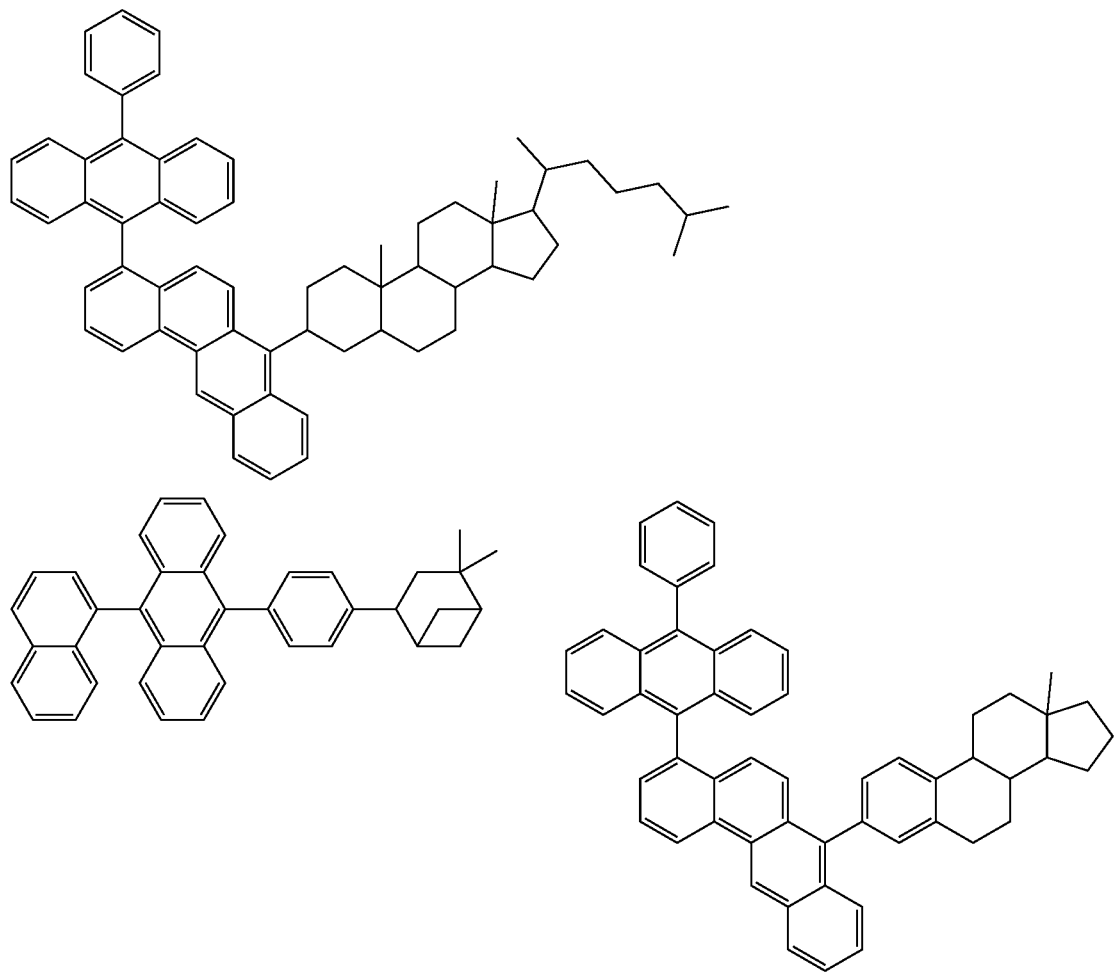

-continued
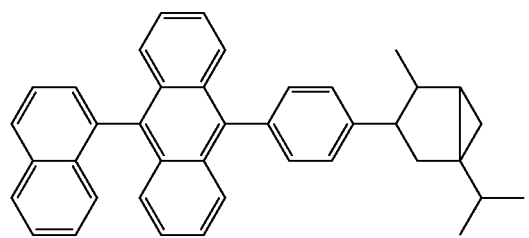
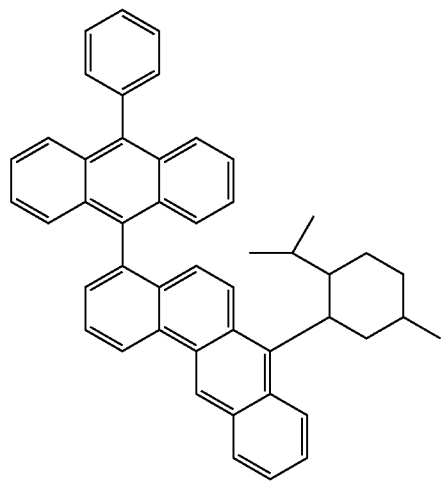
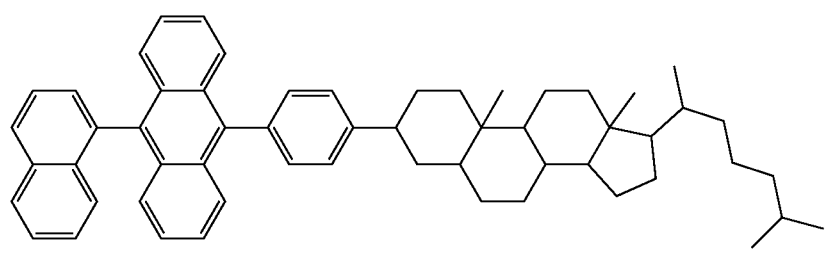
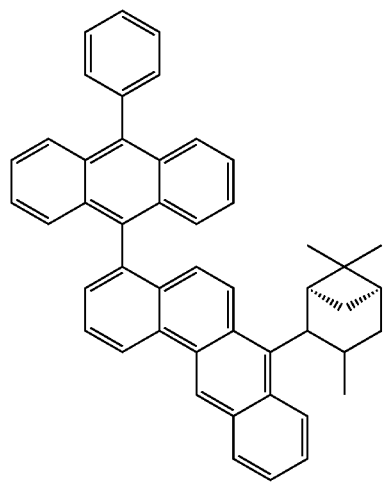
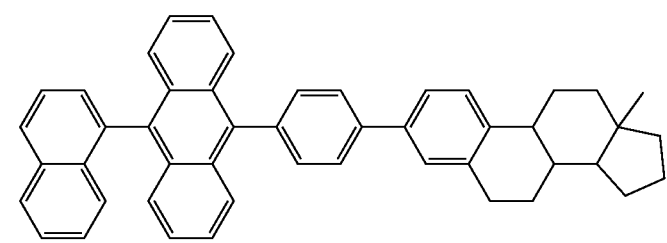
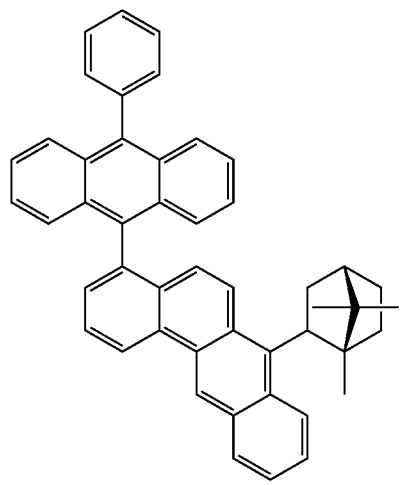
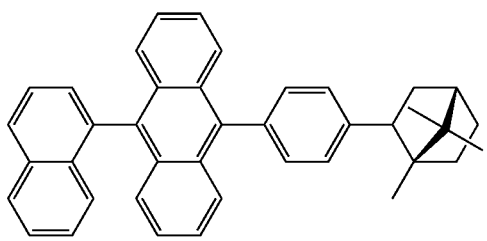

-continued
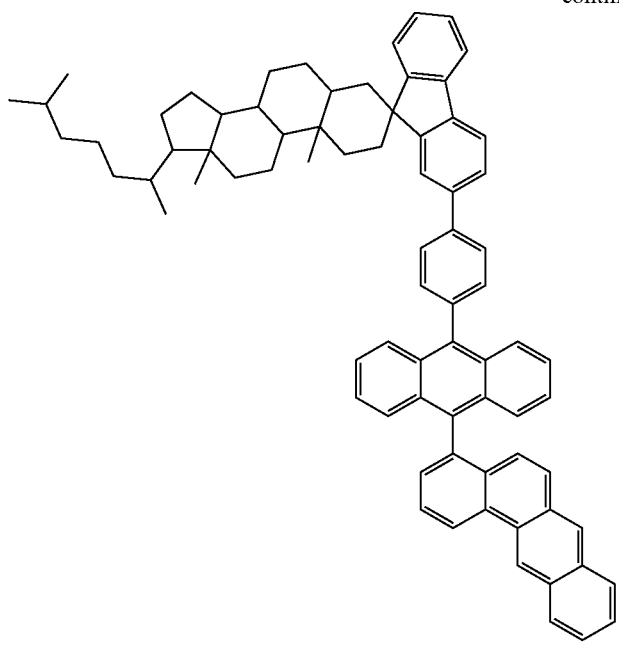
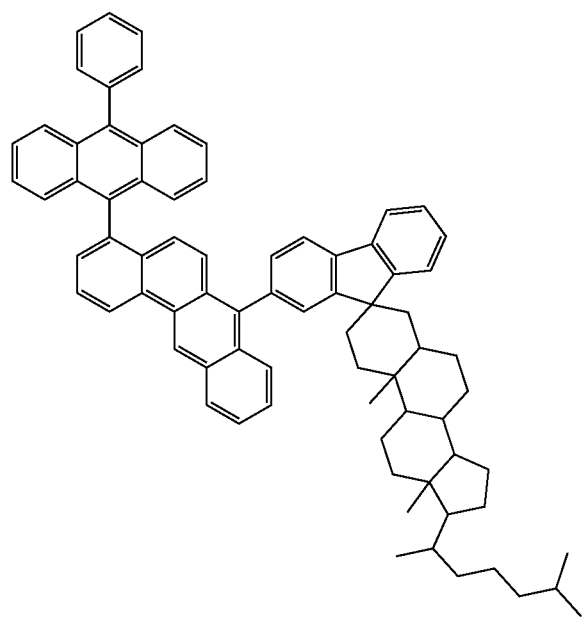

Fluoroescent emitting compounds
-continued
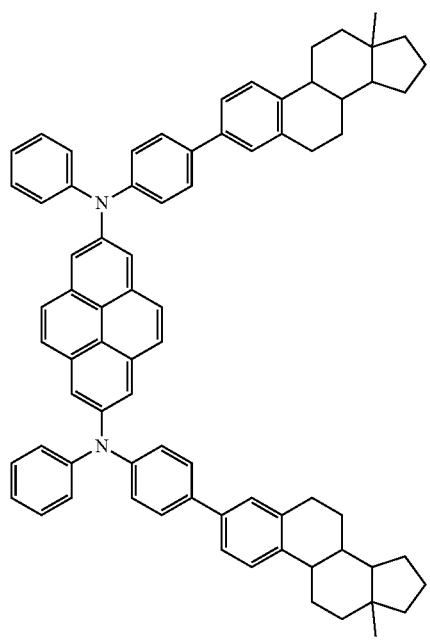
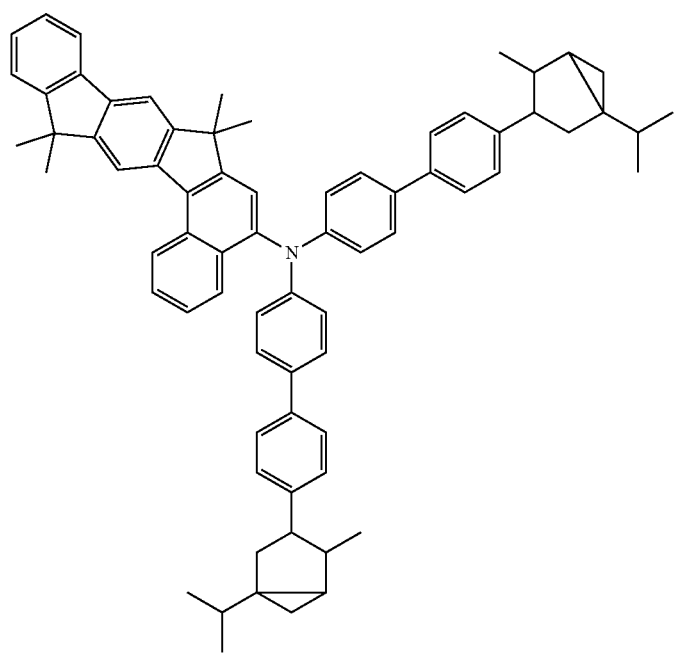

-continued
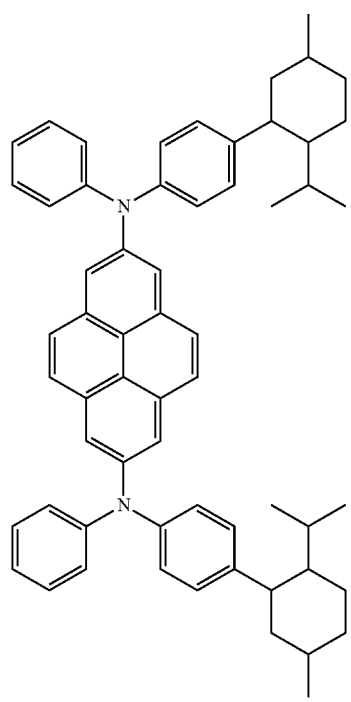
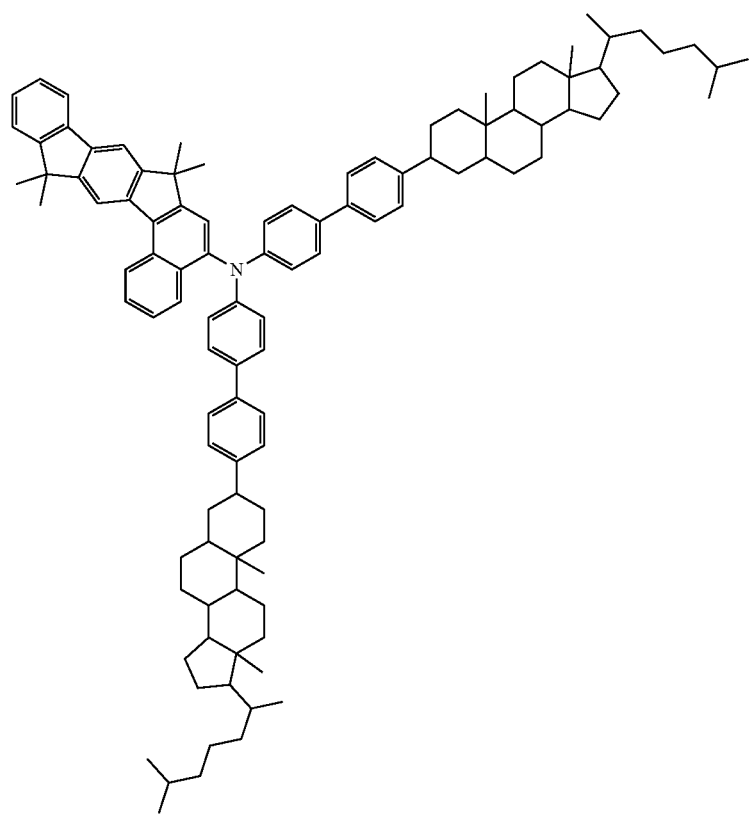

-continued
| 261 | 262 |
|---|---|
| 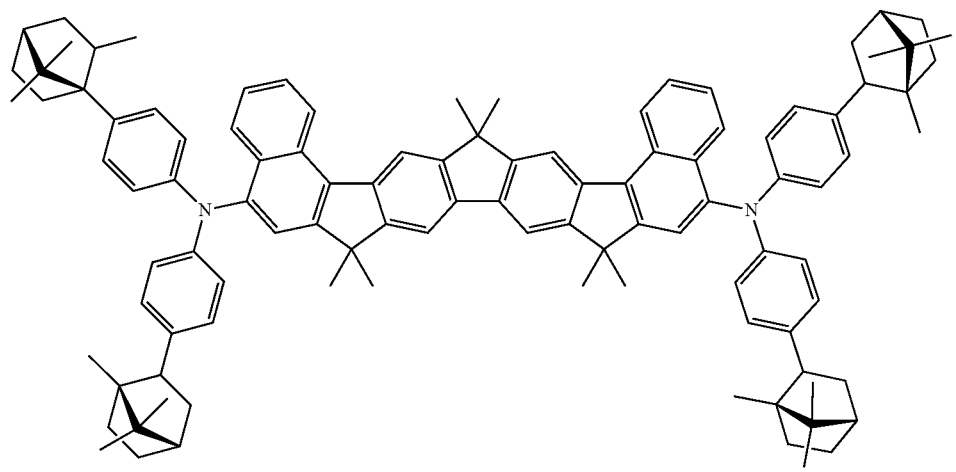 | 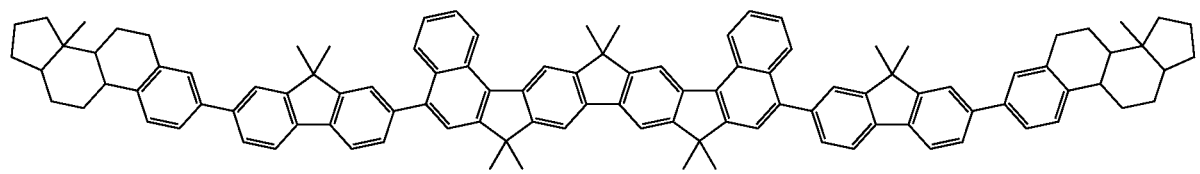 |
| 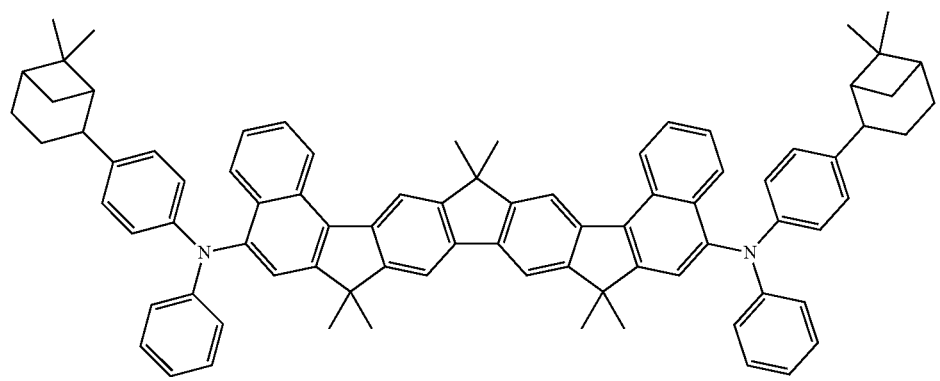 | 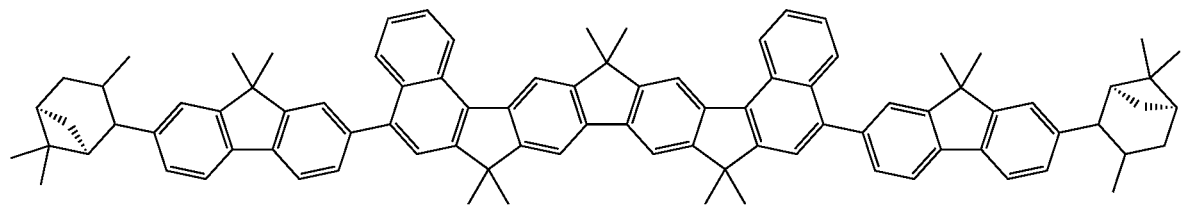 |

-continued
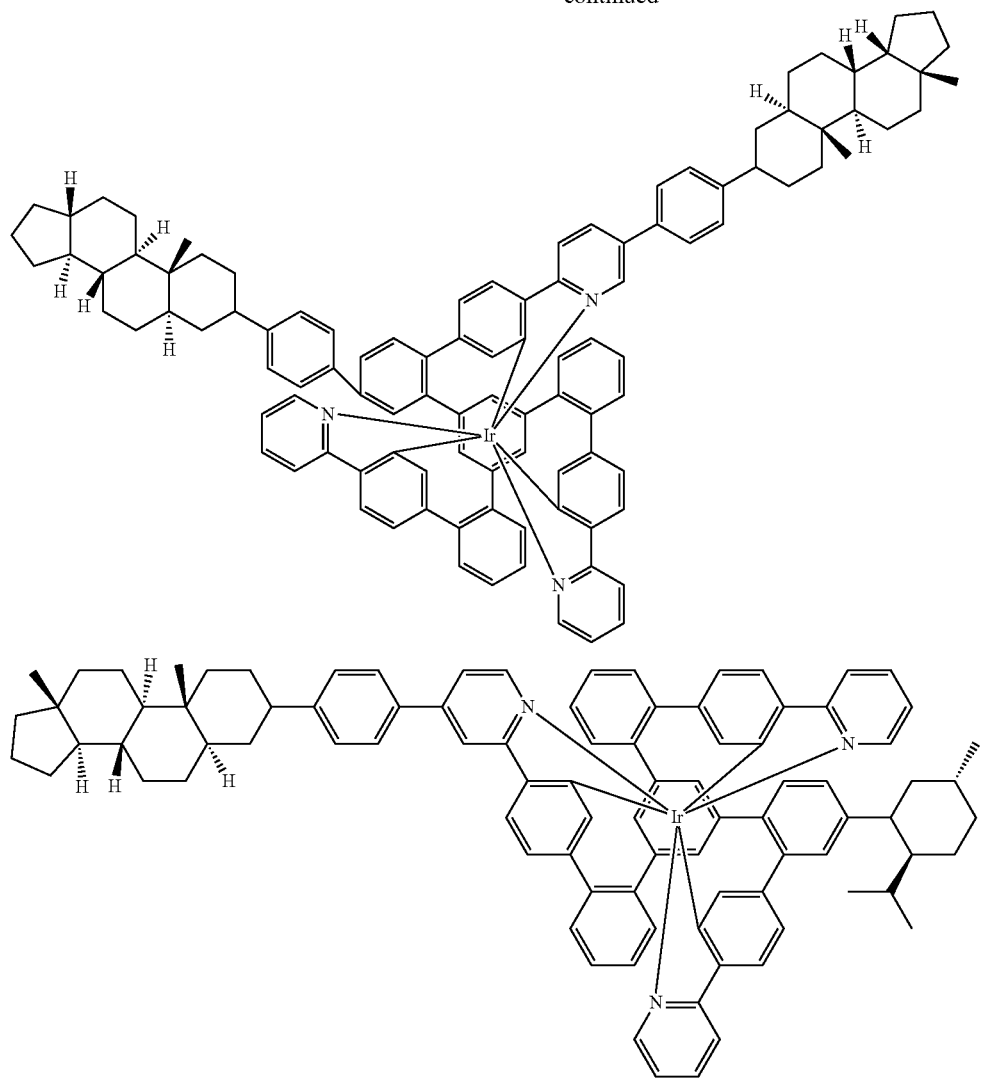
Phosphorescent hosts
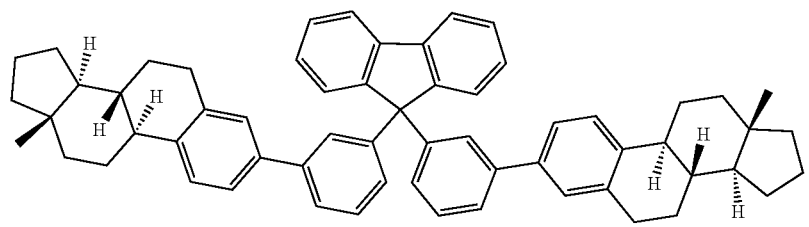
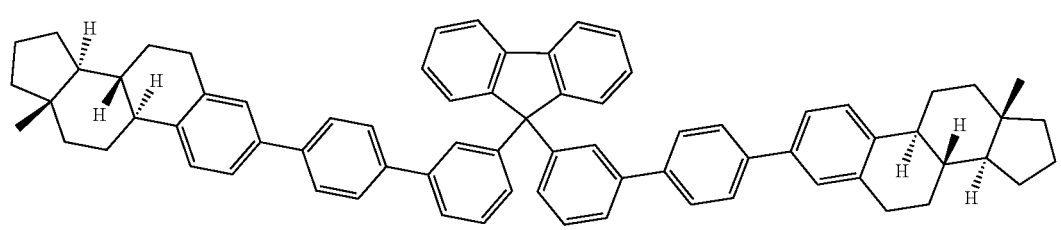

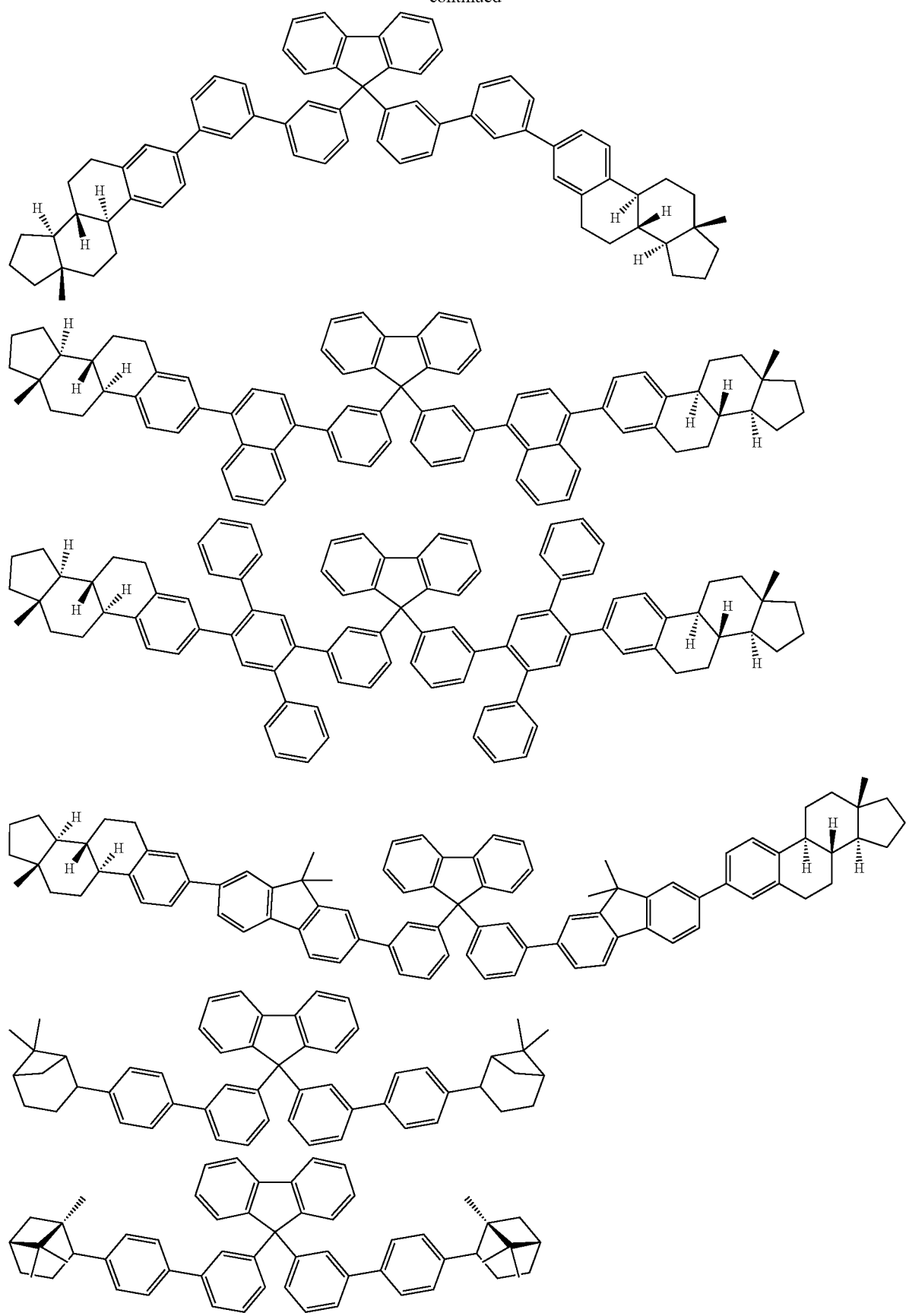

-continued
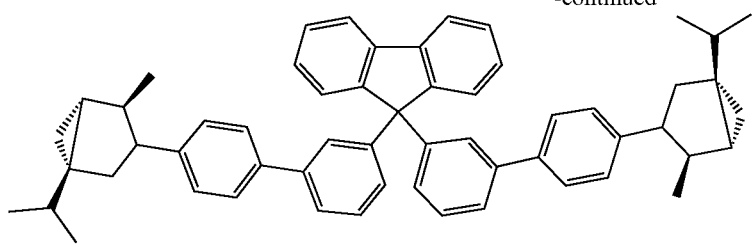
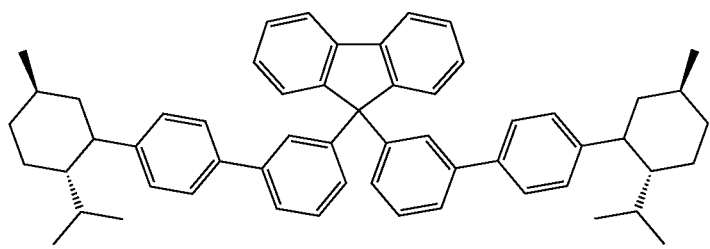
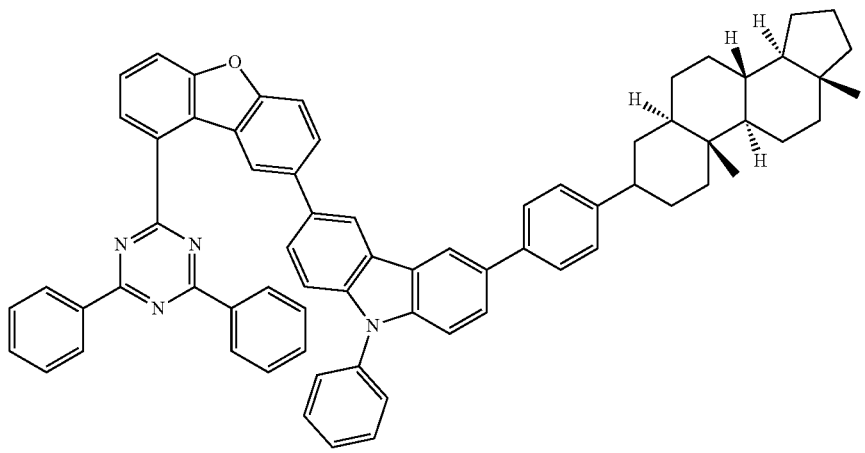
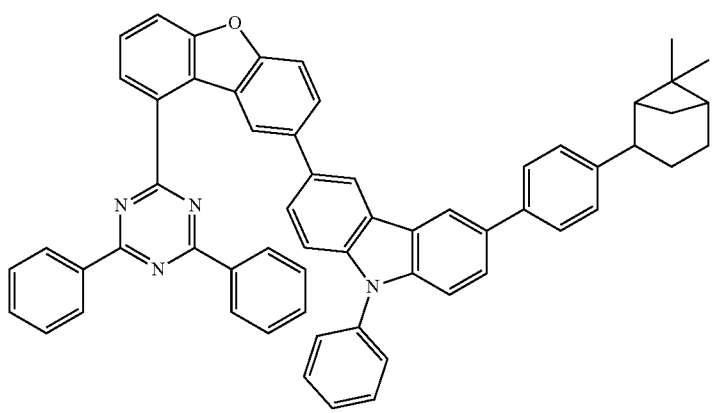

-continued
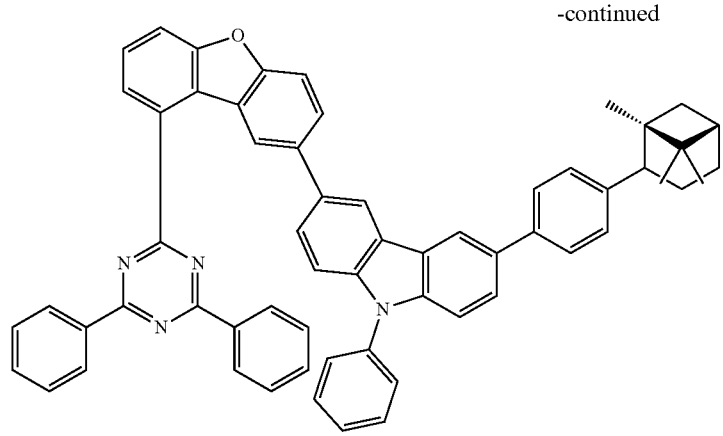
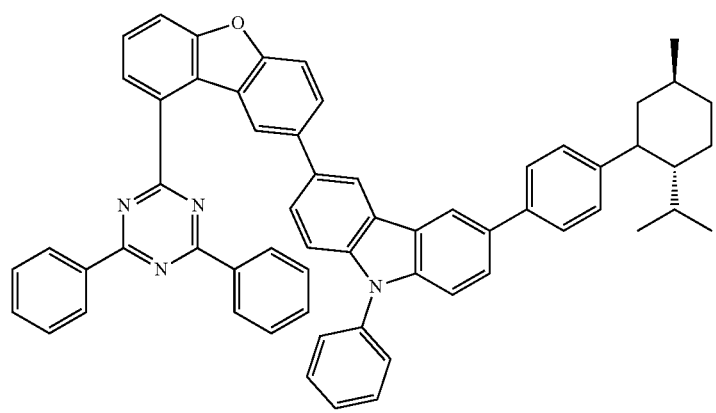
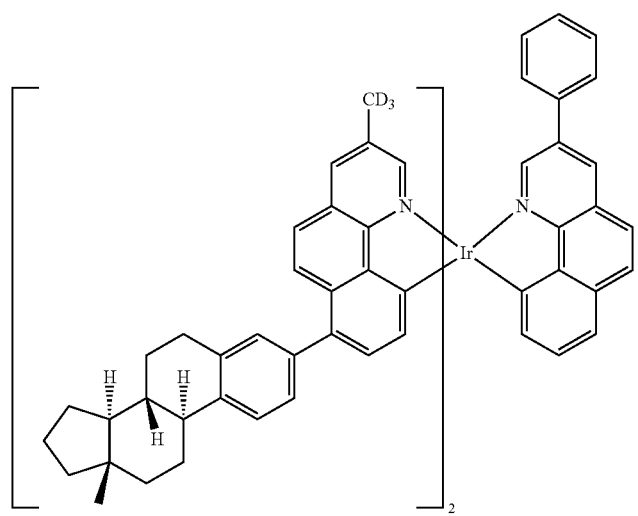

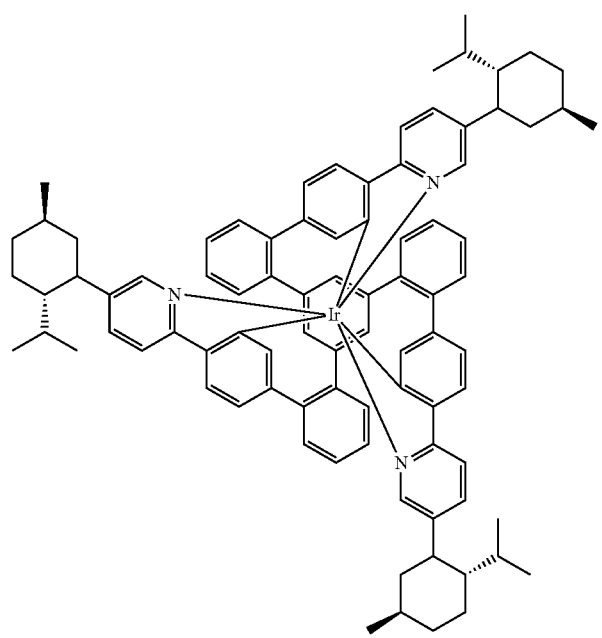
Phosphorescent emitting compounds
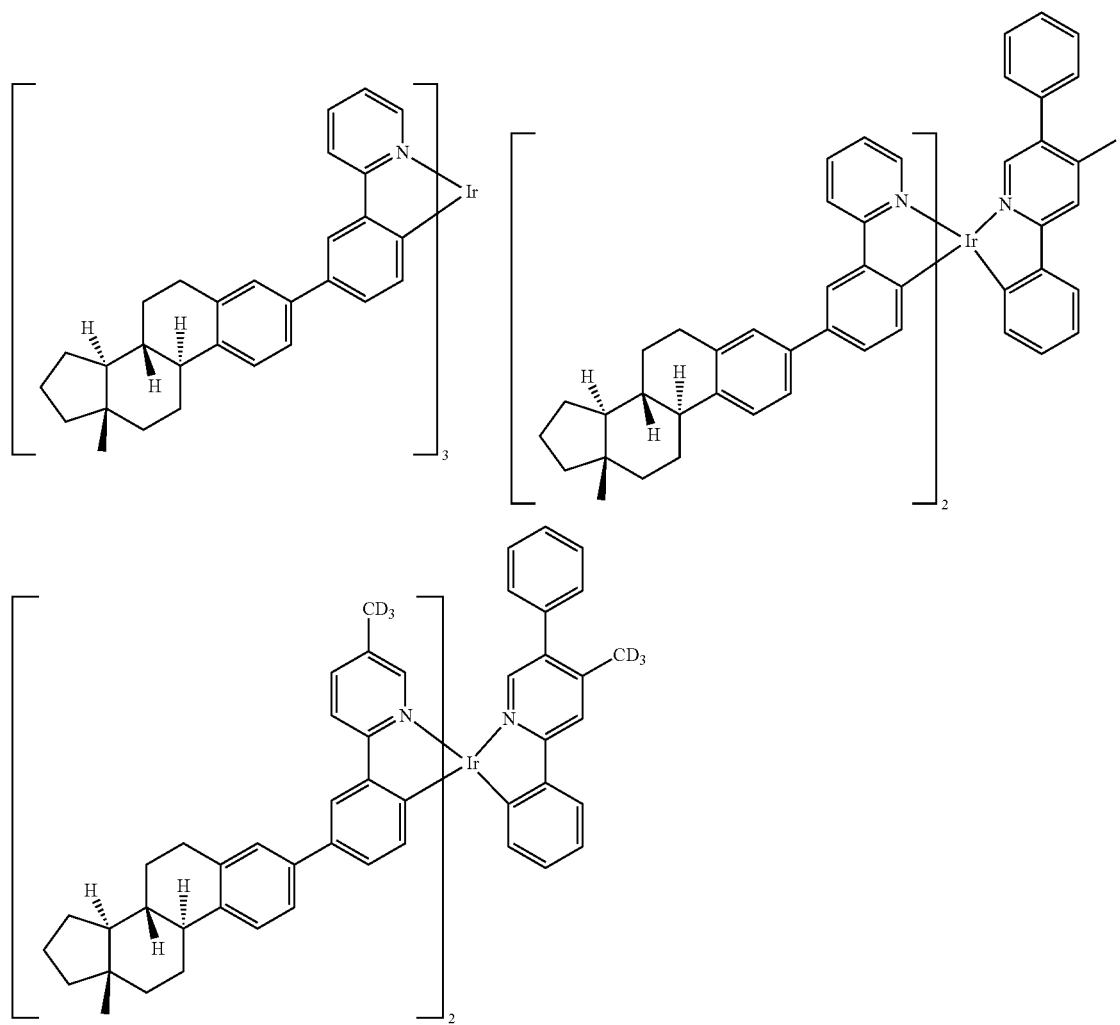

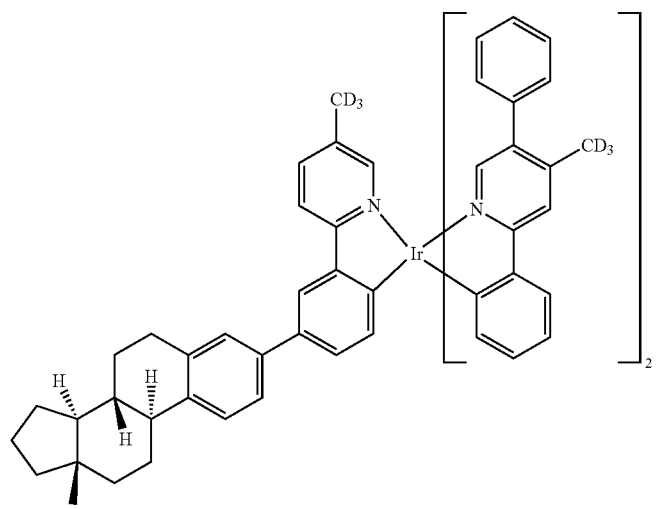
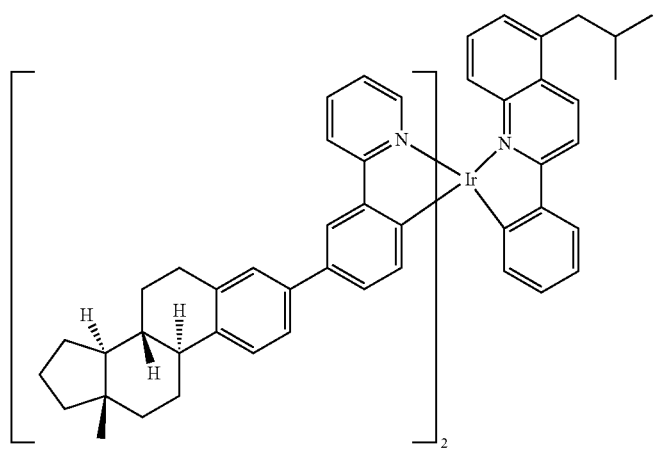
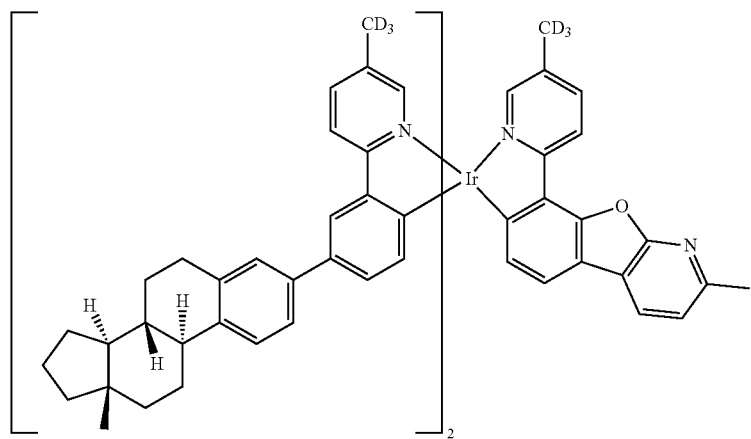

-continued
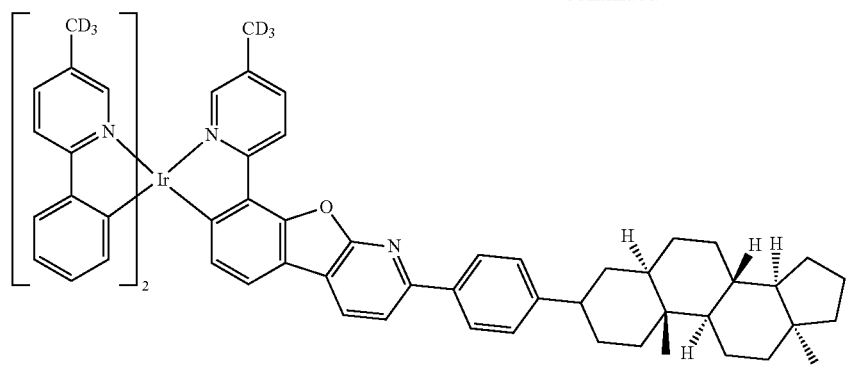
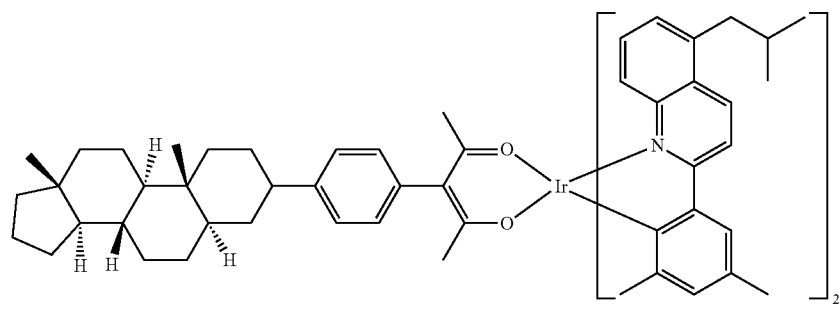
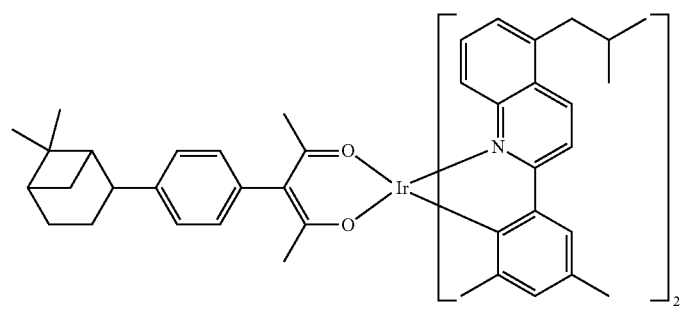
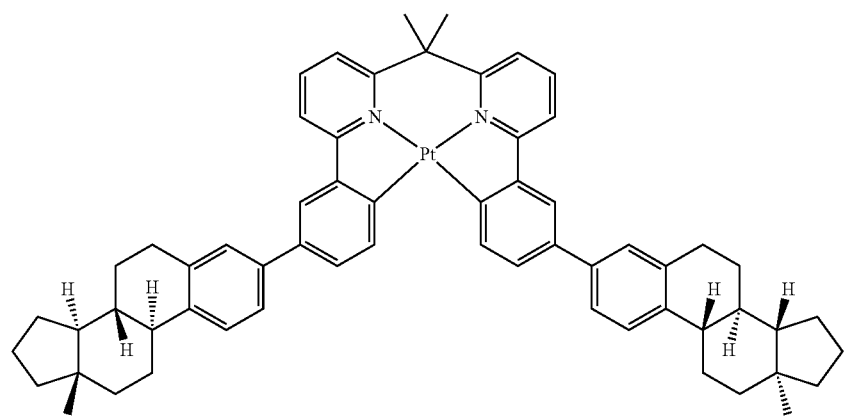

Other examples of compounds according to the invention are the compounds of formula (1) selected from the compounds of formulae PT-3, PT-16, FT-14, FT-17, FT-18, HPT-1, HPT-7, HFT-11 and HFT-26, where m is 0 or 1; and when m is 1, then Ar is selected from a group of formula (Ar-1-1) to (Ar-2-3),

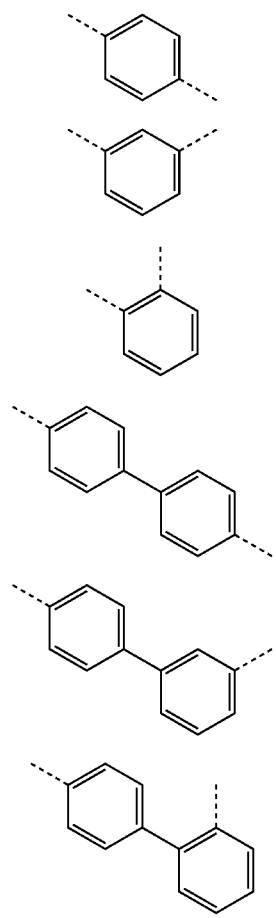

where the dashed bonds indicate the bonding to the groups T and Y and where T is selected from the groups T1, T2, T9, T12, T15 and T18; and where the different groups are combined as presented in the Table below:

| Formula | m | Ar | T |
|---|---|---|---|
| PT-3 | 0 | absent | T1 |
| PT-16 | 0 | absent | T1 |
| FT-14 | 0 | absent | T1 |
| FT-17 | 0 | absent | T1 |
| FT-18 | 0 | absent | T1 |
| HPT-1 | 0 | absent | T1 |
| HPT-7 | 0 | absent | T1 |
| HFT-11 | 0 | absent | T1 |
| HFT-26 | 0 | absent | T1 |
| PT-3 | 0 | absent | T2 |
| PT-16 | 0 | absent | T2 |
| FT-14 | 0 | absent | T2 |
| FT-17 | 0 | absent | T2 |
| FT-18 | 0 | absent | T2 |
| HPT-1 | 0 | absent | T2 |
| HPT-7 | 0 | absent | T2 |
| HFT-11 | 0 | absent | T2 |
| HFT-26 | 0 | absent | T2 |
| PT-3 | 0 | absent | T9 |
| PT-16 | 0 | absent | T9 |
| FT-14 | 0 | absent | T9 |
| FT-17 | 0 | absent | T9 |
| FT-18 | 0 | absent | T9 |
| HPT-1 | 0 | absent | T9 |
| HPT-7 | 0 | absent | T9 |
| HFT-11 | 0 | absent | T9 |
| HFT-26 | 0 | absent | T9 |
| PT-3 | 0 | absent | T12 |
| PT-16 | 0 | absent | T12 |
| FT-14 | 0 | absent | T12 |
| FT-17 | 0 | absent | T12 |
| FT-18 | 0 | absent | T12 |
| HPT-1 | 0 | absent | T12 |
| HPT-7 | 0 | absent | T12 |
| HFT-11 | 0 | absent | T12 |
| HFT-26 | 0 | absent | T12 |
| PT-3 | 0 | absent | T15 |
| PT-16 | 0 | absent | T15 |
| FT-14 | 0 | absent | T15 |
| FT-17 | 0 | absent | T15 |
| FT-18 | 0 | absent | T15 |
| HPT-1 | 0 | absent | T15 |
| HPT-7 | 0 | absent | T15 |
| HFT-11 | 0 | absent | T15 |
| HFT-26 | 0 | absent | T15 |
| PT-3 | 0 | absent | T18 |
| PT-16 | 0 | absent | T18 |
| FT-14 | 0 | absent | T18 |
| FT-17 | 0 | absent | T18 |
| FT-18 | 0 | absent | T18 |
| HPT-1 | 0 | absent | T18 |
| HPT-7 | 0 | absent | T18 |
| HFT-11 | 0 | absent | T18 |
| HFT-26 | 0 | absent | T18 |
| PT-3 | 1 | Ar-1-1 | T1 |
| PT-16 | 1 | Ar-1-1 | T1 |
| FT-14 | 1 | Ar-1-1 | T1 |
| FT-17 | 1 | Ar-1-1 | T1 |
| FT-18 | 1 | Ar-1-1 | T1 |
| HPT-1 | 1 | Ar-1-1 | T1 |
| HPT-7 | 1 | Ar-1-1 | T1 |
| HFT-11 | 1 | Ar-1-1 | T1 |
| HFT-26 | 1 | Ar-1-1 | T1 |
| PT-3 | 1 | Ar-1-1 | T2 |
| PT-16 | 1 | Ar-1-1 | T2 |
| FT-14 | 1 | Ar-1-1 | T2 |
| FT-17 | 1 | Ar-1-1 | T2 |
| FT-18 | 1 | Ar-1-1 | T2 |
| HPT-1 | 1 | Ar-1-1 | T2 |
| HPT-7 | 1 | Ar-1-1 | T2 |
| HFT-11 | 1 | Ar-1-1 | T2 |
| HFT-26 | 1 | Ar-1-1 | T2 |
| PT-3 | 1 | Ar-1-1 | T9 |
| PT-16 | 1 | Ar-1-1 | T9 |
| FT-14 | 1 | Ar-1-1 | T9 |
| FT-17 | 1 | Ar-1-1 | T9 |
| FT-18 | 1 | Ar-1-1 | T9 |
| HPT-1 | 1 | Ar-1-1 | T9 |
| HPT-7 | 1 | Ar-1-1 | T9 |
| HFT-11 | 1 | Ar-1-1 | T9 |
| HFT-26 | 1 | Ar-1-1 | T9 |
| PT-3 | 1 | Ar-1-1 | T12 |
| PT-16 | 1 | Ar-1-1 | T12 |
| FT-14 | 1 | Ar-1-1 | T12 |
| FT-17 | 1 | Ar-1-1 | T12 |
| FT-18 | 1 | Ar-1-1 | T12 |
| HPT-1 | 1 | Ar-1-1 | T12 |
| HPT-7 | 1 | Ar-1-1 | T12 |
| HFT-11 | 1 | Ar-1-1 | T12 |
| HFT-26 | 1 | Ar-1-1 | T12 |
| PT-3 | 1 | Ar-1-1 | T15 |
| PT-16 | 1 | Ar-1-1 | T15 |

| Formula | m | Ar | T |
|---|---|---|---|
| FT-14 | 1 | Ar-1-1 | T15 |
| FT-17 | 1 | Ar-1-1 | T15 |
| FT-18 | 1 | Ar-1-1 | T15 |
| HPT-1 | 1 | Ar-1-1 | T15 |
| HPT-7 | 1 | Ar-1-1 | T15 |
| HFT-11 | 1 | Ar-1-1 | T15 |
| HFT-26 | 1 | Ar-1-1 | T15 |
| PT-3 | 1 | Ar-1-1 | T18 |
| PT-16 | 1 | Ar-1-1 | T18 |
| FT-14 | 1 | Ar-1-1 | T18 |
| FT-17 | 1 | Ar-1-1 | T18 |
| FT-18 | 1 | Ar-1-1 | T18 |
| HPT-1 | 1 | Ar-1-1 | T18 |
| HPT-7 | 1 | Ar-1-1 | T18 |
| HFT-11 | 1 | Ar-1-1 | T18 |
| HFT-26 | 1 | Ar-1-1 | T18 |
| PT-3 | 1 | Ar-1-2 | T1 |
| PT-16 | 1 | Ar-1-2 | T1 |
| FT-14 | 1 | Ar-1-2 | T1 |
| FT-17 | 1 | Ar-1-2 | T1 |
| FT-18 | 1 | Ar-1-2 | T1 |
| HPT-1 | 1 | Ar-1-2 | T1 |
| HPT-7 | 1 | Ar-1-2 | T1 |
| HFT-11 | 1 | Ar-1-2 | T1 |
| HFT-26 | 1 | Ar-1-2 | T1 |
| PT-3 | 1 | Ar-1-2 | T2 |
| PT-16 | 1 | Ar-1-2 | T2 |
| FT-14 | 1 | Ar-1-2 | T2 |
| FT-17 | 1 | Ar-1-2 | T2 |
| FT-18 | 1 | Ar-1-2 | T2 |
| HPT-1 | 1 | Ar-1-2 | T2 |
| HPT-7 | 1 | Ar-1-2 | T2 |
| HFT-11 | 1 | Ar-1-2 | T2 |
| HFT-26 | 1 | Ar-1-2 | T2 |
| PT-3 | 1 | Ar-1-2 | T9 |
| PT-16 | 1 | Ar-1-2 | T9 |
| FT-14 | 1 | Ar-1-2 | T9 |
| FT-17 | 1 | Ar-1-2 | T9 |
| FT-18 | 1 | Ar-1-2 | T9 |
| HPT-1 | 1 | Ar-1-2 | T9 |
| HPT-7 | 1 | Ar-1-2 | T9 |
| HFT-11 | 1 | Ar-1-2 | T9 |
| HFT-26 | 1 | Ar-1-2 | T9 |
| PT-3 | 1 | Ar-1-2 | T12 |
| PT-16 | 1 | Ar-1-2 | T12 |
| FT-14 | 1 | Ar-1-2 | T12 |
| FT-17 | 1 | Ar-1-2 | T12 |
| FT-18 | 1 | Ar-1-2 | T12 |
| HPT-1 | 1 | Ar-1-2 | T12 |
| HPT-7 | 1 | Ar-1-2 | T12 |
| HFT-11 | 1 | Ar-1-2 | T12 |
| HFT-26 | 1 | Ar-1-2 | T12 |
| PT-3 | 1 | Ar-1-2 | T15 |
| PT-16 | 1 | Ar-1-2 | T15 |
| FT-14 | 1 | Ar-1-2 | T15 |
| FT-17 | 1 | Ar-1-2 | T15 |
| FT-18 | 1 | Ar-1-2 | T15 |
| HPT-1 | 1 | Ar-1-2 | T15 |
| HPT-7 | 1 | Ar-1-2 | T15 |
| HFT-11 | 1 | Ar-1-2 | T15 |
| HFT-26 | 1 | Ar-1-2 | T15 |
| PT-3 | 1 | Ar-1-2 | T18 |
| PT-16 | 1 | Ar-1-2 | T18 |
| FT-14 | 1 | Ar-1-2 | T18 |
| FT-17 | 1 | Ar-1-2 | T18 |
| FT-18 | 1 | Ar-1-2 | T18 |
| HPT-1 | 1 | Ar-1-2 | T18 |
| HPT-7 | 1 | Ar-1-2 | T18 |
| HFT-11 | 1 | Ar-1-2 | T18 |
| HFT-26 | 1 | Ar-1-2 | T18 |
| PT-3 | 1 | Ar-1-3 | T1 |
| PT-16 | 1 | Ar-1-3 | T1 |
| FT-14 | 1 | Ar-1-3 | T1 |
| FT-17 | 1 | Ar-1-3 | T1 |
| FT-18 | 1 | Ar-1-3 | T1 |
| HPT-1 | 1 | Ar-1-3 | T1 |
| HPT-7 | 1 | Ar-1-3 | T1 |
| HFT-11 | 1 | Ar-1-3 | T1 |
| HFT-26 | 1 | Ar-1-3 | T1 |
| PT-3 | 1 | Ar-1-3 | T2 |
| PT-16 | 1 | Ar-1-3 | T2 |
| FT-14 | 1 | Ar-1-3 | T2 |
| FT-17 | 1 | Ar-1-3 | T2 |
| FT-18 | 1 | Ar-1-3 | T2 |
| HPT-1 | 1 | Ar-1-3 | T2 |
| HPT-7 | 1 | Ar-1-3 | T2 |
| HFT-11 | 1 | Ar-1-3 | T2 |
| HFT-26 | 1 | Ar-1-3 | T2 |
| PT-3 | 1 | Ar-1-3 | T9 |
| PT-16 | 1 | Ar-1-3 | T9 |
| FT-14 | 1 | Ar-1-3 | T9 |
| FT-17 | 1 | Ar-1-3 | T9 |
| FT-18 | 1 | Ar-1-3 | T9 |
| HPT-1 | 1 | Ar-1-3 | T9 |
| HPT-7 | 1 | Ar-1-3 | T9 |
| HFT-11 | 1 | Ar-1-3 | T9 |
| HFT-26 | 1 | Ar-1-3 | T9 |
| PT-3 | 1 | Ar-2-1 | T1 |
| PT-16 | 1 | Ar-2-1 | T1 |
| FT-14 | 1 | Ar-2-1 | T1 |
| FT-17 | 1 | Ar-2-1 | T1 |
| FT-18 | 1 | Ar-2-1 | T1 |
| HPT-1 | 1 | Ar-2-1 | T1 |
| HPT-7 | 1 | Ar-2-1 | T1 |
| HFT-11 | 1 | Ar-2-1 | T1 |
| HFT-26 | 1 | Ar-2-1 | T1 |
| PT-3 | 1 | Ar-2-1 | T2 |
| PT-16 | 1 | Ar-2-1 | T2 |
| FT-14 | 1 | Ar-2-1 | T2 |
| FT-17 | 1 | Ar-2-1 | T2 |
| FT-18 | 1 | Ar-2-1 | T2 |
| HPT-1 | 1 | Ar-2-1 | T2 |
| HPT-7 | 1 | Ar-2-1 | T2 |
| HFT-11 | 1 | Ar-2-1 | T2 |
| HFT-26 | 1 | Ar-2-1 | T2 |
| PT-3 | 1 | Ar-2-1 | T9 |
| PT-16 | 1 | Ar-2-1 | T9 |
| FT-14 | 1 | Ar-2-1 | T9 |
| FT-17 | 1 | Ar-2-1 | T9 |
| FT-18 | 1 | Ar-2-1 | T9 |
| HPT-1 | 1 | Ar-2-1 | T9 |
| HPT-7 | 1 | Ar-2-1 | T9 |
| HFT-11 | 1 | Ar-2-1 | T9 |
| HFT-26 | 1 | Ar-2-1 | T9 |
| PT-3 | 1 | Ar-2-1 | T12 |
| PT-16 | 1 | Ar-2-1 | T12 |
| FT-14 | 1 | Ar-2-1 | T12 |
| FT-17 | 1 | Ar-2-1 | T12 |
| FT-18 | 1 | Ar-2-1 | T12 |
| HPT-1 | 1 | Ar-2-1 | T12 |
| HPT-7 | 1 | Ar-2-1 | T12 |
| HFT-11 | 1 | Ar-2-1 | T12 |
| HFT-26 | 1 | Ar-2-1 | T12 |
| PT-3 | 1 | Ar-2-1 | T15 |
| PT-16 | 1 | Ar-2-1 | T15 |
| FT-14 | 1 | Ar-2-1 | T15 |
| FT-17 | 1 | Ar-2-1 | T15 |
| FT-18 | 1 | Ar-2-1 | T15 |
| HPT-1 | 1 | Ar-2-1 | T15 |
| HPT-7 | 1 | Ar-2-1 | T15 |
| HFT-11 | 1 | Ar-2-1 | T15 |
| HFT-26 | 1 | Ar-2-1 | T15 |
| PT-3 | 1 | Ar-2-1 | T18 |
| PT-16 | 1 | Ar-2-1 | T18 |
| FT-14 | 1 | Ar-2-1 | T18 |
| FT-17 | 1 | Ar-2-1 | T18 |
| FT-18 | 1 | Ar-2-1 | T18 |
| HPT-1 | 1 | Ar-2-1 | T18 |
| HPT-7 | 1 | Ar-2-1 | T18 |
| HFT-11 | 1 | Ar-2-1 | T18 |
| HFT-26 | 1 | Ar-2-1 | T18 |
| PT-3 | 1 | Ar-2-2 | T1 |
| PT-16 | 1 | Ar-2-2 | T1 |
| FT-14 | 1 | Ar-2-2 | T1 |

| Formula | m | Ar | T |
|---|---|---|---|
| FT-17 | 1 | Ar-2-2 | T1 |
| FT-18 | 1 | Ar-2-2 | T1 |
| HPT-1 | 1 | Ar-2-2 | T1 |
| HPT-7 | 1 | Ar-2-2 | T1 |
| HFT-11 | 1 | Ar-2-2 | T1 |
| HFT-26 | 1 | Ar-2-2 | T1 |
| PT-3 | 1 | Ar-2-2 | T2 |
| PT-16 | 1 | Ar-2-2 | T2 |
| FT-14 | 1 | Ar-2-2 | T2 |
| FT-17 | 1 | Ar-2-2 | T2 |
| FT-18 | 1 | Ar-2-2 | T2 |
| HPT-1 | 1 | Ar-2-2 | T2 |
| HPT-7 | 1 | Ar-2-2 | T2 |
| HFT-11 | 1 | Ar-2-2 | T2 |
| HFT-26 | 1 | Ar-2-2 | T2 |
| PT-3 | 1 | Ar-2-2 | T9 |
| PT-16 | 1 | Ar-2-2 | T9 |
| FT-14 | 1 | Ar-2-2 | T9 |
| FT-17 | 1 | Ar-2-2 | T9 |
| FT-18 | 1 | Ar-2-2 | T9 |
| HPT-1 | 1 | Ar-2-2 | T9 |
| HPT-7 | 1 | Ar-2-2 | T9 |
| HFT-11 | 1 | Ar-2-2 | T9 |
| HFT-26 | 1 | Ar-2-2 | T9 |
| PT-3 | 1 | Ar-2-2 | T12 |
| PT-16 | 1 | Ar-2-2 | T12 |
| FT-14 | 1 | Ar-2-2 | T12 |
| FT-17 | 1 | Ar-2-2 | T12 |
| FT-18 | 1 | Ar-2-2 | T12 |
| HPT-1 | 1 | Ar-2-2 | T12 |
| HPT-7 | 1 | Ar-2-2 | T12 |
| HFT-11 | 1 | Ar-2-2 | T12 |
| HFT-26 | 1 | Ar-2-2 | T12 |
| PT-3 | 1 | Ar-2-2 | T15 |
| PT-16 | 1 | Ar-2-2 | T15 |
| FT-14 | 1 | Ar-2-2 | T15 |
| FT-17 | 1 | Ar-2-2 | T15 |
| FT-18 | 1 | Ar-2-2 | T15 |
| HPT-1 | 1 | Ar-2-2 | T15 |
| HPT-7 | 1 | Ar-2-2 | T15 |
| HFT-11 | 1 | Ar-2-2 | T15 |
| HFT-26 | 1 | Ar-2-2 | T15 |
| PT-3 | 1 | Ar-2-2 | T18 |
| PT-16 | 1 | Ar-2-2 | T18 |
| FT-14 | 1 | Ar-2-2 | T18 |
| FT-17 | 1 | Ar-2-2 | T18 |
| FT-18 | 1 | Ar-2-2 | T18 |
| HPT-1 | 1 | Ar-2-2 | T18 |
| HPT-7 | 1 | Ar-2-2 | T18 |
| HFT-11 | 1 | Ar-2-2 | T18 |
| HFT-26 | 1 | Ar-2-2 | T18 |
| PT-3 | 1 | Ar-2-3 | T1 |
| PT-16 | 1 | Ar-2-3 | T1 |
| FT-14 | 1 | Ar-2-3 | T1 |
| FT-17 | 1 | Ar-2-3 | T1 |
| FT-18 | 1 | Ar-2-3 | T1 |
| HPT-1 | 1 | Ar-2-3 | T1 |
| HPT-7 | 1 | Ar-2-3 | T1 |
| HFT-11 | 1 | Ar-2-3 | T1 |
| HFT-26 | 1 | Ar-2-3 | T1 |
| PT-3 | 1 | Ar-2-3 | T2 |
| PT-16 | 1 | Ar-2-3 | T2 |
| FT-14 | 1 | Ar-2-3 | T2 |
| FT-17 | 1 | Ar-2-3 | T2 |
| FT-18 | 1 | Ar-2-3 | T2 |
| HPT-1 | 1 | Ar-2-3 | T2 |
| HPT-7 | 1 | Ar-2-3 | T2 |
| HFT-11 | 1 | Ar-2-3 | T2 |
| HFT-26 | 1 | Ar-2-3 | T2 |
| PT-3 | 1 | Ar-2-3 | T9 |
| PT-16 | 1 | Ar-2-3 | T9 |
| FT-14 | 1 | Ar-2-3 | T9 |
| FT-17 | 1 | Ar-2-3 | T9 |
| FT-18 | 1 | Ar-2-3 | T9 |
| HPT-1 | 1 | Ar-2-3 | T9 |
| HPT-7 | 1 | Ar-2-3 | T9 |
| HFT-11 | 1 | Ar-2-3 | T9 |
| HFT-26 | 1 | Ar-2-3 | T9 |
| PT-3 | 1 | Ar-2-3 | T12 |
| PT-16 | 1 | Ar-2-3 | T12 |
| FT-14 | 1 | Ar-2-3 | T12 |
| FT-17 | 1 | Ar-2-3 | T12 |
| FT-18 | 1 | Ar-2-3 | T12 |
| HPT-1 | 1 | Ar-2-3 | T12 |
| HPT-7 | 1 | Ar-2-3 | T12 |
| HFT-11 | 1 | Ar-2-3 | T12 |
| HFT-26 | 1 | Ar-2-3 | T12 |
| PT-3 | 1 | Ar-2-3 | T15 |
| PT-16 | 1 | Ar-2-3 | T15 |
| FT-14 | 1 | Ar-2-3 | T15 |
| FT-17 | 1 | Ar-2-3 | T15 |
| FT-18 | 1 | Ar-2-3 | T15 |
| HPT-1 | 1 | Ar-2-3 | T15 |
| HPT-7 | 1 | Ar-2-3 | T15 |
| HFT-11 | 1 | Ar-2-3 | T15 |
| HFT-26 | 1 | Ar-2-3 | T15 |
| PT-3 | 1 | Ar-2-3 | T18 |
| PT-16 | 1 | Ar-2-3 | T18 |
| FT-14 | 1 | Ar-2-3 | T18 |
| FT-17 | 1 | Ar-2-3 | T18 |
| FT-18 | 1 | Ar-2-3 | T18 |
| HPT-1 | 1 | Ar-2-3 | T18 |
| HPT-7 | 1 | Ar-2-3 | T18 |
| HFT-11 | 1 | Ar-2-3 | T18 |
| HFT-26 | 1 | Ar-2-3 | T18 |
| PT-3 | 1 | Ar-1-3 | T12 |
| PT-16 | 1 | Ar-1-3 | T12 |
| FT-14 | 1 | Ar-1-3 | T12 |
| FT-17 | 1 | Ar-1-3 | T12 |
| FT-18 | 1 | Ar-1-3 | T12 |
| HPT-1 | 1 | Ar-1-3 | T12 |
| HPT-7 | 1 | Ar-1-3 | T12 |
| HFT-11 | 1 | Ar-1-3 | T12 |
| HFT-26 | 1 | Ar-1-3 | T12 |
| PT-3 | 1 | Ar-1-3 | T15 |
| PT-16 | 1 | Ar-1-3 | T15 |
| FT-14 | 1 | Ar-1-3 | T15 |
| FT-17 | 1 | Ar-1-3 | T15 |
| FT-18 | 1 | Ar-1-3 | T15 |
| HPT-1 | 1 | Ar-1-3 | T15 |
| HPT-7 | 1 | Ar-1-3 | T15 |
| HFT-11 | 1 | Ar-1-3 | T15 |
| HFT-26 | 1 | Ar-1-3 | T15 |
| PT-3 | 1 | Ar-1-3 | T18 |
| PT-16 | 1 | Ar-1-3 | T18 |
| FT-14 | 1 | Ar-1-3 | T18 |
| FT-17 | 1 | Ar-1-3 | T18 |
| FT-18 | 1 | Ar-1-3 | T18 |
| HPT-1 | 1 | Ar-1-3 | T18 |
| HPT-7 | 1 | Ar-1-3 | T18 |
| HFT-11 | 1 | Ar-1-3 | T18 |
| HFT-26 | 1 | Ar-1-3 | T18 |

Other examples of compounds according to the invention are the compounds of formula (2) selected from the compounds of formulae PT-22, PT-23, FT-24, FT-25, HPT-46, HPT-47, HFT-27 and HFT-28, where m is 0 or 1; and when m is 1, then Ar is selected from a group of formula (Ar-1-1) to (Ar-2-3) and where T is selected from the groups T6, T10, T11 and T16; and where the different groups are combined as follows:

| Formula | m | Ar | T |
|---|---|---|---|
| PT-22 | 0 | absent | T6 |
| PT-23 | 0 | absent | T6 |
| FT-24 | 0 | absent | T6 |
| FT-25 | 0 | absent | T6 |
| HPT-46 | 0 | absent | T6 |

| Formula | m | Ar | T |
|---|---|---|---|
| HPT-47 | 0 | absent | T6 |
| HFT-27 | 0 | absent | T6 |
| HFT-28 | 0 | absent | T6 |
| PT-22 | 0 | absent | T10 |
| PT-23 | 0 | absent | T10 |
| FT-24 | 0 | absent | T10 |
| FT-25 | 0 | absent | T10 |
| HPT-46 | 0 | absent | T10 |
| HPT-47 | 0 | absent | T10 |
| HFT-27 | 0 | absent | T10 |
| HFT-28 | 0 | absent | T10 |
| PT-22 | 0 | absent | T11 |
| PT-23 | 0 | absent | T11 |
| FT-24 | 0 | absent | T11 |
| FT-25 | 0 | absent | T11 |
| HPT-46 | 0 | absent | T11 |
| HPT-47 | 0 | absent | T11 |
| HFT-27 | 0 | absent | T11 |
| HFT-28 | 0 | absent | T11 |
| PT-22 | 0 | absent | T16 |
| PT-23 | 0 | absent | T16 |
| FT-24 | 0 | absent | T16 |
| FT-25 | 0 | absent | T16 |
| HPT-46 | 0 | absent | T16 |
| HPT-47 | 0 | absent | T16 |
| HFT-27 | 0 | absent | T16 |
| HFT-28 | 0 | absent | T16 |
| PT-22 | 1 | Ar-1-1 | T6 |
| PT-23 | 1 | Ar-1-1 | T6 |
| FT-24 | 1 | Ar-1-1 | T6 |
| FT-25 | 1 | Ar-1-1 | T6 |
| HPT-46 | 1 | Ar-1-1 | T6 |
| HPT-47 | 1 | Ar-1-1 | T6 |
| HFT-27 | 1 | Ar-1-1 | T6 |
| HFT-28 | 1 | Ar-1-1 | T6 |
| PT-22 | 1 | Ar-1-1 | T10 |
| PT-23 | 1 | Ar-1-1 | T10 |
| FT-24 | 1 | Ar-1-1 | T10 |
| FT-25 | 1 | Ar-1-1 | T10 |
| HPT-46 | 1 | Ar-1-1 | T10 |
| HPT-47 | 1 | Ar-1-1 | T10 |
| HFT-27 | 1 | Ar-1-1 | T10 |
| HFT-28 | 1 | Ar-1-1 | T10 |
| PT-22 | 1 | Ar-1-1 | T11 |
| PT-23 | 1 | Ar-1-1 | T11 |
| FT-24 | 1 | Ar-1-1 | T11 |
| FT-25 | 1 | Ar-1-1 | T11 |
| HPT-46 | 1 | Ar-1-1 | T11 |
| HPT-47 | 1 | Ar-1-1 | T11 |
| HFT-27 | 1 | Ar-1-1 | T11 |
| HFT-28 | 1 | Ar-1-1 | T11 |
| PT-22 | 1 | Ar-1-1 | T16 |
| PT-23 | 1 | Ar-1-1 | T16 |
| FT-24 | 1 | Ar-1-1 | T16 |
| FT-25 | 1 | Ar-1-1 | T16 |
| HPT-46 | 1 | Ar-1-1 | T16 |
| HPT-47 | 1 | Ar-1-1 | T16 |
| HFT-27 | 1 | Ar-1-1 | T16 |
| HFT-28 | 1 | Ar-1-1 | T16 |
| PT-22 | 1 | Ar-1-2 | T6 |
| PT-23 | 1 | Ar-1-2 | T6 |
| FT-24 | 1 | Ar-1-2 | T6 |
| FT-25 | 1 | Ar-1-2 | T6 |
| HPT-46 | 1 | Ar-1-2 | T6 |
| HPT-47 | 1 | Ar-1-2 | T6 |
| HFT-27 | 1 | Ar-1-2 | T6 |
| HFT-28 | 1 | Ar-1-2 | T6 |
| PT-22 | 1 | Ar-1-2 | T10 |
| PT-23 | 1 | Ar-1-2 | T10 |
| FT-24 | 1 | Ar-1-2 | T10 |
| FT-25 | 1 | Ar-1-2 | T10 |
| HPT-46 | 1 | Ar-1-2 | T10 |
| HPT-47 | 1 | Ar-1-2 | T10 |
| HFT-27 | 1 | Ar-1-2 | T10 |
| HFT-28 | 1 | Ar-1-2 | T10 |
| PT-22 | 1 | Ar-1-2 | T11 |
| PT-23 | 1 | Ar-1-2 | T11 |
| FT-24 | 1 | Ar-1-2 | T11 |
| FT-25 | 1 | Ar-1-2 | T11 |
| HPT-46 | 1 | Ar-1-2 | T11 |
| HPT-47 | 1 | Ar-1-2 | T11 |
| HFT-27 | 1 | Ar-1-2 | T11 |
| HFT-28 | 1 | Ar-1-2 | T11 |
| PT-22 | 1 | Ar-1-2 | T16 |
| PT-23 | 1 | Ar-1-2 | T16 |
| FT-24 | 1 | Ar-1-2 | T16 |
| FT-25 | 1 | Ar-1-2 | T16 |
| HPT-46 | 1 | Ar-1-2 | T16 |
| HPT-47 | 1 | Ar-1-2 | T16 |
| HFT-27 | 1 | Ar-1-2 | T16 |
| HFT-28 | 1 | Ar-1-2 | T16 |
| PT-22 | 1 | Ar-1-3 | T6 |
| PT-23 | 1 | Ar-1-3 | T6 |
| FT-24 | 1 | Ar-1-3 | T6 |
| FT-25 | 1 | Ar-1-3 | T6 |
| HPT-46 | 1 | Ar-1-3 | T6 |
| HPT-47 | 1 | Ar-1-3 | T6 |
| HFT-27 | 1 | Ar-1-3 | T6 |
| HFT-28 | 1 | Ar-1-3 | T6 |
| PT-22 | 1 | Ar-1-3 | T10 |
| PT-23 | 1 | Ar-1-3 | T10 |
| FT-24 | 1 | Ar-1-3 | T10 |
| FT-25 | 1 | Ar-1-3 | T10 |
| HPT-46 | 1 | Ar-1-3 | T10 |
| HPT-47 | 1 | Ar-1-3 | T10 |
| HFT-27 | 1 | Ar-1-3 | T10 |
| HFT-28 | 1 | Ar-1-3 | T10 |
| PT-22 | 1 | Ar-2-1 | T6 |
| PT-23 | 1 | Ar-2-1 | T6 |
| FT-24 | 1 | Ar-2-1 | T6 |
| FT-25 | 1 | Ar-2-1 | T6 |
| HPT-46 | 1 | Ar-2-1 | T6 |
| HPT-47 | 1 | Ar-2-1 | T6 |
| HFT-27 | 1 | Ar-2-1 | T6 |
| HFT-28 | 1 | Ar-2-1 | T6 |
| PT-22 | 1 | Ar-2-1 | T10 |
| PT-23 | 1 | Ar-2-1 | T10 |
| FT-24 | 1 | Ar-2-1 | T10 |
| FT-25 | 1 | Ar-2-1 | T10 |
| HPT-46 | 1 | Ar-2-1 | T10 |
| HPT-47 | 1 | Ar-2-1 | T10 |
| HFT-27 | 1 | Ar-2-1 | T10 |
| HFT-28 | 1 | Ar-2-1 | T10 |
| PT-22 | 1 | Ar-2-1 | T11 |
| PT-23 | 1 | Ar-2-1 | T11 |
| FT-24 | 1 | Ar-2-1 | T11 |
| FT-25 | 1 | Ar-2-1 | T11 |
| HPT-46 | 1 | Ar-2-1 | T11 |
| HPT-47 | 1 | Ar-2-1 | T11 |
| HFT-27 | 1 | Ar-2-1 | T11 |
| HFT-28 | 1 | Ar-2-1 | T11 |
| PT-22 | 1 | Ar-2-1 | T16 |
| PT-23 | 1 | Ar-2-1 | T16 |
| FT-24 | 1 | Ar-2-1 | T16 |
| FT-25 | 1 | Ar-2-1 | T16 |
| HPT-46 | 1 | Ar-2-1 | T16 |
| HPT-47 | 1 | Ar-2-1 | T16 |
| HFT-27 | 1 | Ar-2-1 | T16 |
| HFT-28 | 1 | Ar-2-1 | T16 |
| PT-22 | 1 | Ar-2-2 | T6 |
| PT-23 | 1 | Ar-2-2 | T6 |
| FT-24 | 1 | Ar-2-2 | T6 |
| FT-25 | 1 | Ar-2-2 | T6 |
| HPT-46 | 1 | Ar-2-2 | T6 |
| HPT-47 | 1 | Ar-2-2 | T6 |
| HFT-27 | 1 | Ar-2-2 | T6 |
| HFT-28 | 1 | Ar-2-2 | T6 |
| PT-22 | 1 | Ar-2-2 | T10 |
| PT-23 | 1 | Ar-2-2 | T10 |
| FT-24 | 1 | Ar-2-2 | T10 |
| FT-25 | 1 | Ar-2-2 | T10 |
| HPT-46 | 1 | Ar-2-2 | T10 |
| HPT-47 | 1 | Ar-2-2 | T10 |
| HFT-27 | 1 | Ar-2-2 | T10 |

-continued

| Formula | m | Ar | T |
|---|---|---|---|
| HFT-28 | 1 | Ar-2-2 | T10 |
| PT-22 | 1 | Ar-2-2 | T11 |
| PT-23 | 1 | Ar-2-2 | T11 |
| FT-24 | 1 | Ar-2-2 | T11 |
| FT-25 | 1 | Ar-2-2 | T11 |
| HPT-46 | 1 | Ar-2-2 | T11 |
| HPT-47 | 1 | Ar-2-2 | T11 |
| HFT-27 | 1 | Ar-2-2 | T11 |
| HFT-28 | 1 | Ar-2-2 | T11 |
| PT-22 | 1 | Ar-2-2 | T16 |
| PT-23 | 1 | Ar-2-2 | T16 |
| FT-24 | 1 | Ar-2-2 | T16 |
| FT-25 | 1 | Ar-2-2 | T16 |
| HPT-46 | 1 | Ar-2-2 | T16 |
| HPT-47 | 1 | Ar-2-2 | T16 |
| HFT-27 | 1 | Ar-2-2 | T16 |
| HFT-28 | 1 | Ar-2-2 | T16 |
| PT-22 | 1 | Ar-2-2 | T6 |
| PT-23 | 1 | Ar-2-2 | T6 |
| FT-24 | 1 | Ar-2-2 | T6 |
| FT-25 | 1 | Ar-2-2 | T6 |
| HPT-46 | 1 | Ar-2-2 | T6 |
| HPT-47 | 1 | Ar-2-2 | T6 |
| HFT-27 | 1 | Ar-2-2 | T6 |
| HFT-28 | 1 | Ar-2-2 | T6 |
| PT-22 | 1 | Ar-2-2 | T10 |
| PT-23 | 1 | Ar-2-2 | T10 |
| FT-24 | 1 | Ar-2-2 | T10 |
| FT-25 | 1 | Ar-2-2 | T10 |
| HPT-46 | 1 | Ar-2-2 | T10 |
| HPT-47 | 1 | Ar-2-2 | T10 |
| HFT-27 | 1 | Ar-2-2 | T10 |
| HFT-28 | 1 | Ar-2-2 | T10 |
| PT-22 | 1 | Ar-2-2 | T11 |
| PT-23 | 1 | Ar-2-2 | T11 |
| FT-24 | 1 | Ar-2-2 | T11 |
| FT-25 | 1 | Ar-2-2 | T11 |
| HPT-46 | 1 | Ar-2-2 | T11 |
| HPT-47 | 1 | Ar-2-2 | T11 |
| HFT-27 | 1 | Ar-2-3 | T11 |
| HFT-28 | 1 | Ar-2-3 | T11 |
| PT-22 | 1 | Ar-2-3 | T16 |
| PT-23 | 1 | Ar-2-3 | T16 |
| FT-24 | 1 | Ar-2-3 | T16 |
| FT-25 | 1 | Ar-2-3 | T16 |
| HPT-46 | 1 | Ar-2-3 | T16 |
| HPT-47 | 1 | Ar-2-3 | T16 |
| HFT-27 | 1 | Ar-2-3 | T16 |
| HFT-28 | 1 | Ar-2-3 | T16 |
| PT-22 | 1 | Ar-1-3 | T11 |
| PT-23 | 1 | Ar-1-3 | T11 |
| FT-24 | 1 | Ar-1-3 | T11 |
| FT-25 | 1 | Ar-1-3 | T11 |
| HPT-46 | 1 | Ar-1-3 | T11 |
| HPT-47 | 1 | Ar-1-3 | T11 |
| HFT-27 | 1 | Ar-1-3 | T11 |
| HFT-28 | 1 | Ar-1-3 | T11 |
| PT-22 | 1 | Ar-1-3 | T16 |
| PT-23 | 1 | Ar-1-3 | T16 |
| FT-24 | 1 | Ar-1-3 | T16 |
| FT-25 | 1 | Ar-1-3 | T16 |
| HPT-46 | 1 | Ar-1-3 | T16 |
| HPT-47 | 1 | Ar-1-3 | T16 |
| HFT-27 | 1 | Ar-1-3 | T16 |
| HFT-28 | 1 | Ar-1-3 | T16 |

The functional materials, which are substituted by at least one terpene or terpenoid group, can be prepared by known processes or reaction steps of organic chemistry.

A preferred process for the preparation of functional materials substituted by at least one terpene or terpenoid group is shown below with Scheme 1 or with Scheme 2:

Scheme 1

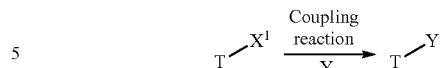

$X^1$: reactive group like Cl, Br, I or another leaving group
T: terpene or terpenoid group
Y: functional material (host or emitter)

Scheme 2

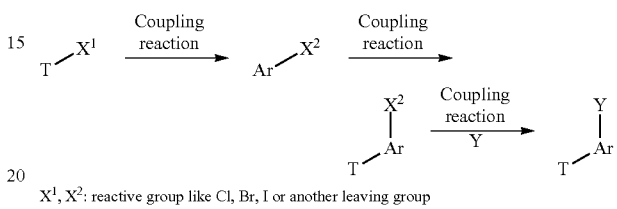

$X^1, X^2$: reactive group like Cl, Br, I or another leaving group
T: terpene or terpenoid group
Ar: aromatic or heteroaromatic group
Y: functional material (host or emitter)

Details on the processes indicated schematically above can be obtained from the working examples.

The person skilled in the art will be able to deviate from the processes indicated schematically above or modify them in order to obtain compounds of the formulae (1) to (4), if this is necessary. This is carried out within the scope of the usual abilities of the person skilled in the art.

The metal-catalysed coupling reaction here is preferably a transition-metal-catalysed coupling reaction, particularly preferably a Suzuki reaction.

The invention furthermore relates to intermediate compounds of formula (Int-1),

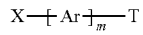

Formula (Int-1)

where the following applies to the symbols and indices used:

X is selected from Cl, Br, I, trifluoromethanesulfonate ($CF_3SO_3$—), tosylate ($CH_3C_6H_4SO_3$—), mesylate ($CH_3SO_3$—), or —$B(OR^B)_2$;

$R^B$ is H, a straight-chain alkyl having 1 to 10 C atoms, where two substituents $R^B$ may form a monocyclic aliphatic ring system that may be substituted by an alkyl group having 1 to 3 C atoms;

Ar is on each occurrence, identically or differently, selected from the group consisting of aromatic or heteroaromatic ring systems having 5 to 60 aromatic ring atoms, which may in each case also be substituted by one or more radicals R;

T is on each occurrence, identically or differently selected from the group consisting of terpene and terpenoid groups, which may in each case be substituted by one or more radicals $R^1$;

R, $R^1$ stand on each occurrence, identically or differently, for H, D, F, Cl, Br, I, CHO, CN, $NO_2$, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals $R^2$, where in each case one or more non-adjacent CH$_2$ groups may be replaced by R$^2$C=CR$^2$, C=C, C=O, C=S, SO, SO$_2$, O or S and where one or more H atoms may be replaced by D, F, Cl, Br, I, CN or NO$_2$, an aromatic or heteroaromatic ring systems having 5 to 60 aromatic ring atoms, which may in each case be substituted by one or more radicals R$^2$, or an aryloxy groups having 5 to 60 aromatic ring atoms, which may be substituted by one or more radicals R$^2$, where two adjacent substituents R and/or two adjacent substituents R$^1$ may form a mono- or polycyclic, aliphatic ring system or aromatic ring system, which may be substituted by one or more radicals R$^2$;

R$^2$ stands on each occurrence, identically or differently, for H, D, F, Cl, Br, I, CN, a straight-chain alkyl, alkoxy or thioalkyl groups having 1 to 20 C atoms or branched or cyclic alkyl, alkoxy or thioalkyl groups having 3 to 20 C atoms, where in each case one or more non-adjacent CH$_2$ groups may be replaced by SO, SO$_2$, O, S and where one or more H atoms may be replaced by D, F, Cl, Br or I, or an aromatic or heteroaromatic ring system having 5 to 24 C atoms;

m is on each occurrence, identically or differently, 1, 2, 3 or 4.

Preferably, X is selected from —B(OR$^B$)$_2$.

More preferably, X is selected from —B(OR$^B$)$_2$ and two substituents R$^B$ form a monocyclic aliphatic ring system that may be substituted by an alkyl group having 1 to 3 C atoms.

Very more preferably, X corresponds to a group (R$^B$-1),

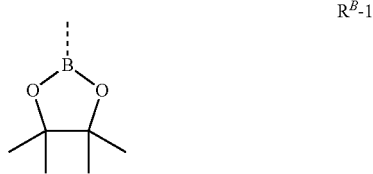

R$^B$-1 where the dashed bond indicates the bonding of B to the group Ar in formula (Int-1).

The compounds according to the invention described above, in particular compounds which are substituted by reactive leaving groups, such as bromine, iodine, chlorine, boronic acid or boronic acid ester, can be used as monomers for the preparation of corresponding oligomers, dendrimers or polymers. Suitable reactive leaving groups are, for example, bromine, iodine, chlorine, boronic acids, boronic acid esters, amines, alkenyl or alkynyl groups containing a terminal C—C double or triple bond respectively, oxiranes, oxetanes, groups which undergo a cycloaddition, for example a 1,3-dipolar cycloaddition, such, as, for example, dienes or azides, carboxylic acid derivatives, alcohols and silanes.

The invention therefore furthermore relates to oligomers, polymers or dendrimers comprising one or more compounds of the formulae (1) to (4), where the bond(s) to the polymer, oligomer or dendrimer may be localised at any desired positions in formulae (1) to (4) which are substituted by R, R$^1$ or R$^2$. Depending on the linking of the compound of the formula (1), (2), (3) or (4), the compound is part of a side chain of the oligomer or polymer or part of the main chain.

An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formulae (1) to (4) may be linked directly to one another or linked to one another via a divalent group, for example via a substituted or unsubstituted alkylene group, via a heteroatom or via a divalent aromatic or heteroaromatic group. In branched and dendritic structures, three or more units of the formulae (1) to (4) may, for example, be linked via a trivalent or polyvalent group, for example via a trivalent or polyvalent aromatic or heteroaromatic group, to give a branched or dendritic oligomer or polymer.

The same preferences as described above for compounds of the formula (1) to (4) apply to the recurring units of the formulae (1) to (4) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 1992/18552), carbazoles (for example in accordance with WO 04/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formulae (1) to (4) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, dichlorobenzene, chlorobenzene, dioxane, phenoxytoluene, in particular 3-phenoxytoluene, (–)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of one of the formulae (1) to (4), and at least one solvent, preferably an organic solvent.

The way in which solutions of this type can be prepared is known to the person skilled in the art and is described, for example, in WO 2002/072714, WO 2003/019694 and the literature cited therein.

Preferably, the formulation according to the invention comprises at least one compound of one of the formulae (1) to (4) and at least one solvent, selected from non-polar solvents and dipolar aprotic solvents and mixtures thereof.

Preferred non-polar solvents are selected from the group consisting of aromatics, alkylaromatics, cyclohexanes and the mixtures thereof and preferred dipolar aprotic solvents are selected from the group consisting of ketones, ethers, esters, amides, sulfones and sulfoxides, such as acetone, butanone, cyclohexanone, di-n-butyl ether, THF, dioxane, 3-phenoxytoluene, anisole, ethyl acetate, butyl acetate, hexyl acetate, benzoic acid methyl ester, DMF, DMAC, NMP, DMSO, dimetylsulfone and sulfolane, and the mixtures thereof.

Preferred concentrations are 1-500 mg/ml, particularly preferred 10-200 mg/ml. This property is of crucial importance for processing from solutions in the form of a solution alone or in combination with other materials, especially with regard to the printing of high-resolution full-color-displays.

The compounds of the formulae (1) to (4) are suitable for use in electronic devices, in particular in organic electroluminescent devices (OLEDs).

The invention therefore furthermore relates to the use of a compound of one of the formulae (1) to (4) in an electronic device. The electronic device here is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention furthermore relates to an electronic device comprising at least one compound of one of the formulae (1) to (4). The electronic device is preferably selected from the devices indicated above. Particular preference is given to an organic electroluminescent device comprising anode, cathode and at least one emitting layer, characterised in that at least one organic layer comprises at least one compound of one of the formulae (1) to (4).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of the organic electroluminescent device is preferably as follows: anode—hole-injection layer—hole-transport layer—emitting layer—electron-transport layer—electron-injection layer—cathode. It is not necessary for all of the said layers to be present, and further layers may additionally be present, for example an electron-blocking layer adjacent to the emitting layer on the anode side, or a hole-blocking layer adjacent to the emitting layer on the cathode side The organic electroluminescent device according to the invention may comprise a plurality of emitting layers. In this case, these emission layers particularly preferably have in total a plurality of emission maxima between 380 nm and 750 nm, resulting overall in white emission, i.e. various emitting compounds which are able to fluoresce or phosphoresce and which emit blue, green, yellow, orange or red light are used in the emitting layers. Particular preference is given to three-layer systems, i.e. systems having three emitting layers, where at least one of these layers preferably comprises at least one compound of one of the formulae (1) to (4) and where the three layers exhibit blue, green, yellow, orange or red emission (for the basic structure see, for example, WO 2005/011013). It should be noted that, for the generation of white light, an emitter compound used individually which emits in a broad wavelength range may also be suitable instead of a plurality of emitter compounds emitting in colour. Alternatively and/or additionally, the compounds according to the invention may also be present in the hole-transport layer or in another layer in an organic electroluminescent device of this type. The various emitting layers may be directly adjacent to one another, or they may be separated from one another by non-emitting layers. According to a preferred embodiment of the invention, a white-emitting OLED is a so-called tandem OLED, i.e. two or more complete OLED layer sequences are present in the OLED, where the OLED layer sequences in each case comprise hole-transport layer, emitting layer and electron-transport layer, which are each separated from one another by a charge-generation layer.

It is preferred for the compound of the formulae (1) to (4) to be employed in an emitting layer. The compound of the formulae (1) to (4) is particularly suitable for use as emitting compound or as a host in an emitting layer.

If the compound according to the invention is employed as emitting compound in an emitting layer, it is preferably employed in combination with one or more host materials.

The proportion of the emitting compound in the mixture of the emitting layer is between 0.1 and 50.0%, preferably between 0.5 and 20.0%, particularly preferably between 1.0 and 10.0%. Correspondingly, the proportion of the host material or hosts materials is between 50.0 and 99.9%, preferably between 80.0 and 99.5%, particularly preferably between 90.0 and 99.0%.

The specifications of the proportions in % are, for the purposes of the present application, taken to mean % by vol. if the compounds are applied from the gas phase and % by weight if the compounds are applied from solution.

If the compound according to the invention is employed as host material, it can be employed in combination with all known emitting compounds.

If the compound of the formulae (1) to (4) is employed as host in combination with a phosphorescent emitter in an emitting layer, the phosphorescent emitter is preferably selected from the embodiments of phosphorescent emitters indicated above for Y. In this case, one or more further host materials are furthermore preferably present in the emitting layer.

So-called mixed-host systems of this type preferably comprise two or three different host materials, particularly preferably two different host materials. One of the two materials here is preferably a material having hole-transporting properties and the other material is a material having electron-transporting properties.

However, the desired electron-transporting and hole-transporting properties of the mixed-hosts components may also be combined principally or completely in a single mixed-host component, where the further mixed-host component(s) fulfil other functions. The two different host materials here may be present in a ratio of 1:50 to 1:1, preferably 1:20 to 1:1, particularly preferably 1:10 to 1:1 and very particularly preferably 1:4 to 1:1. Mixed-hosts systems are preferably employed in phosphorescent organic electroluminescent devices. More precise information on mixed-hosts systems is given, inter alia, in the application WO 2010/108579.

Particularly suitable host materials which can be used in combination with the compounds according to the invention as host components of a mixed-host system are selected from the preferred host materials indicated above for Y, depending on what type of emitting compound is employed in the mixed-host system.

Generally preferred classes of material for use as corresponding functional materials in the organic electroluminescent devices according to the invention, besides those which are already described above, are indicated below.

Besides the phosphorescent emitting compounds described above, other suitable phosphorescent emitting compounds are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as are used in accordance with the prior art for phosphorescent OLEDs and as are known to the person skilled in the art in the area of organic electroluminescent devices are suitable for use in the devices according to the invention. The person skilled in the art will also be able, without inventive step, to employ further phosphorescent complexes in combination with the compounds according to the invention in OLEDs.

Besides the fluorescent emitting compounds described above, other suitable fluorescent emitting compounds are the indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847, and the indenofluorene derivatives containing condensed aryl groups which are disclosed in WO 2010/012328, the pyrenarylamines disclosed in WO 2012/048780 and WO 2013/185871, the benzoindenofluorenamines disclosed in WO 2014/037077, the benzofluorenamines disclosed in EP 2941472 and the indenofluorenes disclosed in EP3057947.

Suitable charge-transport materials, as can be used in the hole-injection or hole-transport layer or electron-blocking layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

Examples of preferred hole-transport materials which can be used besides the compounds of the formulae (1) to (4) in a hole-transport, hole-injection or electron-blocking layer in the electroluminescent device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or WO 2013/120577), fluorenamines (for example in accordance with EP 2875092, EP 2875699 and EP 2875004), spirodibenzopyranamines (for example in accordance with WO 2013/083216) and dihydroacridine derivatives (for example in accordance with WO 2012/150001).

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, Li$_2$O, BaF$_2$, MgO, NaF, CsF, Cs$_2$CO$_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiO$_x$, Al/PtO$_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formulae (1) to (4) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds according to the invention can be employed in displays, as light sources in lighting applications and as light sources in medical and/or cosmetic applications (for example light therapy).

EXAMPLES

A) Y is a Fluorescent Emitting Group a-1) Syntheses Examples

The following syntheses are generally performed under a protective gas atmosphere and with dried solvents.

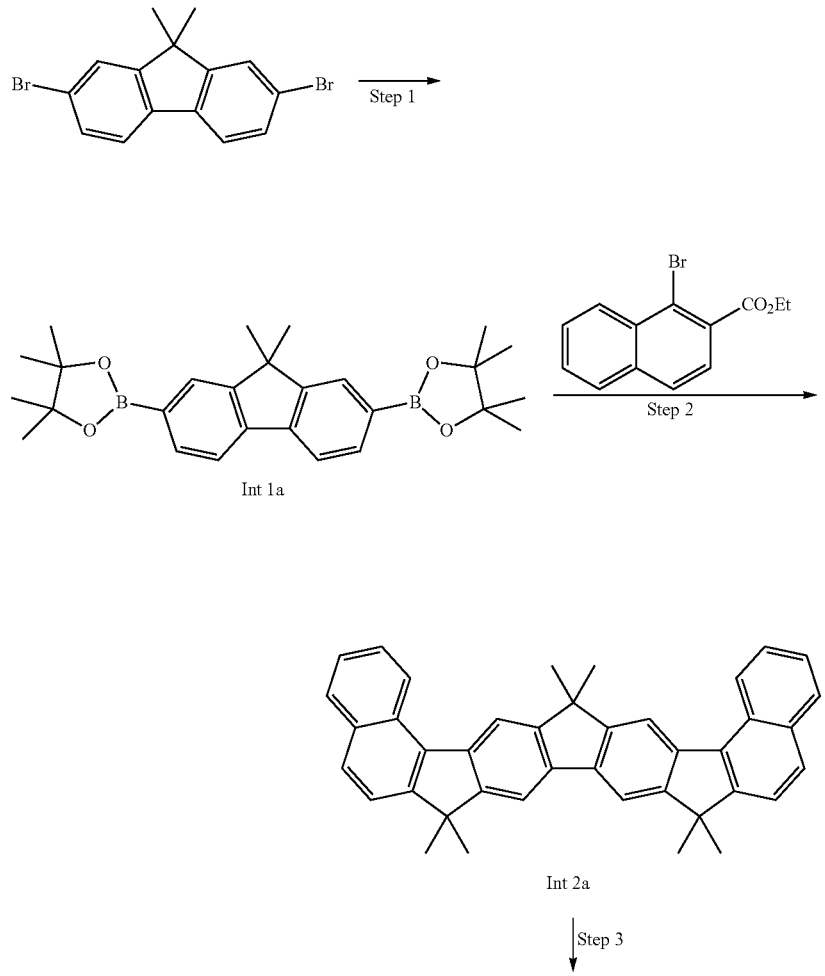

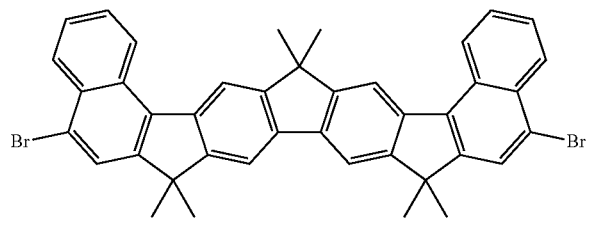

Int 3a

Step 1: Suzuki-Miyaura borylation, Pd catalysis
Step 2: Suzuki cross-coupling (Pd); Me-Grignard addition; Condensation
Step 3: Bromination Int 1a:
2,7-Dibromo-9,9-dioctyl-9H-fluorene (100 g, 0.17 mol), bis(pinacolato)-diboron (94.9 g, 0.37 mol) and potassium acetate (50 g, 0.51 mol) are suspended in 1.4 L dioxane. The solution is saturated with argon. $PdCl_2(dppf)$-$CH_2Cl_2$ (4.2 g, 0.01 mol) is added. The reaction mixture is refluxed for 16 h and then cooled to room temperature. Ethyl acetate and water are added. The organic phase is washed with water (3×500 mL). The organic phase is concentrated under reduced pressure and the residue is purified by recrystallization from ethanol. The desired product Int 1a is obtained as a grey powder. Yield: 98 g (90%).

In analogous manner, the following compounds can be obtained:

| starting material | product Int 1 | yield |
|---|---|---|
| 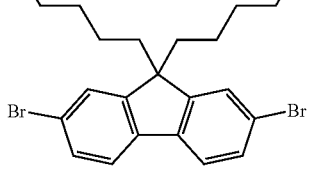 |  | 90% |
| | Int 1b | |

Int 2a:
Step 1: Int 1a (94 g, 0.146 mol), 1-bromo-naphthaline-2-carboxylic acid ethyl ester (104 g, 0.37 mmol) and sodium carbonate (56 g, 0.5 mol) are added to water/toluene/dioxane (1:1:1, 1.5 L). The solution is saturated with argon. Tetrakis(triphenylphosphin)-palladium(0) (15.2 g, 0.01 mol) is added and the reaction mixture is refluxed for 6 hours. After cooling down to room temperature toluene (500 mL) is added and the organic phase is washed with water (3×500 mL) and then concentrated under reduced pressure. The residue is purified by recrystallization from ethanol.

To 115 g (0.145 mol) of the recrystallized intermediate are added 145 g (0.60 mol) cerium(III) chloride and 500 mL THF, and the mixture is stirred for 30 minutes and cooled to 0° C. 390 mL (1.17 mol) methyl magnesiumchloride (3M in THF) is diluted in 1 L THF and added dropwise to the reaction mixture at 0° C. The reaction mixture is allowed to warm to room temperature. After 16 hours 800 ml sat. aq. ammonium chloride is added at 0° C. Ethyl acetate (2×500 mL) is added, the combined organic phases are washed with water (2×500 mL) and concentrated under reduced pressure. The residue is purified by recrystallization from ethanol.

To 103 g (0.14 mol) of the recrystallized intermediate is added 275 g amberlyst 15 and 1.5 L toluene. The reaction mixture is refluxed for 16 hours using a Dean-Stark apparatus. After cooling down to room temperature, the amberlyst is removed by filtration and the organic phase is concentrated under reduced pressure. The residue is purified by several recrystallizations from ethanol or heptane/toluene. The desired product Int 2a is obtained as a yellow solid. Yield: 73 g (70% over three steps).

In analogous manner, the following compounds can be obtained:

| starting material | product Int 2 | yield |
|---|---|---|
| 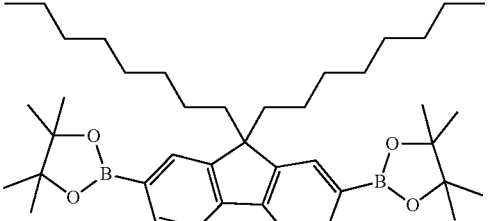<br>Int 1b | 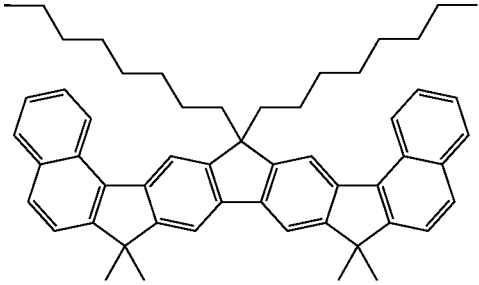<br>Int 2b | 70% |

Int 3a:

Int 2a (73 g, 101 mmol) is dissolved in 1 L DCM and cooled to −10° C. $Br_2$ (33.1 g, 207 mmol) in 500 mL DCM is added dropwise. The reaction mixture is stirred one hour at 0° C. and then allowed to warm to room temperature. After 16 hours, 20 mL sodium thiosulfate solution is added and the mixture is stirred for 15 minutes. Water (1 L) is added, the organic phase is washed with water (3×500 mL) and the combined organic phases are concentrated under reduced pressure. The purified product Int 3a is obtained by multiple recrystallizations from ethanol or heptane/toluene. Yield: 66.4 g (74%).

In analogous manner, the following compounds can be obtained:

| starting material | product Int 3 | yield |
|---|---|---|
| 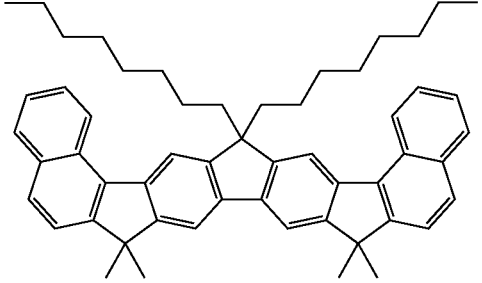<br>Int 2b | 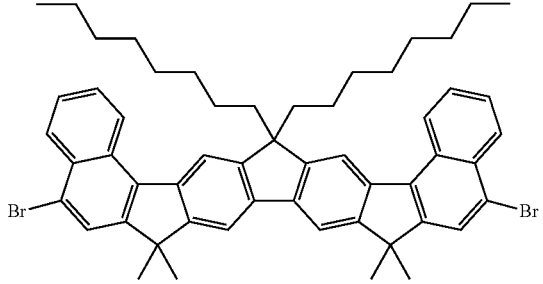<br>Int 3b | 70% |

General synthesis scheme 2

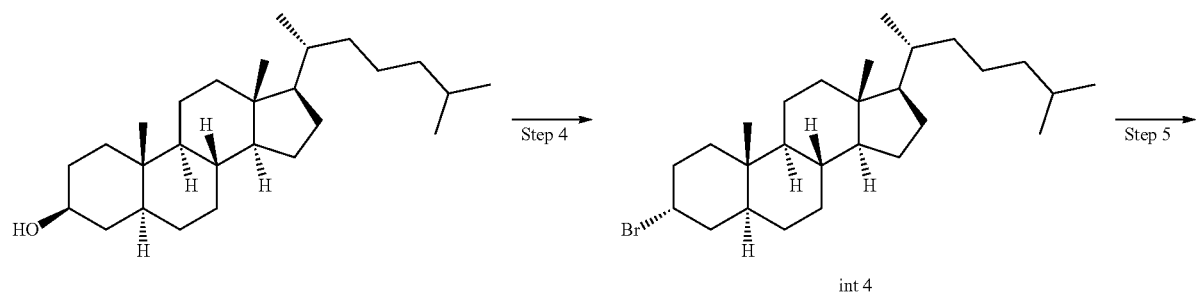
int 4

-continued

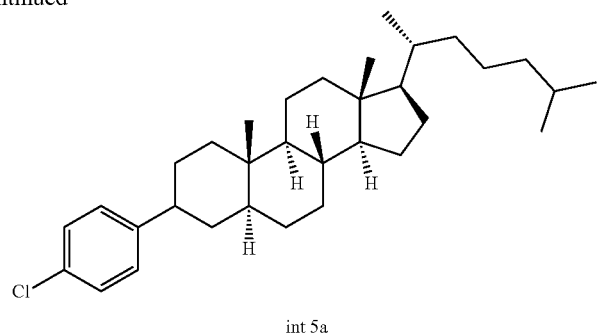
int 5a

Step 6 ↓

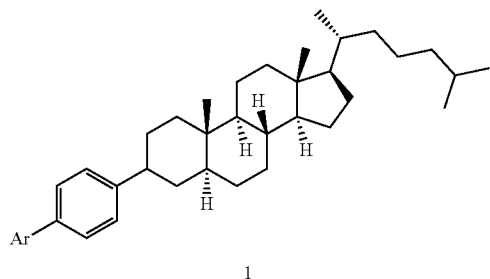
1

← Step 7

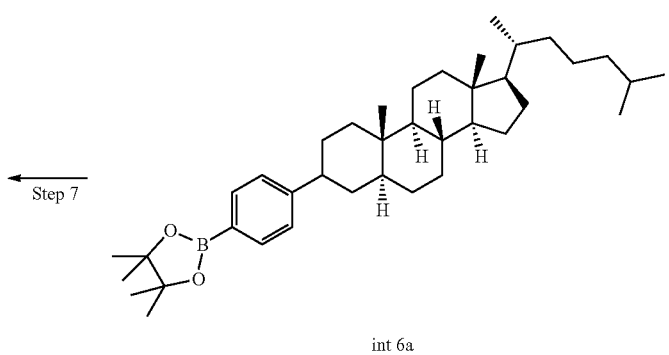
int 6a

Step 4: Appel reaction
Step 5: Alkyl Suzuki cross-coupling, Ni catalysis
Step 6: Suzuki-Miyaura borylation, Pd catalysis
Step 7: Suzuki cross-coupling, Pd catalysis Int 4:

To 5α-Cholestan-3β-ol (104 g, 267 mmol) and triphenylphosphine (140 g, 534 mmol) stirring in THF (500 mL) at 0° C. is added N-bromosuccinimide (95.0 g, 534 mmol) portionwise over 1 h. The heterogeneous orange reaction mixture is warmed to RT and stirred overnight. The reaction is quenched by addition of 2N aqueous HCl, and diluted with 500 mL EtOAc. The reaction mixture is filtered, and the precipitate washed further with EtOAc. The organic phase is collected, and the aqueous phase extracted with EtOAc. The combined organic phases are dried with Na2SO4, filtered, concentrated to a brown oil, and combined with the initial collected precipitate. The crude is extracted with heptane, filtered and concentrated. The filtrate is concentrated, and purified by recrystallization from a heptane/ethanol mixture. The desired product Int 4 is obtained as a colorless powder. Yield: 93.8 g (78%).

Int 5a:

To a dried reaction flask under Ar is added 4-chlorophenylboronic acid (44.1 g, 282 mmol), nickel(II) iodide (4.41 g, 14.1 mmol), trans-2-aminocyclohexanol (3.08 g, 14.1 mmol) and NaHMDS (86.1 g, 469 mmol). The flask is cooled to 0° C. and anhydrous iPrOH (500 ml) is added by addition funnel to the reagents over 30 min (caution: exothermic), resulting in a free flowing heterogeneous mixture. The reaction mixture is warmed to RT and Int 4 (106 g, 235 mmol) is added as a solid. The reaction mixture is heated to 70° C. and stirred overnight. The reaction mixture is then cooled to RT, and diluted with 1 L heptane and passed through a plug of SiO2. The eluent is concentrated to dryness, taken up in 1 L refluxing EtOH, and cooled to RT. The resulting precipitate is collected by filtration, washing with EtOH. The desired product Int 5a is collected as a colorless powder. Yield: 81.6 g (72%).

In analogous manner, the following compounds can be obtained:

| starting material | product Int 5 | yield |
|---|---|---|
| 3-chlorophenylboronic acid | Int 5b | 33% |
| 4'-chloro-[1,1'-biphenyl]-4-ylboronic acid | Int 5c | 53% |

Int 6a:

A mixture of Int 5a (81.5 g, 169 mmol), bispinacolatodiboron (78.7 g, 304 mmol), and potassium acetate (49.7 g, 506 mmol) in 1,4-dioxane (500 mL) is degassed by bubbling with Ar for 10 min, then trans-dichlorobis(tricyclohexylphosphine)palladium(II) (7.55 g, 10.1 mmol) is added and the reaction mixture is stirred under Ar at 100° C. overnight. The reaction mixture is cooled to RT, diluted with 500 mL toluene and filtered through Celite. The filtrate is concentrated, taken up in DCM and filtered through a plug of SiO2, and the eluent concentrated to dryness. The resulting crude material is purified by recrystallization from EtOH. The desired product Int 6a is obtained as a light gray powder. Yield: 88.1 g (91%).

In analogous manner, the following compounds can be obtained:

| starting material Int 5 | product Int 6 | yield |
|---|---|---|
| Int 5b | Int 6b | 83% |

| starting material Int 5 | product Int 6 | yield |
|---|---|---|
| Int 5c | 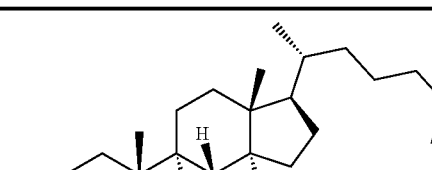 Int 6c | 88% |

Compound 1:

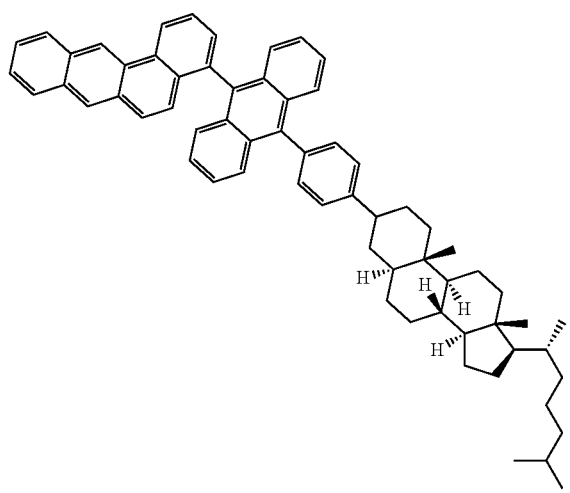

A mixture of 4-(10-Bromo-anthracen-9-yl)benzo[a]anthracene (4.83 g, 10.0 mmol), Int 6a (6.61 g, 11.5 mmol), and sodium carbonate (2.12 g, 20.0 mmol) in a toluene (100 ml)/dioxane (100 ml)/water (100 ml) solvent mixture is degassed by Ar sparging for 15 min. To the reaction mixture is then added tetrakis(triphenylphosphine)palladium(0) (580 mg, 0.50 mmol), and the mixture is heated to 95° C. with stirring overnight. The reaction mixture is cooled to RT, and the organic phase is extracted with toluene. The combined organics are concentrated and further purified by filtration through silica (eluting with toluene) and hot extraction through basic aluminum oxide (eluting with a toluene/heptane mixture). The desired product 1 is obtained as a colorless powder. Yield: 7.8 g (92%).

In analogous manner, the following compounds can be obtained:

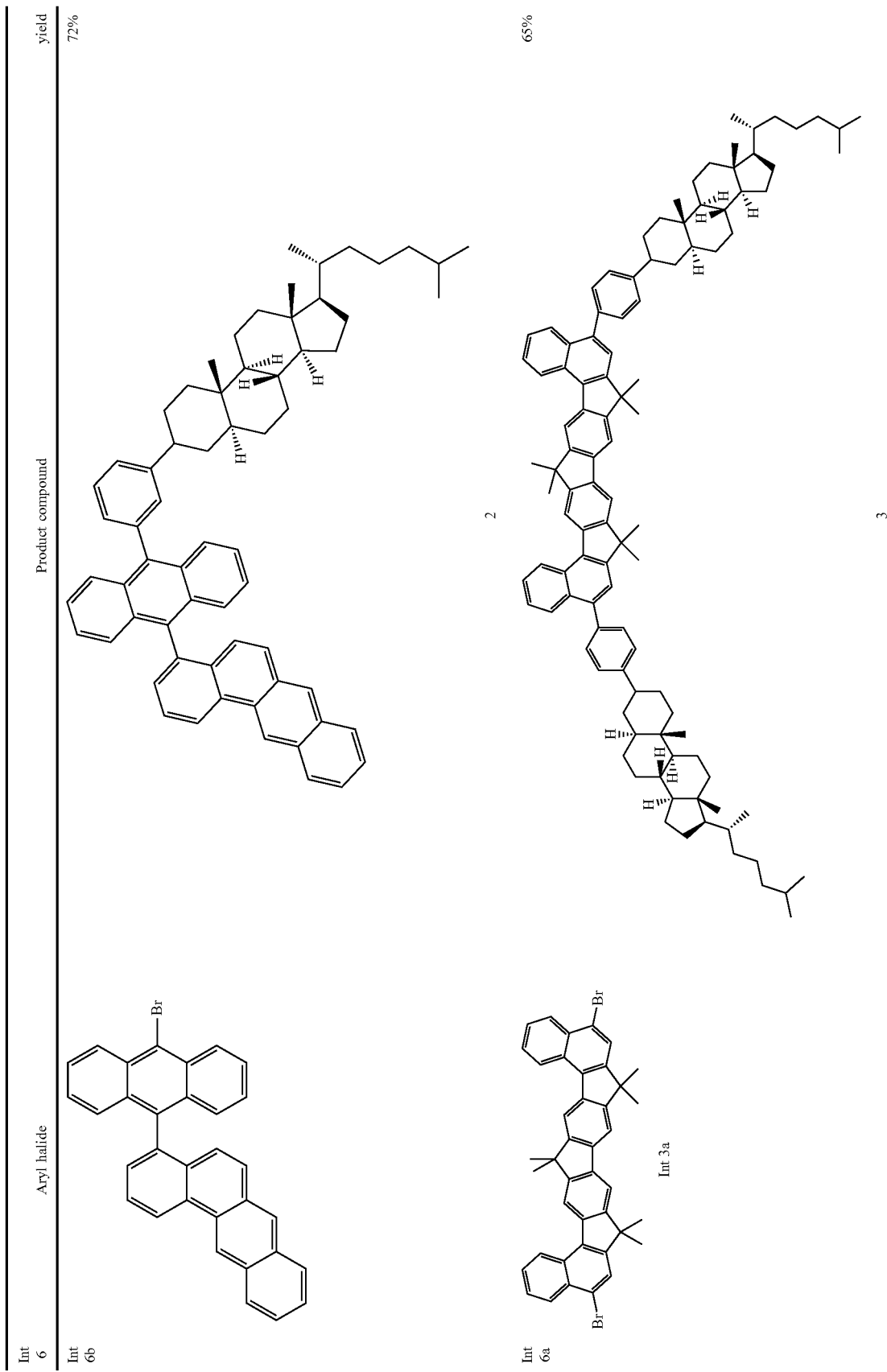

| Int | Aryl halide | Product compound | yield |
|---|---|---|---|
| 6 | | | |
| Int 6c | 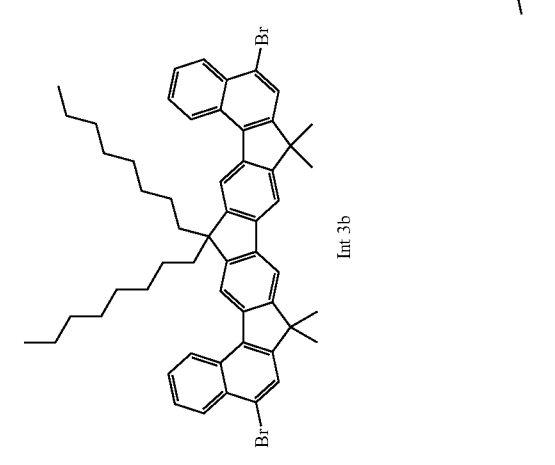 Int 3b | 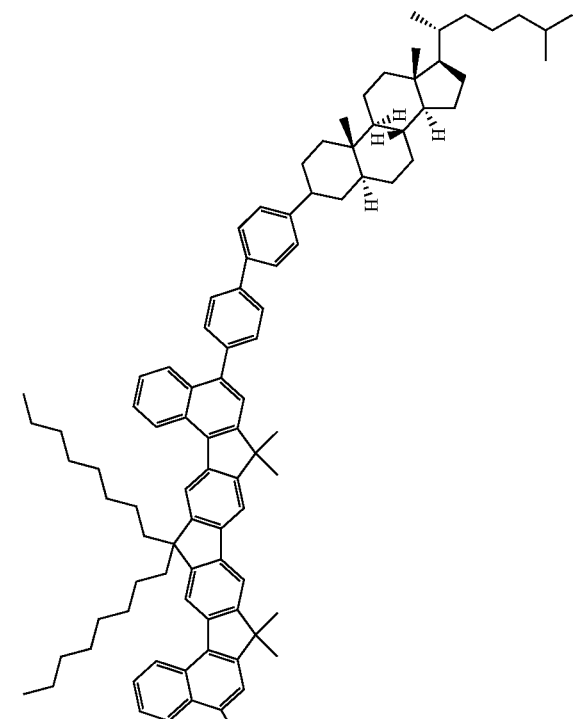 4 | 90% | a-2) Fabrication of OLEDs

Device Examples Processed from Solution

The production of solution-based OLEDs is described in principle in the literature, for example in WO 2004/037887 and WO 2010/097155. In the following examples, the two production methods (application from gas phase and solution processing) were combined, so that processing up to and including the emission layer was carried out from solution and the subsequent layers (hole-blocking layer/electron-transport layer) were applied by vacuum vapour deposition. The general processes described above are for this purpose adapted to the circumstances described here (layer-thickness variation, materials) and combined as follows.

The device structure used is thus as follows:
substrate,
ITO (50 nm),
PEDOT (20 nm),
hole-transport layer (HTL) (20 nm),
emission layer (92% of host, 8% of dopant) (60 nm),
electron-transport layer (ETL) (20 nm),
electron-injection layer (EIL) (3 nm)
cathode (Al) (100 nm).

The substrates used are glass plates coated with structured ITO (indium tin oxide) in a thickness of 50 nm. For better processing, these are coated with the buffer (PEDOT) Clevios P VP Al 4083 (Heraeus Clevios GmbH, Leverkusen). The spin coating of the buffer is carried out from water in air. The layer is subsequently dried by heating at 180° C. for 10 minutes. The hole-transport and emission layers are applied to the glass plates coated in this way.

The hole-transport layer is the polymer of the structure shown in Table 2, which was synthesised in accordance with WO 2010/097155. The polymer is dissolved in toluene, so that the solution typically has a solid content of approx. 5 g/l if, as here, the layer thickness of 20 nm which is typical for a device is to be achieved by means of spin coating. The layers are applied by spin coating in an inert-gas atmosphere, in the present case argon, and dried by heating at 180° C. for 60 min.

The emission layer (EML) is always composed of at least one matrix material (host=H) and an emitting dopant (emitter=D). An expression such as H1 (92%): D1 (8%) here means that material H1 is present in the emission layer in a proportion by weight of 92% and dopant D1 is present in the emission layer in a proportion by weight of 8%. The mixture for the emission layer is dissolved in toluene. The typical solid content of such solutions is approx. 18 g/l if, as here, the layer thickness of 60 nm which is typical for a device is to be achieved by means of spin coating. The layers are applied by spin coating in an inert-gas atmosphere, in the present case argon, and dried by heating at 140° C. for 10 minutes. The materials used are shown in Table 2.

The materials for the electron-transport layer, the electron-injection layer and for the cathode are applied by thermal vapour deposition in a vacuum chamber. The electron-transport layer, for example, may consist of more than one material, which are admixed with one another in a certain proportion by volume by co-evaporation. An expression such as ETM:EIL (50%:50%) would mean that materials ETM and EIL are present in the layer in a proportion by volume of 50% each. The materials used in the present case are shown in Table 2.

The OLEDs are characterised by standard methods. For this purpose, the electroluminescence spectra are recorded, the current efficiency (measured in cd/A) and the external quantum efficiency (EQE, measured in percent) as a function of the luminous density assuming Lambert emission characteristics are calculated from current/voltage/luminous density characteristic lines (IUL characteristic lines), and finally the lifetime of the components is determined. The electroluminescence spectra are recorded at a luminous density of 1000 cd/m$^2$, and the CIE 1931 x and y colour coordinates are calculated from this data. The term EQE @ 1000 cd/m$^2$ denotes the external quantum efficiency at an operating luminous density of 1000 cd/m$^2$. The data obtained for the various OLEDs are summarised in Table 1.

Use of Compounds According to the Invention as Fluorescent Emitting Compounds in Organic Light Emitting Diodes Emitting compounds D1 and D2 correspond to compounds according to the invention. The state-of-the-art compound for comparison is represented by V-D1. All emitting compounds are used in combination with either host H1 or H2.

Examples E1 to E4 show in a comparative examination with Comparative Examples V1 and V2 that according to the invention, compounds D1 and D2 achieve an improved external quantum efficiency (EQE) with deeper-blue emission as compared to comparative material V-D1. Especially the comparison of material V-D1 (Examples V1 and V2) with D2 (Examples E5 and E6) shows the technical effect of the present invention, in which appending a terpene-derived motif leads to an improved device performance compared to the state-of-the-art.

TABLE 1

OLED data

| Example | Host 92% | Emitting compound 8% | EQE @ 1000 cd/m$^2$ % | CIE x | CIE y |
|---|---|---|---|---|---|
| V1 | H1 | V-D1 | 6.0 | 0.145 | 0.105 |
| V2 | H2 | V-D1 | 5.7 | 0.145 | 0.108 |
| E1 | H1 | D1 | 6.5 | 0.147 | 0.076 |
| E2 | H2 | D1 | 6.5 | 0.148 | 0.078 |
| E3 | H1 | D2 | 7.5 | 0.146 | 0.090 |
| E4 | H2 | D2 | 7.3 | 0.145 | 0.094 |

TABLE 2
Structures of the materials used
| HTL | H1 | H2 |
|---|---|---|
| 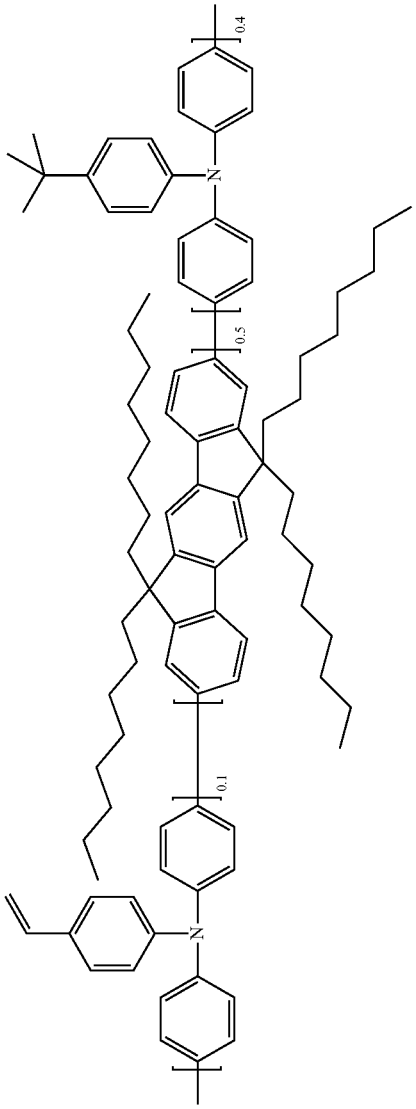 | 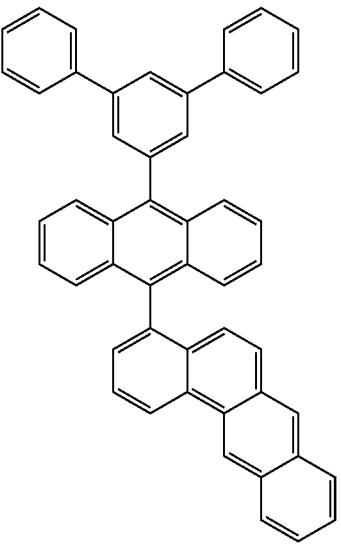 | 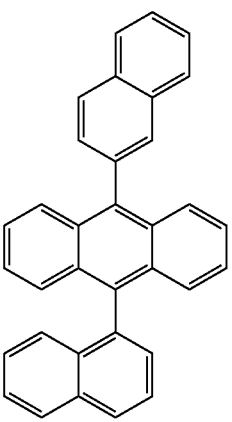 |

TABLE 2-continued
Structures of the materials used
| | |
|---|---|
| V-D1 | 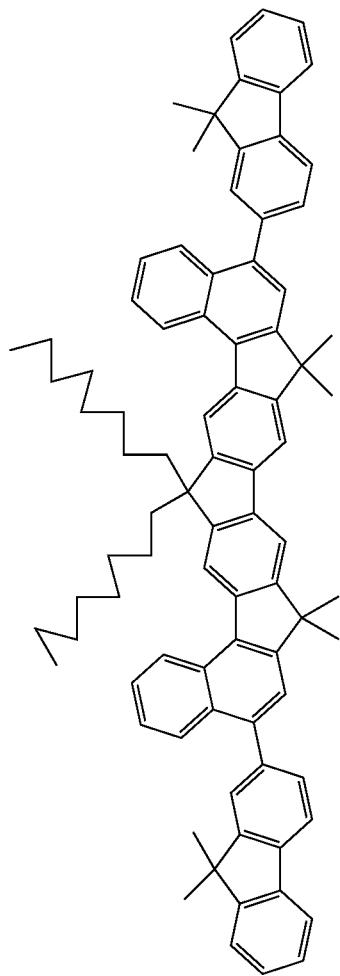 |
| D1 (compound 3) | 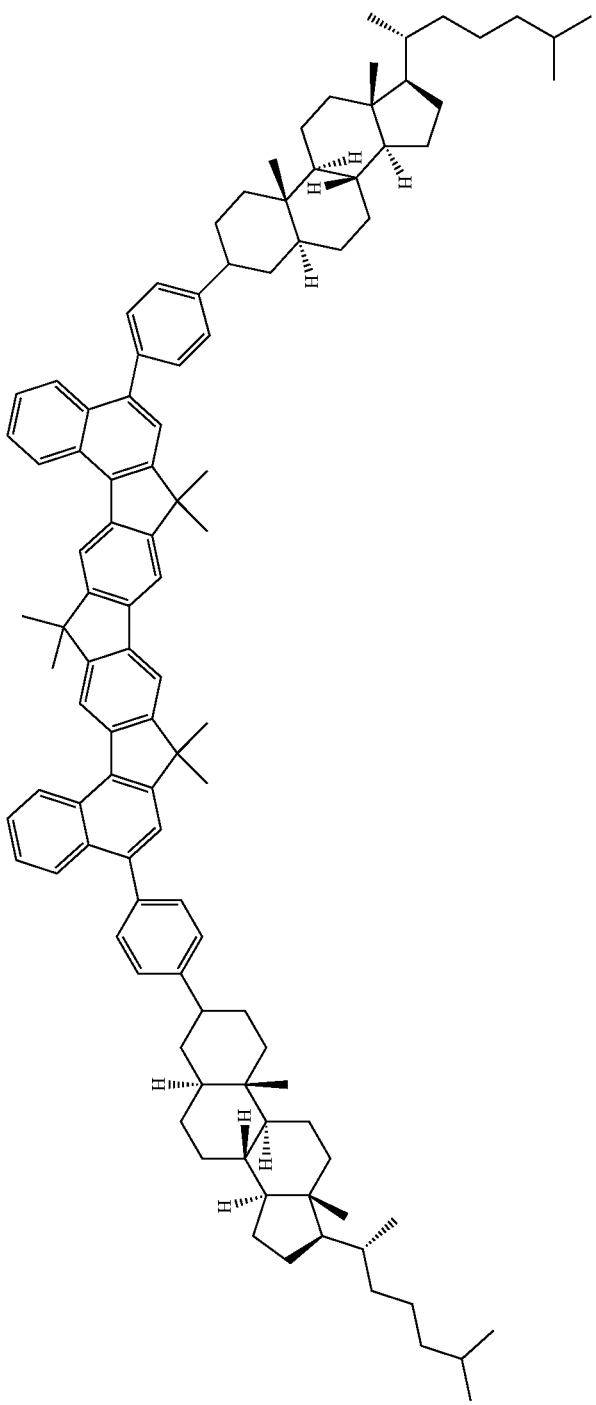 |

TABLE 2-continued
Structures of the materials used
| D2 (compound 4) | EIL |
|---|---|
| 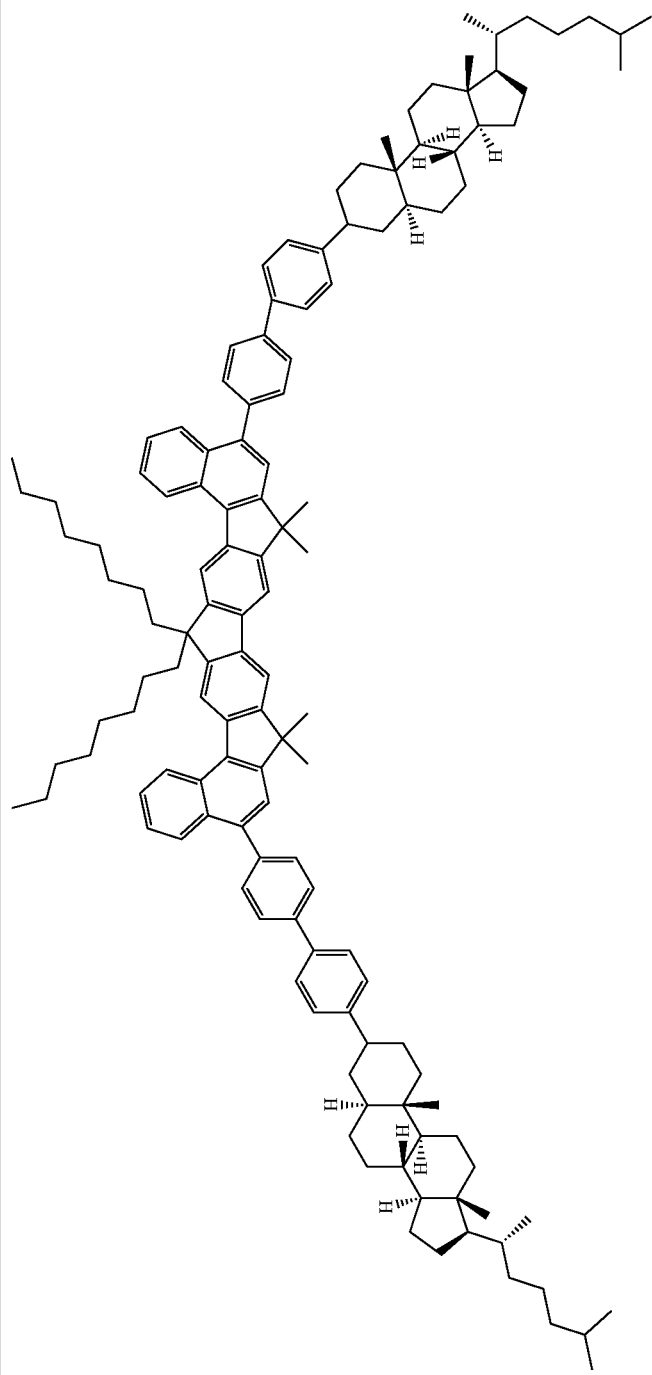 | 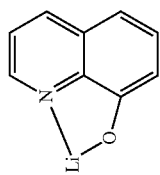 |

TABLE 2-continued
Structures of the materials used
ETL
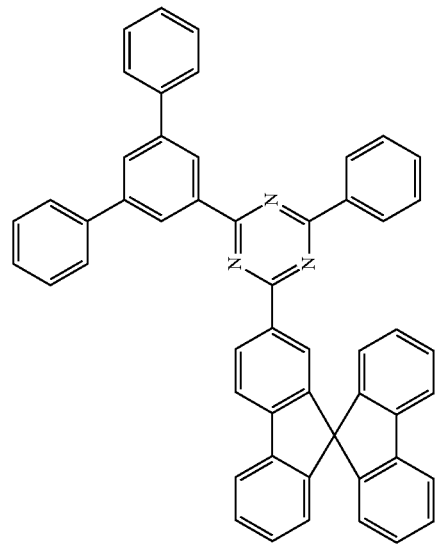

Compounds according to the invention possess good solubility and thus are well suitable for solution processing. By this technique, electronic devices based on blue fluorescent emitting compounds with excellent performance data can be generated.

Alternatively, or in addition, the compounds according to the invention may serve as host materials inside the emission layer (EML), as hole injection material (HIL), as hole transporting material (HTL), as electron transporting material (ETL) or as electron-injection material (EIL) in an organic light emitting diode.

B) Y is a Phosphorescent Emitting Group

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective FIGURES in square brackets or the numbers quoted for individual compounds relate to the CAS numbers of the compounds known from the literature.

b-1) Metal Organic Synthones Known from the Literature b-1-1) Bidentate Complexes Bromo-Functionalized Ligands MS

MS1

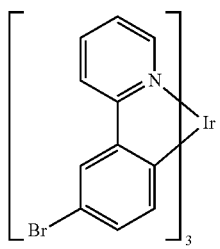

454454-92-3

MS2

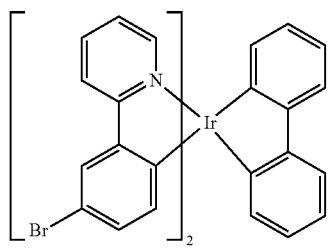

453538-21-1

MS3

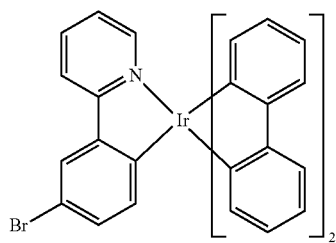

4554454-89-8

MS4

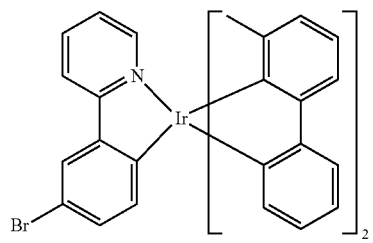

1149344-63-7

MS5

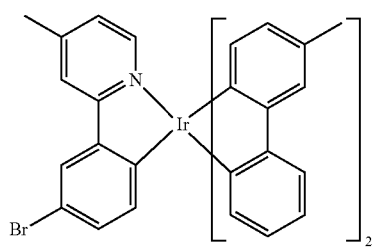

1149344-9-9

MS6

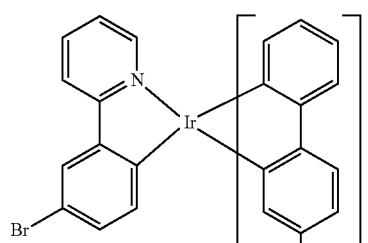

1252029-21-1

-continued
MS7
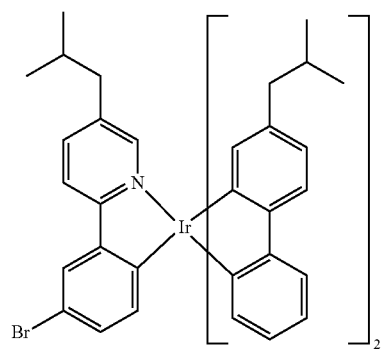
1149344-55-7
MS8
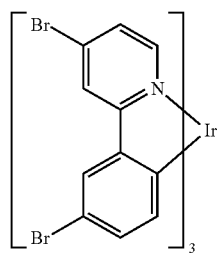
1309878-11-1
MS9
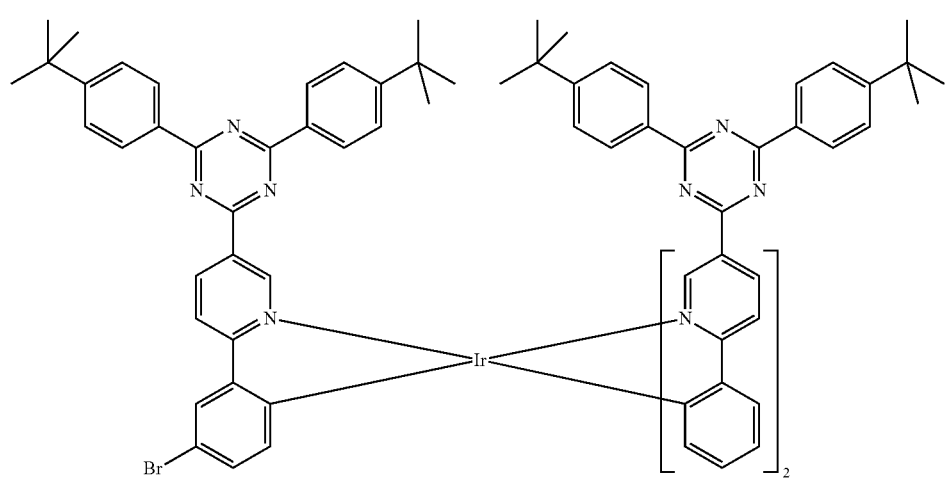
1820909-79-2
MS10
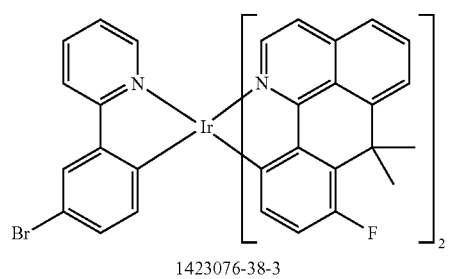
1423076-38-3
MS11
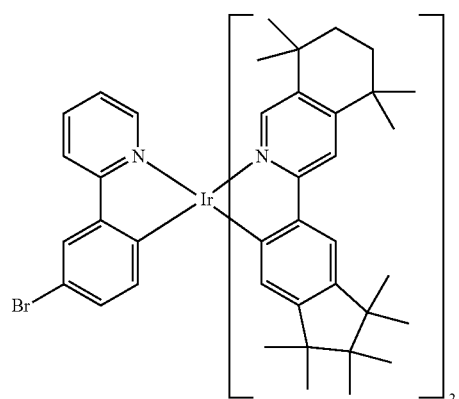
1803296-02-7

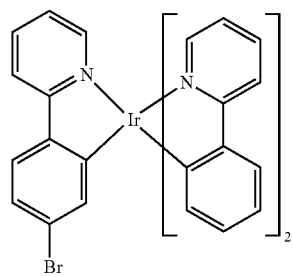
501330-36-5
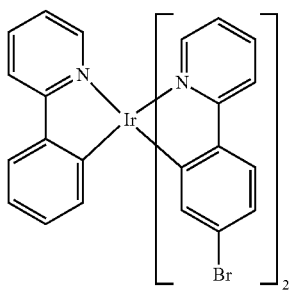
MS12
1627953-70-1
MS13
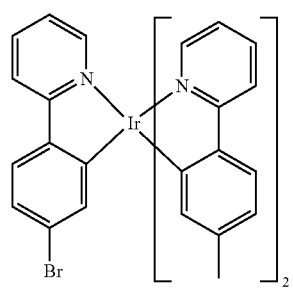
1455513-03-7
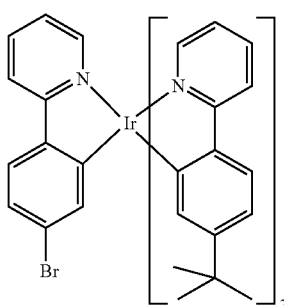
MS14
1252029-10-9
MS15
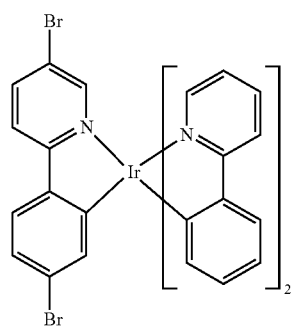
929088-09-5
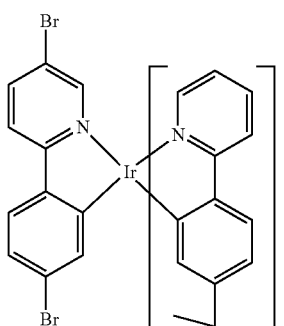
MS16
1252029-11-0
MS17
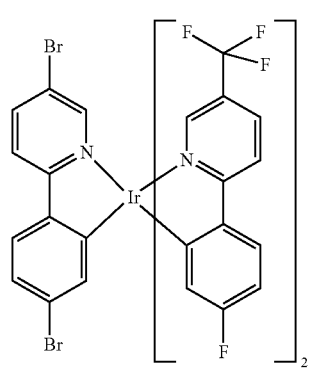
387859-69-0
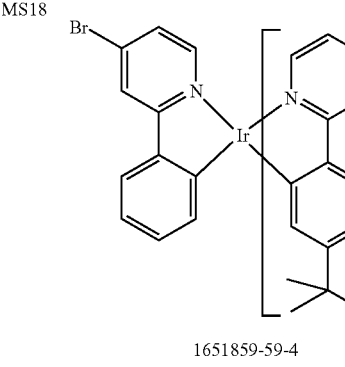
MS18
1651859-59-4
MS19

MS20
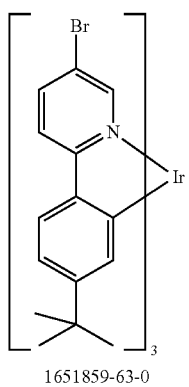
1651859-63-0
MS21
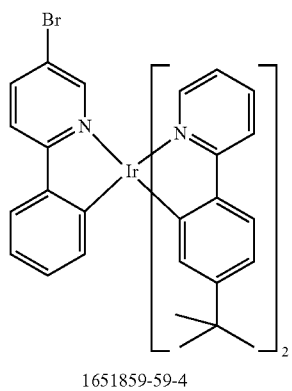
1651859-59-4
MS22
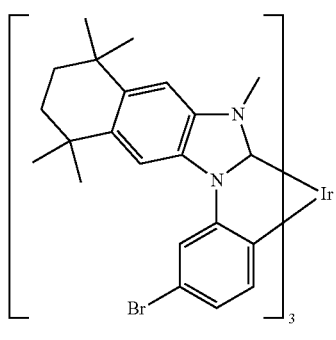
1803319-99-4
MS23
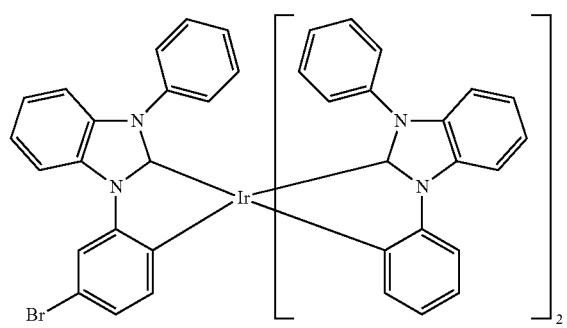
1651822-19-3
MS24
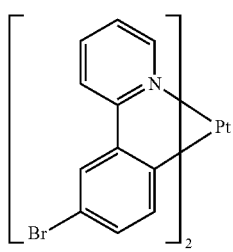
690269-08-0 b-1-2) Tripodale Complexes With Bromo-Functionalized Ligands PS (Syntheses are Described in the Patent Application WO2016/124304)
Tribromide
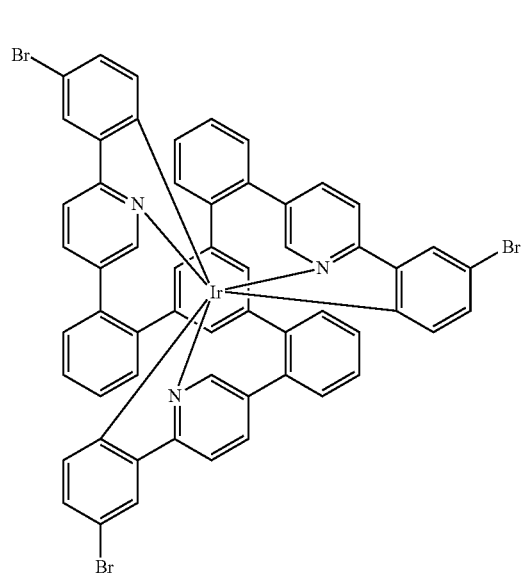
PS1
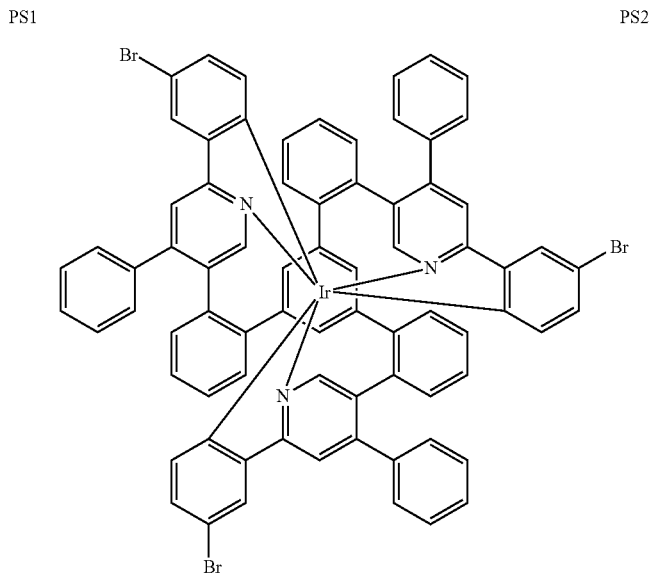
PS2
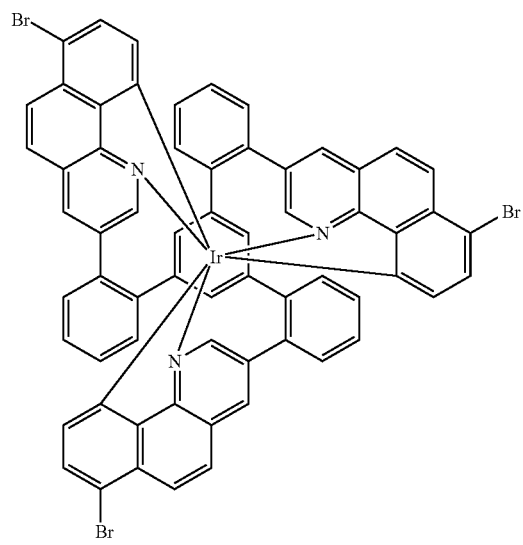
PS3
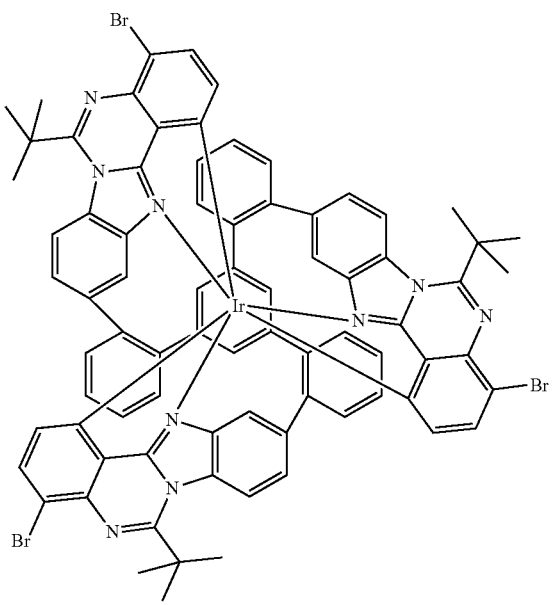
PS4

PS5
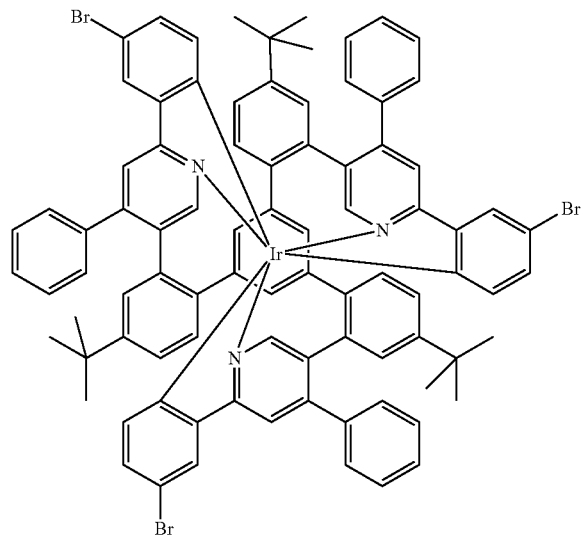
PS6
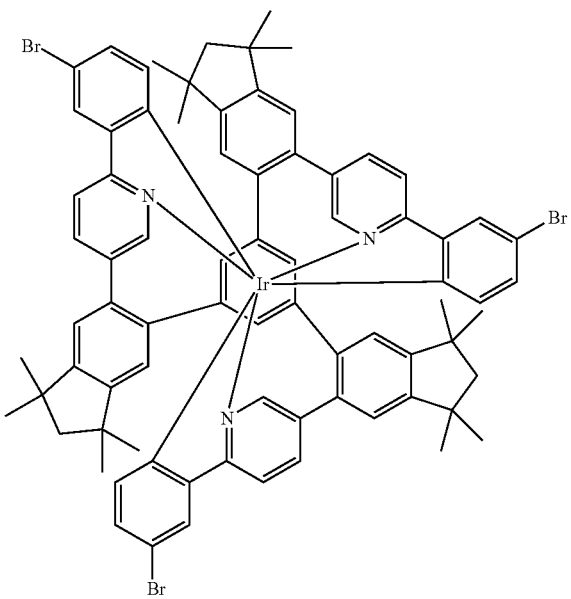
PS7
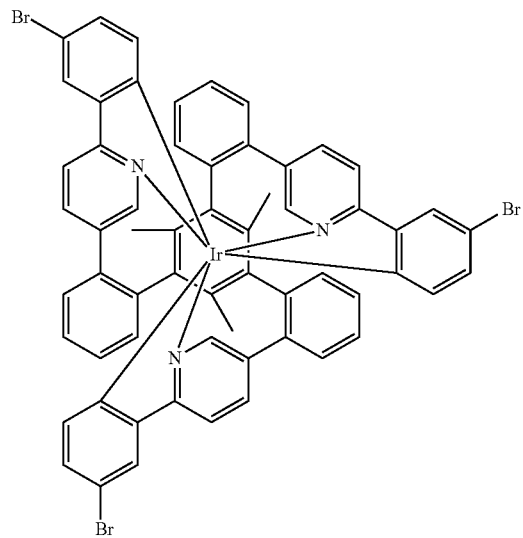
PS8
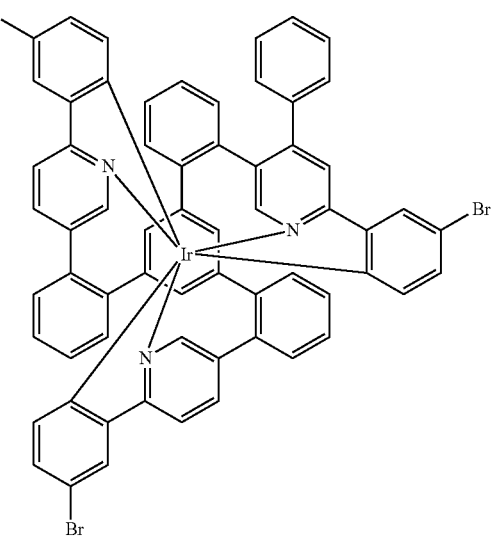

-continued
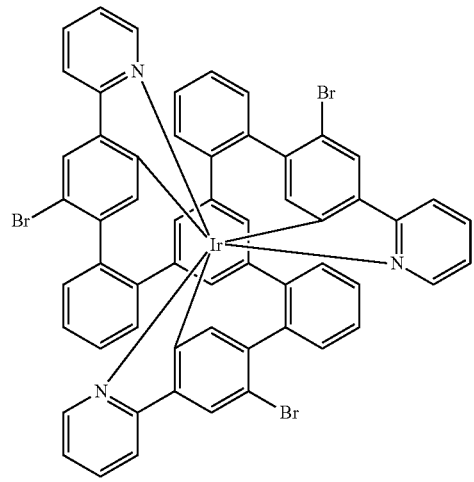
PS9
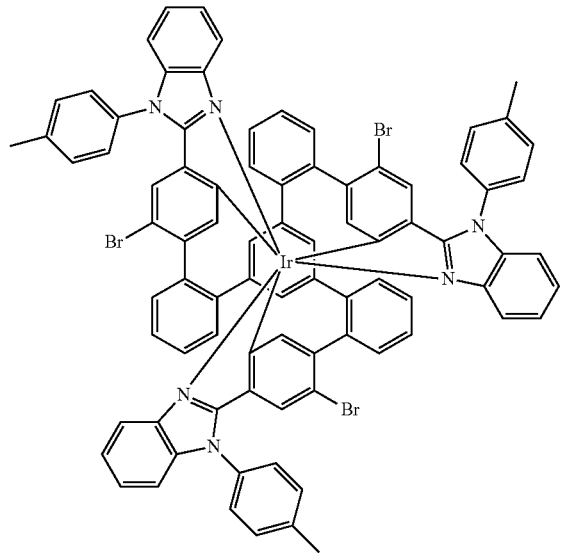
PS10
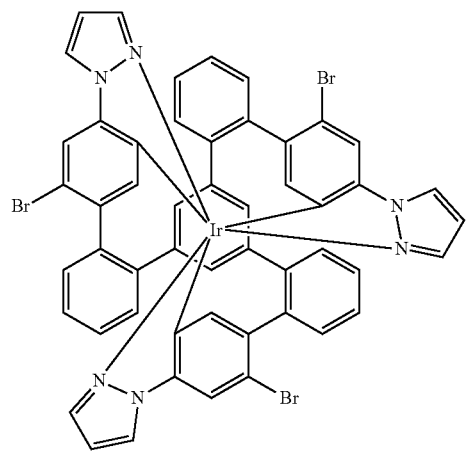
PS11
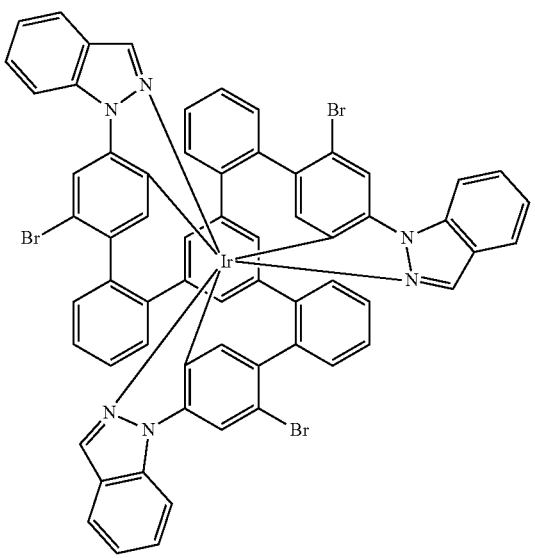
PS12

-continued
PS13
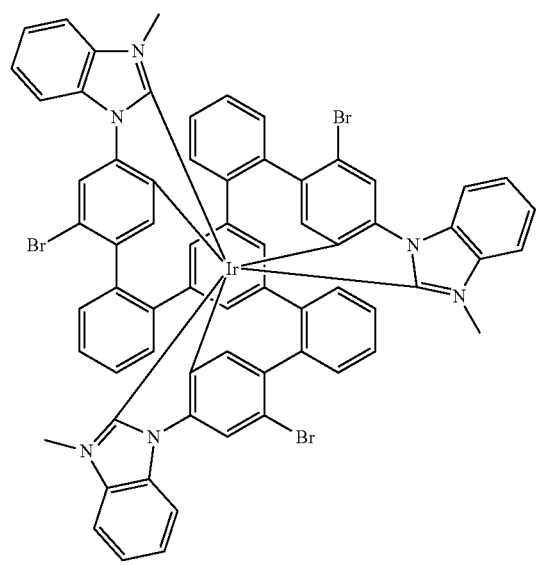
PS14
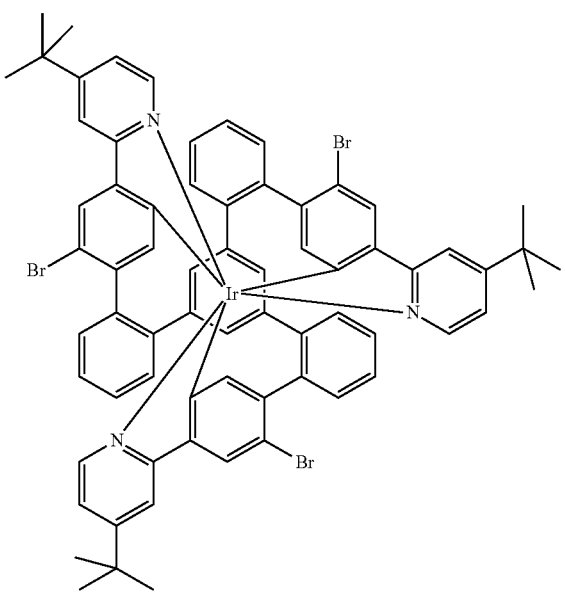
PS15
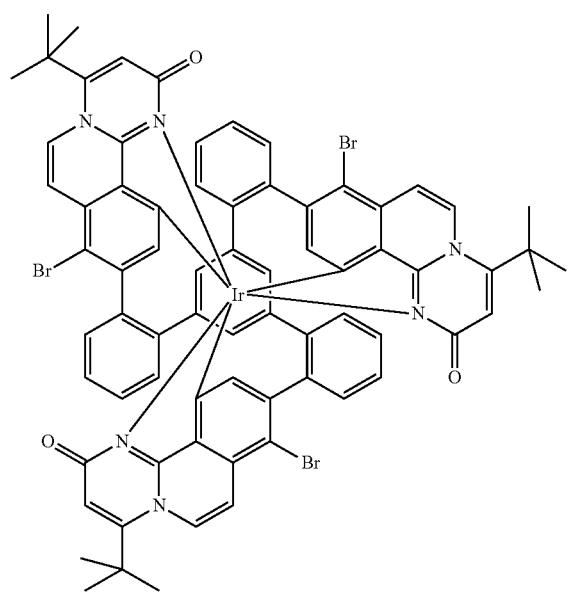
PS16
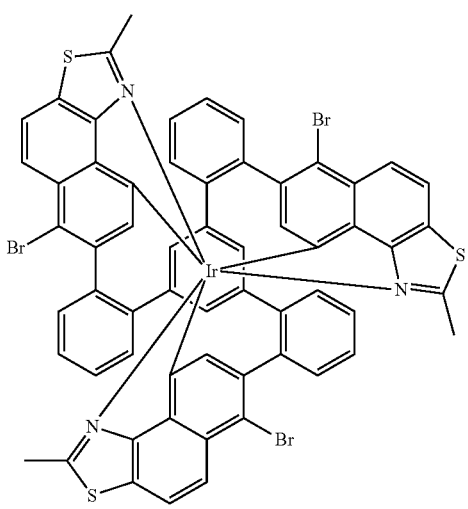

PS17
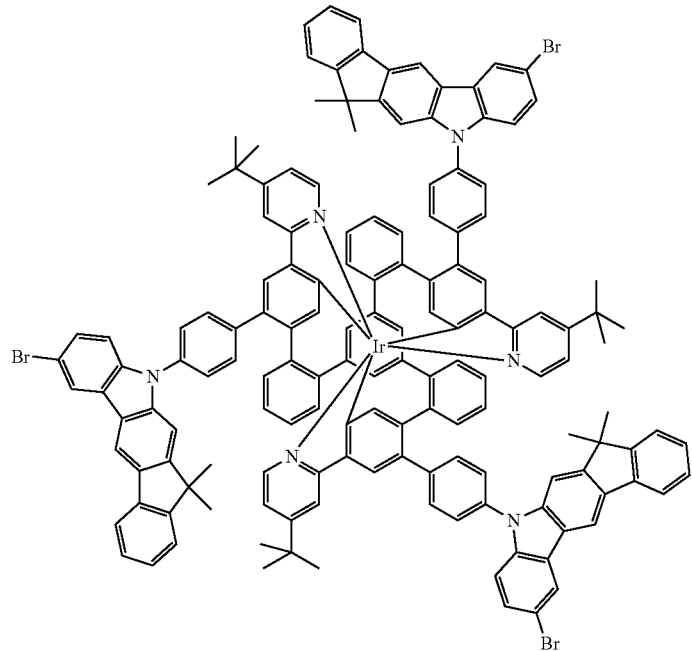
PS18
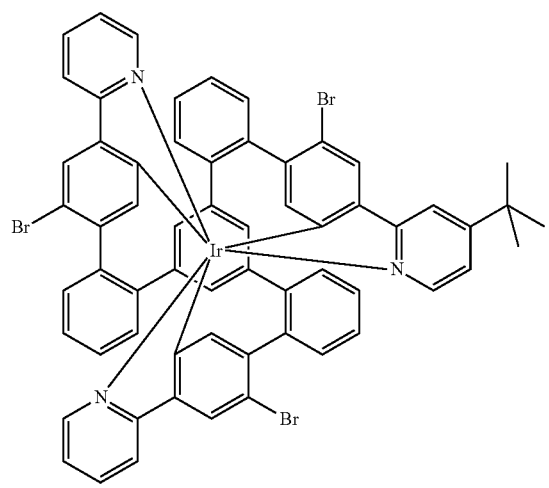
PS19
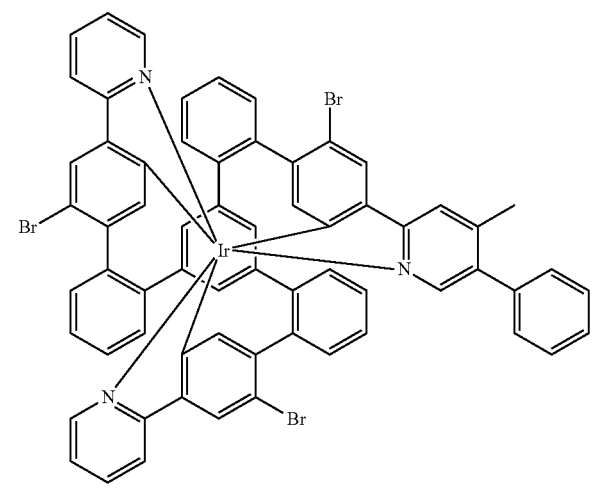

PS20
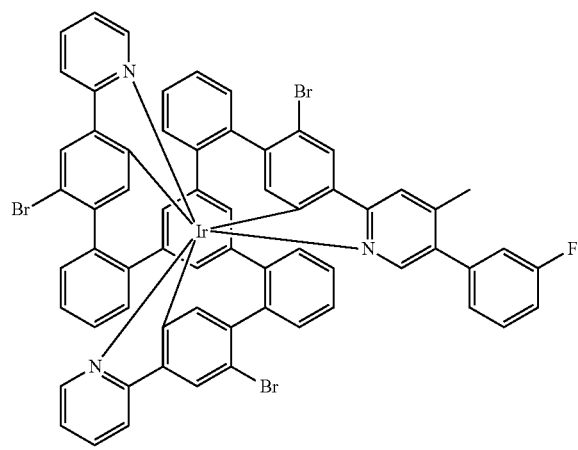
PS21
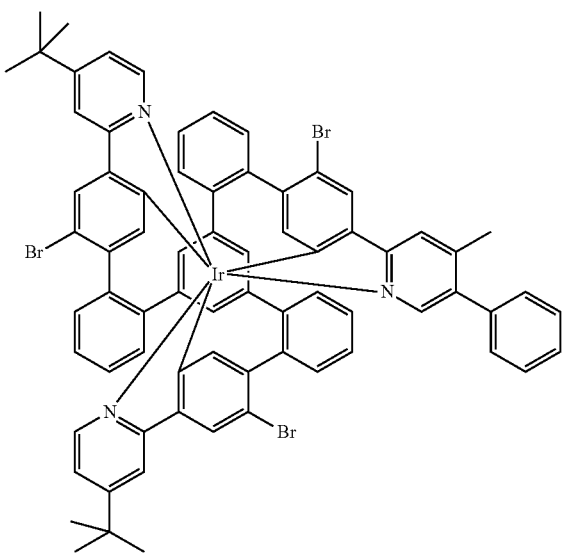
Dibromide
PS22
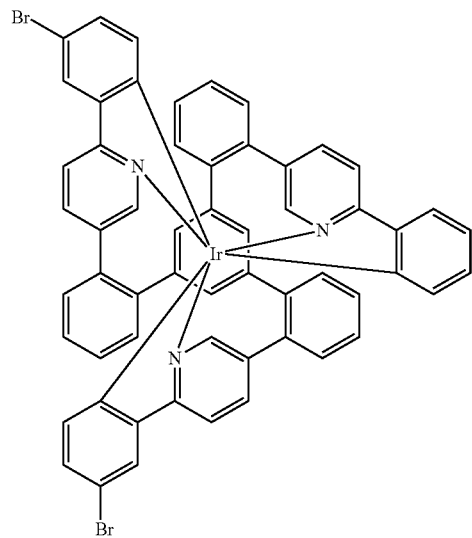
PS23
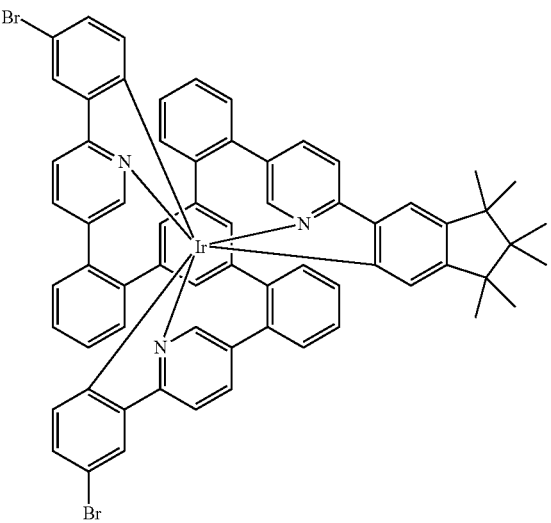

PS24
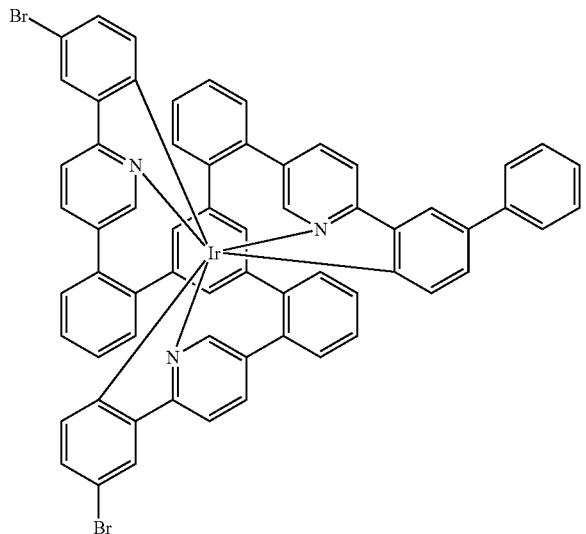
PS25
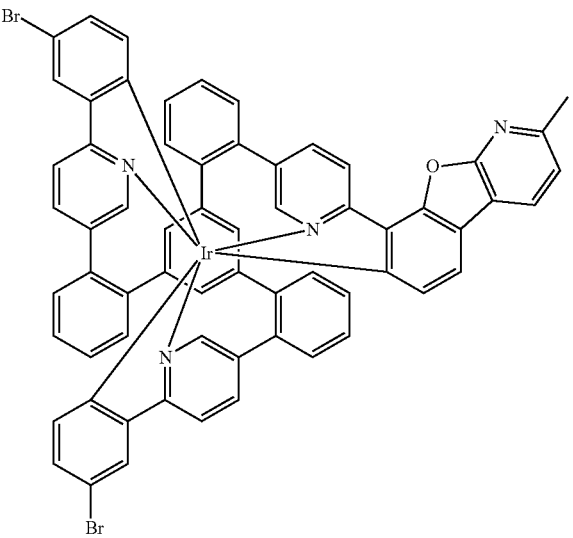
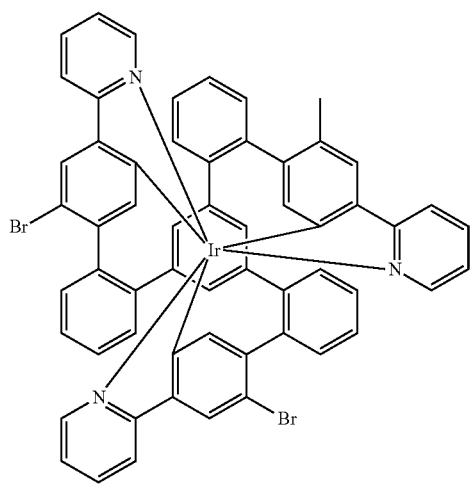
Monobromide
PS26
PS27
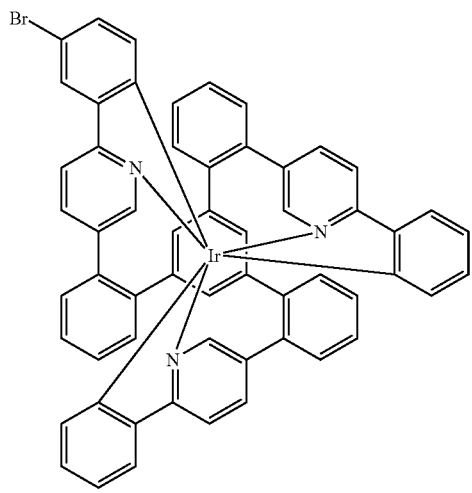
PS28
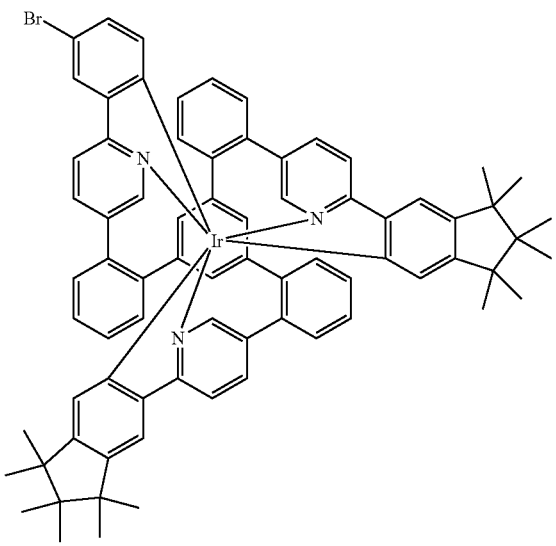

-continued

PS29
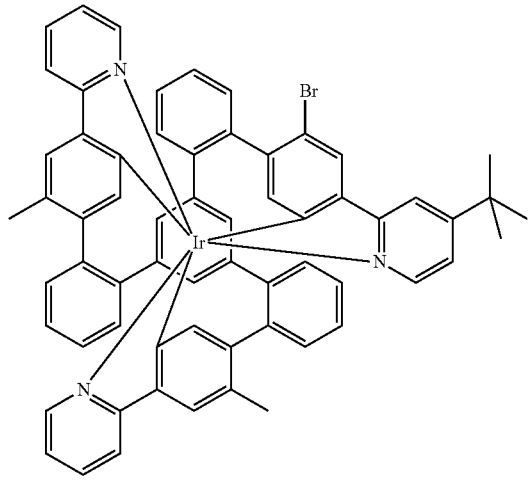

PS30
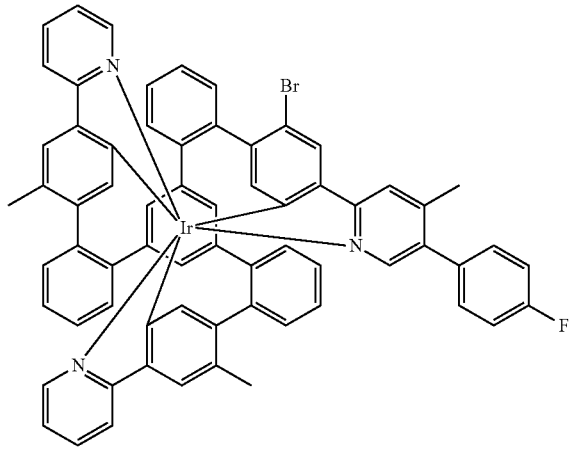

PS31
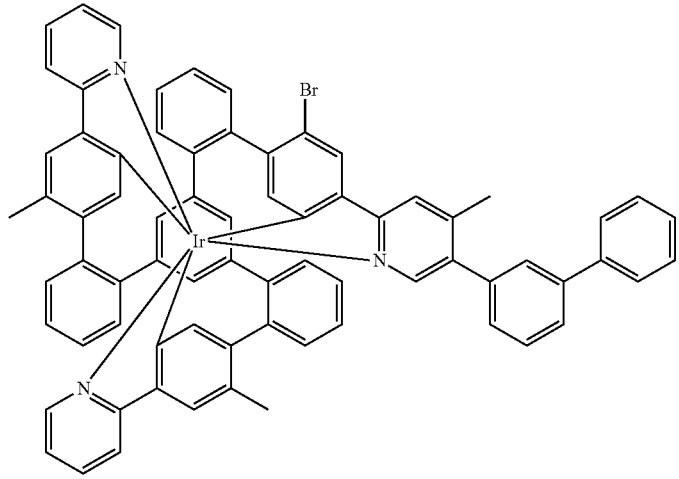

b-2) Synthesis of the Compounds According to the Invention: Suzuki Coupling with the Bromo-Functionalized Iridium Complexes Variant a, Two-Phase Reaction Mixture:

A suspension consisting of 10 mmol of a brominated complex, 12-20 mmol of boronic acid or boronic acid ester per Br-function and 40-90 mmol of tripotassium phosphate in a mixture of 200 ml of toluene, 100 ml of dioxane and 200 ml of water is mixed with 0.6 mmol Tri-o-tolylphosphine and then with 0.1 mmol of palladium(II)acetate and heated under reflux for 16 h. After cooling, 500 ml of water and 200 ml of toluene are added, the aqueous phase is separated from the organic phase, the organic phase is washed three times with 200 ml of water, then once with 200 ml of a saturated saline solution and dried over magnesium sulfate. The mixture is filtered through a Celite bed, washed with toluene, the toluene is removed almost completely in vacuum, 300 ml of methanol are added, the precipitated crude product is filtered, washed three times with 50 ml of methanol each time, and dried in vacuum. The crude product run through a silica gel column. The metal complex is finally annealed or sublimed. The annealing is carried out in the high vacuum (p approx. 10 6 mbar) in the temperature range of approx. 200-300° C.

Variant B, Single-Phase Reaction Mixture:

A suspension of 10 mmol of a brominated complex, 12-20 mmol of boronic acid or boronic acid ester per Br-function and 60-100 mmol of the base (potassium fluoride, tripotassium phosphate (anhydrous or monohydrate or trihydrate), potassium carbonate, cesium carbonate, etc.) and 100 g of glass beads (3 mm diameter) in 100 ml-500 ml of an aprotic solvent (THF, dioxane, xylene, mesitylene, dimethylacetamide, NMP, DMSO, etc.) is mixed with 0.6 mmol of tri-o-tolylphosphine and then with 0.1 mmol of palladium (II)Acetate and heated under reflux for 1-2 h. Alternatively, other phosphines such as, for example, triphenylphosphine, tri-tert-butylphosphine, Sphos, Xphos, RuPhos and Xanth-Phos can be used, the phosphine: palladium ratio being 3:1 to 1.2:1. The solvent is removed under vacuum, the product is mixed with a suitable solvent (toluene, dichloromethane, ethyl acetate, etc.) and purified as described in Variant A.

Variant C:

In the case of educt complexes, which are not very soluble, it may be advantageous to first carry out the Suzuki coupling according to variant B and to subject the obtained crude product to a new Suzuki coupling according to variant A in order to achieve a conversion as complete as possible. After the crude product has been isolated, remaining trace impurities of bromine can be removed by heating the crude product in toluene (100 ml) with 10 mg of palladium(II) cetate and 1 ml of hydrazine hydrate for 16 h. The crude product is then purified as described above.

Synthese Von Ir1

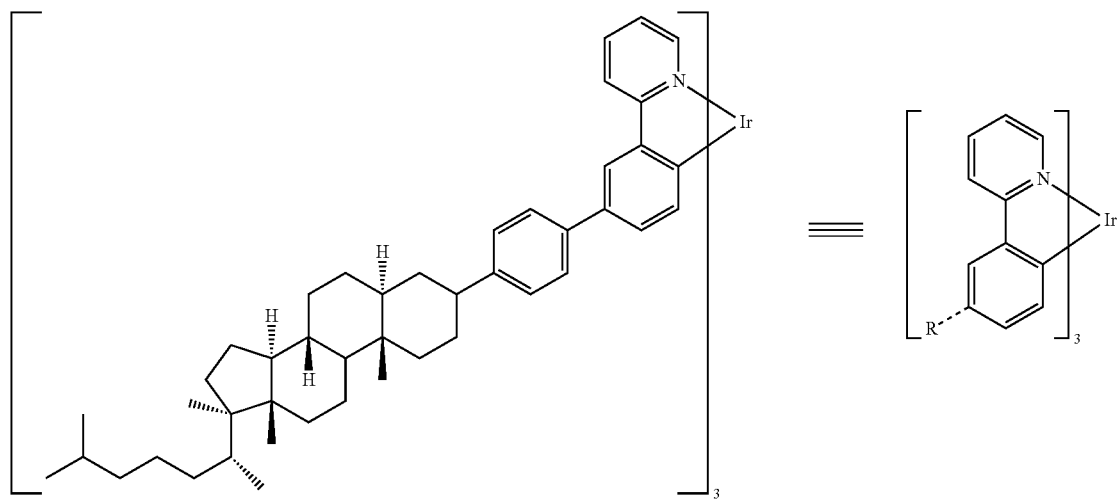

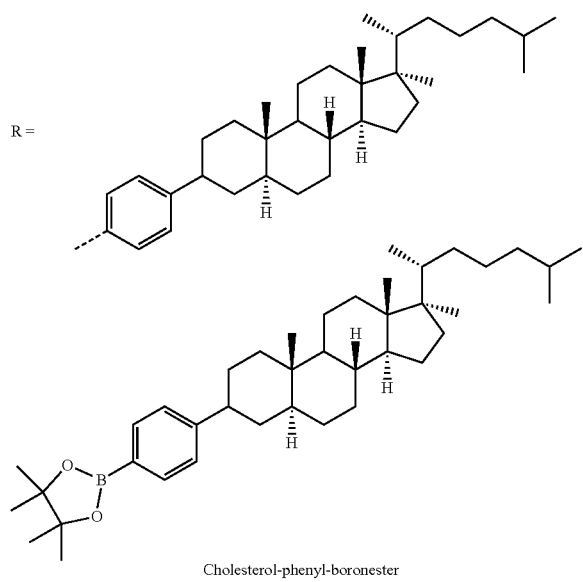

Cholesterol-phenyl-boronester

Variant A:

The reaction is carried out using 892 mg (1.0 mmol) of MS1 and 2355 mg (4 mmol) of cholesterol phenylboronester (see synthesis above), 1911 mg (9 mmol) of tripotassium phosphate (anhydrous), 183 mg (0.6 mmol) of tri-o-tolylphosphine [6163-58-2], 23 mg (0.1 mmol) of palladium (II)acetate, 20 ml of toluene, 10 ml of dioxane and 20 ml of water, under reflux for 16 h. Two chromatographic separation in silica gel with toluene/ethyl acetate are performed using an automatic column chromatography Torrent, Company A. Semrau. Yield: 1.365 g (0.67 mmol) 67%; Purity: approx. 99.9% after HPLC.

Analogously, the following compounds can be prepared by adapting the proportion of the molar amount of reactant with the molar amount of the bromine functionalities of the metal complexes:

| Product |
|---|
| Metal complex educt |
| Variant |
| Yield |
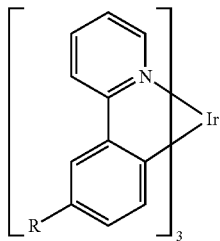
Ir1
MS1
B
53%
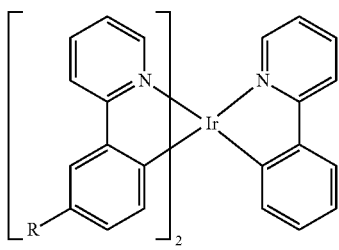
Ir2
MS2
A
57%
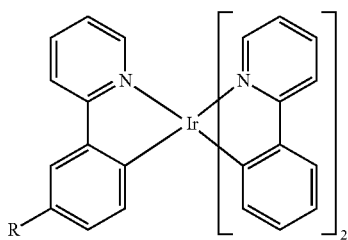
Ir3
MS3
C
65%
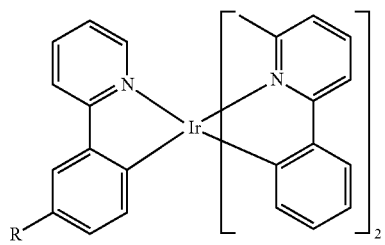
Ir4
MS4
C
63%

-continued
| Product |
|---|
| Metal complex educt |
| Variant |
| Yield |
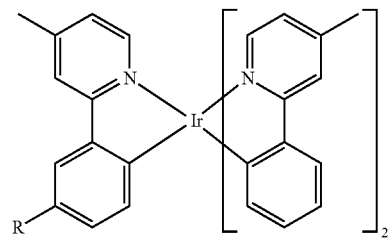
Ir5
MS5
C
60%
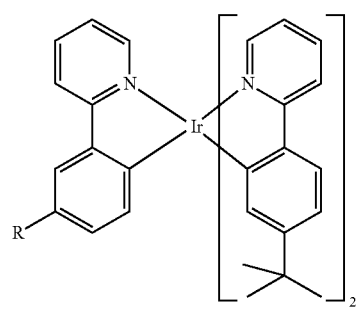
Ir6
MS6
B
64%
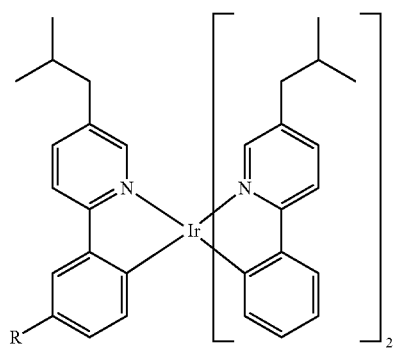
Ir7
MS7
C
67%

| |
|---|
| Product |
| Metal complex educt |
| Variant |
| Yield |
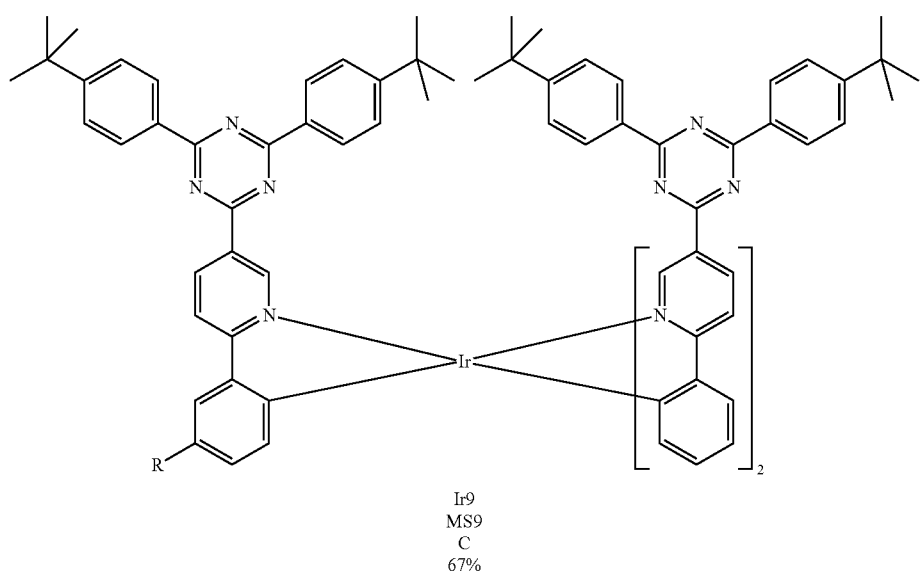
Ir8
MS8
C
45%
Ir9
MS9
C
67%
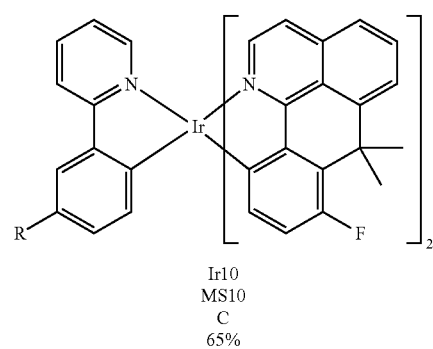
Ir10
MS10
C
65%

| Product |
| --- |
| Metal complex educt |
| Variant |
| Yield |
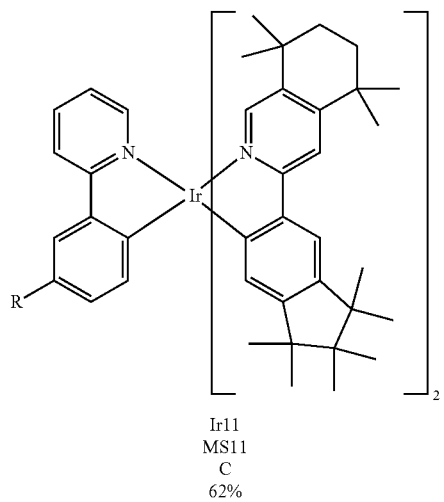
Ir11
MS11
C
62%
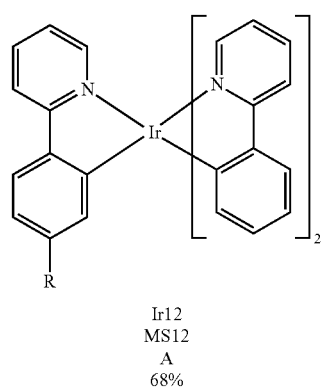
Ir12
MS12
A
68%
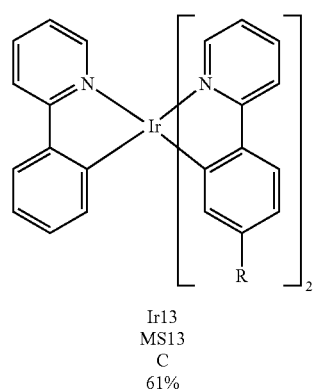
Ir13
MS13
C
61%

-continued
| Product |
|---|
| Metal complex educt |
| Variant |
| Yield |
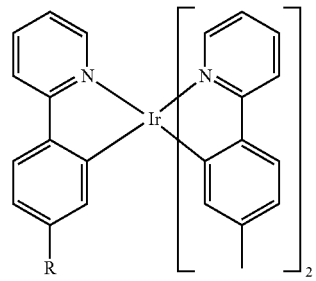
Ir14
MS14
C
68%
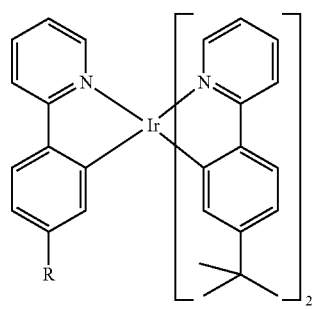
Ir15
MS15
B
66%
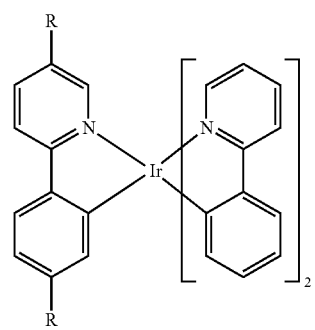
Ir16
MS16
C
59%

-continued

| Product |
|---|
| Metal complex educt |
| Variant |
| Yield |

Ir17
MS17
C
56%

Ir18
MS18
C
55%

Ir19
MS19
C
64%

-continued
| Product Metal complex educt Variant Yield |
|---|
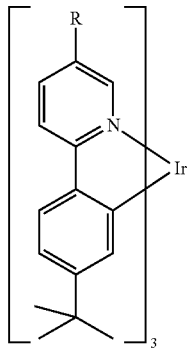
Ir20
MS20
C
47%
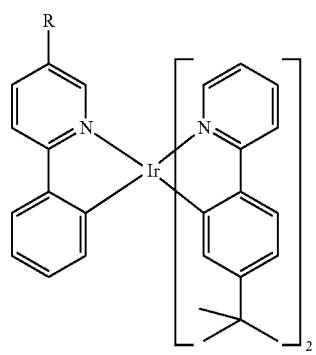
Ir21
MS21
C
67%
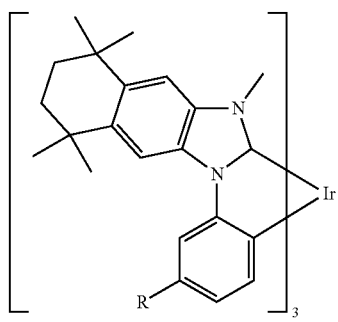
Ir22
MS22
C
55%

-continued

| Product |
|---|
| Metal complex educt |
| Variant |
| Yield |

Ir23
MS23
C
64%

Ir24
MS24
C
53%

Ir25
PS1
B
60%

| Product |
|---|
| Metal complex educt |
| Variant |
| Yield |
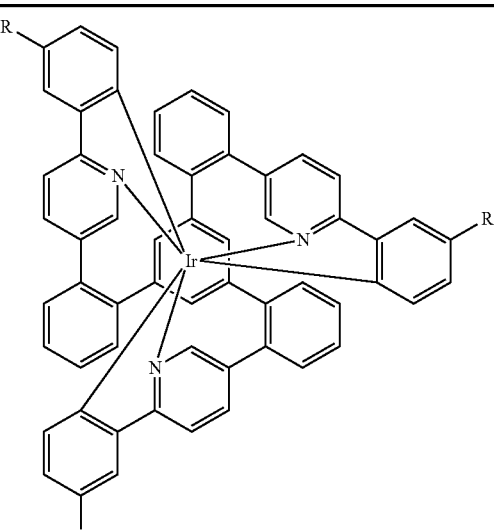
Ir25
PS1
C
56%
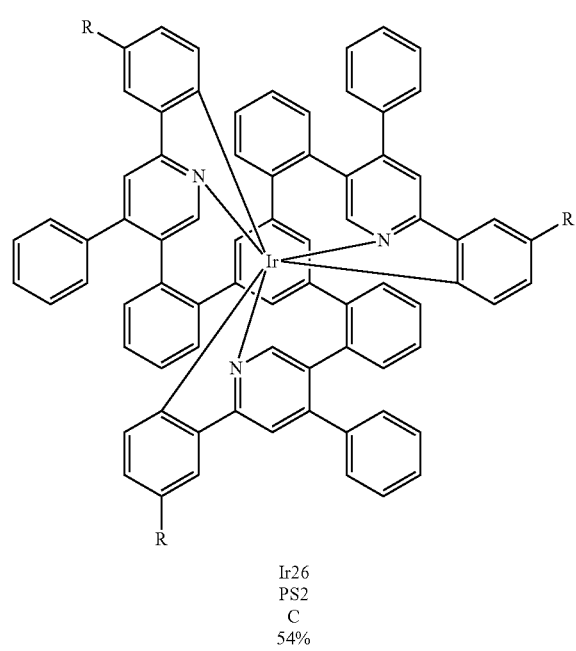
Ir26
PS2
C
54%

| Product |
| --- |
| Metal complex educt |
| Variant |
| Yield |
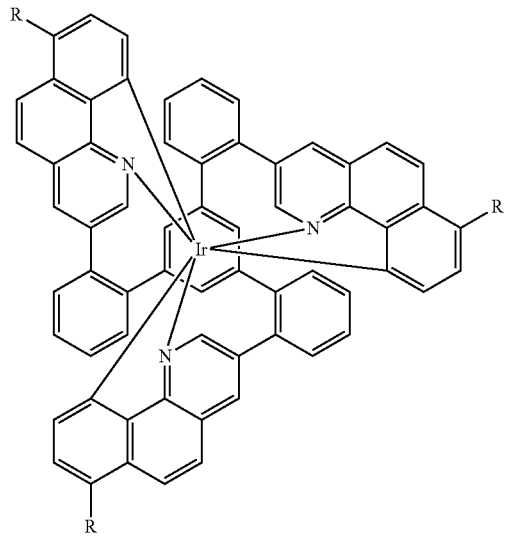
Ir27
PS3
C
50%
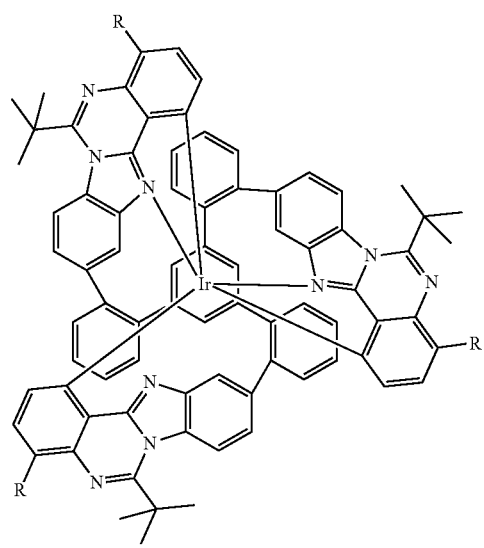
Ir28
PS4
C
51%

-continued
Product
Metal complex educt
Variant
Yield
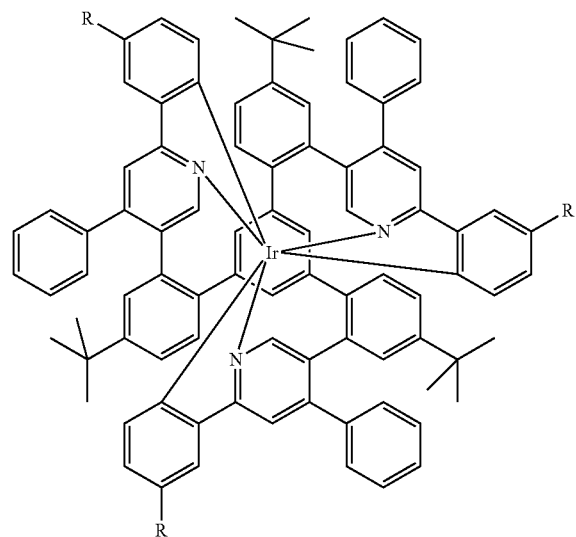
Ir29
PS5
C
57%
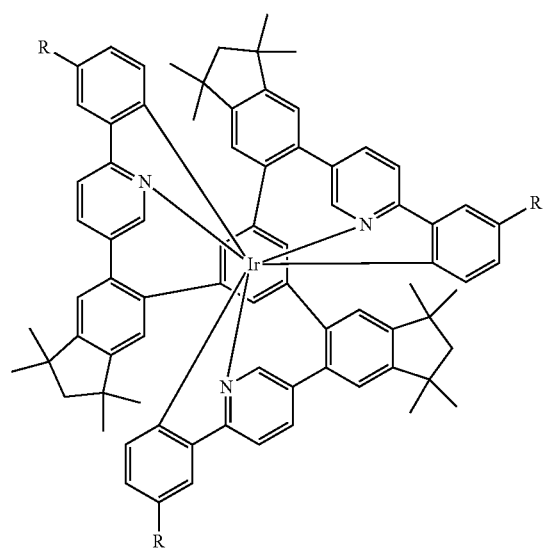
Ir30
PS6
C
57%

-continued
| Product |
| Metal complex educt |
| Variant |
| Yield |
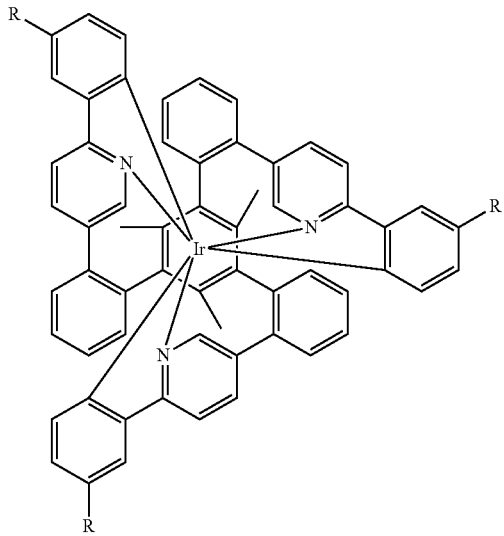
Ir31
PS7
C
56%
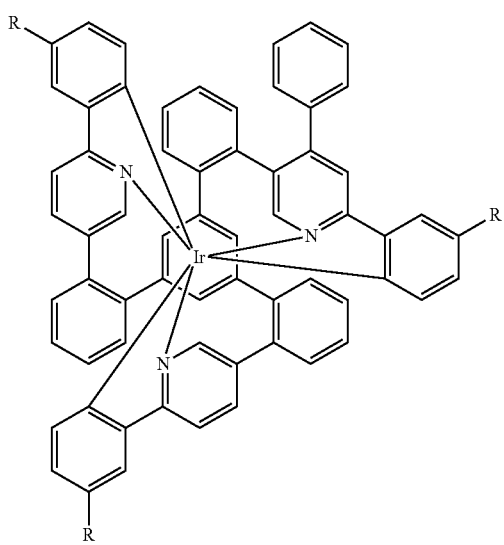
Ir32
PS8
B
63%

-continued
| Product |
| --- |
| Metal complex educt |
| Variant |
| Yield |
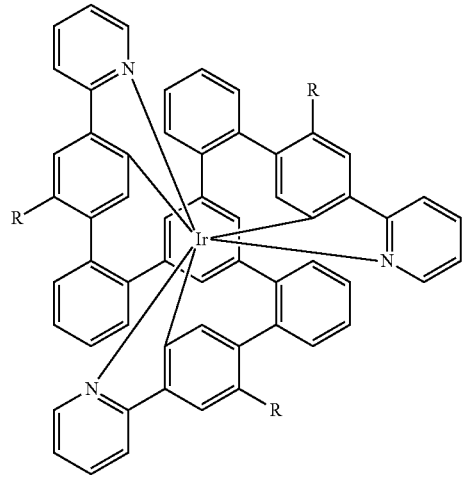
Ir33
PS9
C
60%
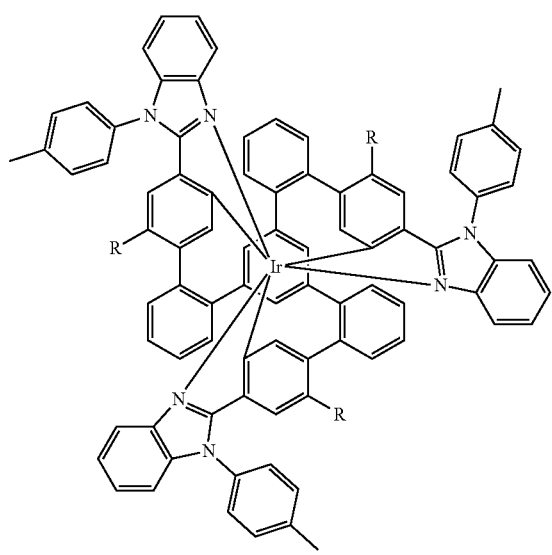
Ir34
PS10
C
55%

| Product |
| --- |
| Metal complex educt |
| Variant |
| Yield |
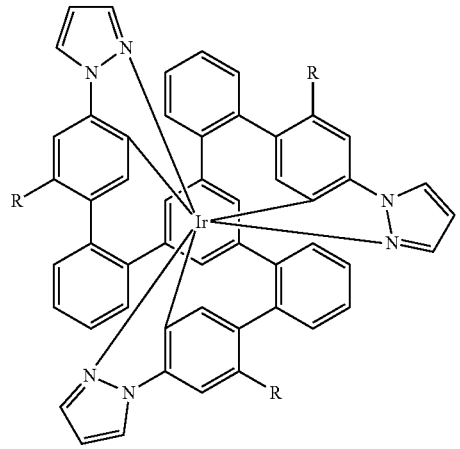
Ir35
PS11
C
51%
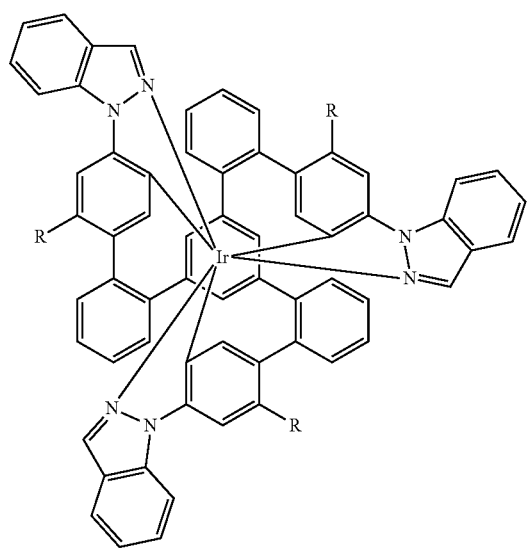
Ir36
PS12
C
53%

-continued
| Product Metal complex educt Variant Yield |
|---|
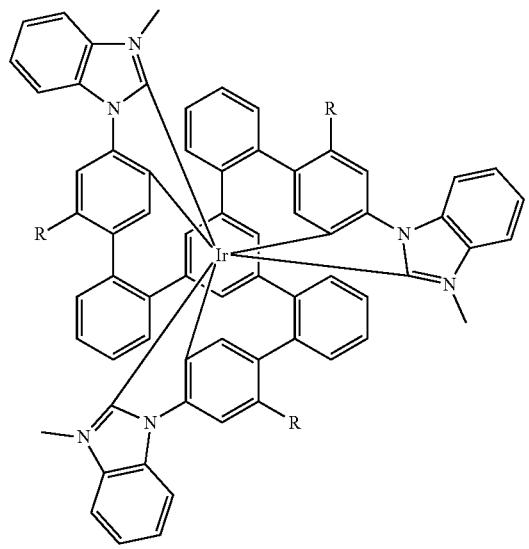
Ir37
PS1
C
53%
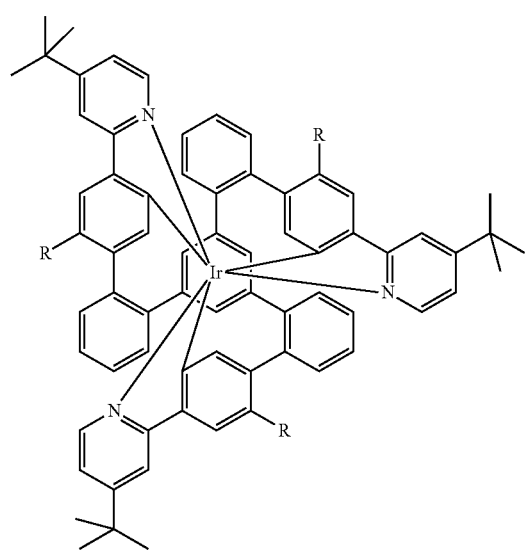
Ir38
PS14
C
54%

-continued
Product
Metal complex educt
Variant
Yield
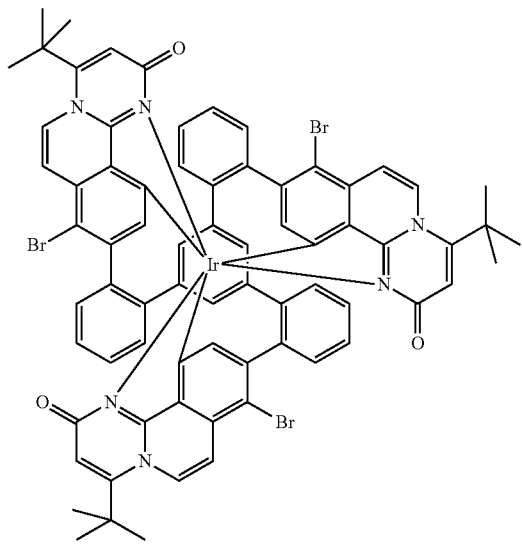
Ir39
PS15
C
47%
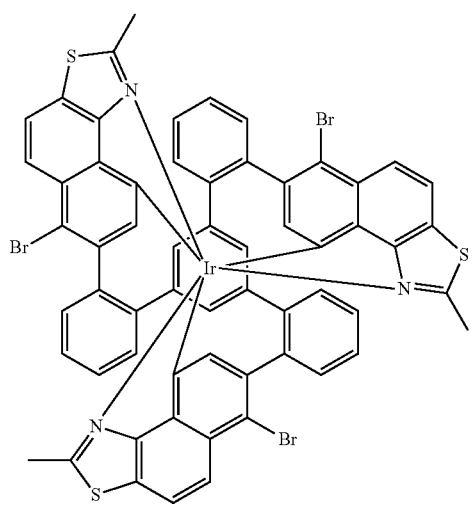
Ir40
PS16
C
45%

| Product |
| --- |
| Metal complex educt |
| Variant |
| Yield |
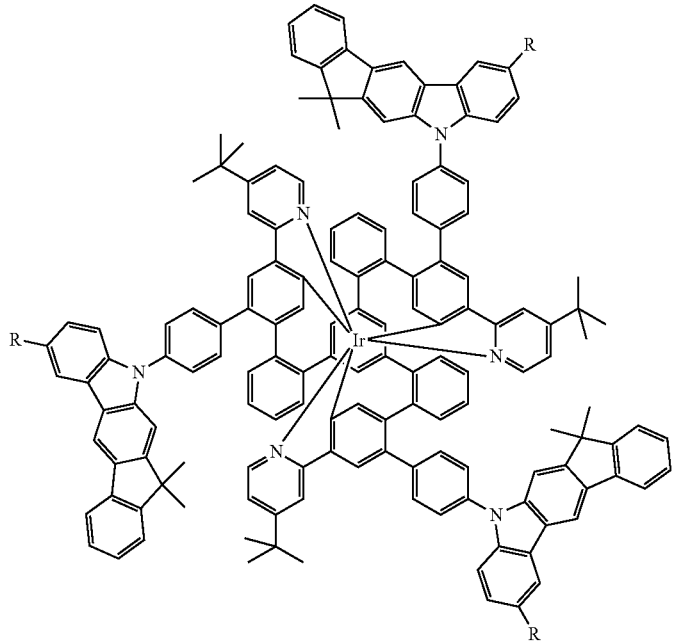
Ir41
PS17
C
67%
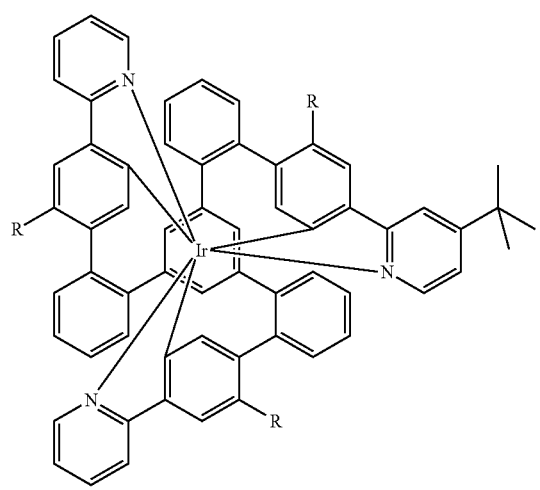
Ir42
PS18
C
55%

-continued
Product
Metal complex educt
Variant
Yield
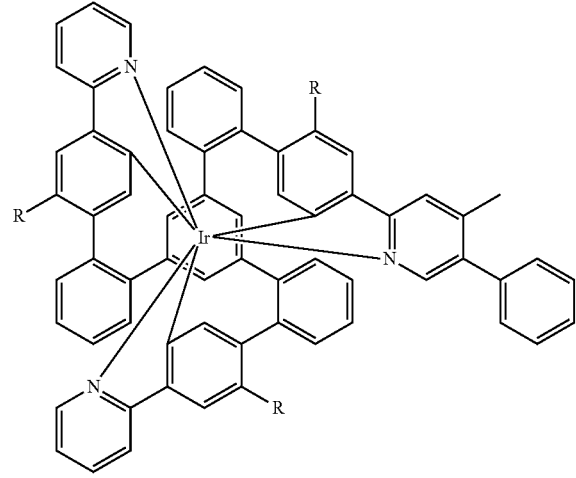
Ir43
PS19
C
57%
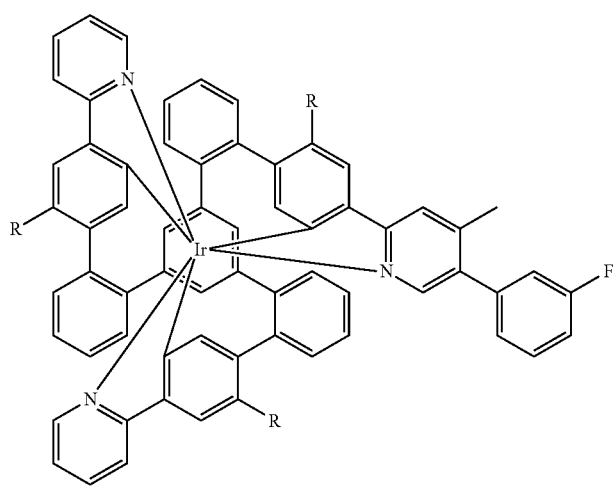
Ir44
PS20
C
54%

-continued
| Product |
|---|
| Metal complex educt |
| Variant |
| Yield |
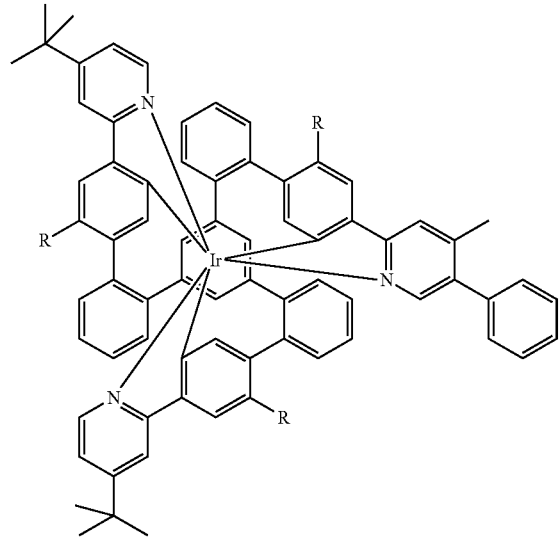
Ir45
PS21
C
52%
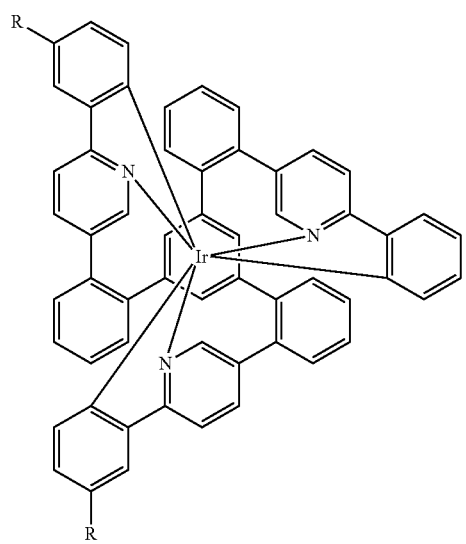
Ir46
PS22
C
54%

| Product Metal complex educt Variant Yield |
|---|
| 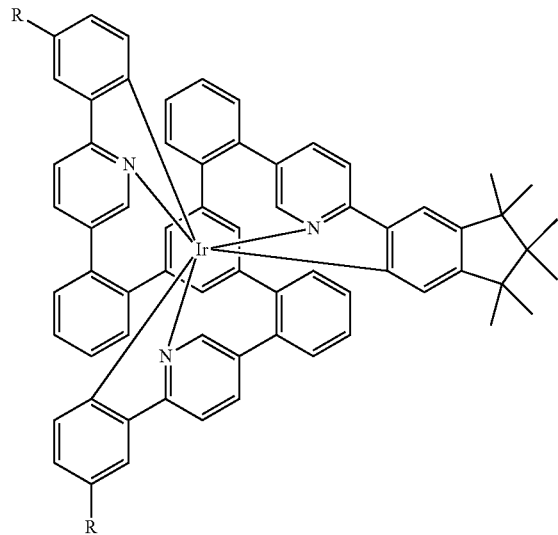 Ir47 PS23 C 49% |
| 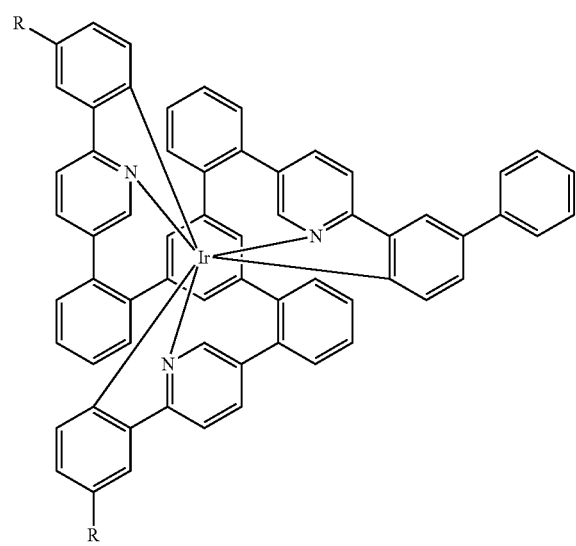 Ir48 PS24 C 59% |

| Product |
|---|
| Metal complex educt |
| Variant |
| Yield |
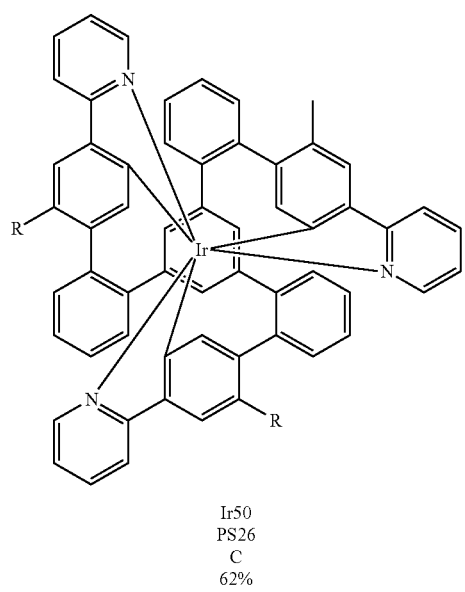
Ir49
PS25
C
64%
Ir50
PS26
C
62%

-continued
| Product |
| Metal complex educt |
| Variant |
| Yield |
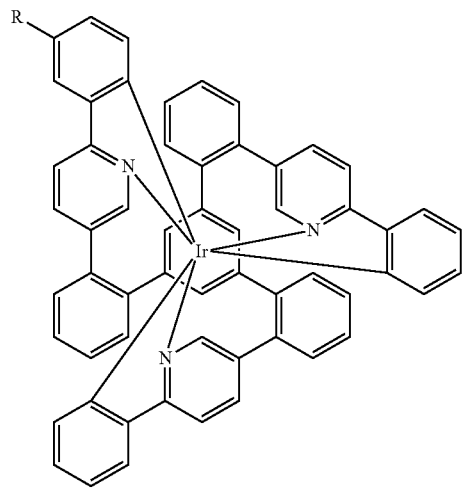
Ir51
PS27
C
65%
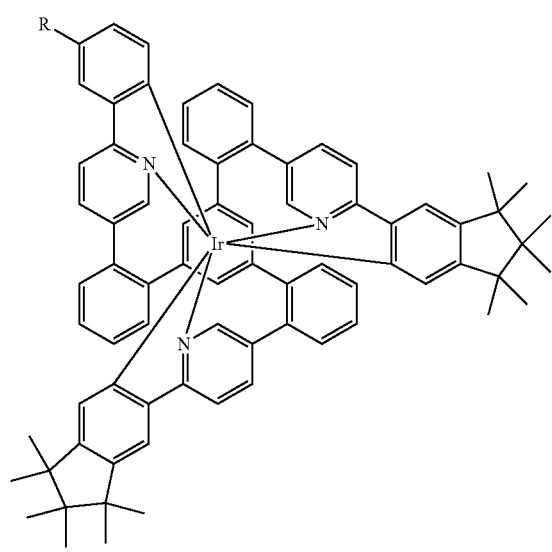
Ir52
PS28
C
64%

-continued
| Product |
|---|
| Metal complex educt |
| Variant |
| Yield |
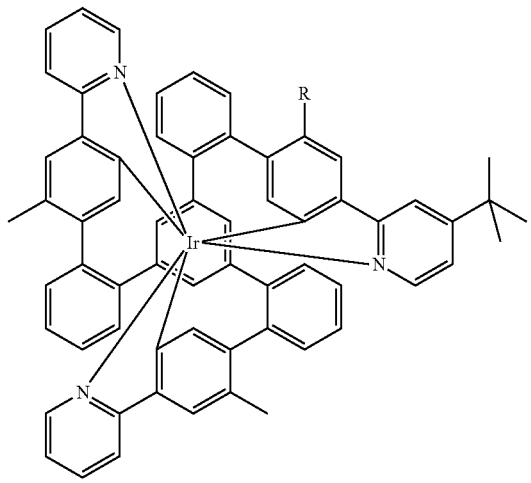
Ir53
PS29
C
63%
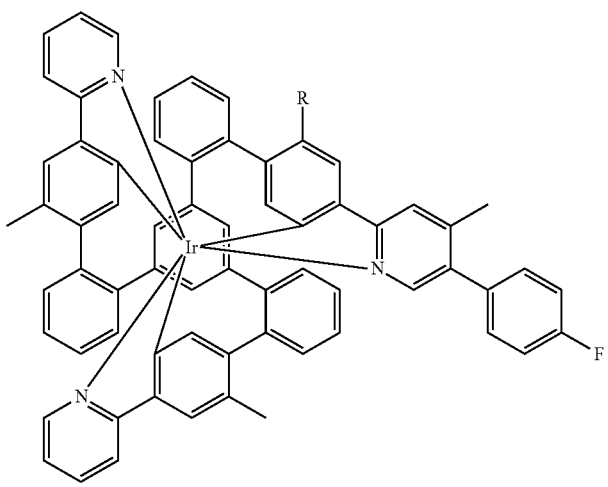
Ir54
PS30
C
64%

-continued

Product
Metal complex educt
Variant
Yield

Ir55
PS31
C
60% b-3) Fabrication of OLEDs

Solution-Processed Devices:

Obtained from Low Molecular Weight Soluble Functional Materials

The iridium complexes according to the invention can also be processed from solution, which is also desirable owing to the high technical complexity in the case of vacuum processes. The production of such components is based on the production of polymer light-emitting diodes (PLEDs), which has already been described in many ways in the literature (eg in WO 2004/037887). The structure of such OLEDs is generally the following one: substrate/ITO/hole injection layer (60 nm)/interlayer (20 nm)/emission layer (60 nm)/hole blocking layer (10 nm)/electron transport layer (40 nm)/cathode. For this purpose, substrates of the company Technoprint (Sodalimeglas) are used, to which the ITO film (indium tin oxide, a transparent, conductive anode) is applied. The substrates are cleaned in the clean room with DI water and a detergent (Deconex 15 PF) and then activated by a UV/ozone plasma treatment. A hole injection layer (20 nm) is then also applied by spin coating in the clean room. The required spin rate depends on the degree of dilution and of the specific spin-coater geometry. In order to remove residual water from the layer, the substrates are heated for 30 minutes at 200° C. on a heating plate. The interlayer used is for hole transport, in this case a HL-X from Merck is used. The interlayer can alternatively be replaced by one or more layers, which only have to fulfill the condition, by which the downstream processing step of the EML deposition from solution do not lead to the dissolution of the interlayer(s). For the production of the emission layer, the triplet emitters according to the invention are dissolved together with the matrix materials in toluene or chlorobenzene or 3-phenoxy-toluene. The typical solid content of such solutions is between 16 and 25 g/L when, as in this case, the typical layer thickness of 60 nm is to be achieved by means of spin coating. The solution-processed devices of type 1 contain an emission layer of M1: M2: IrL (30%: 45%: 25%), and the solution-processed devices of type 2 contain an emission layer of M1:M2:IrLa:IrLb (30%: 35%: 30%: 5%), i.e they contain two different Ir complexes. The emission layer is spun in an inert gas atmosphere, in the present case argon, and is heated at 160° C. for 10 minutes. The hole blocking layer (15 nm ETM1) and the electron transport layer (35 nm ETM1 (50%)/ETM2 (50%)) are evaporated thereon (Vapor deposition system from Lesker, typical vaporization pressure $5\times10^{-6}$ mbar). Finally, a cathode of aluminum (100 nm) (high-purity metal from Aldrich) is evaporated. In order to protect the device from air and air moisture, the device is finally encapsulated and then characterized. The OLED examples mentioned are not yet optimized, Table 1 summarizes the data obtained.

TABLE 1

Results obtained with materials processed from solution

| Ex. | Emitting compound | EQE (%) 1000 cd/m² | Voltage (V) 1000 cd/m² | CIE x/y | LT50 (h) 1000 cd/m² |
|---|---|---|---|---|---|
| Yellow - Green Typ 1 | | | | | |
| Ref-Green | IrRef1 | 18.1 | 5.2 | 0.34/0.61 | 210000 |
| G1 | Ir1 | 19.4 | 5.3 | 0.34/0.62 | 220000 |
| G2 | Ir3 | 19.7 | 5.1 | 0.35/0.62 | 230000 |
| G3 | Ir8 | 19.5 | 5.0 | 0.48/0.50 | 270000 |
| G4 | Ir14 | 20.3 | 5.2 | 0.37/0.60 | 250000 |
| G5 | Ir16 | 21.4 | 5.1 | 0.41/0.57 | 250000 |
| G6 | Ir19 | 20.7 | 5.2 | 0.45/0.52 | 270000 |
| G7 | Ir25 | 21.7 | 4.7 | 0.32/0.63 | 270000 |
| G8 | Ir26 | 21.8 | 4.5 | 0.46/0.52 | 350000 |
| G9 | Ir38 | 22.1 | 4.3 | 0.33/0.63 | 330000 |
| G10 | Ir43 | 20.9 | 4.3 | 0.36/0.61 | 340000 |

TABLE 1-continued
Results obtained with materials processed from solution
| Ex. | Emitting compound | EQE (%) 1000 cd/m² | Voltage (V) 1000 cd/m² | CIE x/y | LT50 (h) 1000 cd/m² |
|---|---|---|---|---|---|
| G11 | Ir48 | 22.2 | 4.4 | 0.34/0.62 | 350000 |
| G12 | Ir55 | 21.9 | 4.3 | 0.36/0.61 | 360000 |
| Red Typ 2 | | | | | |
| R1 | IrRef1 Ir9 | 18.9 | 4.0 | 0.66/0.34 | 290000 |
| R2 | Ir26 Ir9 | 19.3 | 4.1 | 0.66/0.34 | 360000 |
TABLE 2
Structures of the materials
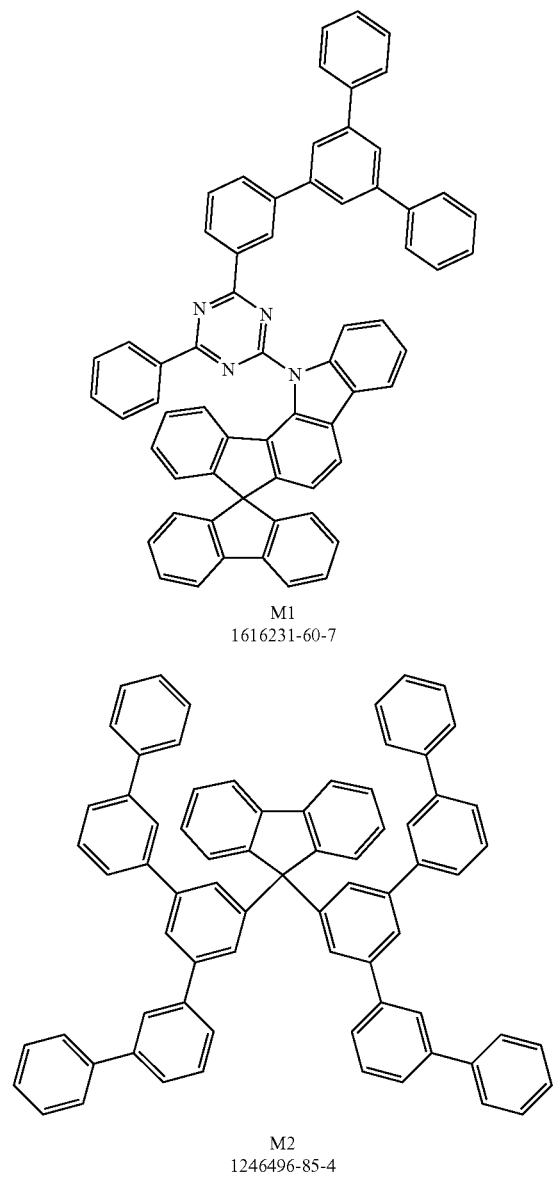
M1
1616231-60-7
M2
1246496-85-4
TABLE 2-continued
Structures of the materials
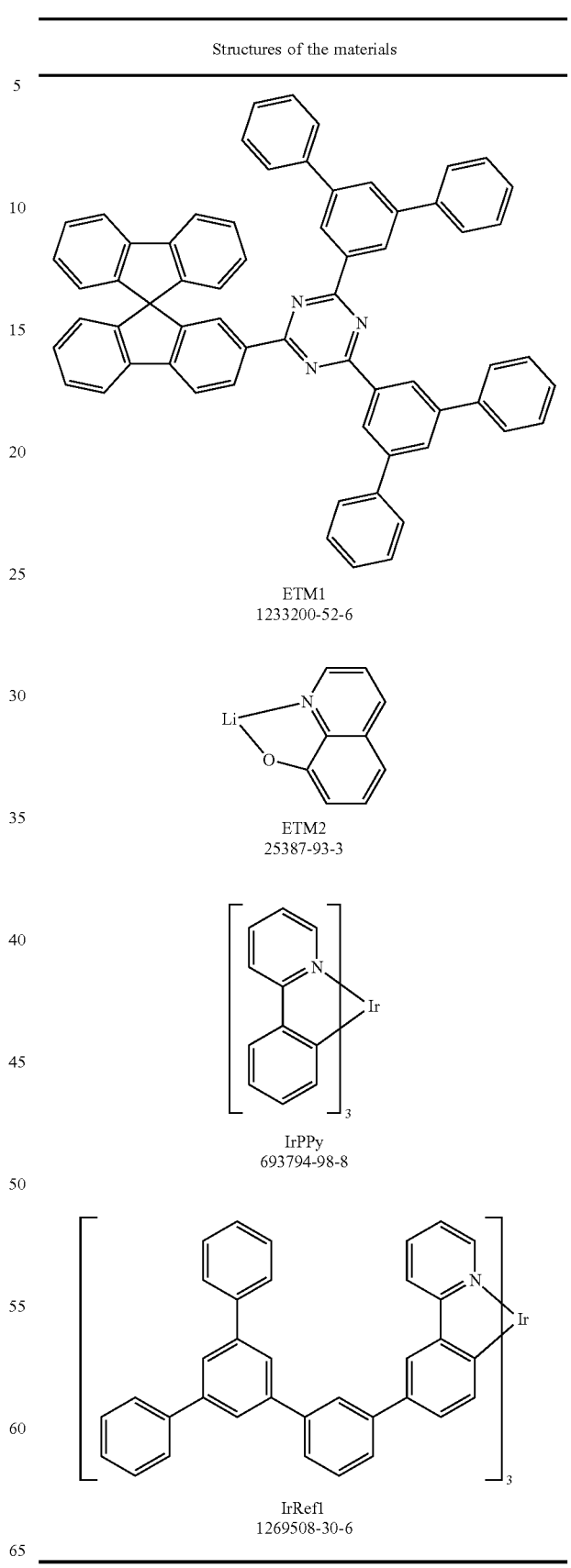
ETM1
1233200-52-6
ETM2
25387-93-3
IrPPy
693794-98-8
IrRef1
1269508-30-6

C) Y is a Host Group c-1) Syntheses Examples

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective FIGURES in square brackets or the numbers quoted for individual compounds relate to the CAS numbers of the compounds known from the literature.

c-1-1) Organic Synthones Known from the Literature

Syn-1

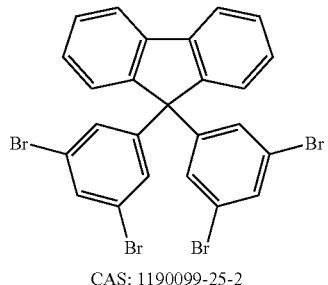

CAS: 1190099-25-2

Syn-2

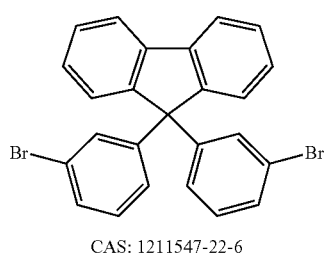

CAS: 1211547-22-6

Syn-3

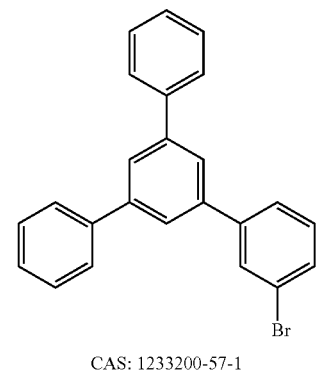

CAS: 1233200-57-1

Syn-4

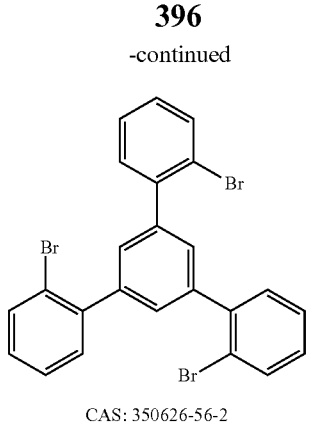

CAS: 350626-56-2

Syn-5

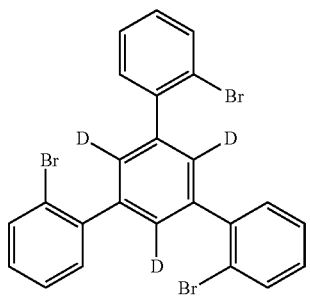

CAS: 1272029-05-6

Syn-6

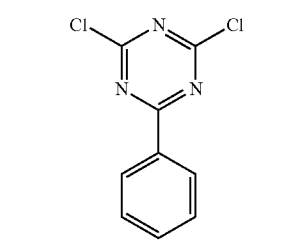

CAS: 1700-02-3

Syn-6

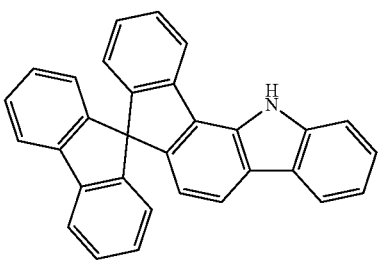

CAS: 1615703-28-0

Syn-7

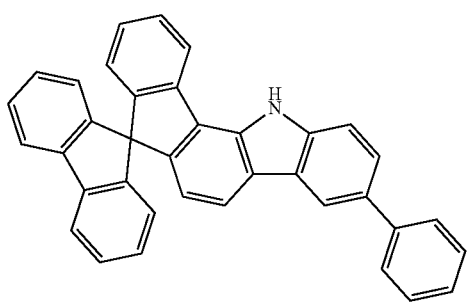

CAS: 1616231-28-7

-continued
Syn-8
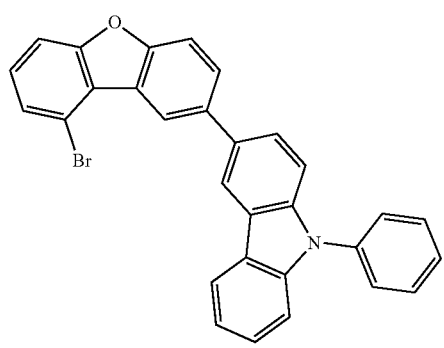
CAS: 1822311-15-8
Syn-9
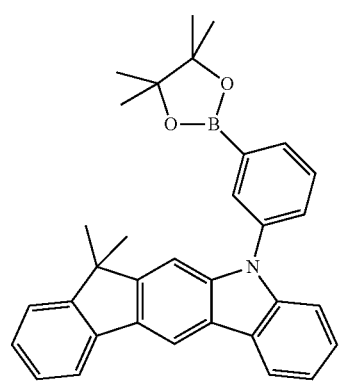
CAS: 180905-57-7
Syn-10
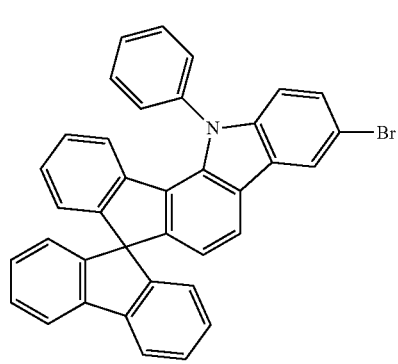
CAS: 1616231-96-9
Syn-11
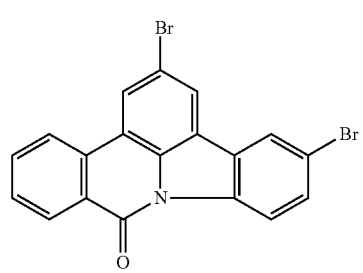
CAS: 1346571-48-9
-continued
Syn-12
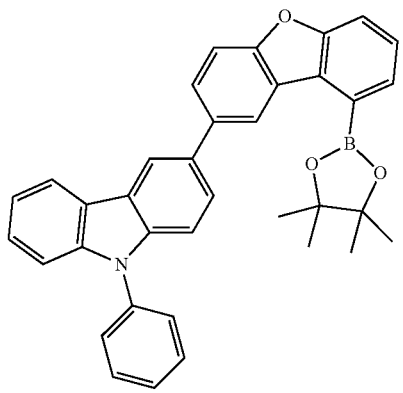
CAS: 1257220-47-5
Syn-13
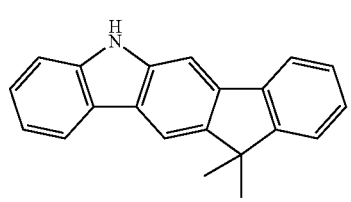
CAS: 1257220-47-5
Syn-14
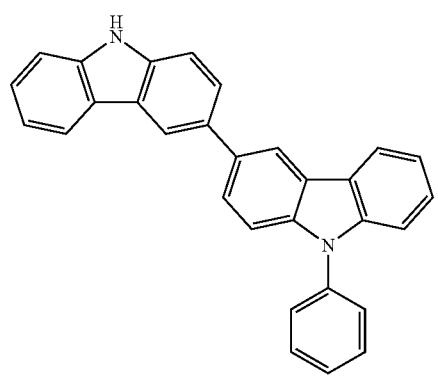
CAS: 1060735-14-9
Syn-15
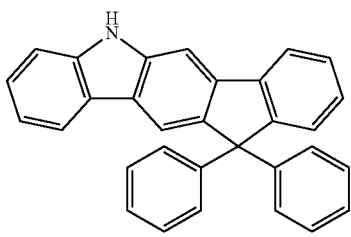
CAS: 1257220-52-2

-continued
Syn-16
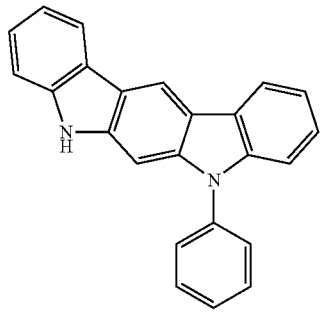
CAS: 1448296-00-1
Syn-17
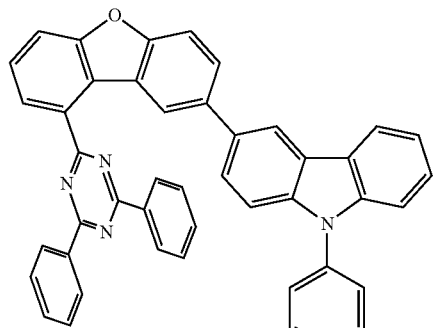
CAS: 1822310-78-0
Syn-18
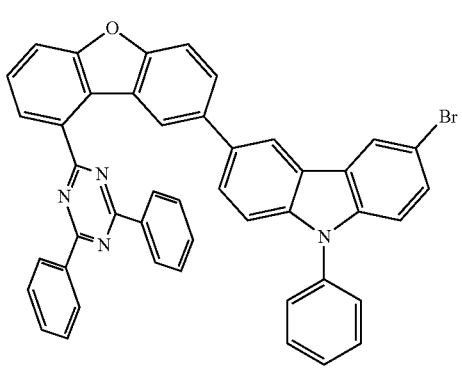
Syn-20
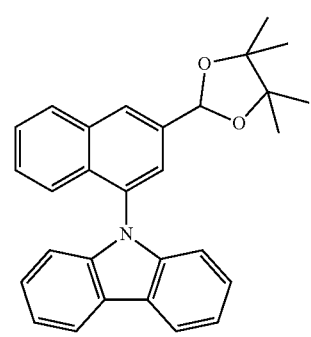
CAS: 1819346-26-3
-continued
Syn-21
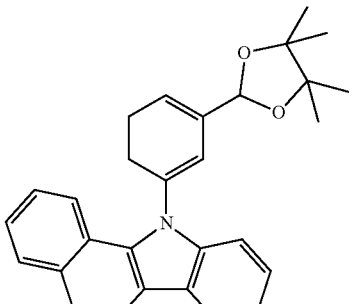
CAS: 1819346-34-3
Syn-22
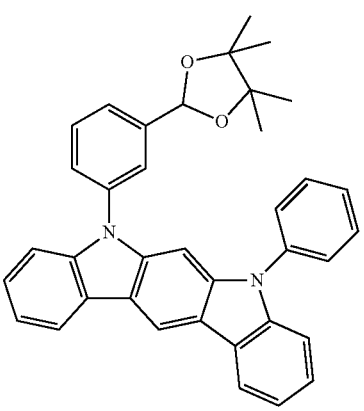
CAS: 1689576-02-0
Syn-23
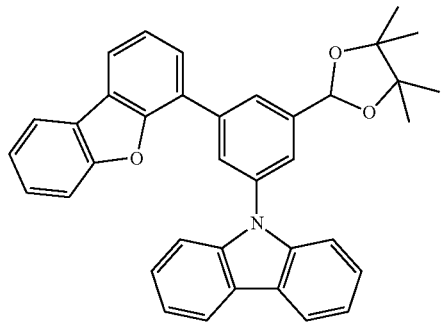
CAS: 1699755-96-8 c-1-2) Synthesis of the Used Synthones

1)

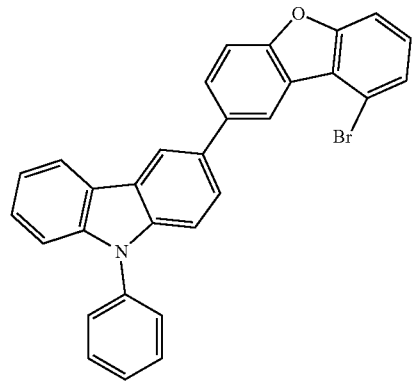

+

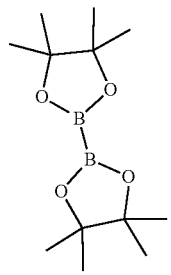

→

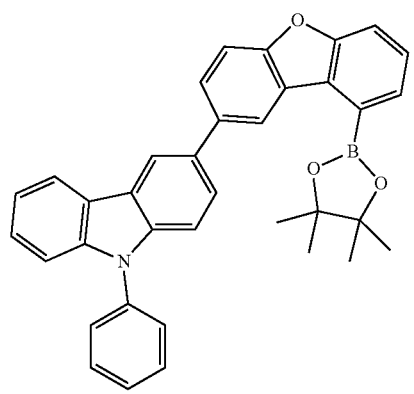

22.8 g (46.7 mmol) of Syn-8, 26.6 g (100 mmol, 2.20 eq) bis(pinacolato)diboron (CAS: 73183-34-3) and 13.89 g (140 mmol, 3.0 eq) of potassium acetate are dissolved in 1000 ml of anhydrous DMF and degassed into a heated 2000 ml 4-neck flask with KPG stirrer, reflux condenser, thermometer, dropping funnel and inert gas connection.

0.73 g (3.27 mmol, 0.07 eq) of palladium(II)acetate are added to the reaction mixture and the mixture is stirred at 100° C. for 24 hours. After cooling to room temperature, 1000 ml of water are added and the precipitated solid is filtered. The solid is collected with dichloromethane, washed with water, filtered through celite, and the solvent is removed under vacuum. The solid is dissolved in ethyl acetate and filtered over silica gel. A colorless solid Syn-12 is obtained as a product (11.7 g, 46.8 mmol, 47% yield).

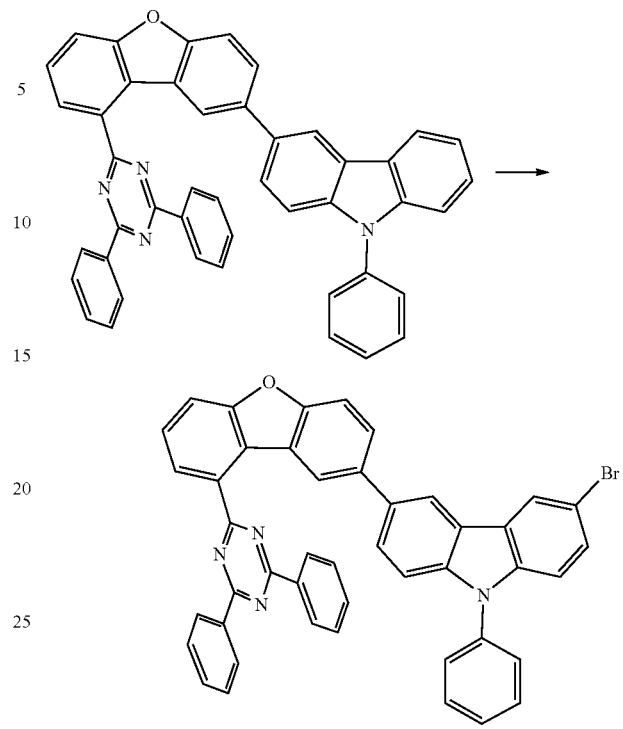

30 g (46.8 mmol) of Syn-17 are dissolved in 1250 ml of anhydrous THF in a 4000 ml 4-neck flask equipped with KPG stirrer, reflux condenser, thermometer, dropping funnel and inert gas connection and degassed.

8.33 g (46.8 mmol, 1 eq) of N-bromosuccinimide are added and the mixture is stirred at 50° C. for 4 days. The solvent is removed in vacuum, the residue is slurried with ethyl acetate, filtered, washed with ethyl acetate and dried in vacuum. A colorless solid Syn-18 is obtained as a product (32.8 g, 45.6 mmol, 97%).

c-1-3) Synthesis of Synthones According to the Invention

BB-1

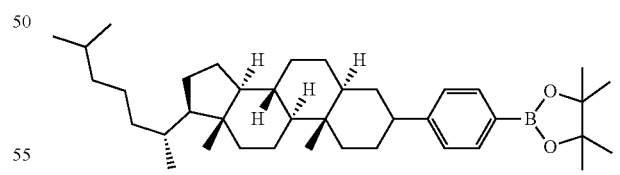

BB-2

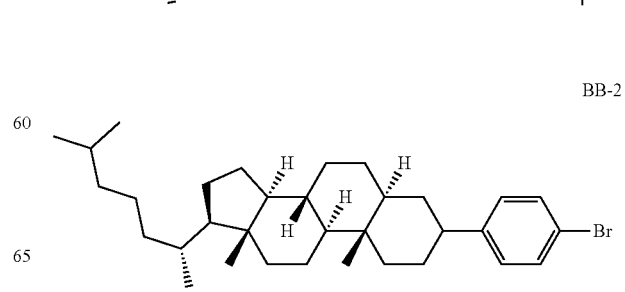

-continued
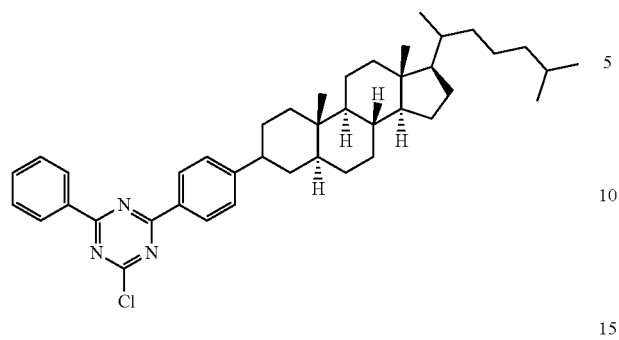
BB-3
Synthesis of BB-3
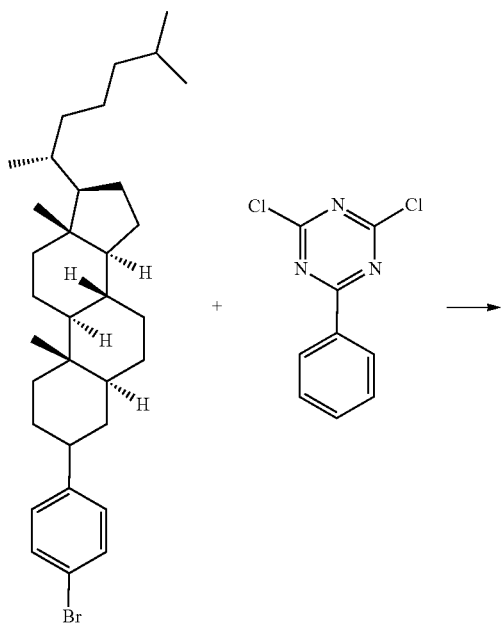
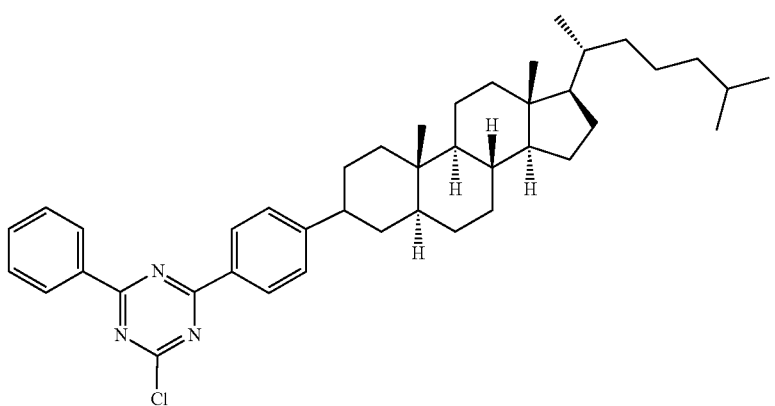

1.15 g magnesium chips are weighed in a heated 500 ml 4-neck flask with KPG stirrer, reflux condenser, thermometer, dropping funnel and inert gas connection. 25 g (47.4 mmol) of BB-1 are weighed in the dropping funnel and mixed with 100 ml of anhydrous THF and 9.2 ml of ethylglycol dimethyl ether (99.5 mmol, 2.1 eq). The solution is slowly added dropwise to the magnesium so that the solvent boils slightly. The reaction mixture is boiled under reflux for 60 minutes and then cooled to 0° C.

10.7 g (47.4 mmol, 1 eq) of 2,4-dichloro-6-phenyl-[1,3,5]-triazine are added into a heated 500 ml 4-necked flask with a KPG stirrer, reflux condenser, thermometer, dropping funnel and mixed with 50 ml of anhydrous THF and cooled to 0° C. The cooled Grignard solution is slowly added to the reaction mixture so that the internal temperature does not rise above 5° C. The reaction mixture is slowly warmed to room temperature, then boiled under reflux for 48 hours. The mixture is cooled to room temperature and diluted with 100 ml of anhydrous THF. Under ice-cooling, 20 ml of water are carefully added, the mixture is stirred at room temperature and ethyl acetate is added. The organic phase is separated, extracted with water, removed from the solvent and dried. A colorless solid BB-3 is obtained as a product (17.1 g, 26.8 mmol, 57%).

c-1-4) Synthesis of Host Compounds According to the Invention

1)

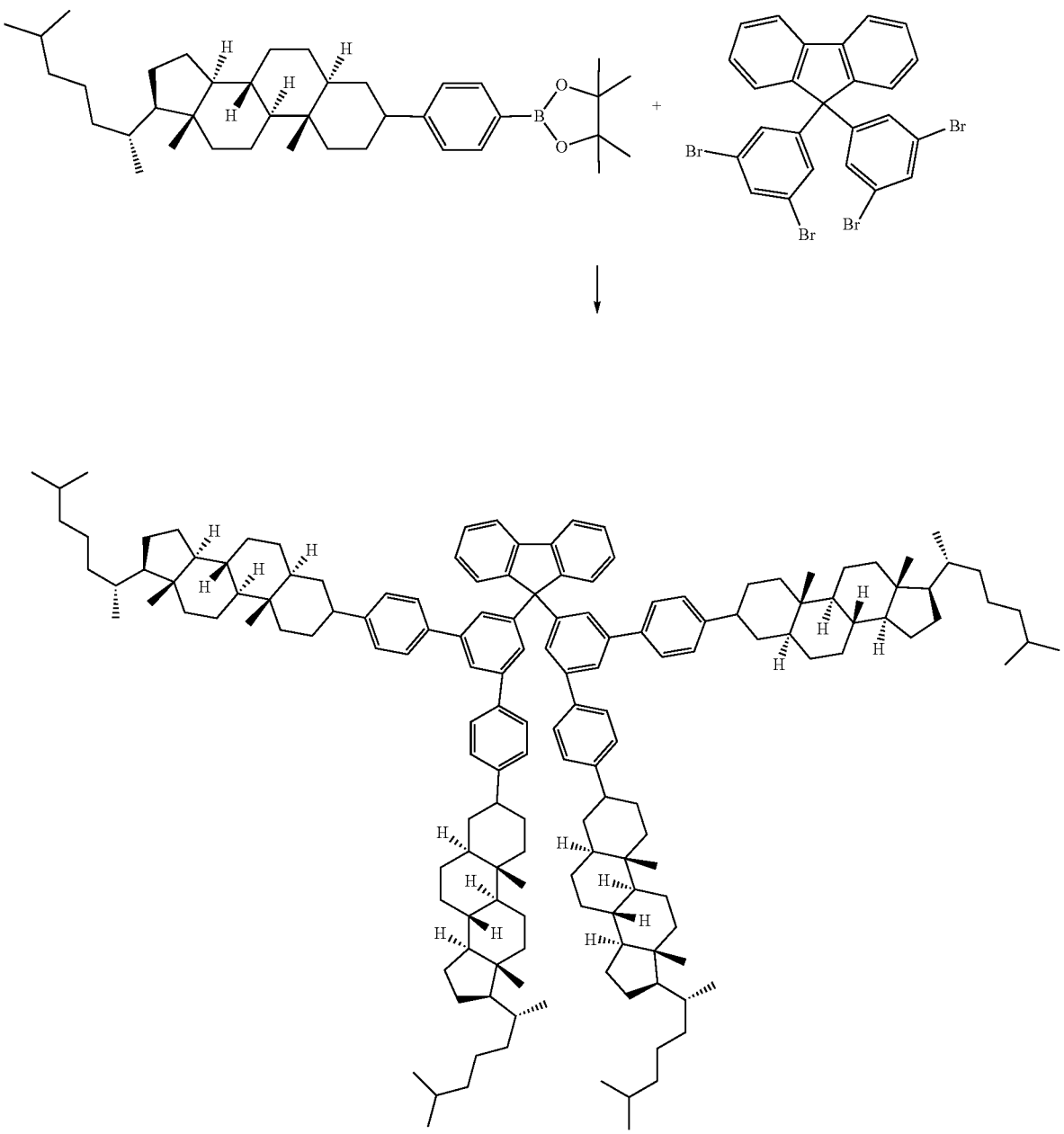

26 g (0.045 mol) of BB-1, 7.17 g (0.011 mol, 0.25 eq) of Syn-1 and 22.9 g of potassium phosphate monohydrate (0.1 mol, 2.2 eq) are weighed in a 1000 ml four-necked flask with KPG stirrer, heating head, reflux condenser and argon connection and mixed with 400 ml of toluene, 200 ml of 1,4-dioxane and 100 ml of water. The reaction solution is degassed and mixed with 253 mg (0.001 mol, 0.025 eq) of palladium(II)acetate and 688 mg of tri-o-tolylphosphine (0.002 mol, 0.05 eq). The reaction mixture is refluxed for 24 hours, then allowed to cool and mixed with water. The phases are separated, the aqueous phase is extracted several times with toluene, and the combined organic phases are separated from the solvent. Recrystallization from toluene/ethanol and heptane gives 7.8 g (0.003 mol, 27% yield) of the colorless solid H-1.

Analogously, Syn-2 can be used instead of Syn-1 so that H-2 is obtained with a yield of 25%.

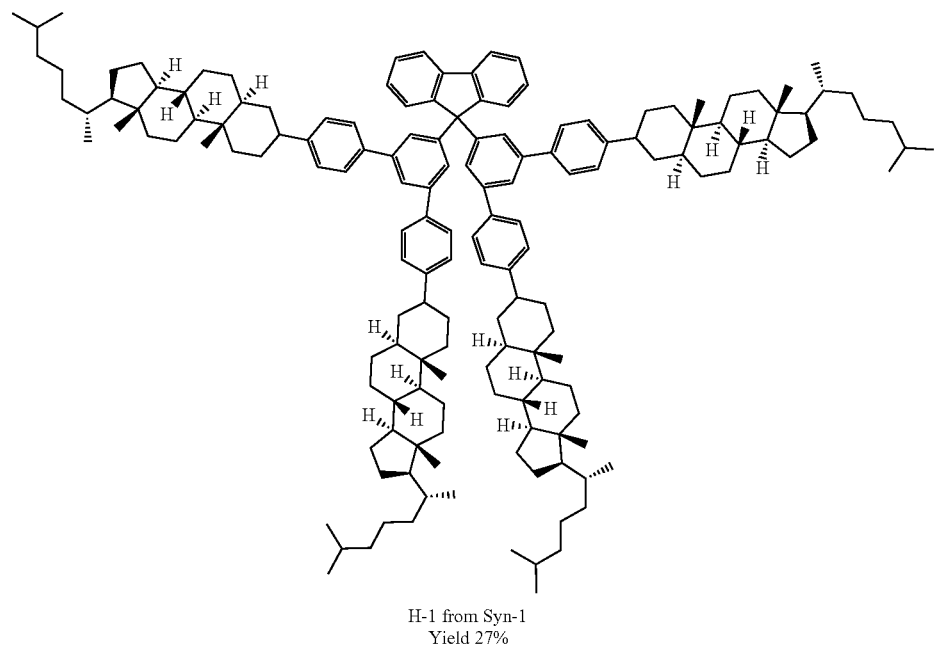

H-1 from Syn-1
Yield 27%

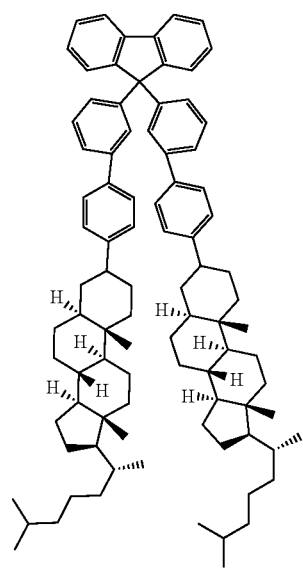

H-2 from Syn-2
Yield 32%

2)
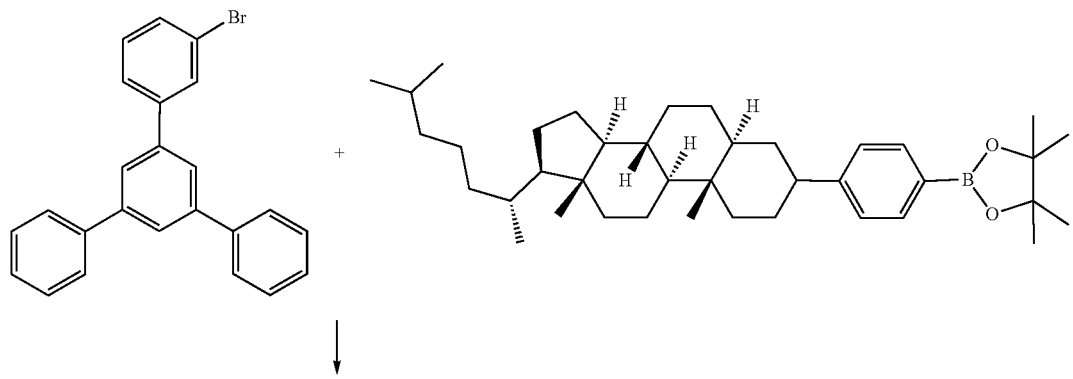
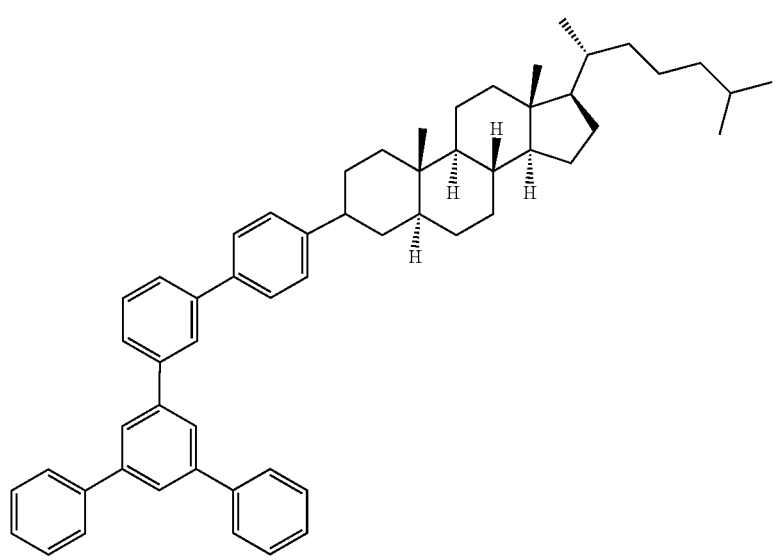

19 g (0.033 mol) of BB-1, 12.7 g (0.033 mol, 1 eq) of Syn-3 and 30.9 g of potassium phosphate monohydrate (0.145 mol, 4.4 eq) are weighed in a 1000 ml four-neck flask with KPG stirrer, heating head, reflux condenser and argon overlay and mixed with 250 ml THF and 135 ml water. The reaction solution is degassed and treated with 2.8 g (0.003 mol, 0.1 eq) XPhos Palladacycle (CAS: 1028206-56-5). The reaction mixture is refluxed for 24 hours and then allowed to cool. Ethanol is added to the reaction mixture, the precipitated solid is filtered, washed with ethanol and dried. Recrystallization from methyl ethyl ketone and cyclohexane gives a colorless solid H-3 (4.2 g, 0.006 mol, 17% yield).

The compounds H-4 to H-9 are obtained analogously by replacing Syn-3 with other synthons, see Table below:

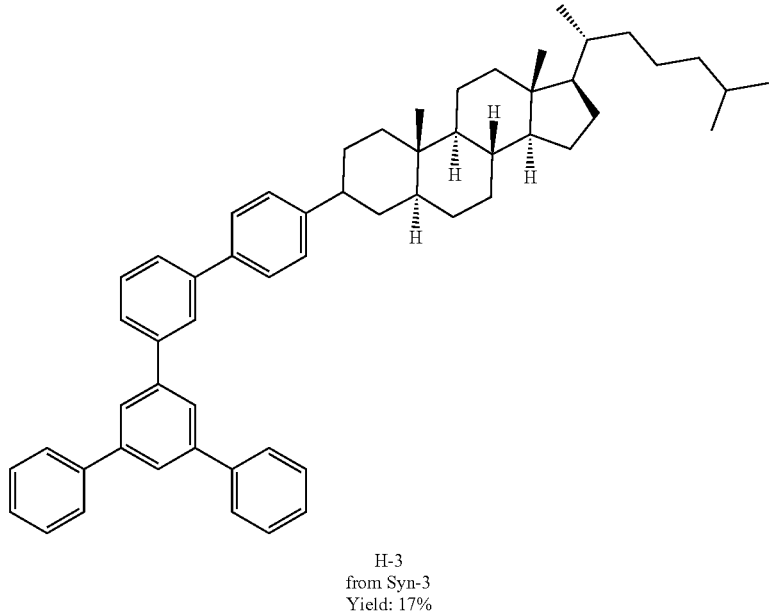

H-3
from Syn-3
Yield: 17%

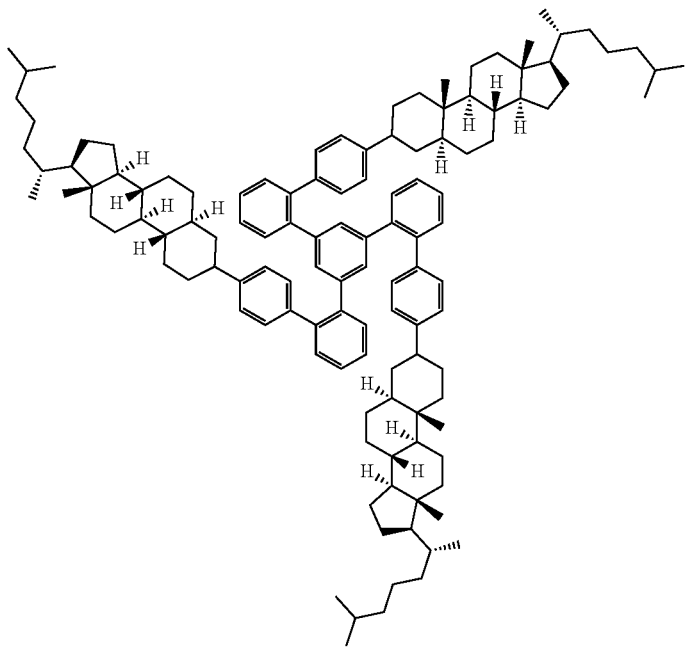

H-4
from Syn-4
Yield: 8%

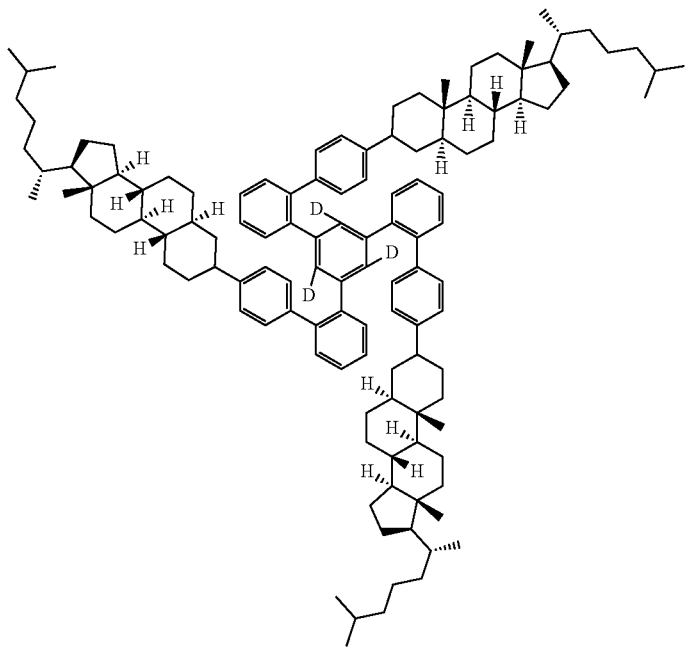
H-5
from Syn-5
Yield: 7%
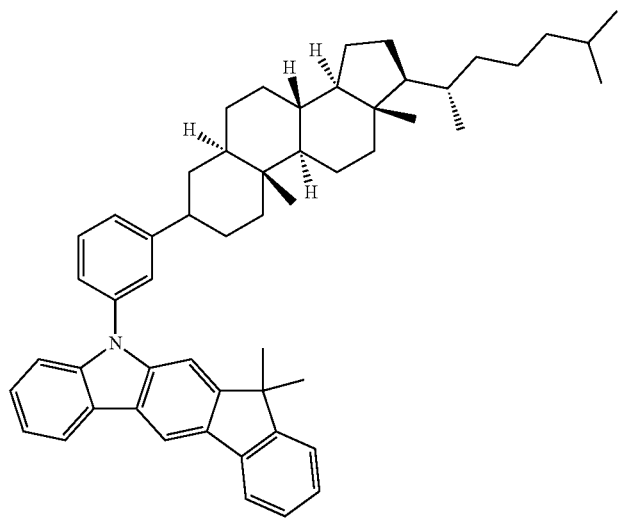
H-6
from Syn-9
Yield: 23%

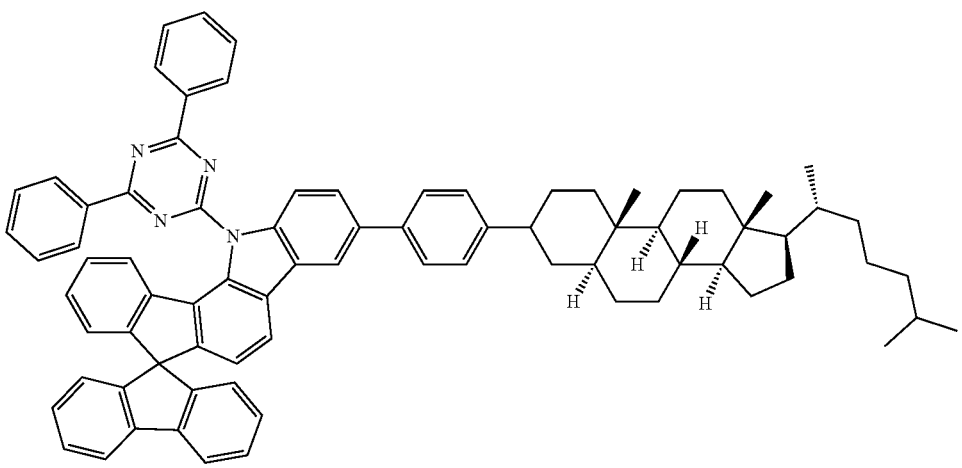
H-7
From Syn-10
Yield: 21%
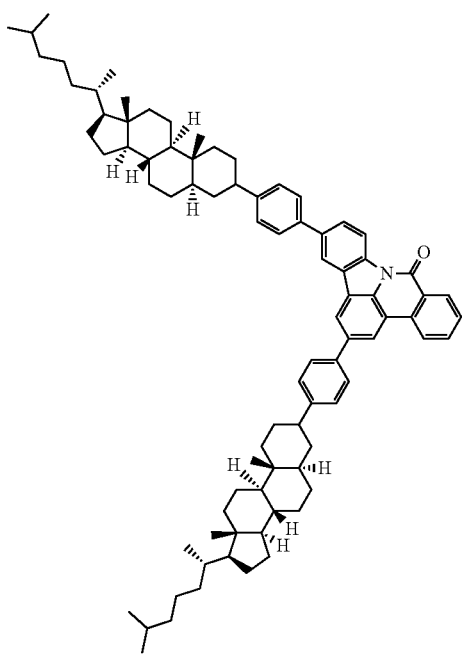 [SMILES: CC(C)CCC[C@H](C)[C@@H]1CC[C@@H]2[C@H]3CC[C@@H]4CC(c5ccc(-c6ccc7c(c6)c6cc(-c8ccc(C9CC[C@]%10(C)[C@H](CC[C@H]%11[C@H]%10CC[C@]%10(C)[C@@H]%11CC[C@H]%10[C@@H](C)CCCC(C)C)C9)cc8)cc8c9ccccc9c(=O)n7c86)cc5)CC[C@@]4(C)[C@@H]3CC[C@]21C]
H-8
From Syn-11
Yield: 18%

-continued
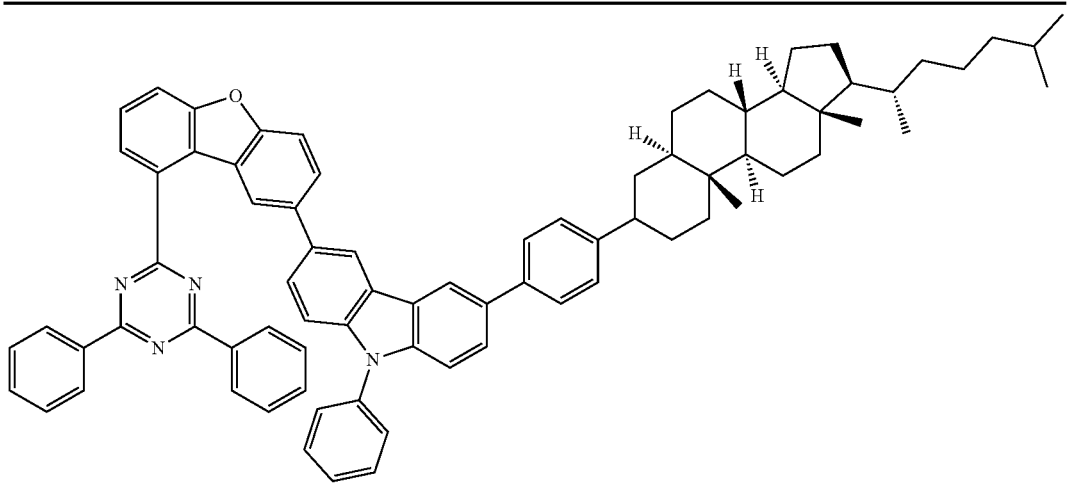
H-9
From Syn-17
Yield 15%
3)
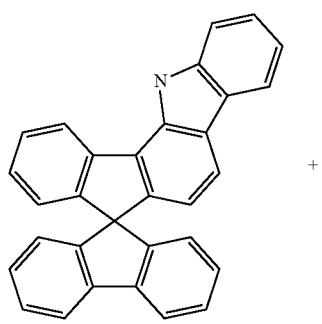   +
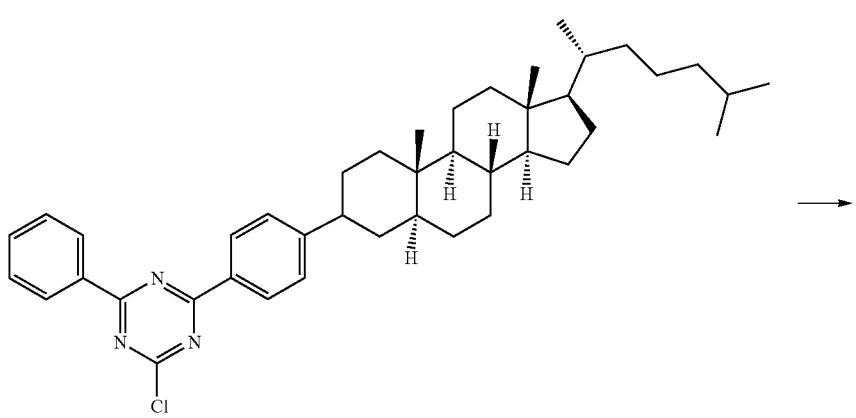

-continued

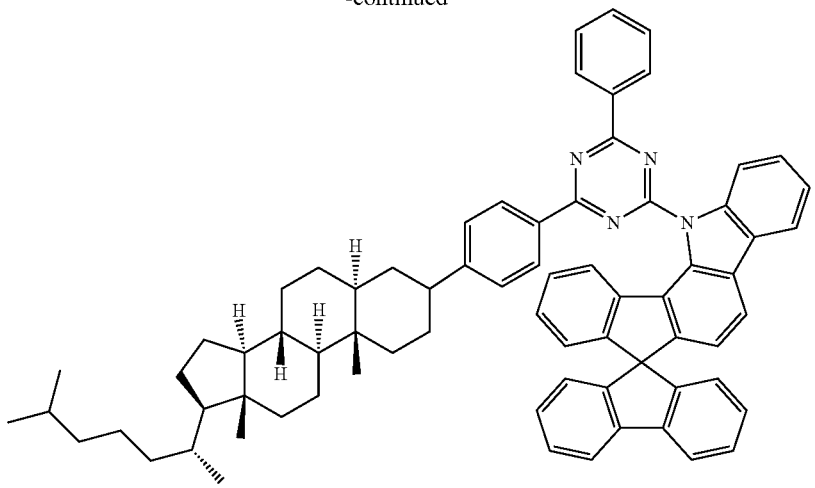

1.657 g of sodium hydride (0.041 mol) are weighed in a 2000 ml four-neck flask equipped with a KPG stirrer, heating head, reflux condenser and argon overlay, mixed with 150 ml of anhydrous dimethylformamide (DMF) and degassed. 14 g (0.035 mol, 0.83 eq) of Syn-6 are dissolved in 200 ml of anhydrous DMF, slowly added dropwise to the sodium hydride solution and the mixture is further stirred for 2 hours. 22.04 g (34.5 mmol, 0.83 eq) of BB-3 are dissolved in 250 ml of anhydrous DMF, slowly added dropwise to the reaction mixture and stirred for 24 hours at room temperature. 500 ml of water are added dropwise to the reaction solution, the precipitated solid is filtered and washed with water. The solid is recrystallized from ethanol and dried to give 29.5 g (29.5 mmol, 85% yield) of the colorless solid H-10.

The compounds H-11 to H-15 are obtained analogously by replacing Syn-6 with other synthons, see Table below:

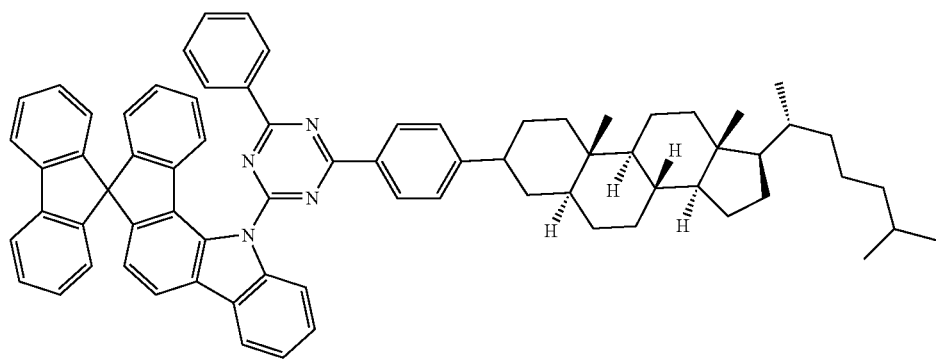

H-10
From Syn-6
Yield 85%

-continued
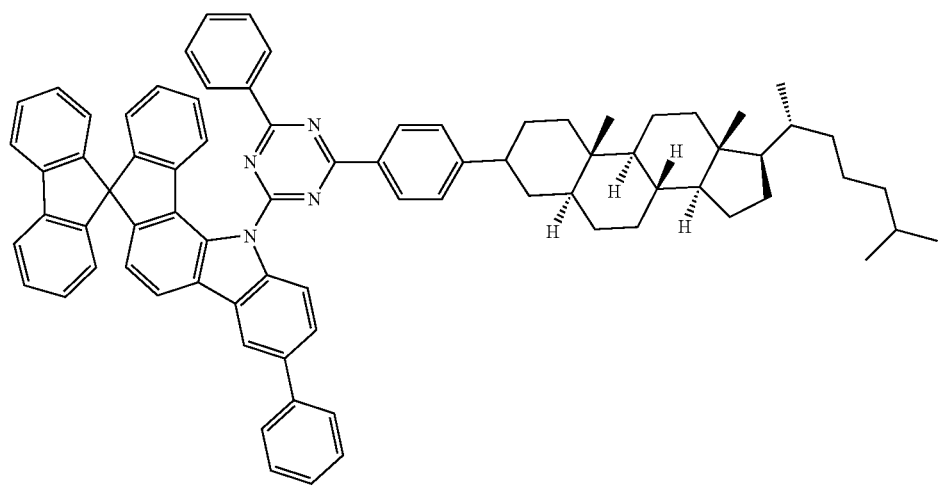
H-11
From Syn-7
Yield 81%
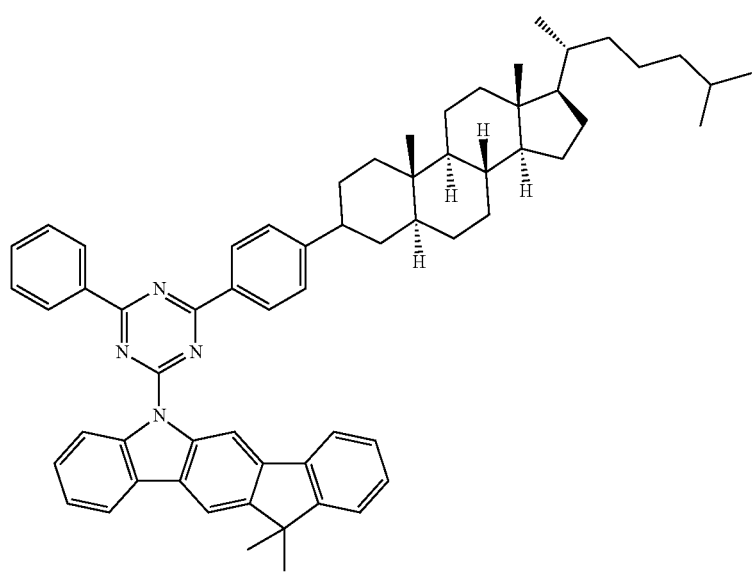
H-12
from Syn-13
Yield 73%

-continued
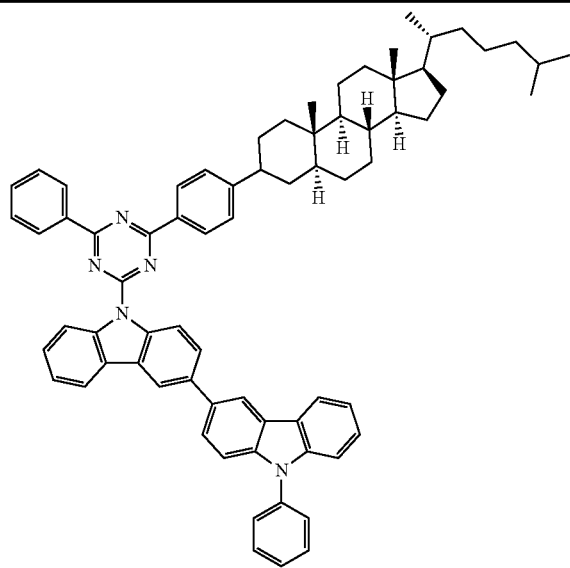
H-13
from Syn-14
Yield 85%
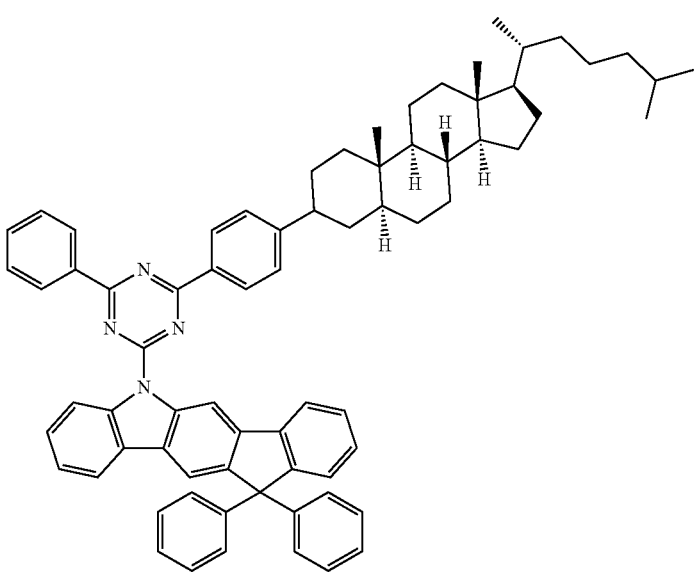
H-14
from Syn-15
Yield 79%

-continued
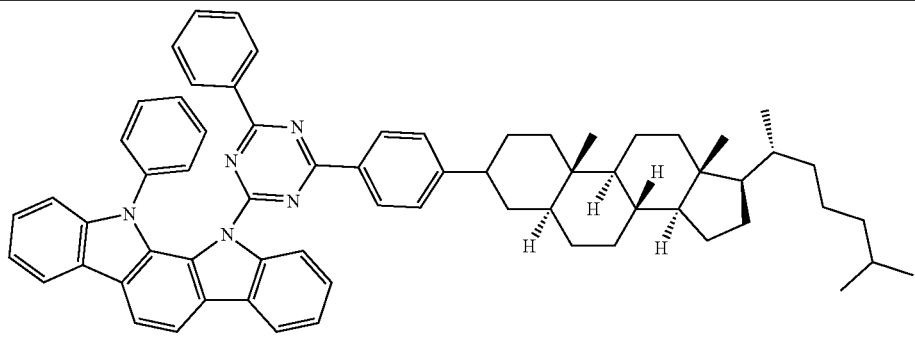
H-15
from Syn-16
Yield 45%
4)
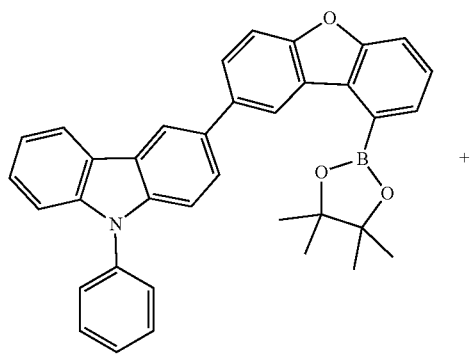 +
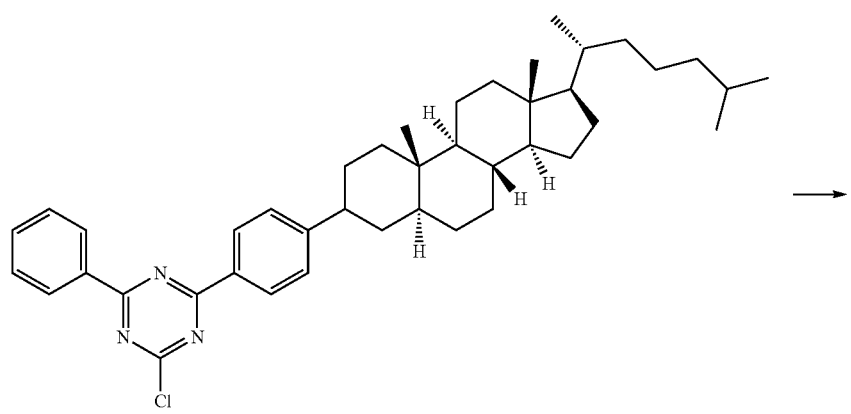

-continued

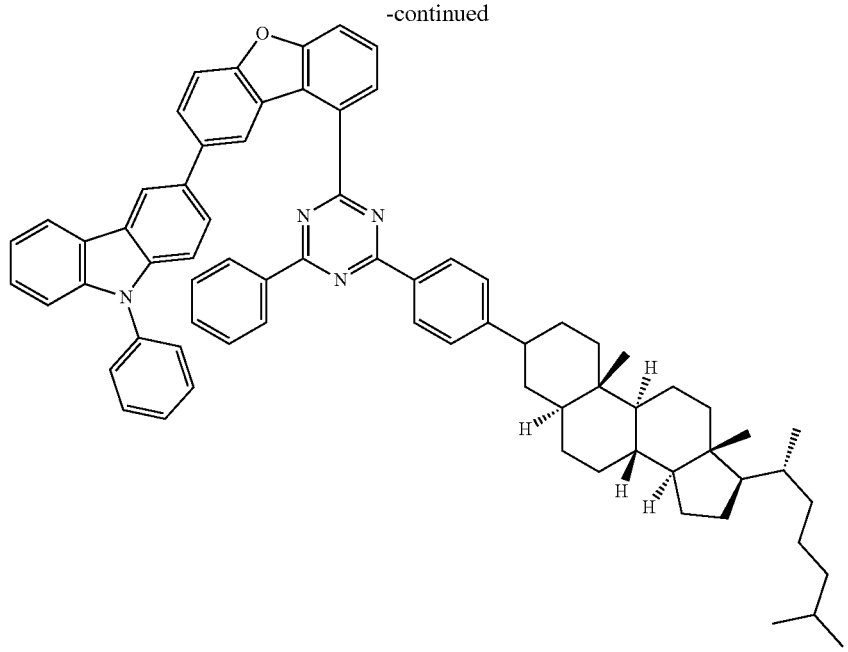

12.7 g (23.7 mmol) of Syn-12, 15.14 g (23.7 mmol, 1 eq) of BB-3 and 5.5 g (52.2 mmol, 2.2 eq) of sodium carbonate are weighed in a 500 ml four-neck flask with KPG stirrer, heating head, reflux condenser and argon overlay and dissolved in 50 ml of water and 100 ml 1,4-Dioxane, and degassed. 411 mg (0.36 mmol, 0.015 eq) of tetrakis(triphenylphosphine)palladium(0) (CAS: 14221-01-3) are added and the reaction mixture is refluxed for 24 hours. After cooling to room temperature, the solid is collected by filtration and purified by repeated recrystallization from methyl-ethylketone. A colorless solid H-16 is obtained as a product (10.1 g, 9.96 mmol, 42% yield).

The compounds H-17 to H-22 are obtained analogously by replacing Syn-6 with other synthons, see Table below:

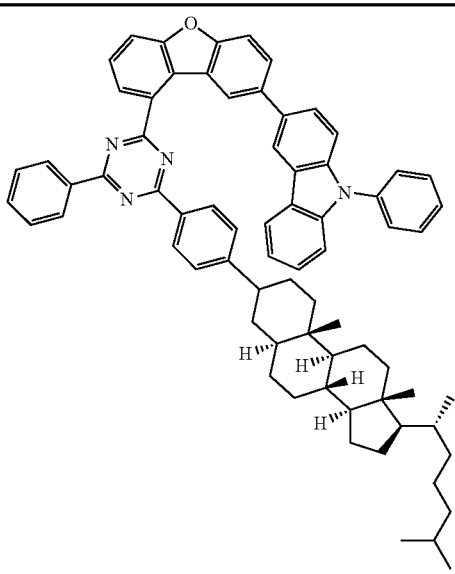

H-16
from Syn-12
Yield: 42%

-continued
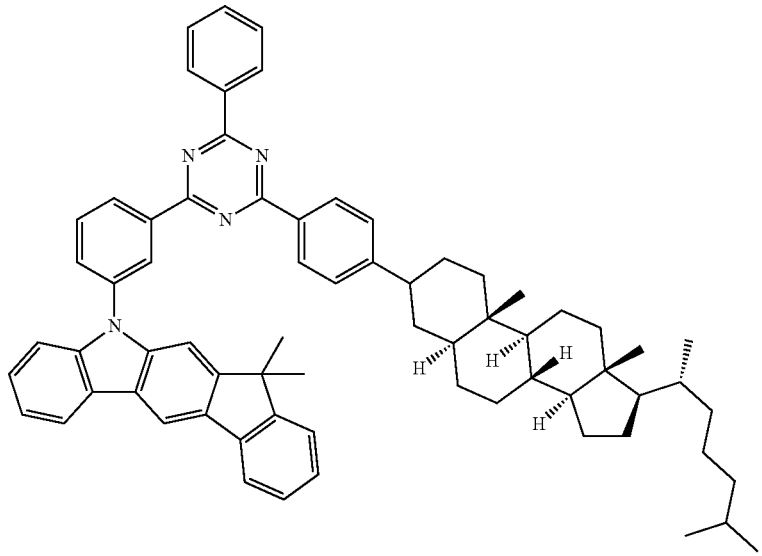
H-17
from Syn-7
Yield: 63%
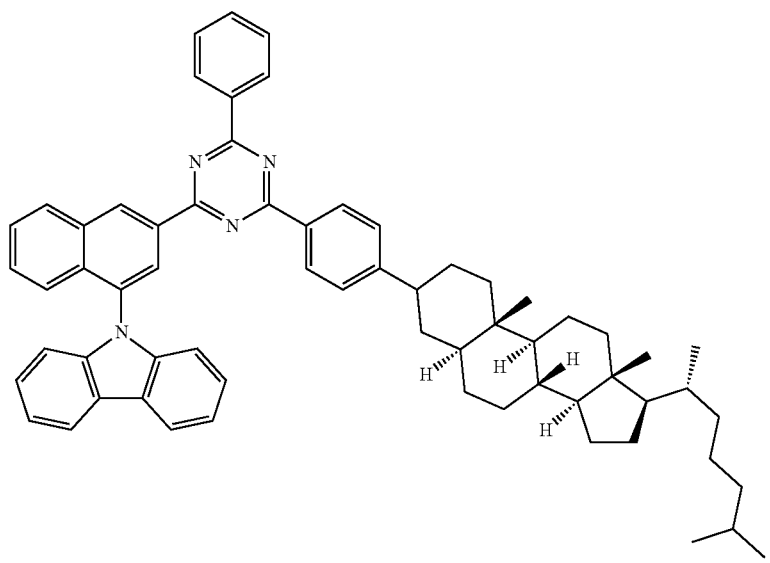
H-19
from Syn-20
Yield: 34%

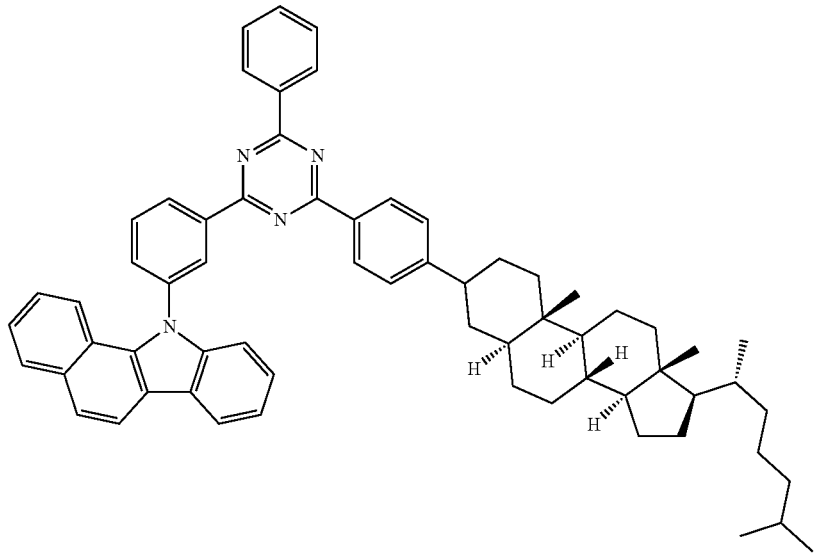
H-20
from Syn-21
Yield: 60%
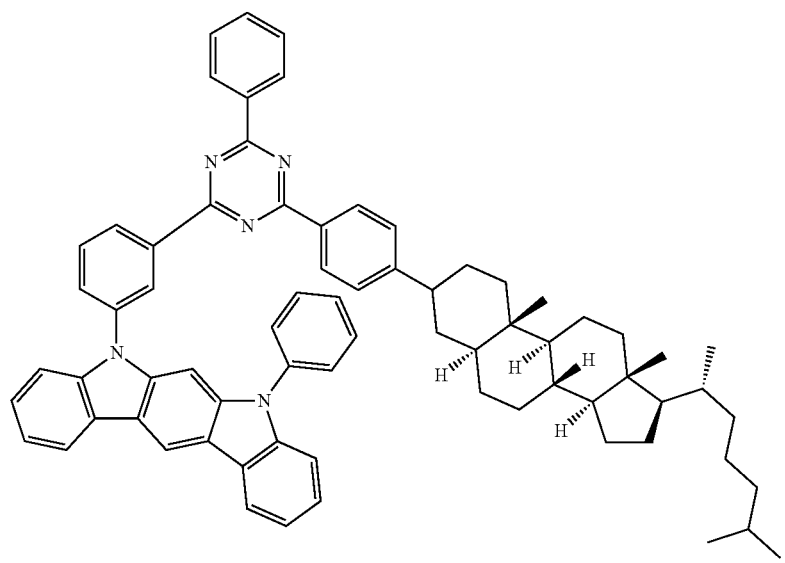
H-21
from Syn-22
Yield: 42%

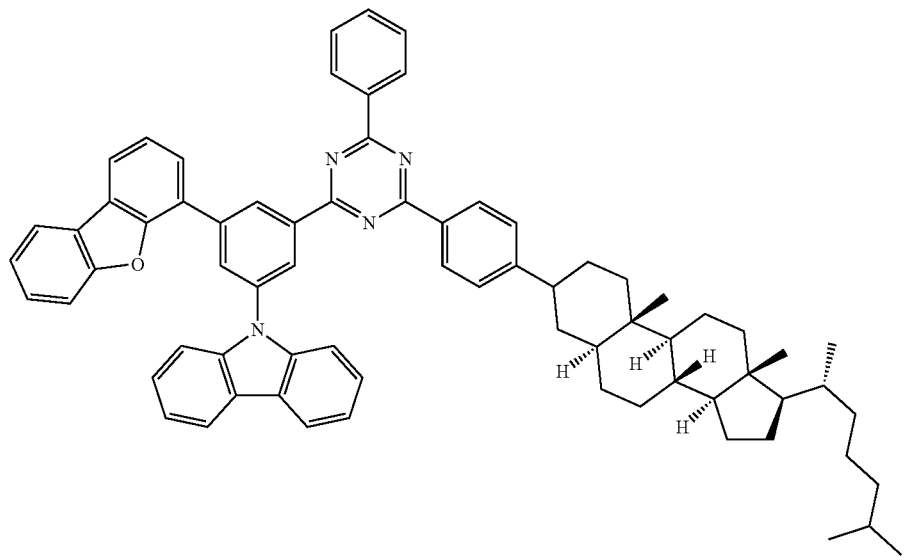
H-22
from Syn-23
Yield: 36%
5)
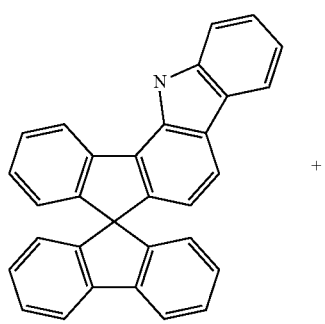   +
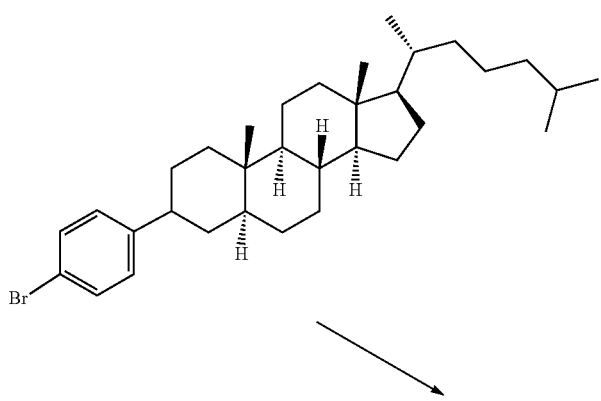

-continued

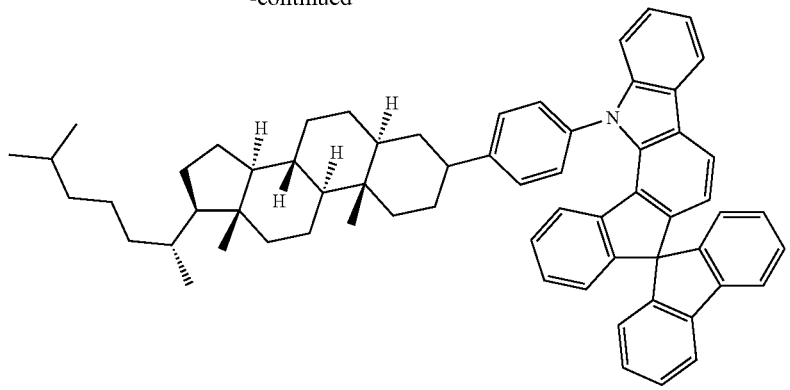

18.1 g (44.6 mmol) of Syn-6, 40 g (75.9 mmol, 1.7 eq) of BB-2, 6.61 g (66.7 mmol, 1.5 eq) of sodium tert-butylate are weighed in a 1000 ml four-neck flask with KPG stirrer, heating head, reflux condenser and argon overlay and degassed. 0.3 g (1.35 mmol, 0.03 eq) of palladium(II) acetate, 982 mg (2.67 mmol, 0.06 eq) of tricyclohexylphosphine tetrafluoroborate (CAS: 58656-04-5) and 450 ml of anhydrous o-xylene are added to the reaction mixture, which is boiled for 48 hours under reflux. After cooling to room temperature, the solvent is removed in vacuum, 300 ml of ethanol are added to the residue and the mixture is stirred at 50° C. for 3 hours. The solid is filtered, washed with ethanol and dried. Multiple recrystallization from toluene/heptane mixtures are performed. A colorless solid H-23 is obtained as a product (12.17 g, 14.3 mmol, 32%).

The compounds H-24 to H-28 are obtained analogously by replacing Syn-6 with other synthons, see Table below:

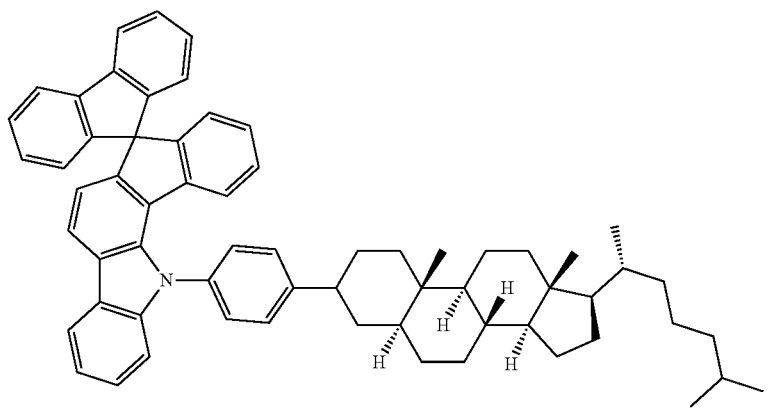

H-23
from Syn-6
Yield 32%

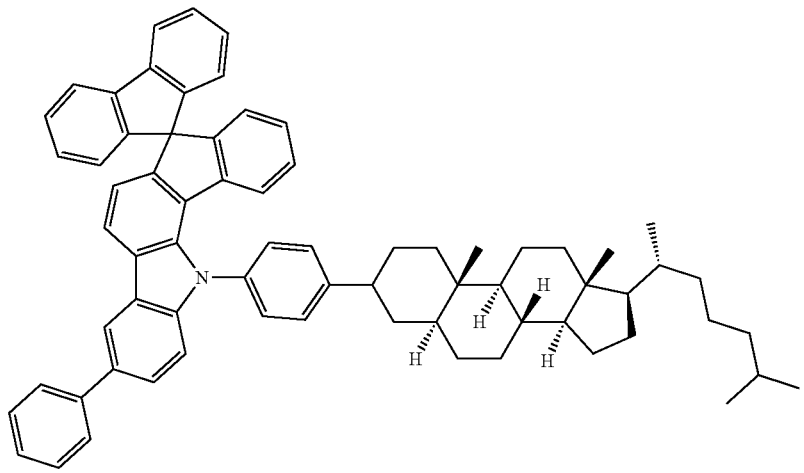
H-24
from Syn-7
Yield 27%
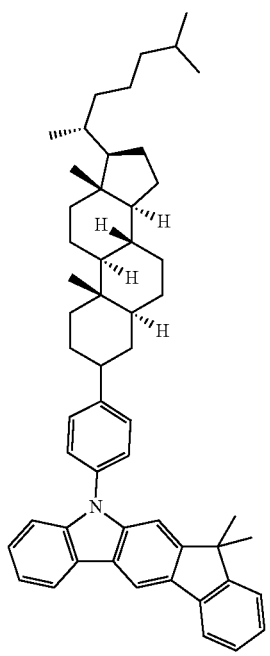
H-25
from Syn-13
Yield 29%

-continued
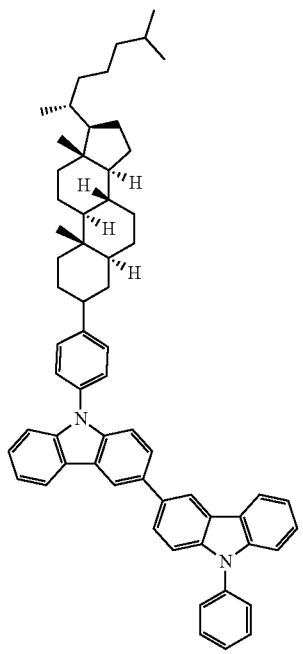
H-26
from Syn-14
Yield 36%
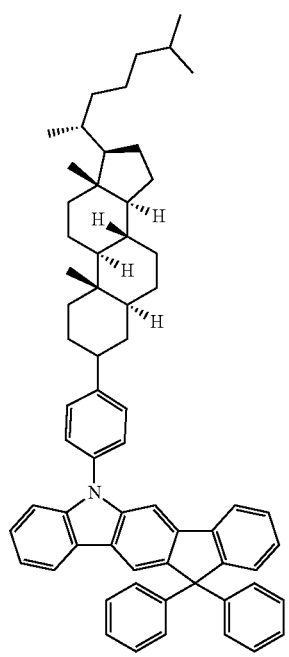
H-27
from Syn-15
Yield 33%

-continued

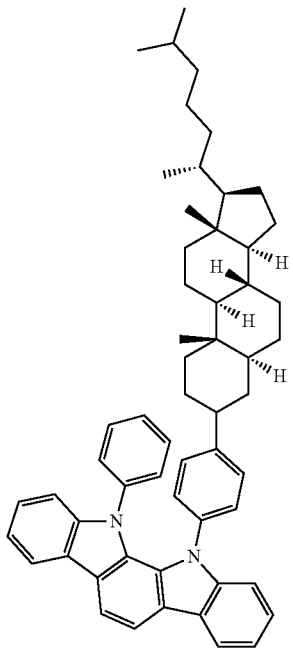

H-28
from Syn-16
Yield 21% c-5) Fabrication of OLEDs

The host compounds H-1 to H-28 can be used as host compounds in the OLEDs described above in point b-3) instead of M1 and/or M2.

The invention claimed is:
1. A compound of one of the formulae (1) to (4),

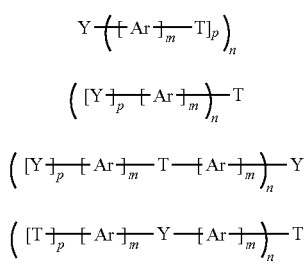

Formula (1)
Formula (2)
Formula (3)
Formula (4)

where the following applies to the symbols and indices used:

Y is selected from the group consisting of fluorescent emitting groups, phosphorescent emitting groups, host groups for fluorescent emitting compounds and host groups for phosphorescent emitting compounds, having a molecular weight equal or less than 3000 g/mol, and which may in each case be substituted by one or more radicals $R^1$;

Ar is on each occurrence, identically or differently, selected from the group consisting of aromatic ring systems having 6 to 18 aromatic ring atoms, which may in each case also be substituted by one or more radicals R, where two groups Ar are allowed to be connected via a single bond or a divalent bridge;

T is on each occurrence, identically or differently selected from the group consisting of T1 to T19, T1
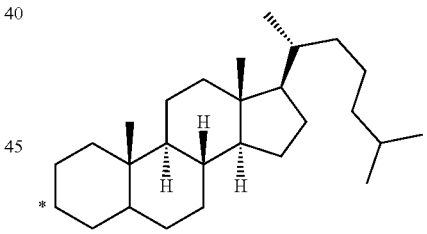

T2
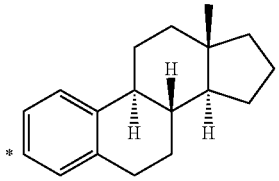

T3
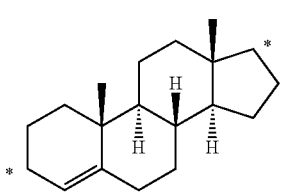

-continued

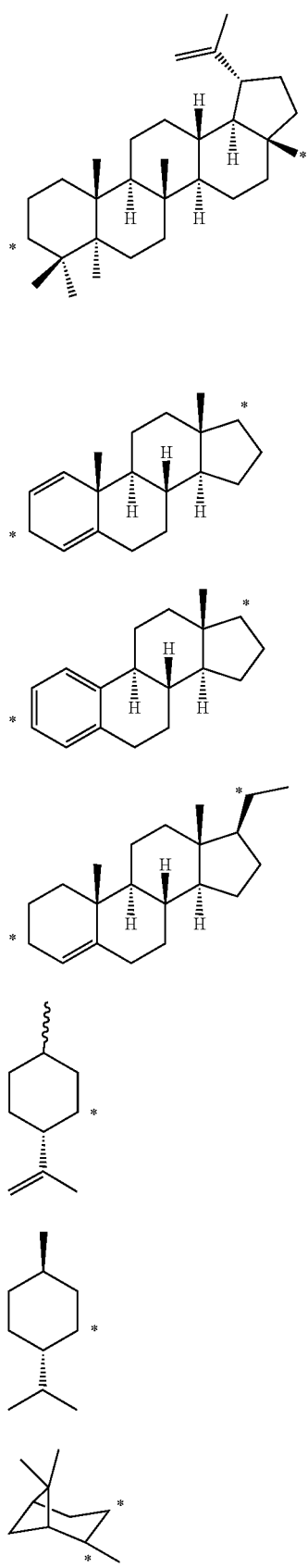

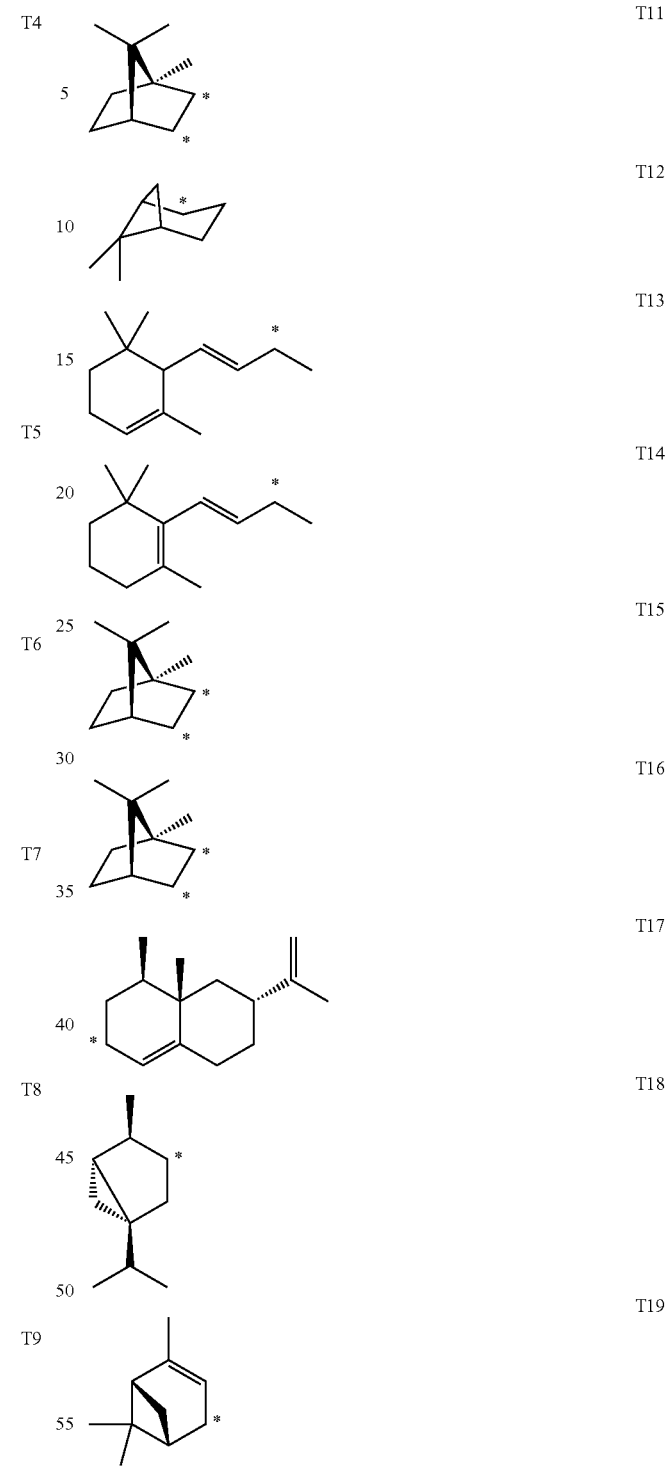

where the symbol(s) * in T1 to T19 indicates the bonding to the group(s) —(Ar)$_m$—Y in formulae (1) to (4);

R and R$^1$ stand on each occurrence, identically or differently, for H, D, F, Cl, Br, I, CHO, CN, NO$_2$, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals R$^2$, where in each case one or more non-adjacent CH$_2$ groups may be replaced by $R^2C=CR^2$, $C\equiv$, $C=O$, $C=S$, SO, $SO_2$, O or S and where one or more H atoms may be replaced by D, F, Cl, Br, I, CN or $NO_2$, an aromatic or heteroaromatic ring systems having 5 to 60 aromatic ring atoms, which may in each case be substituted by one or more radicals $R^2$, or an aryloxy groups having 5 to 60 aromatic ring atoms, which may be substituted by one or more radicals $R^2$, where two adjacent substituents R and/or two adjacent substituents $R^1$ may form a mono- or polycyclic, aliphatic ring system or aromatic ring system, which may be substituted by one or more radicals $R^2$;

$R^2$ stands on each occurrence, identically or differently, for H, D, F, Cl, Br, I, CN, a straight-chain alkyl, alkoxy or thioalkyl groups having 1 to 20 C atoms or branched or cyclic alkyl, alkoxy or thioalkyl groups having 3 to 20 C atoms, where in each case one or more non-adjacent $CH_2$ groups may be replaced by SO, $SO_2$, O, S and where one or more H atoms may be replaced by D, F, Cl, Br or I, or an aromatic or heteroaromatic ring system having 5 to 24 C atoms;

m is on each occurrence, identically or differently, 1, 2, 3 or 4;

n is an integer from 1 to 8; and p is on each occurrence, identically or differently, 0 or 1, with the proviso that at least one p is equal to 1 in formulae (1) and (2).

2. The compound according to claim 1, wherein m is on each occurrence, identically or differently, 1 or 2.

3. The compound according to claim 1, wherein the group Y is a phosphorescent emitting group selected from the group consisting of iridium, platinum and copper complexes.

4. The compound according to claim 1, wherein the group Y is a fluorescent emitting group selected from the group consisting of arylamines, indenofluorene derivatives and anthracene derivatives.

5. The compound according to claim 1, wherein the group Y is a host group for a phosphorescent emitting compound selected from spirobifluorene amines, aromatic ketones, aromatic phosphine oxides or aromatic sulfoides or sulfones, triarylamines, carbazole derivatives, indolocarbazole derivatives, indenocarbazole derivatives, azacarbazole derivatives, silanes, azaboroles or boronic esters, triazine derivatives, zinc complexes, fluorene derivatives, diazasilole or tetraazasilole derivatives, diazaphosphole derivatives or bridged carbazole derivatives.

6. The compound according to claim 1, wherein the group Y is a host group for a fluorescent emitting compound selected from the group consisting of oligoarylenes comprising naphthalene, anthracene, benzanthracene, benzophenanthrene, pyrene, oligoarylenevinylenes, indenofluorene derivatives, ketones, phosphine oxides and sulfoxides.

7. The compound according to claim 1, wherein the group T has a molecular weight equal or superior to 350 g/mol.

8. A formulation comprising at least one compound according to claim 1 and at least one solvent.

9. The formulation according to claim 8, wherein the solvents is selected from the group consisting of aromatics, alkylaromatics, cyclohexanes, ketones, ethers, esters, amides, sulfones, sulfoxides and mixtures thereof.

10. A process for the preparation of the compound according to claim 1, which comprises bonding group T to a group Y, or in which a group T, which is previously substituted by a group Ar, is bonded to a group Y via the group Ar, where T, Y and Ar have the same meaning as in claim 1.

11. An electronic device comprising at least one compound according to claim 1, wherein the electronic device is selected from the group consisting of organic electroluminescent device, organic integrated circuit, organic field-effect transistor, organic thin-film transistor, organic light-emitting transistor, organic solar cell, dye-sensitised organic solar cell, organic optical detector, organic photoreceptor, organic field-quench device, light-emitting electrochemical cell, organic laser diode, organic plasmon emitting device and liquid-crystal device.

12. An organic electroluminescent device which comprises an emitting layer, where the said emitting layer comprises at least one compound according to claim 1.

13. The compound according to claim 1, wherein the group T is selected from the group consisting of T1, T2, T6, T9, T10, T11, T12, T15, T16 and T18.

14. The compound according to claim 1, wherein the group T is selected from the group consisting of T1, T2 and T6.

15. The compound according to claim 1, wherein the group T is selected from the group consisting of T1 and T2.

* * * * *